(12) United States Patent
Stoddart et al.

(10) Patent No.: US 11,649,480 B2
(45) Date of Patent: May 16, 2023

(54) METHOD FOR MODIFYING A TEMPLATE DOUBLE STRANDED POLYNUCLEOTIDE

(71) Applicant: Oxford Nanopore Technologies PLC, Oxford (GB)

(72) Inventors: David Jackson Stoddart, Oxford (GB); James White, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 1119 days.

(21) Appl. No.: 16/304,114

(22) PCT Filed: May 25, 2017

(86) PCT No.: PCT/GB2017/051490
§ 371 (c)(1),
(2) Date: Nov. 21, 2018

(87) PCT Pub. No.: WO2017/203267
PCT Pub. Date: Nov. 30, 2017

(65) Prior Publication Data
US 2019/0194722 A1    Jun. 27, 2019

(30) Foreign Application Priority Data

May 25, 2016 (GB) ..................... 1609220

(51) Int. Cl.
*C12Q 1/6806* (2018.01)
*C12Q 1/6869* (2018.01)

(52) U.S. Cl.
CPC ......... *C12Q 1/6806* (2013.01); *C12Q 1/6869* (2013.01); *C12Q 2521/10* (2013.01); *C12Q 2521/513* (2013.01); *C12Q 2522/101* (2013.01); *C12Q 2525/155* (2013.01); *C12Q 2525/191* (2013.01); *C12Q 2535/122* (2013.01); *C12Q 2565/631* (2013.01)

(58) Field of Classification Search
CPC ................ C12Q 1/6806; C12Q 1/6869; C12Q 2521/10; C12Q 2521/513; C12Q 2522/101; C12Q 2525/155; C12Q 2525/191; C12Q 2535/122; C12Q 2565/631
See application file for complete search history.

(56) References Cited

U.S. PATENT DOCUMENTS

| | | |
|---|---|---|
| 5,215,899 A | 6/1993 | Dattagupta |
| 5,424,413 A | 6/1995 | Hogan et al. |
| 5,561,043 A | 10/1996 | Cantor et al. |
| 5,714,320 A | 2/1998 | Kool |
| 5,777,078 A | 7/1998 | Bayley et al. |
| 5,795,782 A | 8/1998 | Church et al. |
| 5,817,771 A | 10/1998 | Bayley et al. |
| 5,866,328 A | 2/1999 | Bensimon et al. |
| 5,866,336 A | 2/1999 | Nazarenko et al. |
| 5,985,834 A | 11/1999 | Engel et al. |
| 6,015,714 A | 1/2000 | Baldarelli et al. |
| 6,087,099 A | 7/2000 | Gupte et al. |
| 6,123,819 A | 9/2000 | Peeters |
| 6,127,166 A | 10/2000 | Bayley et al. |
| 6,251,610 B1 | 6/2001 | Gupte et al. |
| 6,274,320 B1 | 8/2001 | Rothberg et al. |
| 6,362,002 B1 | 3/2002 | Denison et al. |
| 6,403,319 B1 | 6/2002 | Lizardi et al. |
| 6,426,231 B1 | 7/2002 | Bayley et al. |
| 6,451,563 B1 | 9/2002 | Wittig et al. |
| 6,451,593 B1 | 9/2002 | Wittig et al. |
| 6,465,193 B2 | 10/2002 | Akeson et al. |
| 6,498,023 B1 | 12/2002 | Abarzua |
| 6,627,067 B1 | 9/2003 | Branton et al. |
| 6,709,861 B2 | 3/2004 | Mead et al. |
| 6,787,308 B2 | 9/2004 | Balasubramanian et al. |
| 6,824,659 B2 | 11/2004 | Bayley et al. |
| 6,863,833 B1 | 3/2005 | Bloom et al. |
| 6,916,665 B2 | 7/2005 | Bayley et al. |
| 6,927,070 B1 | 8/2005 | Bayley et al. |
| 7,087,729 B1 | 8/2006 | Prive |
| 7,189,503 B2 | 3/2007 | Akeson et al. |
| 7,238,485 B2 | 7/2007 | Akeson et al. |
| 7,361,466 B2 | 4/2008 | Korlach et al. |
| 7,507,575 B2 | 3/2009 | Bedingham et al. |
| 7,700,281 B2 | 4/2010 | Kubu et al. |
| 7,745,116 B2 | 6/2010 | Williams |
| 8,105,846 B2 | 1/2012 | Bayley et al. |
| 8,143,030 B2 | 3/2012 | Maxham et al. |
| 8,153,375 B2 | 4/2012 | Travers et al. |

(Continued)

FOREIGN PATENT DOCUMENTS

| | | |
|---|---|---|
| CN | 101495656 | 7/2009 |
| CN | 102245760 | 11/2011 |

(Continued)

OTHER PUBLICATIONS

[No Author Listed], Multiplex sequencing. https://www.illumina.com/science/technology/next-generation-sequencing/multiplex-sequencing.html. Printed on Nov. 4, 2021. 1 page.

(Continued)

*Primary Examiner* — Narayan K Bhat

(74) *Attorney, Agent, or Firm* — Wolf, Greenfield & Sacks, P.C.

(57) ABSTRACT

The invention relates to a method for modifying a template double stranded polynucleotide, especially for characterisation using nanopore sequencing. The method produces from the template a plurality of modified double stranded polynucleotides. These modified polynucleotides can then be characterised.

20 Claims, 6 Drawing Sheets
Specification includes a Sequence Listing.

(56) References Cited

U.S. PATENT DOCUMENTS

| | | |
|---|---|---|
| 8,343,746 B2 | 1/2013 | Rank et al. |
| 8,383,369 B2 | 2/2013 | Maxham et al. |
| 8,628,940 B2 | 1/2014 | Sorenson et al. |
| 8,652,779 B2 | 2/2014 | Turner et al. |
| 8,785,211 B2 | 7/2014 | Bayley et al. |
| 8,822,160 B2 | 9/2014 | Bayley et al. |
| 8,889,348 B2 | 11/2014 | Ju |
| 9,057,102 B2 | 6/2015 | Turner et al. |
| 9,116,118 B2 | 8/2015 | Turner et al. |
| 9,145,623 B2 | 9/2015 | Kavanagh et al. |
| 9,150,918 B2 | 10/2015 | Turner et al. |
| 9,542,527 B2 | 1/2017 | Travers et al. |
| 9,546,400 B2 | 1/2017 | Turner et al. |
| 9,551,023 B2 | 1/2017 | Turner et al. |
| 9,556,480 B2 | 1/2017 | Turner et al. |
| 9,582,640 B2 | 2/2017 | Travers et al. |
| 9,600,626 B2 | 3/2017 | Travers et al. |
| 9,670,526 B2 | 6/2017 | Kokoris et al. |
| 9,678,056 B2 | 6/2017 | Turner et al. |
| 9,738,929 B2 | 8/2017 | Turner et al. |
| 9,957,560 B2 | 5/2018 | Brown et al. |
| 10,131,944 B2 | 11/2018 | Bernick et al. |
| 10,221,450 B2 | 3/2019 | Heron et al. |
| 10,227,632 B2 | 3/2019 | Jarvius |
| 10,501,767 B2 | 12/2019 | Stoddart et al. |
| 10,570,440 B2 | 2/2020 | White et al. |
| 10,597,713 B2 | 3/2020 | Brown et al. |
| 10,669,578 B2 | 6/2020 | Clarke et al. |
| 10,851,409 B2 | 12/2020 | Brown et al. |
| 11,155,860 B2 | 10/2021 | White et al. |
| 11,168,363 B2 | 11/2021 | Brown et al. |
| 11,186,857 B2 | 11/2021 | Stoddart et al. |
| 11,261,487 B2 | 3/2022 | Brown et al. |
| 11,268,139 B2 | 3/2022 | Lu |
| 11,352,664 B2 | 6/2022 | Mckeown |
| 11,390,904 B2 | 7/2022 | White |
| 11,459,606 B2 | 10/2022 | Mckeown |
| 2001/0039039 A1 | 11/2001 | Weissman et al. |
| 2002/0028458 A1 | 3/2002 | Lexow |
| 2002/0094526 A1 | 7/2002 | Bayley et al. |
| 2002/0098530 A1 | 7/2002 | Pfeifer et al. |
| 2002/0132350 A1 | 9/2002 | Suzuki et al. |
| 2002/0142331 A1 | 10/2002 | Fu et al. |
| 2002/0177701 A1 | 11/2002 | Weissman et al. |
| 2002/0197618 A1 | 12/2002 | Sampson |
| 2003/0044816 A1 | 3/2003 | Denison et al. |
| 2003/0059778 A1 | 3/2003 | Berlin et al. |
| 2003/0087232 A1 | 5/2003 | Christians et al. |
| 2003/0099951 A1 | 5/2003 | Akeson et al. |
| 2003/0108902 A1 | 6/2003 | Abarzua |
| 2003/0118595 A1 | 6/2003 | Niemeyer et al. |
| 2003/0165936 A1 | 9/2003 | Rabbani et al. |
| 2003/0166137 A1 | 9/2003 | Zuker et al. |
| 2003/0211502 A1 | 11/2003 | Sauer et al. |
| 2003/0215881 A1 | 11/2003 | Bayley et al. |
| 2004/0055901 A1 | 3/2004 | Petersen et al. |
| 2004/0214177 A1 | 10/2004 | Bension |
| 2004/0229315 A1 | 11/2004 | Lee et al. |
| 2005/0042633 A1 | 2/2005 | Williams |
| 2005/0053961 A1 | 3/2005 | Akeson et al. |
| 2005/0142559 A1 | 6/2005 | Makrigiorgos |
| 2005/0221316 A1 | 10/2005 | Pedersen et al. |
| 2005/0227239 A1 | 10/2005 | Joyce |
| 2005/0260655 A1 | 11/2005 | Liu et al. |
| 2006/0063171 A1 | 3/2006 | Akeson et al. |
| 2006/0086626 A1 | 4/2006 | Joyce |
| 2006/0141516 A1 | 6/2006 | Kobold et al. |
| 2006/0147935 A1 | 7/2006 | Linnarsson |
| 2006/0292611 A1 | 12/2006 | Berka et al. |
| 2007/0015182 A1 | 1/2007 | Abarzua |
| 2007/0020640 A1 | 1/2007 | McCloskey |
| 2007/0031857 A1 | 2/2007 | Makarov et al. |
| 2007/0122885 A1 | 5/2007 | Reeves et al. |
| 2007/0224613 A1 | 9/2007 | Strathmann |
| 2007/0269825 A1 | 11/2007 | Wang et al. |
| 2007/0287151 A1 | 12/2007 | Linnarsson |
| 2008/0108082 A1 | 5/2008 | Rank et al. |
| 2008/0166724 A1 | 7/2008 | Gerber et al. |
| 2008/0206252 A1 | 8/2008 | Pennica et al. |
| 2008/0311582 A1 | 12/2008 | Bayley et al. |
| 2009/0098612 A1 | 4/2009 | Rhee et al. |
| 2009/0191598 A1 | 7/2009 | Ruan et al. |
| 2009/0256116 A1 | 10/2009 | Shumaker-Parry et al. |
| 2009/0269771 A1 | 10/2009 | Schroeder |
| 2009/0280538 A1 | 11/2009 | Patel et al. |
| 2009/0298075 A1 | 12/2009 | Travers et al. |
| 2010/0003560 A1 | 1/2010 | Shibata |
| 2010/0035254 A1 | 2/2010 | Williams |
| 2010/0035260 A1 | 2/2010 | Olasagasti et al. |
| 2010/0075309 A1 | 3/2010 | Maxham et al. |
| 2010/0075327 A1 | 3/2010 | Maxham et al. |
| 2010/0075328 A1 | 3/2010 | Bjornson et al. |
| 2010/0092960 A1 | 4/2010 | Fehr |
| 2010/0120098 A1 | 5/2010 | Grunenwald et al. |
| 2010/0121582 A1 | 5/2010 | Pan et al. |
| 2010/0221212 A1 | 9/2010 | Stagliano et al. |
| 2010/0221716 A1 | 9/2010 | Flusberg et al. |
| 2010/0276588 A1 | 11/2010 | Syms |
| 2010/0331194 A1 | 12/2010 | Turner et al. |
| 2011/0019186 A1 | 1/2011 | Himmelhaus et al. |
| 2011/0124518 A1 | 5/2011 | Cantor |
| 2011/0136676 A1 | 6/2011 | Greene |
| 2011/0214991 A1 | 9/2011 | Kim et al. |
| 2011/0224106 A1 | 9/2011 | Eshoo et al. |
| 2011/0281768 A1 | 11/2011 | Travers et al. |
| 2011/0287435 A1 | 11/2011 | Grunenwald et al. |
| 2011/0311965 A1 | 12/2011 | Maglia et al. |
| 2012/0010085 A1 | 1/2012 | Rava et al. |
| 2012/0015821 A1 | 1/2012 | Raymond |
| 2012/0058468 A1 | 3/2012 | Mckeown |
| 2012/0100530 A1 | 4/2012 | Moysey et al. |
| 2012/0107802 A1 | 5/2012 | Stoddart et al. |
| 2012/0196279 A1 | 8/2012 | Underwood et al. |
| 2012/0244525 A1 | 9/2012 | Hendrickson |
| 2013/0017978 A1 | 1/2013 | Kavanagh et al. |
| 2013/0048499 A1 | 2/2013 | Mayer et al. |
| 2013/0078624 A1 | 3/2013 | Holmes et al. |
| 2013/0143802 A1 | 6/2013 | Chilkoti |
| 2013/0195908 A1 | 8/2013 | Leonetti et al. |
| 2013/0203123 A1 | 8/2013 | Nelson et al. |
| 2013/0327644 A1 | 12/2013 | Turner et al. |
| 2014/0134618 A1 | 5/2014 | Kokoris et al. |
| 2014/0134629 A1 | 5/2014 | Turner et al. |
| 2014/0186823 A1 | 7/2014 | Clarke et al. |
| 2014/0206842 A1 | 7/2014 | Majeed et al. |
| 2014/0262784 A1 | 9/2014 | Clarke et al. |
| 2014/0296089 A1 | 10/2014 | Holmes et al. |
| 2014/0308661 A1 | 10/2014 | Holmes et al. |
| 2015/0008126 A1 | 1/2015 | Maglia et al. |
| 2015/0045257 A1 | 2/2015 | Kavanagh et al. |
| 2015/0152492 A1 | 6/2015 | Brown et al. |
| 2015/0167075 A1 | 6/2015 | Turner et al. |
| 2015/0175663 A1 | 6/2015 | Yokoi et al. |
| 2015/0197796 A1 | 7/2015 | White et al. |
| 2015/0218629 A1 | 8/2015 | Heron et al. |
| 2015/0265994 A1 | 9/2015 | Hyde et al. |
| 2015/0285781 A1 | 10/2015 | Heron et al. |
| 2015/0307934 A1 | 10/2015 | Turner et al. |
| 2016/0010147 A1 | 1/2016 | Heron et al. |
| 2016/0010148 A1 | 1/2016 | Turner et al. |
| 2016/0011169 A1 | 1/2016 | Turner et al. |
| 2016/0194677 A1 | 7/2016 | Stoddart et al. |
| 2016/0257942 A1 | 9/2016 | Bruce et al. |
| 2016/0281159 A1 | 9/2016 | Brown et al. |
| 2016/0362739 A1 | 12/2016 | Brown et al. |
| 2017/0002406 A1 | 1/2017 | Bowen et al. |
| 2017/0067101 A1 | 3/2017 | Clarke et al. |
| 2017/0226503 A1 | 8/2017 | Strachan et al. |
| 2017/0240955 A1 | 8/2017 | White |
| 2017/0314062 A1 | 11/2017 | Kokoris et al. |
| 2017/0321266 A1 | 11/2017 | Mckeown |
| 2018/0030506 A1 | 2/2018 | Fujioka |
| 2018/0051277 A1 | 2/2018 | Godfrey et al. |
| 2018/0291440 A1 | 10/2018 | Mckeown |

(56) References Cited

U.S. PATENT DOCUMENTS

| | | | |
|---|---|---|---|
| 2018/0291441 A1 | 10/2018 | Brown et al. | |
| 2019/0194722 A1 | 6/2019 | Stoddart et al. | |
| 2019/0211390 A1 | 7/2019 | Heron et al. | |
| 2019/0376132 A1 | 12/2019 | Mckeown | |
| 2020/0002761 A1 | 1/2020 | Mckeown | |
| 2020/0024655 A1 | 1/2020 | Brown et al. | |
| 2020/0032248 A1 | 1/2020 | White et al. | |
| 2020/0109396 A1 | 4/2020 | Tsai et al. | |
| 2020/0131549 A1 | 4/2020 | Stoddart et al. | |
| 2020/0239950 A1 | 7/2020 | Brown et al. | |
| 2020/0291452 A1 | 9/2020 | White | |
| 2020/0318179 A1 | 10/2020 | Clarke et al. | |
| 2022/0127669 A1 | 4/2022 | Brown et al. | |
| 2022/0145383 A1 | 5/2022 | White et al. | |
| 2022/0186274 A1 | 6/2022 | Stoddart et al. | |

FOREIGN PATENT DOCUMENTS

| | | |
|---|---|---|
| CN | 105209634 A | 12/2015 |
| CN | 105705656 A | 6/2016 |
| DE | 112016000293 T5 | 9/2017 |
| EP | 2682460 A1 | 1/2014 |
| EP | 3470529 A1 | 4/2019 |
| GB | 2130219 | 5/1984 |
| GB | 2237390 | 5/1991 |
| GB | 2453377 | 4/2009 |
| JP | H11-137260 | 5/1999 |
| JP | 2012-506704 A | 3/2012 |
| WO | WO 1994/23065 | 10/1994 |
| WO | WO 1999/05167 | 2/1999 |
| WO | WO 2000/28312 | 5/2000 |
| WO | WO 2001/40516 | 6/2001 |
| WO | WO 2001/42782 | 6/2001 |
| WO | WO 2001/59453 | 8/2001 |
| WO | WO 2002/42496 | 5/2002 |
| WO | WO 2003/095669 | 11/2003 |
| WO | WO 2005/056750 | 6/2005 |
| WO | WO 2005/068656 A1 | 7/2005 |
| WO | WO 2005/118877 | 12/2005 |
| WO | WO 2005/124888 | 12/2005 |
| WO | WO 2006/020775 | 2/2006 |
| WO | WO 2006/028508 | 3/2006 |
| WO | WO 2006/100484 | 9/2006 |
| WO | WO 2007/057668 | 5/2007 |
| WO | WO 2007/075987 | 7/2007 |
| WO | WO 2007/084103 | 7/2007 |
| WO | WO 2007/114693 A2 | 10/2007 |
| WO | WO 2007/146158 | 12/2007 |
| WO | WO 2008/045575 | 4/2008 |
| WO | WO 2008/083554 | 7/2008 |
| WO | WO 2008/102120 | 8/2008 |
| WO | WO 2008/102121 | 8/2008 |
| WO | WO 2008/124107 | 10/2008 |
| WO | WO 2009/035647 | 3/2009 |
| WO | WO 2009/044170 A1 | 4/2009 |
| WO | WO 2009/077734 A2 | 6/2009 |
| WO | WO 2009/120372 A2 | 10/2009 |
| WO | WO 2009/120374 A2 | 10/2009 |
| WO | WO 2010/004265 | 1/2010 |
| WO | WO 2010/004273 | 1/2010 |
| WO | WO 2010/030683 A1 | 3/2010 |
| WO | WO 2010/034018 | 3/2010 |
| WO | WO 2010/048605 A1 | 4/2010 |
| WO | WO 2010/051773 | 5/2010 |
| WO | WO 2010/086602 A1 | 8/2010 |
| WO | WO 2010/086603 | 8/2010 |
| WO | WO 2010/086622 | 8/2010 |
| WO | WO 2010/094040 | 8/2010 |
| WO | WO 2010/109107 A1 | 9/2010 |
| WO | WO 2010/109197 | 9/2010 |
| WO | WO 2010/122293 | 10/2010 |
| WO | WO 2010/146349 A1 | 12/2010 |
| WO | WO 2011/067559 | 6/2011 |
| WO | WO 2012/033524 A2 | 3/2012 |
| WO | WO 2012/061832 | 5/2012 |
| WO | WO 2012/083249 A2 | 6/2012 |
| WO | WO 2012/098561 A2 | 7/2012 |
| WO | WO 2012/098562 A2 | 7/2012 |
| WO | WO 2012/103545 A1 | 8/2012 |
| WO | WO 2012/107778 A2 | 8/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/131962 A1 | 9/2013 |
| WO | WO 2013/153359 A1 | 10/2013 |
| WO | WO 2013/185137 A1 | 12/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A2 | 5/2014 |
| WO | WO 2014/064444 A1 | 5/2014 |
| WO | WO 2014/108810 A2 | 7/2014 |
| WO | WO 2014/135838 A1 | 9/2014 |
| WO | WO 2014/153408 | 9/2014 |
| WO | WO 2015/022544 A1 | 2/2015 |
| WO | WO 2015/031909 A1 | 3/2015 |
| WO | WO 2015/055981 A2 | 4/2015 |
| WO | WO 2015/056028 A1 | 4/2015 |
| WO | WO 2015/110777 A1 | 7/2015 |
| WO | WO 2015/110813 A1 | 7/2015 |
| WO | WO 2015/189636 A1 | 12/2015 |
| WO | WO 2015/200609 A1 | 12/2015 |
| WO | WO 2016/003814 A1 | 1/2016 |
| WO | WO 2016/022557 A1 | 2/2016 |
| WO | WO 2016/028887 A1 | 2/2016 |
| WO | WO 2016/034591 A2 | 3/2016 |
| WO | WO 2016/055777 A2 | 4/2016 |
| WO | WO 2016/059363 A1 | 4/2016 |
| WO | WO 2017/215500 A1 | 12/2017 |

OTHER PUBLICATIONS

[No Author Listed], Single-molecule real-time sequencing. Wikipedia entry/ Sep. 19, 2021. Retrieved from https://en.wikipedia.org/w/index.php?title+Singlemolecule_real-time_sequencing&oldid=1045146197. Printed on Nov. 4, 2021. 10 pages.

Dong et al., Amplified detection of nucleic acid by G-quadruplex based hybridization chain reaction. Biosens Bioelectron. Oct.-Dec. 2012;38(1):258-63. doi: 10.1016/j.bios.2012.05.042. Epub Jun. 8, 2012.

Faller et al., The structure of a mycobacterial outer-membrane channel. Science. Feb. 20, 2004;303(5661):1189-92. doi: 10.1126/science.1094114.

Gill et al., Nucleic acid isothermal amplification technologies: a review. Nucleosides Nucleotides Nucleic Acids. Mar. 2008;27(3):224-43. doi: 10.1080/15257770701845204.

He et al., The carboxyl-terminal domain of bacteriophage T7 single-stranded DNA-binding protein modulates DNA binding and interaction with T7 DNA polymerase. J Biol Chem. Aug. 8, 2003;278(32):29538-45. doi: 10.1074/jbc.M304318200. Epub May 24, 2003.

Hollis et al., Structure of the gene 2.5 protein, a single-stranded DNA binding protein encoded by bacteriophage T7. Proc Natl Acad Sci U S A. Aug. 14, 2001;98(17):9557-62. doi: 10.1073/pnas.171317698. Epub Jul. 31, 2001.

Hyland et al., The DNA binding domain of the gene 2.5 single-stranded DNA-binding protein of bacteriophage T7. J Biol Chem. Feb. 28, 2003;278(9):7247-56. doi: 10.1074/jbc.M210605200. Epub Dec. 20, 2002.

Kahvejian et al., Making single-molecule sequencing a reality. American Laboratory. Jan. 1, 2008;40(20):48-53. www.americanlaboratory.com/913-Technical-Articles/780-Making-Single-Molecule-Sequencing-a-Reality/. Last accessed Dec. 10, 2021.

Kuipers, Random mutagenesis by using mixtures of dNTP and dITP in PCR. Methods Mol Biol. 1996;57:351-6. doi: 10.1385/0-89603-332-5:351.

(56) References Cited

OTHER PUBLICATIONS

Liang, Structure of outer membrane protein G by solution NMR spectroscopy. Proc Natl Acad Sci U S A. Oct. 9, 2007;104(41):16140-5. doi: 10.1073/pnas.0705466104. Epub Oct. 2, 2007.

Locher et al., Transmembrane signaling across the ligand-gated FhuA receptor: crystal structures of free and ferrichrome-bound states reveal allosteric changes. Cell. Dec. 11, 1998;95(6):771-8. doi: 10.1016/s0092-8674(00)81700-6.

Manosas et al., Magnetic tweezers for the study of DNA tracking motors. Methods Enzymol. 2010;475:297-320. doi: 10.1016/80076-6879(10)75013-8.

Matson et al., The gene 4 protein of bacteriophage T7. Characterization of helicase activity. J Biol Chem. Nov. 25, 1983;258(22):14017-24.

Miner et al., Molecular barcodes detect redundancy and contamination in hairpin-bisulfite PCR. Nucleic Acids Res. 2004; 32(17): e135. EPub Sep. 30, 2004. doi: 10.1093/nar/gnh132.

Pettersson et al., Generations of sequencing technologies. Genomics. Feb. 2009;93(2):105-11. doi: 10.1016/j.ygeno.2008.10.003. Epub Nov. 21, 2008.

Rezende et al., Essential amino acid residues in the single-stranded DNA-binding protein of bacteriophage T7. Identification of the dimer interface. J Biol Chem. Dec. 27, 2002;277(52):50643-53. doi: 10.1074/jbc.M207359200. Epub Oct. 12, 2002.

Shendure et al., Overview of DNA sequencing strategies. Curr Protoc Mol Biol. Jan. 2008;Chapter 7:Unit 7.1. doi: 10.1002/0471142727.mb0701s81.

Spee et al., Efficient random mutagenesis method with adjustable mutation frequency by use of PCR and dITP. Nucleic Acids Res. Feb. 11, 1993;21(3):777-8. doi: 10.1093/nar/21.3.777.

Wang et al., A simple and reproducible method for directed evolution: combination of random mutation with dITP and DNA fragmentation with endonuclease V. Mol Biotechnol. Jan. 2013;53(1):49-54. doi: 10.1007/s12033-012-9516-9.

Yamashita et al., Crystal structures of the OmpF porin: function in a colicin translocon. EMBO J. Aug. 6, 2008;27(15):2171-80. doi: 10.1038/emboj.2008.137. Epub Jul. 17, 2008.

International Search Report and Written Opinion for Application No. PCT/GB2017/051490, dated Aug. 28, 2017.

International Preliminary Report on Patentability for Application No. PCT/GB2017/051490, dated Dec. 6, 2018.

Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Amblard et al., Cu(I)-catalyzed Huisgen azide-alkyne 1,3-dipolar cycloaddition reaction in nucleoside, nucleotide, and oligonucleotide chemistry. Chem Rev. Sep. 2009;109(9):4207-20. doi: 10.1021/cr9001462.

Ashkenasy et al., Recognizing a single base in an individual DNA strand: a step toward DNA sequencing in nanopores. Angew Chem Int Ed Engl. Feb. 18, 2005;44(9): 1401-4.

Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.

Astier et al., Stochastic detection of motor protein-RNA complexes by single-channel current recording. Chemphyschem. Oct. 22, 2007;8(15):2189-94.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006; 128(5): 1705-10.

Avrameas, Coupling of enzymes to proteins with glutaraldehyde. Use of the conjugates for the detection of antigens and antibodies. Immunochemistry. Jan. 1969;6(1):43-52.

Bayley et al., Stochastic sensors inspired by biology. Nature. Sep. 13, 2001;413(6852):226-30.

Bayley, Sequencing single molecules of DNA. Curr Opin Chem Biol. Dec. 2006;10(6):628-37. Epub Nov. 20, 2006.

Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.

Berger et al., Universal bases for hybridization, replication and chain termination. Nucleic Acids Res. Aug. 1, 2000;28(15):2911-4.

Bowie et al., Deciphering the message in protein sequences: tolerance to amino acid substitutions. Science. Mar. 16, 1990;247(4948):1306-10.

Braha et al., Carriers versus adapters in stochastic sensing. Chemphyschem. May 2005;6(5):889-92.

Braha et al., Designed protein pores as components for biosensors. Chem Biol. Jul. 1997;4(7):497-505.

Branton et al., The potential and challenges of nanopore sequencing. Nat Biotechnol. Oct. 2008;26(10): 1146-53. doi:10.1038/nbt.1495.

Braslavsky et al., Sequence information can be obtained from single DNA molecules. Proc Natl Acad Sci U S A. Apr. 1, 2003;100(7):3960-4. Epub Mar. 21, 2003.

Budanova et al., Heptakis(6-amino-6-deoxy)-beta-cyclodextrin as a chiral selector for the separation of anionic analyte enantiomers by capillary electrophoresis. Electrophoresis. Aug. 2004;25(16):2795-800.

Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.

Busam, Structure of *Escherichia coli* exonuclease I in complex with thymidine 5'-monophosphate. Acta Crystallogr D Biol Crystallogr. Feb. 2008;64(Pt 2):206-10. doi: 10.1107/S090744490706012X. Epub Jan. 16, 2008.

Butler et al., Determination of RNA orientation during translocation through a biological nanopore. Biophys J. Jan. 1, 2006;90(1):190-9. Epub Oct. 7, 2005.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Chan, Advances in sequencing technology. Mutat Res. Jun. 3, 2005;573(1-2):13-40.

Cheley et al., A functional protein pore with a "retro" transmembrane domain. Protein Sci. Jun. 1999;8(6):1257-67.

Cheley et al., A genetically encoded pore for the stochastic detection of a protein kinase. Chembiochem. Dec. 2006;7(12):1923-7.

Cheley et al., Spontaneous oligomerization of a staphylococcal alpha-hemolysin conformationally constrained by removal of residues that form the transmembrane beta-barrel. Protein Eng. Dec. 1997;10(12):1433-43.

Cheley et al., Stochastic sensing of nanomolar inositol 1,4,5-trisphosphate with an engineered pore. Chem Biol. Jul. 2002;9(7):829-38.

Chen et al., Atomic Layer Deposition to Fine-Tune the Surface Properties and Diameters of Fabricated Nanopores. Nano Lett. Jun. 25, 2004;4(7):1333-1337.

Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.

Cheng, et al., Functional characterization of the multidomain F plasmid TraI relaxase-helicase. J Biol Chem. Apr. 8, 2011;286(14): 12670-82. doi: 10.1074/jbc.M110.207563. Epub Feb. 2, 2011.

Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.

Colas et al., Microscopical investigations of nisin-loaded nanoliposomes prepared by Mozafari method and their bacterial targeting. Micron. 2007;38(8):841-7. Epub Jul. 3, 2007.

(56) References Cited

OTHER PUBLICATIONS

Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Comai et al., Protein engineering modulates the transport properties and ion selectivity of the pores formed by staphylococcal gamma-haemolysins in lipid membranes. Mol Microbiol. Jun. 2002;44(5):1251-67.
Comer et al., Microscopic mechanics of hairpin DNA translocation through synthetic nanopores. Biophys J. Jan. 2009;96(2):593-608. doi: 10.1016/j.bpj.2008.09.023.
Cudic et al., Binding of Nucleotides in Water by Phenathridinium Bis(intercaland) Receptor Molecules. J. Chem. Soc., Chem. Commun., 1995:1073-75.
Dapprich, Single-molecule DNA digestion by lambda-exonuclease. Cytometry. Jul. 1, 1999;36(3):163-8.
Deamer et al., Characterization of nucleic acids by nanopore analysis. Acc Chem Res. Oct. 2002;35(10):817-25.
Deamer et al., Nanopores and nucleic acids: prospects for ultrarapid sequencing. Trends Biotechnol. Apr. 2000;18(4):147-51.
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Devereux et al., A comprehensive set of sequence analysis programs for the VAX. Nucleic Acids Res. Jan. 11, 1984; 12(1 Pt 1):387-95.
Dorre et al., Techniques for single molecule sequencing. Bioimaging, vol. 5:139-152 (1997).
Eid et al., Real-time DNA sequencing from single polymerase molecules. Science. Jan. 2, 2009;323(5910):133-8.doi:10.1126/science.1162986. Epub Nov. 20, 2008.
Eliseev et al., Aminocyclodextrins as Selective Hosts with Several Binding Sites for Nucleotides. Angew. Chem. Int. Ed. Engl., vol. 32(9):1331-1333 (1993).
Eliseev et al., Molecular Recognition of Nucleotides, Nucleosides, and Sugars by Aminocyclodextrins. J. Am. Chem. Soc., vol. 116:6081-6088 (1994).
El-Sagheer et al., Synthesis and polymerase chain reaction amplification of DNA strands containing an unnatural triazole linkage. J Am Chem Soc. Mar. 25, 2009;131(11):3958-64. doi: 10.1021/ja8065896.
Erie et al., A dumbbell-shaped, double-hairpin structure of DNA: a thermodynamic investigation. Biochemistry. Nov. 3, 1987;26(22):7150-9.
Fairman-Williams et al., SF1 and SF2 helicases: family matters. Curr Opin Struct Biol. Jun. 2010;20(3):313-24. doi: 10.1016/j.sbi.2010.03.011. Epub Apr. 22, 2010.
Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.
Flusberg et al., Direct detection of DNA methylation during single-molecule, real-time sequencing. Nat Methods. Jun. 2010;7(6):461-5. doi: 10.1038/nmeth.1459. Epub May 9, 2010.
Gacillàn-Barcia et al., The diversity of conjugative relaxases and its application in plasmid classification. FEMS Microbiol Rev. May 2009;33(3):657-87.
Genschel et al., Interaction of E. coli single-stranded DNA binding protein (SSB) with exonuclease I. The carboxy-tei minus of SSB is the recognition site for the nuclease. Biol Chem. Mar. 2000;381(3):183-92.
Gershow et al., Recapturing and trapping single molecules with a solid-state nanopore. Nat Nanotechnol. Dec. 2007;2(12):775-9. doi:10.1038/nnano.2007.381. Epub Dec. 2, 2007.
Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Grant et al., A facile method for attaching nitroxide spin labels at the 5' terminus of nucleic acids. Nucleic Acids Res. 2007;35(10):e77. Epub May 21, 2007.
Gu et al., Capture of a single molecule in a nanocavity. Science. Jan. 26, 2001;291(5504):636-40.
Gu et al., Electroosmotic enhancement of the binding of a neutral molecule to a transmembrane pore. Proc Natl Acad Sci U S A, Dec. 23, 2003;100(26):15498-503, Epub Dec. 15, 2003.
Gu et al., Prolonged residence time of a noncovalent molecular adapter, beta-cyclodextrin, within the lumen of mutant alpha-hemolysin pores. J Gen Physiol. Nov. 2001;118(5):481-94.
Gu et al., Reversal of charge selectivity in transmembrane protein pores by using noncovalent molecular adapters. Proc Natl Acad Sci U S A. Apr. 11, 2000;97(8):3959-64.
Gu et al., Single molecule sensing by nanopores and nanopore devices. Analyst. Mar. 2010;135(3):441-51. doi: 10.1039/b907735a. Epub Dec. 22, 2009.
Gu et al., Stochastic sensing of organic analytes by a pore-forming protein containing a molecular adapter. Nature. Apr. 22, 1999;398(6729):686-90.
Guan et al., Stochastic sensing of TNT with a genetically engineered pore. Chembiochem. Oct. 2005;6(10):1875-81.
Hammerstein et al., Subunit dimers of alpha-hemolysin expand the engineering toolbox for protein nanopores. J Biol Chem. Apr. 22, 2011;286(16):14324-34. doi: 10.1074/jbc.M111.218164. Epub Feb. 15, 2011.
Han et al., Characterization and optimization of an entropic trap for DNA separation. Anal Chem. Jan. 15, 2002;74(2):394-401.
Han et al., RecJ exonuclease: substrates, products and interaction with SSB. Nucleic Acids Res. Feb. 18, 2006;34(4):1084-91. Print 2006.
He et al., The T4 Phage SF1B Helicase Dda is Structurally Optimized to Perform DNA Strand Separation. Structure. Jul. 3, 2012; 20(7): 1189-1200. EPub May 31, 2012. doi: 10.1016/j.str.2012.04.013.
Hein et al., Click chemistry, a powerful tool for pharmaceutical sciences. Pharm Res. Oct. 2008;25(10):2216-30. doi: 10.1007/s11095-008-9616-1. Epub May 29, 2008.
Henrickson et al., Driven DNA transport into an asymmetric nanometer-scale pore. Phys Rev Lett. Oct. 2, 2000;85(14):3057-60.
Heredia et al., In vitro double transposition for DNA identification. Anal Biochem. Apr. 1, 2010;399(1):78-83. doi:10.1016/j.ab.2009.11.030. Epub Nov. 26, 2009.
Heron et al., Simultaneous measurement of ionic current and fluorescence from single protein pores. J Am Chem Soc. Feb. 11, 2009;131(5):1652-3. doi: 10.1021/ja808128s.
Hobbs et al., SSB protein limits RecOR binding onto single-stranded DNA. J Biol Chem. Apr. 13, 2007;282(15):11058-67. Epub Feb. 1, 2007.
Holden et al., Direct introduction of single protein channels and pores into lipid bilayers. J Am Chem Soc. May 11, 2005;127(18):6502-3.
Holden et al., Functional bionetworks from nano liter water droplets. J Am Chem Soc. Jul. 11, 2007;129(27):8650-5. Epub Jun. 16, 2007.
Hornblower et al., Single-molecule analysis of DNA-protein complexes using nanopores. Nat Methods. Apr. 2007;4(4):315-7. Epub Mar. 4, 2007.
Howorka et al., DNA Duplex Formation of Individual DNA Strands within a Single Protein Pore. Biophysical Journal, vol. 82{1, pt. 2):508a, No. 2482-Plat (2002).
Howorka et al., Improved protocol for high-throughput cysteine scanning mutagenesis. Biotechniques. Nov. 1998;25(5):764-6, 768, 770 passim.
Howorka et al., Kinetics of duplex formation for individual DNA strands within a single protein nanopore. Proc Natl Acad Sci U S A. Nov. 6, 2001;98(23):12996-3001. Epub Oct. 23, 2001.
Howorka et al., Probing distance and electrical potential within a protein pore with tethered DNA. Biophys J. Dec. 2002;83(6):3202-10.
Howorka et al., Sequence-specific detection of individual DNA strands using engineered nanopores. Nat Biotechnol. Jul. 2001;19(7):636-9.

(56) References Cited

OTHER PUBLICATIONS

Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.

Hwang et al., Electrical behavior of droplet interface bilayer networks: experimental analysis and modeling. J Am Chem Soc. Sep. 26, 2007;129(38):11854-64. Epub Sep. 1, 2007.

Ivanov et al., DNA tunneling detector embedded in a nanopore. Nano Lett. Jan. 12, 2011;11(1):279-85. doi: 10.1021/nl103873a. Epub Dec. 6, 2010.

Jayasinghe et al., The leukocidin pore: evidence for an octamer with four LukF subunits and four LukS subunits alternating around a central axis. Protein Sci. Oct. 2005;14(10):2550-61.

Jung et al., The internal cavity of the staphylococcal alpha-hemolysin pore accommodates approximately 175 exogenous amino acid residues. Biochemistry. Jun. 28, 2005;44(25):8919-29.

Kalisch et al., Covalently linked sequencing primer linkers (splinkers) for sequence analysis of restriction fragments. Gene. 1986;44(2-3):263-70.

Kanan et al., Reaction discovery enabled by DNA-templated synthesis and in vitro selection. Nature. Sep. 30, 2004;431(7008):545-9.

Kang et al., Single protein pores containing molecular adapters at high temperatures. Angew Chem Int Ed Engl. Feb. 25, 2005;44(10):1495-9.

Kasianowicz et al., Characterization of individual polynucleotide molecules using a membrane channel. Proc Natl Acad Sci U S A. Nov. 26, 1996;93(24):13770-3.

Keyser, Controlling molecular transport through nanopores. J R Soc Interface. Oct. 7, 2011;8(63):1369-78. doi: 10.1098/rsif.2011.0222. Epub Jun. 29, 2011.

Khulbe et al., DNA translocation through a-hemolysin nanopores with potential application to macromolecular data storage. Journal Applied Physics, vol. 97(104317): 1-7 (2005).

Kocalka et al., Rapid and efficient DNA strand cross-linking by click chemistry. Chembiochem. May 23, 2008;9(8):1280-5. doi:10.1002/cbic.200800006.

Kolb et al., Click Chemistry: Diverse Chemical Function from a Few Good Reactions. Angew Chem Int Ed Engl. Jun. 1, 2001;40(11):2004-2021.

Kovall et al., Toroidal structure of lambda-exonuclease. Science. Sep. 19, 1997;277(5333):1824-7.

Kozarewa et al., 96-plex molecular barcoding for the Illumina Genome Analyzer. Methods Mol Biol. 2011;733:279-98. doi: 10.1007/978-1-61779-089-8_20.

Kozlov et al., Regulation of Single-stranded DNA Binding by the C Termini of Esherichia coli Single-stranded DNA-binding (SBB) Protein. J. Biol. Chem. May 28, 2010;285(22): 17246-52.

Kumar et al., Nomadioactive labeling of synthetic oligonucleotide probes with terminal deoxynucleotidyl transferase. Anal Biochem. Mar. 1988;169(2):376-82. Erratum in: Anal Biochem Sep. 1988;173(2):469.

Langecker et al., Synthetic lipid membrane channels formed by designed DNA nanostructures. Science. Nov. 16, 2012;338(6109):932-6. doi: 10.1126/science.1225624.

Lazar et al., Transforming growth factor alpha: mutation of aspartic acid 47 and leucine 48 results in different biological activities. Mol Cell Biol. Mar. 1988;8(3):1247-52.

Lee et al., Importance of the conserved CA dinucleotide at Mu termini. J Mol Biol. Nov. 30, 2001;314(3):433-44.

Li et al., DNA molecules and configurations in a solid-state nanopore microscope. Nat Mater. Sep. 2003;2(9):611-5. Epub Aug. 24, 2003.

Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.

Liu et al., Adding new chemistries to the genetic code. Annu Rev Biochem. 2010;79:413-44. doi: 10.1146/annurev.biochem.052308.105824.

Liu et al., Structure of the DNA repair helicase XPD. Cell. May 30, 2008;133(5):801-12. doi: 10.1016/j.cell.2008.04.029.

Lohman et al., Non-hexameric DNA helicases and translocases: mechanisms and regulation. Nat Rev Mol Cell Biol. May 2008;9(5):391-401. doi: 10.1038/nrm2394.

Lovett et al., Identification and purification of a single-stranded-DNA-specific exonuclease encoded by the recJ gene of Escherichia coli. Proc Natl Acad Sci U S A. Apr. 1989;86(8):2627-31.

Lovrinovic et al., Rapid synthesis of DNA-cysteine conjugates for expressed protein ligation. Biochem Biophys Res Commun. Sep. 30, 2005;335(3):943-8.

Lu et al., Peptide inhibitors identify roles for SSB C-terminal residues in SSB/Exonuclease I complex formation. Biochemistry. Jul. 28, 2009; 48(29): 6764-6771. doi: 10.1021/bi900361r. Author Manuscript.

Lu et al., Structural basis of Escherichia coli single-stranded DNA-binding protein stimulation of exonuclease I. Proc Natl Acad Sci U S A. Jul. 8, 2008;105(27):9169-74. doi: 10.1073/pnas.0800741105. Epub Jun. 30, 2008.

Luo et al., Influence of polymer-pore interactions on translocation. Phys Rev Lett. Oct. 5, 2007;99(14):148102. Epub Oct. 1, 2007.

Lutz et al., Efficient construction of therapeutics, bioconjugates, biomaterials and bioactive surfaces using azide-alkyne "click" chemistry. Adv Drug Deliv Rev. Jun. 10, 2008;60(9):958-70. doi: 10.1016/j.addr.2008.02.004. Epub Mar. 4, 2008.

Ma et al., Bright functional rotaxanes. Chem Soc Rev. Jan. 2010;39(1):70-80. doi: 10.1039/b901710k. Epub Jul. 21, 2009.

Maglia et al., Analysis of single nucleic acid molecules with protein nanopores. Methods Enzymol. 2010;475:591-623. doi: 10.1016/S0076-6879(10)75022-9.

Maglia et al., Enhanced translocation of single DNA molecules through alpha-hemolysin nanopores by manipulation of internal charge. Proc Natl Acad Sci U S A. Dec. 16, 2008;105(50):19720-5. doi:10.1073/pnas.0808296105. Epub Dec. 5, 2008.

Martin et al., Nanoscale protein pores modified withPAMAM dendrimers. J Am Chem Soc. Aug. 8, 2007;129(31):9640-9. Epub Jul. 18, 2007.

Martinez et al., The mRNA cap structure stimulates rate of poly(A) removal and amplifies processivity of degradation, J Biol Chem. Jul. 27, 2001;276(30):27923-9, Epub May 18, 2001.

Marziali et al., New DNA sequencing methods. Annu Rev Biomed Eng. 2001;3:195-223.

Mathé et al., Orientation discrimination of single-stranded DNA inside the alpha-hemolysin membrane channel. Proc Natl Acad Sci U S A. Aug. 30, 2005;102(35): 12377-82. Epub Aug. 19, 2005.

Matsuura et al., Real-time observation of a single DNA digestion by lambda exonuclease under a fluorescence microscope field. Nucleic Acids Res. Aug. 15, 2001;29(16):E79.

Meller et al., Rapid nanopore discrimination between single polynucleotide molecules. Proc Natl Acad Sci U S A. Feb. 1, 2000;97(3):1079-84.

Meller et al., Single molecule measurements of DNA transport through a nanopore. Electrophoresis. Aug. 2002;23(16):2583-91.

Meller, Dynamics of polynucleotide transport through nanometre-scale pores. Journal Physics: Condensed Matter, vol. 15:R581-R607 (2003).

Merzlyak et al., Conductance and ion selectivity of a mesoscopic protein nanopore probed with cysteine scanning mutagenesis. Biophys J. Nov. 2005;89(5):3059-70. Epub Aug. 5, 2005.

Miles et al., Single molecule sensing with solid-state nanopores: novel materials, methods, and applications. Chem Soc Rev. Jan. 7, 2013;42(1):15-28. doi: 10.1039/c2cs35286a. Epub Sep. 19, 2012.

Mitchell et al., Chemical tags facilitate the sensing of individual DNA strands with nanopores. Angew Chem Int Ed Engl. 2008;47(30):5565-8. doi: 10.1002/anie.200800183.

Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.

Mol et al., Structure and function of the multifunctional DNA-repair enzyme exonuclease III. Nature. Mar. 23, 1995;374(6520):381-6.

Montal et al., Formation of bimolecular membranes from lipid monolayers and a study of their electrical properties. Proc Natl Acad Sci U S A. Dec. 1972;69(12):3561-6.

(56) References Cited

OTHER PUBLICATIONS

Movileanu et al., Detecting protein analytes that modulate transmembrane movement of a polymer chain within a single protein pore. Nat Biotechnol. Oct. 2000;18(10):1091-5.
Movileanu et al., Location of a constriction in the lumen of a transmembrane pore by targeted covalent attachment of polymer molecules. J Gen Physiol. Mar. 2001;117(3):239-52.
Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.
Nakane et al., A nanosensor for transmembrane capture and identification of single nucleic Acid molecules. Biophys J. Jul. 2004;87(1):615-21. Erratum in: Biophys J. Nov. 2004;87(5):3618.
Nakane et al., Nanopore sensors for nucleic acid analysis. J. Phys.: Condens. Matter, vol. 15: R 1365-R1393 (2003).
Niemeyer et al., DNA-directed assembly of bienzymic complexes from in vivo biotinylated NAD(P)H:FMN oxidoreductase and luciferase. Chembiochem. Mar. 1, 2002;3(2-3):242-5.
Nikolov et al., Behavior of giant vesicles with anchored DNA molecules. Biophys J. Jun. 15, 2007;92(12):4356-68. Epub Mar. 23, 2007.
North et al., Host factors that promote transpososome disassembly and the PriA-PriC pathway for restart primosome assembly. Mol Microbiol. Jun. 2005;56(6):1601-16.
Nwe et al., Growing applications of "click chemistry" for bioconjugation in contemporary biomedical research. Cancer Biother Radiopharm. Jun. 2009;24(3):289-302. doi: 10.1089/cbr.2008.0626.
O'Shea et al., X-ray structure of the GCN4 leucine zipper, a two-stranded, parallel coiled coil. Science. Oct. 25, 1991;254(5031):539-44.
Paner et al., Studies of DNA dumbbells. III. Theoretical analysis of optical melting curves of dumbbells with a 16 base-pair duplex stem and Tn end loops (n=2, 3, 4, 6, 8, 10, 14). Biopolymers. Jul. 1992;32(7):881-92.
Paner et al., Studies of DNA dumbbells. VI. Analysis of optical melting curves of dumbbells with a sixteen-base pair duplex stem and end-loops of variable size and sequence. Biopolymers. Dec. 1996;39(6):779-93.
Pfeiffer et al., Bivalent cholesterol-based coupling of oligonucletides to lipid membrane assemblies. J Am Chem Soc. Aug. 25, 2004;126(33):10224-5.
Phoenix et al., OmpF-Lpp signal sequence mutants with varying charge hydrophobicity ratios provide evidence for a phosphatidylglycerol-signal sequence interaction during protein translocation across the *Escherichia coli* inner membrane. J Biol Chem. Aug. 15, 1993;268(23):17069-73.
Purnell et al., Nucleotide identification and orientation discrimination of DNA homopolymers immobilized in a protein nanopore. Nano Lett. Sep. 2008;8(9):3029-34. doi: 10.1021/n1802312f. Epub Aug. 13, 2008.
Remaut et al., Protein-protein interaction through beta-strand addition. Trends Biochem Sci. Aug. 2006;31(8):436-44. Epub Jul. 7, 2006.
Saariaho et al., Characteristics of MuA transposase-catalyzed processing of model transposon end DNA hairpin substrates. Nucleic Acids Res. Jun. 6, 2006;34(10):3139-49. Print 2006.
Sanchez-Quesada et al., Cyclic Peptides as Molecular Adapters for a Pore-Forming Protein. Journal American Chemical Society, vol. 122(48): 11757-11766 (2000).
Sanchez-Quesada et al., Single DNA rotaxanes of a transmembrane pore protein. Angew Chem Int Ed Engl. Jun. 7, 2004;43(23):3063-7.
Sanderson, Personal genomes: Standard and pores. Nature. Nov. 6, 2008;456(7218):23-5. doi: 10.1038/456023a.
Satapathy et al., ATPase activity of RecD is essential for growth of the Antarctic Pseudomonas syringae Lz4W at low temperature. FEBS J. Apr. 2008;275(8):1835-51. doi: 10.1111/j.1742-4658.2008.06342.X. Epub Mar. 9, 2008.
Sauer-Budge et al., Unzipping kinetics of double-stranded DNA in a nanopore. Phys Rev Lett. Jun. 13, 2003;90(23):238101. Epub Jun. 9, 2003.
Schneider et al., DNA sequencing with nanopores. Nat Biotechnol. Apr. 10, 2012;30(4):326-8. doi: 10.1038/nbt.2181.
Seeman, Nucleic acid junctions and lattices. J TheorBiol. Nov. 21, 1982;99(2):237-47.
Seo et al., Click chemistry to construct fluorescent oligonucleotides for DNA sequencing. J Org Chem. Jan. 24, 2003;68(2):609-12.
Seol et al., Stretching of homopolymeric RNA reveals single-stranded helices and basestacking. Phys Rev Lett. Apr. 13, 2007;98(15):158103. Epub Apr. 12, 2007.
Shank et al., Redesigning channel-forming peptides: amino acid substitutions that enhance rates of supramolecular self-assembly and raise ion transport activity. Biophys J. Mar. 15, 2006;90(6):2138-50. Epub Dec. 30, 2005.
Shin et al., Kinetics of a reversible covalent-bond-forming reaction observed at the single-molecule level. Angew Chem Int Ed Engl. Oct. 4, 2002;41(19):3707-9; 3523.
Smeets et al., Salt dependence of ion transport and DNA translocation through solid-state nanopores. Nano Lett. Jan. 2006;6(1):89-95.
Song et al., Structure of staphylococcal alpha-hemolysin, a heptameric transmembrane pore. Science. Dec. 13, 1996;274(5294):1859-66.
Soni et al., Synchronous optical and electrical detection of biomolecules traversing through solid-state nanopores. Rev Sci Instrum. Jan. 2010;81(1):014301. doi: 10.1063/1.3277116.
Stoddart et al., Multiple base-recognition sites in a biological nanopore: two heads are better than one. Angew Chem Int Ed Engl. 2010;49(3):556-9. doi: 10.1002/anie.200905483.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Sutherland et al., An analysis of mismatched duplex DNA unzipping through a bacterial nanopore. Biochem Cell Biol, Jun. 2004;82(3):407-12.
Tadey et al., Capillary electrophoretic separation of nucleotide isomers via complexation with cyclodextrin and borate. J Chromatogr B Biomed Appl. Jul. 15, 1994;657(2):365-72.
Thomas et al., Processivity of DNA exonucleases. J Biol Chem. Jan. 25, 1978;253(2):424-9.
Tohda et al., "Channel Mimetic Sensing Membranes for Nucleotides Based on Multitopic Hydrogen Bonding," Israel Journal of Chemistry, vol. 37:267-275 (1997).
Travers et al., A flexible and efficient template format for circular consensus sequencing and SNP detection. Nucleic Acids Res. Aug. 2010;38(15):e159. doi: 10.1093/nar/gkq543. Epub Jun. 22, 2010.
Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.
Tung et al., Preparation and applications of peptide-oligonucleotide conjugates. Bioconjug Chem. Sep.-Oct. 2000;11(5):605-18.
Tuteja et al., Unraveling DNA helicases. Motif, structure, mechanism and function. Eur J Biochem. May 2004;271(10):1849-63. Review. Erratum in: Eur J Biochem. Aug. 2004;271(15):3283.
Van De Goor, Nanopore Detection: Threading DNA Through a Tiny Hole. PharmaGenomics, vol. 4 (3):28-30 (2004).
Van Heel et al., Single-particle electron cryo-microscopy: towards atomic resolution. Q Rev Biophys. Nov. 2000;33(4):307-69.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Venkatesan et al., Nanopore sensors for nucleic acid analysis. Nat Nanotechnol. Sep. 18, 2011;6(10):615-24. doi: 10.1038/nnano.2011.129.
Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.
Wang et al., Bioconjugation by copper(I)-catalyzed azide-alkyne [3+2] cycloaddition. J Am Chem Soc. Mar. 19, 2003;125(11):3192-3.

(56) References Cited

OTHER PUBLICATIONS

Wang et al., Nanopores with a spark for single-molecule detection. Nat Biotechnol. Jul. 2001;19(7):622-3.
Wanunu et al., Discrimination of methylcytosine from hydroxymethylcytosine in DNA molecules. J Am Chem Soc. Jan. 26, 2011;133(3):486-92. doi:10.1021/ja107836t. Epub Dec. 14, 2010.
Wanunu et al., DNA translocation governed by interactions with solid-state nanopores. Biophys J. Nov. 15, 2008;95(10):4716-25. doi: 10.1529/biophysj.108.140475. Epub Aug. 15, 2008.
Wemmer et al., Preparation and melting of single strand circular DNA loops. Nucleic Acids Res. Dec. 9, 1985;13(23):8611-21.
Winters-Hilt et al., Highly accurate classification of Watson-Crick basepairs on termini of single DNA molecules. Biophys J. Feb. 2003;84(2 Pt 1):967-76.
Wolfe et al., Catalyzing the translocation of polypeptides through attractive interactions. J Am Chem Soc. Nov. 14, 2007;129(45):14034-41. Epub Oct. 19, 2007.
Wong et al., Polymer capture by electro-osmotic flow of oppositely charged nanopores. J Chem Phys. Apr. 28, 2007;126(16):164903.
Woodman et al., Archaeal Hel308 domain V couples DNA binding to ATP hydrolysis and positions DNA for unwinding over the helicase ratchet. J Mol Biol. Dec. 14, 2007;374(5): 1139-44. Epub Oct. 10, 2007.
Wu et al., Protein nanopores with covalently attached molecular adapters. J Am Chem Soc. Dec. 26, 2007;129(51):16142-8. Epub Nov. 30, 2007.
Xie, et al., Single-molecule observation of the catalytic subunit of cAMP-dependent protein kinase binding to an inhibitor peptide. Chem Biol. Jan. 2005;12(1):109-20.
Yamagata et al., Overexpression, purification and characterization of RecJ protein from Thermus theunophilus HB8 and its core domain. Nucleic Acids Res. Nov. 15, 2001;29(22):4617-24.
Yoshina-Ishii et al., Arrays of mobile tethered vesicles on supported lipid bilayers. J Am Chem Soc. Apr. 2, 2003;125(13):3696-7.
Yusko et al., Controlling the translocation of proteins through nanopores with bioinspired fluid walls. Nat Nanotechnol. Apr. 2011; 6(4): 253-260. EPub Feb. 20, 2011. doi: 10.1038/nnano.2011.12.
Cui et al., Maize Mu transposon and its application in reverse genetic research. Bulletin of Agricultural Science and Technology. Dec. 31, 2010;1:35-38.
Mitchel et al., Heteroduplex DNA position defines the roles of the Sgs1, Srs2, and Mph1 helicases in promoting distinct recombination outcomes. PLoS Genet. 2013;9(3):e1003340. doi: 10.1371/journal.pgen.1003340. Epub Mar. 14, 2013.
Nakai et al., Handoff from recombinase to replisome: insights from transposition. Proc Natl Acad Sci U S A. Jul. 17, 2001;98(15):8247-54. doi: 10.1073/pnas.111007898.
Notomi et al., Loop-mediated isothermal amplification of DNA. Nucleic Acids Res. Jun. 15, 2000;28(12):E63. doi: 10.1093/nar/28.12.e63.
Singleton et al., Structure and mechanism of helicases and nucleic acid translocases. Annu Rev Biochem. 2007;76:23-50. doi: 10.1146/annurev.biochem.76.052305.115300.
Skipper et al., DNA transposon-based gene vehicles—scenes from an evolutionary drive. J Biomed Sci. Dec. 9, 2013;20(1):92. doi: 10.1186/1423-0127-20-92.

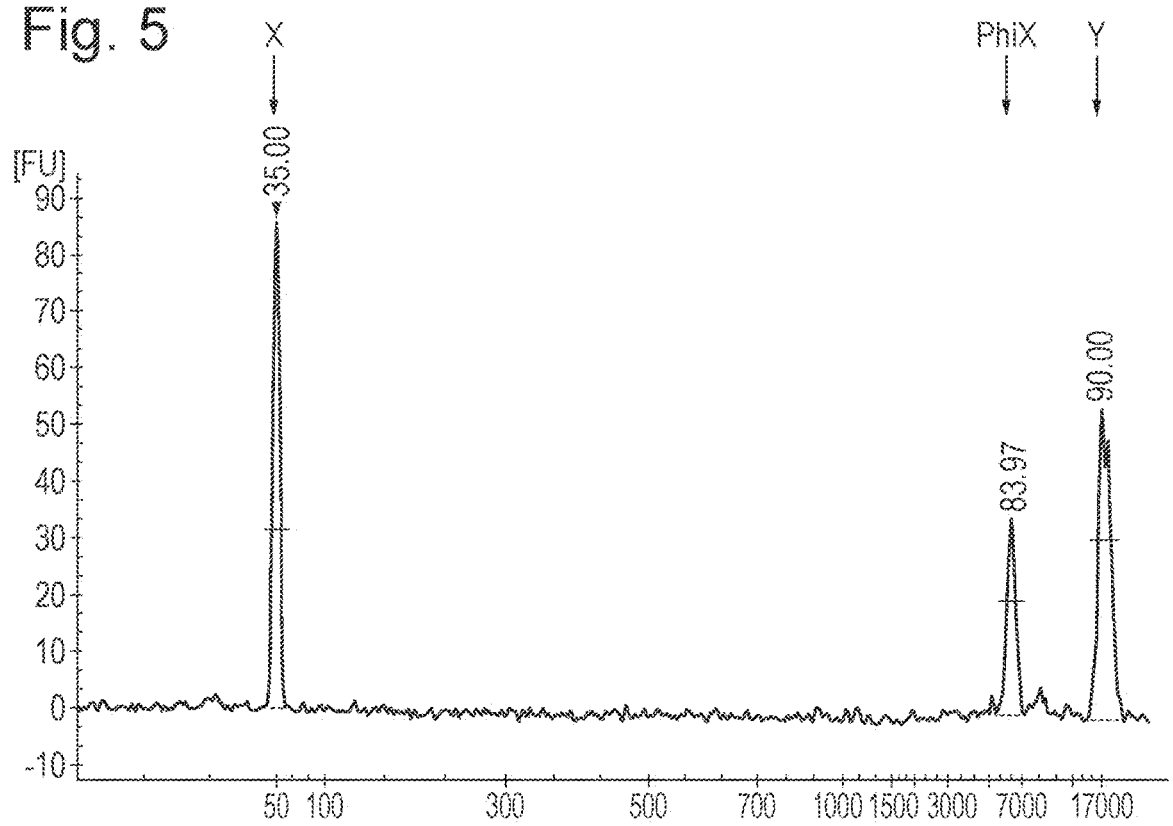
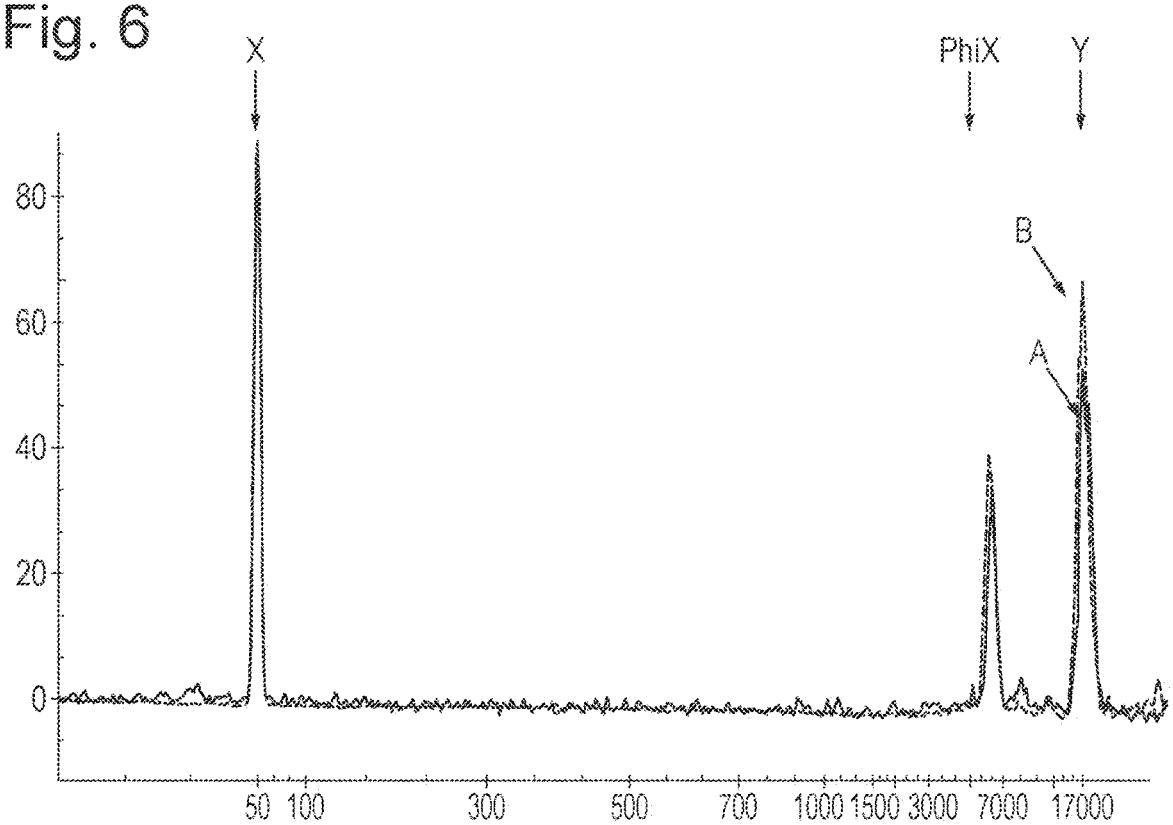

METHOD FOR MODIFYING A TEMPLATE DOUBLE STRANDED POLYNUCLEOTIDE

RELATED APPLICATIONS

This application is a national stage filing under 35 U.S.C. § 371 of international application number PCT/GB2017/051490, filed May 25, 2017, and claims the benefit of GB application number 1609220.7, filed, May 25, 2016, the contents of which is herein incorporated by reference in its entirety.

FIELD OF THE INVENTION

The invention relates to a method for modifying a template double stranded polynucleotide, especially for characterisation using nanopore sequencing.

BACKGROUND OF THE INVENTION

There are many commercial situations which require the preparation of a nucleic acid library. This is frequently achieved using a transposase. Depending on the transposase which is used to prepare the library it may be necessary to repair the transposition events in vitro before the library can be used, for example in sequencing.

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identity of the nucleotides are derived. Strand sequencing can involve the use of a molecular brake to control the movement of the polynucleotide through the pore.

International Application No. PCT/GB2014/052505 (published as WO 2015/022544) discloses using a MuA transposase and a population of MuA substrates to produce a plurality of shorter, modified double stranded polynucleotides from a template double stranded polynucleotide. The modified polynucleotides can be designed such that they are each easier to characterise, such as by strand sequencing, than the original template polynucleotide. The MuA transposase is inactivated by heat.

SUMMARY OF THE INVENTION

The invention relates to a method for modifying a template double stranded polynucleotide, especially for characterisation using nanopore sequencing. The method produces from the template a plurality of modified double stranded polynucleotides. These modified polynucleotides can then be characterised.

The inventors have surprisingly demonstrated that it is possible to remove a MuA transposase from modified polynucleotides using a translocase. This avoids the need to heat inactivate the MuA transposase, which may also inactivate any other enzymes or proteins being used in the preparation or characterisation of the modified polynucleotides. Removing the heat inactivation step also dispenses with the need for additional equipment such as a thermal cycler or water bath, used for heating up the sample.

The invention therefore provides a method for modifying a template double stranded polynucleotide, comprising:

(a) contacting the template polynucleotide with a MuA transposase and a population of double stranded MuA substrates each comprising an overhang at one or both ends of one strand such that the transposase fragments the template polynucleotide and ligates a substrate to one or both ends of the double stranded fragments and thereby producing a plurality of fragment/substrate constructs; and (b) using a translocase to remove the MuA transposases from the constructs and thereby producing a plurality of modified double stranded polynucleotides.

DESCRIPTION OF THE FIGURES

FIG. 5 shows an Agilent 2100 Bioanalyser trace. The lower marker is labelled X and the upper marker is labelled Y. A PhiX peak was observed between the upper and lower markers for transpososome 2 (labelled 1) when incubated with Hel308Mbu-E284C/S615C-STrEP (SEQ ID NO: 10 with mutations E284C/S615C with a streptavidin tag attached at its C terminus).

FIG. 6 shows an Agilent 2100 Bioanalyser trace. The lower marker is labelled X and the upper marker is labelled Y. A PhiX peak was observed between the upper and lower markers for transpososome 2 (labelled 1) when incubated with either A) Hel308Mbu-E284C/S615C-STrEP(C) (SEQ ID NO: 10 with mutations E284C/S615C with a streptavidin tag attached at its C terminus) or B) at 75° C. for 10 minutes. A comparison between PhiX with transpososome 2 treated with heat and with Hel308. Red is heat treated, blue is Hel308 treated.

Line 2 corresponds to sample (ii) which has been incubated at 75° C. A tagmentation peak was observed between the upper and lower markers with sample (ii).

Figure 8:
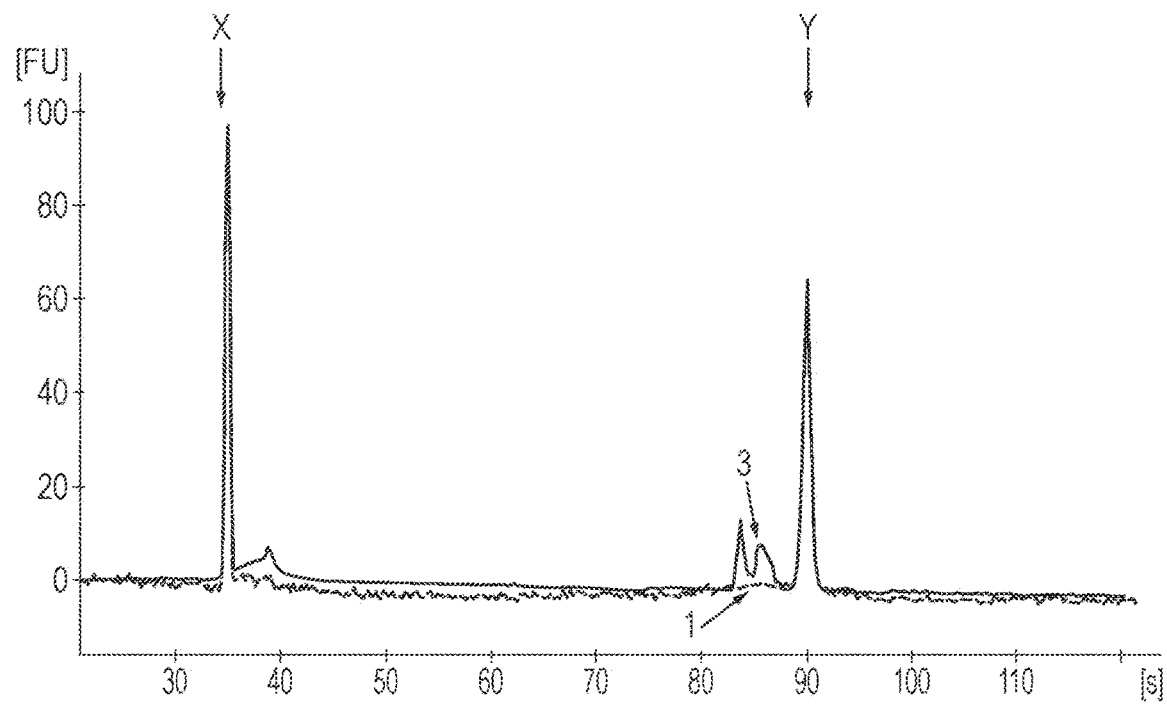

FIG. 8 shows an Agilent 2100 Bioanalyser trace. The lower marker is labelled X and the upper marker is labelled Y. Line 1 corresponds to control sample (i) which has been incubated at room temperature in the absence of a translocase. No tragmentation peak was observed for sample (i). Line 3 corresponds to sample (iii) which has been incubated at room temperature with Hel308Mbu-E284C-STrEP(C) (SEQ ID NO: 10 with mutation E284C with a streptavidin tag attached at its C terminus). A tagmentation peak was observed between the upper and lower markers with sample (iii).

Figure 9:
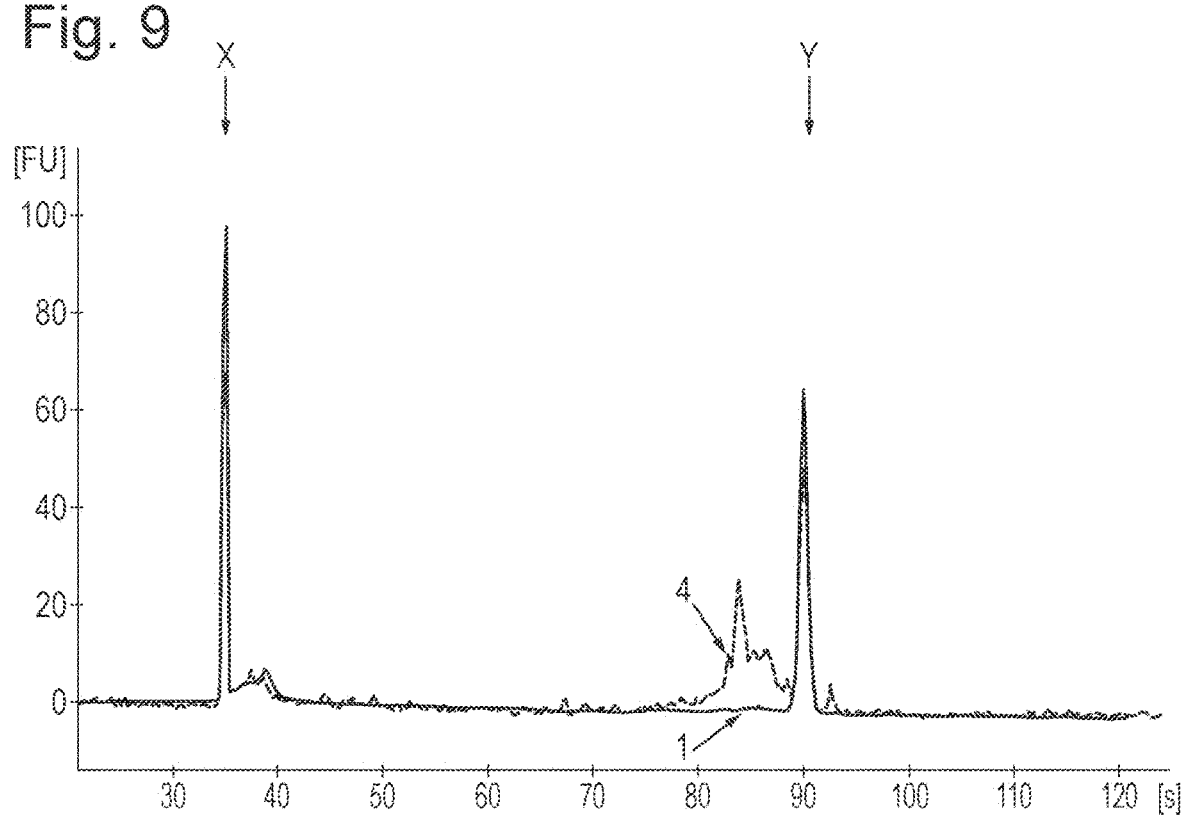

FIG. 9 shows an Agilent 2100 Bioanalyser trace. The lower marker is labelled X and the upper marker is labelled Y. Line 1 corresponds to control sample (i) which has been incubated at room temperature in the absence of a translocase. No tragmentation peak was observed for sample (i). Line 4 corresponds to sample (iv) which has been incubated at room temperature with T4 Dda-(E94C/F98W/C109A/C136A/A360C) (SEQ ID NO: 97 with mutations E94C/F98W/C109A/C136A/A360C and then (ΔM1)G1G2 (where (ΔM1)G1G2=deletion of M1 and then addition G1 and G2). A tagmentation peak was observed between the upper and lower markers with sample (iv).

Figure 10:
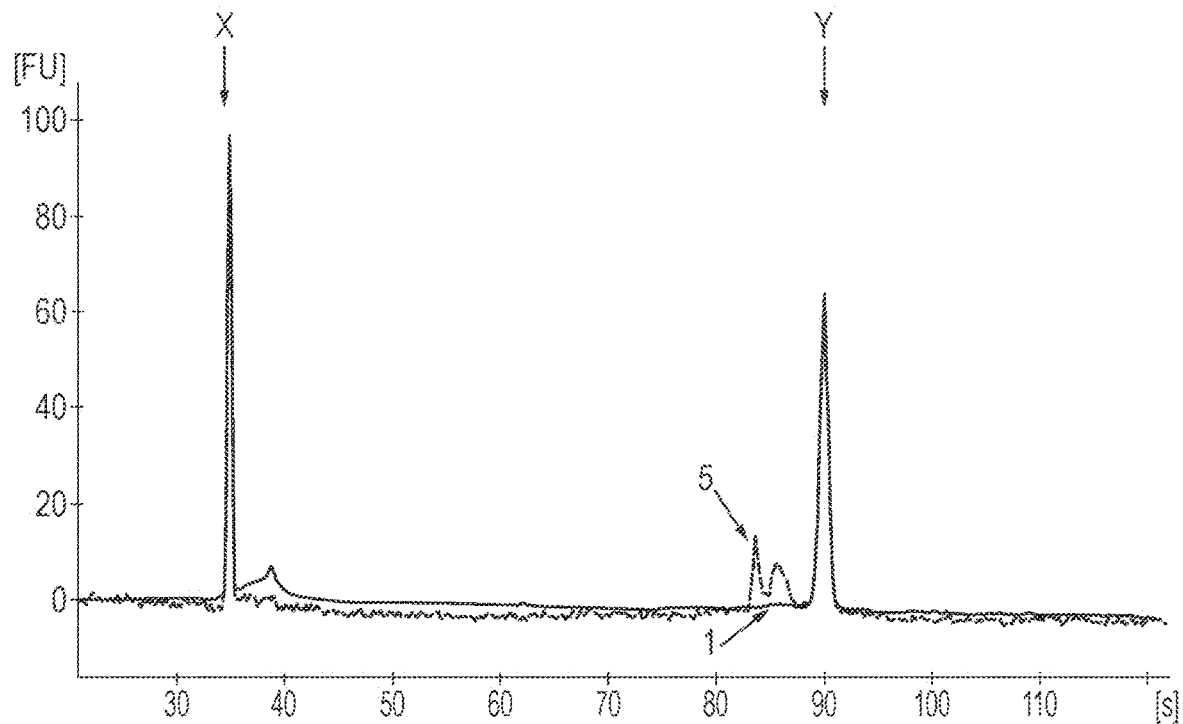

FIG. 10 shows an Agilent 2100 Bioanalyser trace. The lower marker is labelled X and the upper marker is labelled Y. Line 1 corresponds to control sample (i) which has been incubated at room temperature in the absence of a translocase. No tragmentation peak was observed for sample (i). Line 5 corresponds to sample (v) which has been incubated at room temperature with UvrD Eco-(E117C/M380C)-STrEP (SEQ ID NO: 122 with mutations E177C/M380C with a streptavidin tag attached at the C terminus). A tagmentation peak was observed between the upper and lower markers with sample (v).

Figure 11:
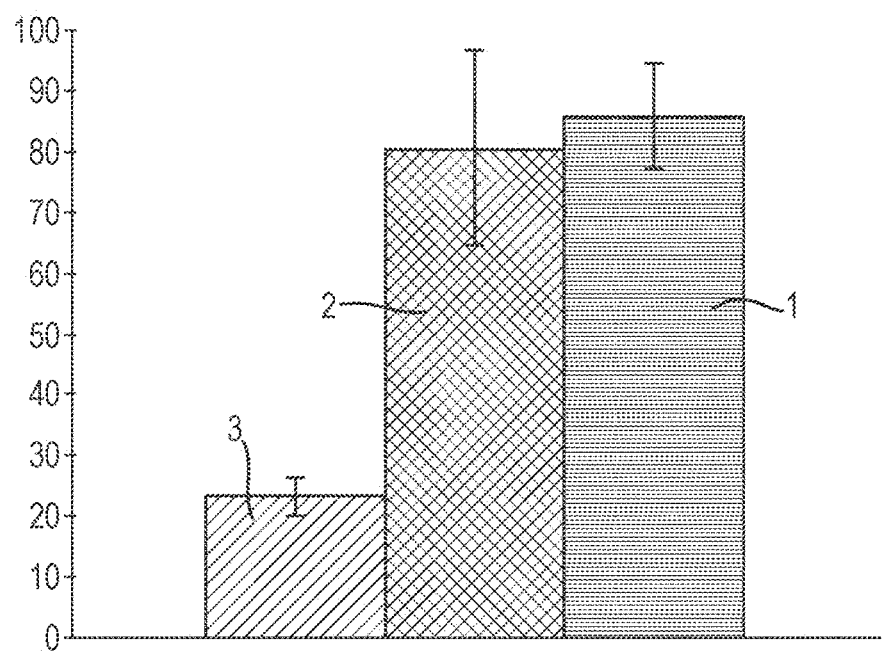

FIG. 11 shows a bar chart of throughput (y-axis label=kb/nanopore/hr) for samples 1-3 (sample 1=incubation at room temperature with Hel308Mbu-E284C/S615C-STrEP(C) using transpososome with 3' overhang, sample 2=incubation at 75° C. for 10 minutes and sample 3=incubation at room temp in absence of Hel308Mbu-E284C/S615C-STrEP(C)).

Figure 12:
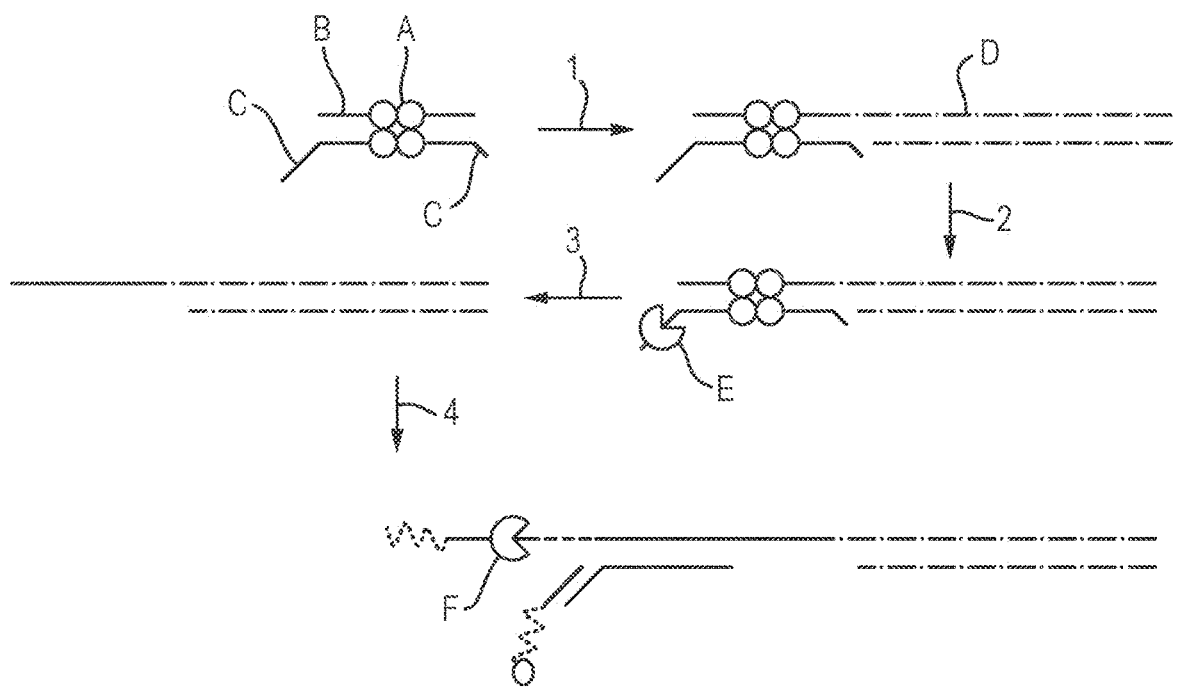

FIG. 12 shows a cartoon representation of a translocase being used to remove a MuA transposase from a construct. The MuA transposase (labelled A) is bound to a double stranded MuA substrate (labelled B) which has two overhangs labelled C at each end of one of the strands. In step 1 the MuA fragments the template polynucleotide and ligates a double stranded MuA substrate to one end producing construct D. In step 2 the translocase (labelled E) was allowed to bind to the construct at one of the overhangs. In step 3 the translocase removes the MuA from the construct producing a modified double stranded polynucleotide. In step 4 a leader was attached to the double stranded polynucleotide which had an enzyme (labelled F) pre-bound which was capable of controlling the movement of the polynucleotide through a nanopore.

It is to be understood that the Figures are for the purpose of illustrating particular embodiments of the invention only, and are not intended to be limiting.

DESCRIPTION OF THE SEQUENCE LISTING

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the amino acid sequence of the Hel308 motif.

SEQ ID NO: 9 shows the amino acid sequence of the extended Hel308 motif.

SEQ ID NOs: 10 to 58 show the amino acid sequences of Hel308 helicases in Table 1.

SEQ ID NO: 59 shows the RecD-like motif I.

SEQ ID NOs: 60 to 62 show the extended RecD-like motif I.

SEQ ID NO: 63 shows the RecD motif I.

SEQ ID NO: 64 shows a preferred RecD motif I, namely G-G-P-G-T-G-K-T.

SEQ ID NOs: 65 to 67 show the extended RecD motif I.

SEQ ID NO: 68 shows the RecD-like motif V.

SEQ ID NO: 69 shows the RecD motif V.

SEQ ID NOs: 70 to 77 show the MobF motif III.

SEQ ID NOs: 78 to 84 show the MobQ motif III.

SEQ ID NO: 85 shows the amino acid sequence of TraI Eco.

SEQ ID NO: 86 shows the RecD-like motif I of TraI Eco.

SEQ ID NO: 87 shows the RecD-like motif V of TraI Eco.

SEQ ID NO: 88 shows the MobF motif III of TraI Eco.

SEQ ID NO: 89 shows the XPD motif V.

SEQ ID NO: 90 shows XPD motif VI.

SEQ ID NO: 91 shows the amino acid sequence of XPD Mbu.

SEQ ID NO: 92 shows the XPD motif V of XPD Mbu.

SEQ ID NO: 93 shows XPD motif VI of XPD Mbu.

SEQ ID NO: 94 shows the polynucleotide sequence of the double stranded portion of a MuA substrate of the invention.

SEQ ID NO: 95 shows the polynucleotide sequence of the double stranded portion of a MuA substrate of the invention. This sequence is complementary to SEQ ID NO: 94 except that it contains a U at the 3' end.

SEQ ID NO: 96 shows polynucleotide sequence of the overhang strand of the double stranded MuA substrate of the invention.

SEQ ID NO: 97 shows the amino acid sequence of Dda 1993.

SEQ ID NOs: 98 to 112 show the amino acid sequences of other Dda helicases for use in the invention.

SEQ ID NO: 113 shows the codon optimised polynucleotide sequence encoding the wild-type CsgG monomer from *Escherichia coli* Str. K-12 substr. MC4100. This monomer lacks the signal sequence.

SEQ ID NO: 114 shows the amino acid sequence of the mature form of the wild-type CsgG monomer from *Escherichia coli* Str. K-12 substr. MC4100. This monomer lacks the signal sequence. The abbreviation used for this CsgG=CsgG-Eco.

SEQ ID NO: 115 to 121 show polynucleotide sequences used in the Examples.

SEQ ID NO: 122 shows the amino acid sequence of UvrD-Eco wild-type.

It is to be understood that the sequences are not intended to be limiting.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polynucleotide" includes "polynucleotides", reference to "a substrate" includes two or more such substrates, reference to "a transmembrane protein pore" includes two or more such pores, and the like.

In this specification, where different amino acids at a specific position are separated by the symbol "/", the symbol "/" means "or". For instance, P108R/K means P108R or P108K. In this specification, where different positions or different substitutions are separated by the symbol "/", the "/" symbol means "and". For example, E94/P108 means E94 and P108 or E94D/R108K means E94D and P108K.

All publications, patents and patent applications cited herein, whether supra or infra, are hereby incorporated by reference in their entirety.

Modification Method

The present invention provides a method of modifying a template polynucleotide. The template may be modified for any purpose. The method is preferably for modifying a template polynucleotide for characterisation, such as for strand sequencing. The template polynucleotide is typically the polynucleotide that will ultimately be characterised, or sequenced, in accordance with the invention. This is discussed in more detail below.

The method provided is a method for modifying a double stranded polynucleotide template, comprising: (a) contacting the polynucleotide template with a MuA transposase in the presence of a double stranded MuA substrate that comprises an overhang at one or both ends of one strand, such that the MuA transposase (i) processes the template polynucleotide to produce a plurality of double stranded fragments and (ii) ligates the double stranded MuA substrate to one or both ends of a double stranded fragment of the plurality, thereby producing a ligation product to which is bound a MuA transposase; and (b) contacting the ligation product with a translocase, such that the translocase processes the ligation product to remove the MuA transposase, thereby producing a plurality of modified double stranded polynucleotides.

The method involves the formation of a plurality of modified double stranded polynucleotides. These modified double stranded polynucleotides are typically easier to characterise than the template polynucleotide, especially using strand sequencing. The plurality of modified double stranded polynucleotides may themselves be characterised in order to facilitate the characterisation of the template polynucleotide. For instance, the sequence of the template polynucleotide can be determined by sequencing each of the modified double stranded polynucleotides.

The modified double stranded polynucleotides are shorter than the template polynucleotide and so it is more straightforward to characterise them using strand sequencing. The modified double stranded polynucleotides may be of any length. The length is determined by the length of the template polynucleotide and the action of the MuA transposase which fragments the polynucleotide. Typically, the modified double stranded polynucleotide is less than about 5000 kb.

The modified double strand polynucleotides can be selectively labelled by including the labels in the MuA substrates. Labelling is selective in that only the modified double stranded polynucleotides produced by the MuA transposase are labelled. A label is an entity that enables sample identification, barcoding and/or tracking of the modified double stranded polynucleotide. Suitable labels include, but are not limited to, calibration sequences, coupling moieties and adaptor bound enzymes. Examples of coupling moieties include, for example, azide, DBCO, pyridyldithiol and malemide. Calibration sequences include any sequence of a known composition. Adaptor bound enzymes include, for example, translocases, polymerases, helicases and other polynucleotide binding proteins.

In some embodiments, the method introduces into the double stranded polynucleotides modifications which facilitate their characterisation using strand sequencing. It is well-established that coupling a polynucleotide to the membrane containing the nanopore lowers by several orders of magnitude the amount of polynucleotide required to allow its characterisation or sequencing. This is discussed in International Application No. PCT/GB2012/051191 (published as WO 2012/164270). The method of the invention allows the production of a plurality of double stranded polynucleotides each of which include a means for coupling the polynucleotides to a membrane. This is discussed in more detail below.

The characterisation of double stranded polynucleotides using a nanopore typically requires the presence of a leader sequence designed to preferentially thread into the nanopore. The method of the invention allows the production of a plurality of double stranded polynucleotides each of which include a single stranded leader sequence. This is discussed in more detail below.

It is also well established that linking the two strands of a double stranded polynucleotide by a bridging moiety, such as hairpin loop, allows both strands of the polynucleotide to be characterised or sequenced by a nanopore. This is advantageous because it doubles the amount of information obtained from a single double stranded polynucleotide. Moreover, because the sequence in the template complement strand is necessarily orthogonal to the sequence of the template strand, the information from the two strands can be combined informatically. Thus, this mechanism provides an orthogonal proof-reading capability that provides higher confidence observations. This is discussed in International Application No. PCT/GB2012/051786 (published as WO 2013/014451). The method of the invention allows the production of a plurality of modified double stranded polynucleotides in which the two strands of each polynucleotide are linked using a hairpin loop.

Template Polynucleotide

The method of the invention modifies a template double stranded polynucleotide, preferably for characterisation. The template polynucleotide is typically the polynucleotide that will ultimately be characterised, or sequenced, in accordance with the invention. It may also be called the target double stranded polynucleotide or the double stranded polynucleotide of interest.

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the template polynucleotide can be oxidized or methylated. One or more nucleotides in the template polynucleotide may be damaged. For instance, the polynucleotide may comprise a pyrimidine dimer. Such dimers are typically associated with damage by ultraviolet light and are the primary cause of skin melanomas. One or more nucleotides in the template polynucleotide may be modified, for instance with a label or a tag. Suitable labels are described below. The template polynucleotide may comprise one or more spacers.

A nucleotide typically contains a nucleobase, a sugar and at least one phosphate group. The nucleobase and sugar form a nucleoside.

The nucleobase is typically heterocyclic. Nucleobases include, but are not limited to, purines and pyrimidines and more specifically adenine (A), guanine (G), thymine (T), uracil (U) and cytosine (C).

The sugar is typically a pentose sugar. Nucleotide sugars include, but are not limited to, ribose and deoxyribose. The sugar is preferably a deoxyribose.

The template double stranded polynucleotide preferably comprises the following nucleosides: deoxyadenosine (dA), deoxyuridine (dU) and/or thymidine (dT), deoxyguanosine (dG) and deoxycytidine (dC).

The nucleotide is typically a ribonucleotide or deoxyribonucleotide. The nucleotide is preferably a deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP. The nucleotides are most preferably selected from dAMP, dTMP, dGMP, dCMP and dUMP.

The template double stranded polynucleotide preferably comprises the following nucleotides: dAMP, dUMP and/or dTMP, dGMP and dCMP.

A nucleotide may be abasic (i.e. lack a nucleobase). A nucleotide may also lack a nucleobase and a sugar (i.e. is a C3 spacer).

The nucleotides in the template polynucleotide may be attached to each other in any manner. The nucleotides are typically attached by their sugar and phosphate groups as in nucleic acids. The nucleotides may be connected via their nucleobases as in pyrimidine dimers.

The template polynucleotide is double stranded. The template polynucleotide may contain some single stranded regions, but at least a portion of the template polynucleotide is double stranded.

The template polynucleotide can be a nucleic acid, such as deoxyribonucleic acid (DNA) or ribonucleic acid (RNA). The template polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

The template polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The template polynucleotide is typically present in any suitable sample. The invention is typically carried out on a sample that is known to contain or suspected to contain the template polynucleotide. Alternatively, the invention may be carried out on a sample to confirm the identity of one or more template polynucleotides whose presence in the sample is known or expected.

The sample may be a biological sample. The invention may be carried out in vitro using at least one sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on at least one sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep, fish, chickens or pigs or may alternatively be pets such as cats or dogs. Alternatively, the sample may be of plant origin, such as a sample obtained from a commercial crop, such as a cereal, legume, fruit or vegetable, for example wheat, barley, oats, canola, maize, soya, rice, rhubarb, bananas, apples, tomatoes, potatoes, grapes, tobacco, beans, lentils, sugar cane, cocoa, broccoli or cotton.

The sample may be a non-biological sample. The non-biological sample is preferably a fluid sample. Examples of non-biological samples include surgical fluids, water such as drinking water, sea water or river water, and reagents for laboratory tests.

The sample is typically processed prior to being used in the invention, for example by centrifugation or by passage through a membrane that filters out unwanted molecules or cells, such as red blood cells. The sample may be measured immediately upon being taken. The sample may also be typically stored prior to assay, preferably below −70° C.

MuA and Conditions

The template polynucleotide is contacted with a MuA transposase. This contacting occurs under conditions which allow the transposase to function, e.g. to fragment the template polynucleotide and to ligate MuA substrates to the one or both ends of the fragments. MuA transposase is commercially available, for instance from Thermo Scientific (Catalogue Number F-750C, 20 μL (1.1 μg/μL)). The MuA translocase may be a wild type MuA translocase or a modified MuA translocase. Conditions under which MuA transposase will function are known in the art. Examples of suitable conditions are described in the Examples.

Population of Substrates

The template polynucleotide is contacted with a population of double stranded MuA substrates. The MuA substrates contain a known MuA recognition sequence. Incubation of the template polynucleotide and MuA substrates with MuA results in adaptor formation. The double stranded substrates are polynucleotide substrates and may be formed from any of the nucleotides or nucleic acids discussed above. The MuA substrates are typically formed from the same nucleotides as the template polynucleotide, except for the universal nucleotides or at least one nucleotide which comprises a nucleoside that is not present in the template polynucleotide.

The population of substrates is typically homogenous (i.e. typically contains a plurality of identical substrates). The population of substrates may be heterogeneous (i.e. may contain a plurality of different substrates).

Suitable substrates for a MuA transposase are known in the art (Saariaho and Savilahti, Nucleic Acids Research, 2006; 34(10): 3139-3149 and Lee and Harshey, J. Mol. Biol., 2001; 314: 433-444).

Each substrate typically comprises a double stranded portion which provides its activity as a substrate for MuA transposase. The double stranded portion is typically the same in each substrate. The population of substrates may comprise different double stranded portions.

The double stranded portion in each substrate is typically at least 50 nucleotide pairs in length, such as at least 55, at least 60 or at least 65 nucleotide pairs in length. The double stranded portion may have a length of up to 10 kb, such as 5 kb, 1 kb or 100 base pairs. The double stranded portion in each substrate preferably comprises a dinucleotide comprising deoxycytidine (dC) and deoxyadenosine (dA) at the 3' end of each strand. The dC and dA are typically in different orientations in the two strands of the double stranded portion, i.e. one strand has dC/dA and the other strand has dA/dC at the 3' end when reading from 5' to 3'.

One strand of the double stranded portion preferably comprises the sequence shown in SEQ ID NO: 94 and the other strand of the double stranded portion preferably comprises a sequence which is complementary to the sequence shown in SEQ ID NO: 94.

Overhangs

Each substrate comprises an overhang at one or both ends of one strand, i.e. at least one overhang on one strand. The one strand in the double stranded substrate having an overhang at one or both ends is also called the one substrate strand.

If there is only one overhang, it is preferably located at the 5' end of the one substrate strand. After fragmentation of the template polynucleotide and ligation of the MuA substrate to the fragments of the template polynucleotide (tagmentation), constructs comprising a fragment of the template polynucleotide and one or more MuA substrates are formed. In such embodiments, a translocase that moves in the 5' to 3' may be used to remove the MuA transposases from the constructs.

If there are two overhangs, i.e. one at each end of one substrate strand, a translocase that moves in either direction, i.e. from 5' to 3' or from 3' to 5', may be used to remove the MuA transposases from the constructs.

Each substrate preferably comprises a double stranded portion which comprises the sequence shown in SEQ ID NO: 94 hybridised to a sequence which is complementary to the sequence shown in SEQ ID NO: 94. The one overhang is preferably at the 5' end of the sequence which is complementary to the sequence shown in SEQ ID NO: 94. The sequence complementary to the sequence shown in SEQ ID NO: 94 may have overhangs at both ends. The sequence complementary to the sequence shown in SEQ ID NO: 94 is the one substrate strand.

The overhang may be at least 3, at least 4, at least 5, at least 6 or at least 7 nucleotides in length. The overhang may have a length of up to about 200 nucleotides, such as about 100, 50, 25 or 10 nucleotides. The overhang is preferably 5 nucleotides in length. The overhang may comprise any of the nucleotides discussed above.

If the overhang at the 5' end of the one substrate strand is not closed after formation of the constructs, the translocase will remove both the MuA transposase and the one substrate strand, i.e. the substrate strand with the overhang. If the overhang at the 5' end of the one substrate strand is closed after formation of the constructs, the translocase will remove only the MuA transposase.

Closure of the overhang occurs for example where the 5' end of the overhang is ligated to the adjacent 3' end of a strand of the template polynucleotide fragment.

Universal Nucleotides

In one embodiment, each substrate comprises an overhang at both ends of one strand and the overhang at the 5' end is formed from universal nucleotides. The overhang preferably consists of universal nucleotides. This allows the overhang to be closed after formation of the constructs. Each substrate preferably comprises a double stranded portion which comprises the sequence shown in SEQ ID NO: 94 hybridised to a sequence which is complementary to the sequence shown in SEQ ID NO: 94. The overhang formed from universal nucleotides is at the 5' end of the sequence which is complementary to the sequence shown in SEQ ID NO: 94.

The overhangs may be at least 3, at least 4, at least 5, at least 6 or at least 7 nucleotides in length. The overhangs are preferably 5 nucleotides in length.

A universal nucleotide is one which will hybridise to some degree to all of the nucleotides in the template polynucleotide. A universal nucleotide is preferably one which will hybridise to some degree to nucleotides comprising the nucleosides adenosine (A), thymine (T), uracil (U), guanine (G) and cytosine (C). The universal nucleotide may hybridise more strongly to some nucleotides than to others. For instance, a universal nucleotide (I) comprising the nucleoside, 2'-deoxyinosine, will show a preferential order of pairing of I-C>I-A>I-G approximately=I-T. For the purposes of the invention, it is only necessary that the universal nucleotide used in the oligomers hybridises to all of the nucleotides in the template polynucleotide.

The universal nucleotide preferably comprises one of the following nucleobases: hypoxanthine, 4-nitroindole, 5-nitroindole, 6-nitroindole, 3-nitropyrrole, nitroimidazole, 4-nitropyrazole, 4-nitrobenzimidazole, 5-nitroindazole, 4-aminobenzimidazole or phenyl (C6-aromatic ring. The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside or phenyl C-2'-deoxyribosyl nucleoside. The universal nucleotide is most preferably comprises 2'-deoxyinosine.

The universal nucleotides in each overhang may be different from one another. The universal nucleotides in each overhang are preferably the same. All of the universal nucleotides in the population of substrates are preferably the same universal nucleotide.

The method of the invention preferably comprises (a) contacting the template polynucleotide with a MuA transposase and a population of double stranded MuA substrates each comprising an overhang at both ends of one strand, wherein the overhang at the 5' end of the one strand consists of universal nucleotides, such that the transposase fragments the template polynucleotide into fragments and ligates a substrate to one or both ends of the double stranded fragments and thereby producing a plurality of fragment/substrate constructs;

(b) allowing the overhangs consisting of universal nucleotides to hybridise to the opposite fragment strands in the constructs;

(c) ligating the overhangs consisting of universal nucleotides to the adjacent fragment strands in the constructs; and (d) using a translocase to remove the MuA transposases from the constructs and thereby producing a plurality of modified double stranded polynucleotides. In this embodiment, the translocase binds to the overhangs at the 3' ends of the one substrate strands in the constructs and moves 3' to 5' to remove the MuA transposase. Since the 5' overhang is closed, the one substrate strands remain in the constructs.

The overhang(s) of universal nucleotides may further comprise a reactive group, preferably at the 5' end. The reactive group may be used to ligate the overhangs to the fragments in the constructs as discussed below. The reactive group may be used to ligate the fragments to the overhangs using click chemistry. Click chemistry is a term first introduced by Kolb et al. in 2001 to describe an expanding set of powerful, selective, and modular building blocks that work reliably in both small- and large-scale applications (Kolb H C, Finn, M G, Sharpless K B, Click chemistry: diverse chemical function from a few good reactions, Angew. Chem. Int. Ed. 40 (2001) 2004-2021). They have defined the set of stringent criteria for click chemistry as follows: "The reaction must be modular, wide in scope, give very high yields, generate only inoffensive by-products that can be removed by nonchromatographic methods, and be stereospecific (but not necessarily enantioselective). The required process characteristics include simple reaction conditions (ideally, the process should be insensitive to oxygen and water), readily available starting materials and reagents, the use of no solvent or a solvent that is benign (such as water) or easily removed, and simple product isolation. Purification if required must be by nonchromatographic methods, such as crystallization or distillation, and the product must be stable under physiological conditions".

Suitable examples of click chemistry include, but are not limited to, the following:

(a) copper-free variant of the 1,3 dipolar cycloaddition reaction, where an azide reacts with an alkyne under strain, for example in a cyclooctane ring;

(b) the reaction of an oxygen nucleophile on one linker with an epoxide or aziridine reactive moiety on the other; and (c) the Staudinger ligation, where the alkyne moiety can be replaced by an aryl phosphine, resulting in a specific reaction with the azide to give an amide bond.

Any reactive group may be used in the invention. The reactive group may be one that is suitable for click chemistry. The reactive group may be any of those disclosed in International Application No. PCT/GB10/000132 (published as WO 2010/086602), particularly in Table 4 of that application.

In a further embodiment, the modification method uses a MuA transposase and a population of MuA substrates each comprising at least one overhang comprising a reactive group. The overhang(s) may be any length and may comprise any combination of any nucleotide(s). Suitable lengths and nucleotides are disclosed above. Suitable reactive groups are discussed above. Accordingly, the invention provides a method for modifying a template double stranded polynucleotide, comprising:

(a) contacting the template polynucleotide with a MuA transposase and a population of double stranded MuA substrates each comprising an overhang at both ends of one strand, wherein the overhang at the 5' end of the one strand comprises a reactive group, such that the transposase fragments the template polynucleotide and ligates a substrate to one or both ends of the double stranded fragments and thereby producing a plurality of fragment/substrate constructs; and (b) ligating the overhangs to the fragments in the constructs using the reactive group;

(c) using a translocase to remove the MuA transposases from the constructs and thereby producing a plurality of modified double stranded polynucleotides. In this embodiment, the translocase binds to the overhangs at the 3' ends of the one substrate strands in the constructs and moves 3' to 5' to remove the MuA transposase. Since the 5' overhang is closed, the one substrate strands remain in the constructs.

Nucleosides that are not Present in the Template Polynucleotide

In one embodiment, each substrate comprises (i) an overhang at both ends of one strand and (ii) at least one nucleotide 10 nucleotides or fewer from the overhang at the 5' end of the one strand which comprises a nucleoside that is not present in the template polynucleotide. For example, the nucleotide that is not present in the template polynucleotide is typically a non-natural nucleotide where the template polynucleotide comprises only natural nucleotides.

As discussed above, the double stranded portion in each substrate preferably comprises a dinucleotide comprising deoxycytidine (dC) and deoxyadenosine (dA) at the 3' end of each strand and a dinucleotide comprising thymidine (dT) and deoxyguanosine (dG) at the 5' end of each strand. In some embodiments, one or both of the nucleotides in the dT and dG dinucleotide of the one substrate strand may be replaced with a nucleotide comprising a nucleoside that is not present in the template polynucleotide as discussed below. In a preferred embodiment, the template polynucleotide comprises deoxyadenosine (dA), thymidine (dT), deoxyguanosine (dG) and deoxycytidine (dC), but not deoxyuridine (dU) and the dA in the dC and dA dinucleotide of one strand is replaced with a nucleotide comprising deoxyuridine (dU). This is exemplified below.

The double stranded portion preferably comprises the sequence shown in SEQ ID NO: 94 and a sequence which is complementary to the sequence shown in SEQ ID NO: 94 and which is modified to include at least one nucleotide that is not present in the template polynucleotide. The sequence complementary to SEQ ID NO: 94 further comprises the overhang, i.e. is the one substrate strand. In a more preferred embodiment, the double stranded portion comprises the sequence shown in SEQ ID NO: 94 and the sequence shown in SEQ ID NO: 95 (see below). In SEQ ID NO: 27, the dT in the dT and dG dinucleotide at the 5' end had been replaced with dU. This double stranded portion (shown below) may be used when the template polynucleotide comprises deoxyadenosine (dA), thymidine (dT), deoxyguanosine (dG) and deoxycytidine (dC), but not deoxyuridine (dU).

```
                                                            (SEQ 94)
5'-GTTTTCGCATTTATCGTGAAACGCTTTCGCGTTTTTCGTGCGCCGCT
TCA-3'

(SEQ 95)
3'-CAAAAGCGTAAATAGCACTTTGCGAAAGCGCAAAAAGCACGCGGCGA
AGU-5'
```

The overhangs may be at least 3, at least 4, at least 5, at least 6 or at least 7 nucleotides in length. The overhangs are preferably 4 nucleotides in length. The overhangs may comprise any of the nucleotides discussed above.

Each substrate comprises at least one nucleotide in the one substrate strand which is 10 nucleotides or fewer from the overhang at 5' end and which comprises a nucleoside that is not present in the template polynucleotide. Each substrate may comprise any number of nucleotides which comprise a nucleoside that is not present in the template polynucleotide, such as 2, 3, 4, 5, 6, 7, 8, 9, 10 or more. If a substrate comprises more than one nucleotide that is not present in the template polynucleotide, those nucleotides are typically the same, but may be different.

If the template polynucleotide comprises deoxyadenosine (dA), thymidine (dT), deoxyguanosine (dG) and deoxycytidine (dC) but not deoxyuridine (dU), the nucleoside that is not present in the template polynucleotide is preferably deoxyuridine (dU).

In a preferred embodiment, one strand of the double stranded portion comprises the sequence shown in SEQ ID NO: 94 and the other strand of the double stranded portion comprises the sequence shown in SEQ ID NO: 95 (see above). In SEQ ID NO: 95, the dT in the dT and dG dinucleotide at the 5' end had been replaced with dU. The overhang at the 5' end of SEQ ID NO: 95 is attached to the U.

In a most preferred embodiment, each substrate comprises the sequence shown in SEQ ID NO: 94 and the sequence shown in SEQ ID NO: 96 (see below). This substrate (shown below) may be used when the template polynucleotide comprises deoxyadenosine (dA), thymidine (dT), deoxyguanosine (dG) and deoxycytidine (dC), but not deoxyuridine (dU).

```
                                                            (SEQ 94)
5'-GTTTTCGCATTTATCGTGAAACGCTTTCGCGTTTTTCGTGCGCCGCT
TCA-3'

(SEQ 96)
3'-CAAAAGCGTAAATAGCACTTTGCGAAAGCGCAAAAAGCACGCGGCGA
AGUCTAG-5'
```

Each substrate also comprise an overhang at the 3' end of the sequence shown in SEQ ID NO: 96.

If the template polynucleotide comprises deoxyadenosine (dA), deoxyuridine (dU), deoxyguanosine (dG) and deoxycytidine (dC) but not thymidine (dT), the nucleoside that is not present in the template polynucleotide is preferably thymidine (dT).

The nucleoside that is not present in the template polynucleotide is preferably abasic, adenosine (A), uridine (U), 5-methyluridine ($m^5U$), cytidine (C) or guanosine (G) or preferably comprises urea, 5, 6 dihydroxythymine, thymine glycol, 5-hydroxy-5 methylhydantoin, uracil glycol, 6-hydroxy-5, 6-dihdrothimine, methyltartronylurea, 7, 8-dihydro-8-oxoguanine (8-oxoguanine), 8-oxoadenine, fapy-guanine, methy-fapy-guanine, fapy-adenine, aflatoxin B1-fapy-guanine, 5-hydroxy-cytosine, 5-hydroxy-uracil, 3-methyladenine, 7-methylguanine, 1,N6-ethenoadenine, hypoxanthine, 5-hydroxyuracil, 5-hydroxymethyluracil, 5-formyluracil or a cis-syn-cyclobutane pyrimidine dimer.

The at least one nucleotide is 10 nucleotides or fewer from the overhang at the 5' end, such as 9, 8, 7, 6, 5, 4, 3, 2, 1 or 0 nucleotides from the overhang. In other words, the at least one nucleotide is preferably at any of positions A to K in the Example below. The at least one nucleotide is preferably 0 nucleotides from the overhang (i.e. is adjacent to the overhang). In other words, the at least one nucleotide is preferably at position K in the Example below.

XXXXXXXXXXX
ABCDEFGHIJKXXXX

The at least one nucleotide may be the first nucleotide in the overhang. In other words, the at least one nucleotide may be at position A in the Example below.

XXXXXXXXXX
XXXXXXXXXXXAXXX

All of the nucleotides in the overhang may comprise a nucleoside that is not present in the template polynucleotide. A person skilled in the art is capable of designing suitable substrates.

The method of the invention preferably comprises (a) contacting the template polynucleotide with a MuA transposase and a population of double stranded MuA substrates each comprising (i) an overhang at both ends of one strand and (ii) at least one nucleotide 10 nucleotides or fewer from the overhang at the 5' end of the one strand which comprises a nucleoside that is not present in the template polynucleotide such that the transposase fragments the template polynucleotide into fragments and ligates a substrate at one or both ends of the double stranded fragments and thereby producing a plurality of fragment/substrate constructs;

(b) removing the overhangs at the 5' end of the one substrate strands from the constructs by selectively removing the at least one nucleotide and thereby producing a plurality of double stranded constructs comprising single stranded gaps;

(c) repairing the single stranded gaps in the constructs; and (d) using a translocase to remove the MuA transposases from the constructs and thereby producing a plurality of modified double stranded polynucleotides.

Ligating the Overhangs

In those embodiments in which the MuA substrates comprise overhangs of universal nucleotides, the method comprises ligating the overhangs to the fragments in the constructs. This may be done using any method of ligating nucleotides known in the art. For instance, it may be done using a ligase, such as a DNA ligase. Alternatively, if the overhangs comprise a reactive group, the reactive group may be used to ligate the overhangs to the fragments in the constructs. For instance, a nucleotide comprising a complementary reactive group may be attached to the fragments and the two reactive groups may be reacted together to ligate the overhangs to the fragments. Click chemistry may be used as discussed above.

Selective Removal

Methods are known in the art for selectively removing the nucleotide(s) which comprise(s) a nucleoside that is not present in the template polynucleotide from the ligated constructs. Nucleotides are selectively removed if they are removed (or excised) from the ligated constructs, but the other nucleotides in the ligated constructs (i.e. those comprising different nucleosides) are not removed (or excised).

Nucleotides comprising deoxyuridine (dU) may be selectively removed using Uracil-Specific Excision Reagent (USER®), which is a mixture of Uracil DNA glycosylase (UDG) and the DNA glycosylase-lyase Endonuclease VIII.

Repairing the Gaps

Methods are known in the art for repairing the single stranded gaps in the double stranded constructs. For instance, the gaps can be repaired using a polymerase and a ligase, such as DNA polymerase and a DNA ligase. Alternatively, the gaps can be repaired using random oligonucleotides of sufficient length to bring the gaps and a ligase.

Translocases

Any translocase that is capable of removing the MuA transposase may be used in the invention. This may occur, for example, as a result of the unwinding of double stranded polynucleotide by a translocase.

The translocase is preferably a helicase. Suitable helicases are well-known in the art (M. E. Fairman-Williams et al., Curr. Opin. Struct Biol., 2010, 20 (3), 313-324, T. M. Lohman et al., Nature Reviews Molecular Cell Biology, 2008, 9, 391-401).

The helicase is preferably a member of superfamily 1 or superfamily 2. The helicase is more preferably a member of one of the following families: Pif1-like, Upf1-like, UvrD/Rep, Ski-like, Rad3/XPD, NS3/NPH-II, DEAD, DEAH/RHA, RecG-like, REcQ-like, T1R-like, Swi/Snf-like and Rig-I-like. The first three of those families are in superfamily 1 and the second ten families are in superfamily 2. The helicase is more preferably a member of one of the following subfamilies: RecD, Upf1 (RNA), PcrA, Rep, UvrD, Hel308, Mtr4 (RNA), XPD, NS3 (RNA), Mss116 (RNA), Prp43 (RNA), RecG, RecQ, T1R, RapA and Hef (RNA). The first five of those subfamilies are in superfamily 1 and the second eleven subfamilies are in superfamily 2. Members of the Upf1, Mtr4, NS3, Mss116, Prp43 and Hef subfamilies are RNA helicases. Members of the remaining subfamilies are DNA helicases. The helicase may be Srs2. The helicase may be RecBCD.

The helicase is preferably a Hel308 helicase. Any Hel308 helicase may be used in accordance with the invention. Hel308 helicases are also known as ski2-like helicases and the two terms can be used interchangeably. Suitable Hel308 helicases are disclosed in Table 4 of International Application No. PCT/GB2012/052579 (published as WO 2013/057495).

The Hel308 helicase typically comprises the amino acid motif Q-X1-X2-G-R-A-G-R (hereinafter called the Hel308 motif; SEQ ID NO: 8). The Hel308 motif is typically part of the helicase motif VI (Tuteja and Tuteja, Eur. J. Biochem. 271, 1849-1863 (2004)). X1 may be C, M or L. X1 is preferably C. X2 may be any amino acid residue. X2 is typically a hydrophobic or neutral residue. X2 may be A, F, M, C, V, L, I, S, T, P or R. X2 is preferably A, F, M, C, V, L, I, S, T or P. X2 is more preferably A, M or L. X2 is most preferably A or M.

The Hel308 helicase preferably comprises the motif Q-X1-X2-G-R-A-G-R-P (hereinafter called the extended Hel308 motif; SEQ ID NO: 9) wherein X1 and X2 are as described above.

The most preferred Hel308 helicases, Hel308 motifs and extended Hel308 motifs are shown in the Table 1 below.

TABLE 1

Preferred Hel308 helicases and their motifs

| SEQ ID NO: | Helicase | Names | % Identity Hel308 Pfu | % Identity Hel308 Mbu | Hel308 motif | Extended Hel308 motif |
|---|---|---|---|---|---|---|
| 10 | Hel308 Mbu | Methanococcoides burtonii | 37% | — | QMAGRAGR (SEQ ID NO: 11) | QMAGRAGRP (SEQ ID NO: 12) |
| 13 | Hel308 Pfu | Pyrococcus furiosus DSM 3638 | — | 37% | QMLGRAGR (SEQ ID NO: 14) | QMLGRAGRP (SEQ ID NO: 15) |
| 16 | Hel308 Hvo | Haloferax volcanii | 34% | 41% | QMMGRAGR (SEQ ID NO: 17) | QMMGRAGRP (SEQ ID NO: 18) |
| 19 | Hel308 Hla | Halorubrum lacusprofundi | 35% | 42% | QMCGRAGR (SEQ ID NO: 20) | QMCGRAGRP (SEQ ID NO: 21) |
| 22 | Hel308 Csy | Cenarchaeum symbiosum | 34% | 34% | QLCGRAGR (SEQ ID NO: 23) | QLCGRAGRP (SEQ ID NO: 24) |
| 25 | Hel308 Sso | Sulfolobus solfataricus | 35% | 33% | QMSGRAGR (SEQ ID NO: 26) | QMSGRAGRP (SEQ ID NO: 27) |
| 28 | Hel308 Mfr | Methanogenium frigidum | 37% | 44% | QMAGRAGR (SEQ ID NO: 11) | QMAGRAGRP (SEQ ID NO: 12) |
| 29 | Hel308 Mok | Methanothermococcus okinawensis | 37% | 34% | QCIGRAGR (SEQ ID NO: 30) | QCIGRAGRP (SEQ ID NO: 31) |

TABLE 1-continued

Preferred Hel308 helicases and their motifs

| SEQ ID NO: | Helicase | Names | % Identity Hel308 Pfu | % Identity Hel308 Mbu | Hel308 motif | Extended Hel308 motif |
|---|---|---|---|---|---|---|
| 32 | Hel308 Mig | *Methanotorris igneus Kol 5* | 40% | 35% | QCIGRAGR (SEQ ID NO: 30) | QCIGRAGRP (SEQ ID NO: 31) |
| 33 | Hel308 Tga | *Thermococcus gammatolerans EJ3* | 60% | 38% | QMMGRAGR (SEQ ID NO: 17) | QMMGRAGRP (SEQ ID NO: 18) |
| 34 | Hel308 Tba | *Thermococcus barophilus MP* | 57% | 35% | QMIGRAGR (SEQ ID NO: 35) | QMIGRAGRP (SEQ ID NO: 36) |
| 37 | Hel308 Tsi | *Thermococcus sibiricus MM 739* | 56% | 35% | QMMGRAGR (SEQ ID NO: 17) | QMMGRAGRP (SEQ ID NO: 18) |
| 38 | Hel308 Mba | *Methanosarcina barkeri str. Fusaro* | 39% | 60% | QMAGRAGR (SEQ ID NO: 11) | QMAGRAGRP (SEQ ID NO: 12) |
| 39 | Hel308 Mac | *Methanosarcina acetivorans* | 38% | 60% | QMAGRAGR (SEQ ID NO: 11) | QMAGRAGRP (SEQ ID NO: 12) |
| 40 | Hel308 Mmah | *Methanohalophilus mahii DSM 5219* | 38% | 60% | QMAGRAGR (SEQ ID NO: 11) | QMAGRAGRP (SEQ ID NO: 12) |
| 41 | Hel308 Mmaz | *Methanosarcina mazei* | 38% | 60% | QMAGRAGR (SEQ ID NO: 11) | QMAGRAGRP (SEQ ID NO: 12) |
| 42 | Hel308 Mth | *Methanosaeta thermophila PT* | 39% | 46% | QMAGRAGR (SEQ ID NO: 11) | QMAGRAGRP (SEQ ID NO: 12) |
| 43 | Hel308 Mzh | *Methanosalsum zhilinae DSM 4017* | 39% | 57% | QMAGRAGR (SEQ ID NO: 11) | QMAGRAGRP (SEQ ID NO: 12) |
| 44 | Hel308 Mev | *Methanohalobium evestigatum Z-7303* | 38% | 61% | QMAGRAGR (SEQ ID NO: 11) | QMAGRAGRP (SEQ ID NO: 12) |
| 45 | Hel308 Mma | *Methanococcus maripaludis* | 36% | 32% | QCIGRAGR (SEQ ID NO: 30) | QCIGRAGRP (SEQ ID NO: 31) |
| 46 | Hel308 Nma | *Natrialba magadii* | 37% | 43% | QMMGRAGR (SEQ ID NO: 17) | QMMGRAGRP (SEQ ID NO: 18) |
| 47 | Hel308 Mbo | *Methanoregula boonei 6A8* | 38% | 45% | QMAGRAGR (SEQ ID NO: 11) | QMAGRAGRP (SEQ ID NO: 12) |
| 48 | Hel308 Fac | *Ferroplasma acidarmanus* | 34% | 32% | QMIGRAGR (SEQ ID NO: 35) | QMIGRAGRP (SEQ ID NO: 36) |
| 49 | Hel308 Mfe | *Methanocaldococcus fervens AG86* | 40% | 35% | QCIGRAGR (SEQ ID NO: 30) | QCIGRAGRP (SEQ ID NO: 31) |
| 50 | Hel308 Mja | *Methanocaldococcus jannaschii* | 24% | 22% | QCIGRAGR (SEQ ID NO: 30) | QCIGRAGRP (SEQ ID NO: 31) |
| 51 | Hel308 Mm | *Methanocaldococcus mfernus* | 41% | 33% | QCIGRAGR (SEQ ID NO: 30) | QCIGRAGRP (SEQ ID NO: 31) |

TABLE 1-continued

Preferred Hel308 helicases and their motifs

| SEQ ID NO: | Helicase | Names | % Identity Hel308 Pfu | % Identity Hel308 Mbu | Hel308 motif | Extended Hel308 motif |
|---|---|---|---|---|---|---|
| 52 | Hel308 Mhu | Methanospirillum hungatei JF-1 | 36% | 40% | QMAGRAGR (SEQ ID NO: 11) | QMAGRAGRP (SEQ ID NO: 12) |
| 53 | Hel308 Afu | Archaeoglobus fulgidus DSM 4304 | 40% | 40% | QMAGRAGR (SEQ ID NO: 11) | QMAGRAGRP (SEQ ID NO: 12) |
| 54 | Hel308 Htu | Haloterrigena turkmenica | 35% | 43% | QMAGRAGR (SEQ ID NO: 11) | QMMGRAGRP (SEQ ID NO: 12) |
| 55 | Hel308 Hpa | Haladaptatus paucihalophilus DX253 | 38% | 45% | QMFGRAGR (SEQ ID NO: 56) | QMFGRAGRP (SEQ ID NO: 57) |
| 58 | Hel308 Hsp ski2-like helicase | Halobacterium sp. NRC-1 | 36.8% | 42.0% | QMFGRAGR (SEQ ID NO: 56) | QMFGRAGRP (SEQ ID NO: 57) |

The most preferred Hel308 motif is shown in SEQ ID NO: 17. The most preferred extended Hel308 motif is shown in SEQ ID NO: 18.

The Hel308 helicase preferably comprises the sequence of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 or a variant thereof.

A variant of a Hel308 helicase is an enzyme that has an amino acid sequence which varies from that of the wild-type helicase and which retains polynucleotide binding activity. In particular, a variant of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 is an enzyme that has an amino acid sequence which varies from that of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 and which retains polynucleotide binding activity. Polynucleotide binding activity can be determined using methods known in the art. Suitable methods include, but are not limited to, fluorescence anisotropy, tryptophan fluorescence and electrophoretic mobility shift assay (EMSA). For instance, the ability of a variant to bind a single stranded polynucleotide can be determined as described in the Examples.

The variant retains helicase activity. This can be measured in various ways. For instance, the ability of the variant to translocate along a polynucleotide can be measured using electrophysiology, a fluorescence assay or ATP hydrolysis.

The variant may include modifications that facilitate handling of the polynucleotide encoding the helicase and/or facilitate its activity at high salt concentrations and/or room temperature. Variants typically differ from the wild-type helicase in regions outside of the Hel308 motif or extended Hel308 motif discussed above. However, variants may include modifications within these motif(s).

Over the entire length of the amino acid sequence of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58, a variant will preferably be at least 30% homologous to that sequence based on amino acid identity. More preferably, the variant polypeptide may be at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 over the entire sequence. There may be at least 70%, for example at least 80%, at least 85%, at least 90% or at least 95%, amino acid identity over a stretch of 150 or more, for example 200, 300, 400, 500, 600, 700, 800, 900 or 1000 or more, contiguous amino acids ("hard homology"). Homology is determined as described below. The variant may differ from the wild-type sequence in any of the ways discussed below with reference to SEQ ID NOs: 2 and 4.

A variant of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 preferably comprises the Hel308 motif or extended Hel308 motif of the wild-type sequence as shown in Table 1 above. However, a variant may comprise the Hel308 motif or extended Hel308 motif from a different wild-type sequence. For instance, a variant of SEQ ID NO: 10 may comprise the Hel308 motif or extended Hel308 motif from SEQ ID NO: 13 (i.e. SEQ ID NO: 14 or 15). Variants of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 may also include modifications within the Hel308 motif or extended Hel308 motif of the relevant wild-type sequence. Suitable modifications at X1 and X2 are discussed above when defining the two motifs. A variant of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 preferably comprises one or more substituted cysteine residues and/or one or more substituted Faz residues to facilitate attachment as discussed above.

A variant of SEQ ID NO: 10 may lack the first 19 amino acids of SEQ ID NO: 10 and/or lack the last 33 amino acids of SEQ ID NO: 10. A variant of SEQ ID NO: 10 preferably comprises a sequence which is at least 70%, at least 75%, at least 80%, at least 85%, at least 90% or more preferably at least 95%, at least 97% or at least 99% homologous based on amino acid identity with amino acids 20 to 211 or 20 to 727 of SEQ ID NO: 10.

The Hel308 helicase may be modified as described in International Application No. PCT/GB2015/051925 (published as WO 2014/013260). In particular, two or more parts on the helicase may be connected to reduce the size of the opening in the polynucleotide domain through which a polynucleotide can unbind from the helicase and wherein the helicase retains its ability to control the movement of the polynucleotide. In Hel308 helicases, the polynucleotide domain and opening can be found between domain 2 (one of the ATPase domains) and domain 4 (the ratchet domain) and domain 2 and domain 5 (the molecular brake). The two or more parts connected in accordance with the invention are preferably (a) any amino acid in domain 2 and any amino acid in domain 4 or (b) any amino acid in domain 2 and any amino acid in domain 5. The amino acid residues which define domains 2, 4 and 5 in various Hel308 helicases are listed in Table 2 below.

TABLE 2

Amino acid residues which correspond to domains 2, 4 and 5 in various Hel308 helicases.

| SEQ ID NO: | Hel308 Homologue | Domain 2 Start | Domain 2 End | Domain 4 Start | Domain 4 End | Domain 5 Start | Domain 5 End |
|---|---|---|---|---|---|---|---|
| 10 | Mbu | W200 | E409 | Y506 | G669 | S670 | Q760 |
| 13 | Pfu | W198 | F398 | Y490 | G640 | I641 | S720 |
| 16 | Hvo | W201 | W418 | Y509 | G725 | V726 | E827 |
| 19 | Hla | W201 | W418 | Y513 | G725 | V726 | R824 |
| 22 | Csy | W205 | G414 | Y504 | G644 | I645 | K705 |
| 25 | Sso | W204 | L420 | Y506 | G651 | I652 | S717 |
| 28 | Mfr | W193 | E397 | Y488 | G630 | I631 | I684 |
| 29 | Mok | W198 | G415 | Y551 | G706 | A707 | I775 |
| 32 | Mig | W200 | E408 | Y495 | G632 | A633 | I699 |
| 33 | Tga | W198 | R399 | Y491 | G639 | V640 | R720 |
| 34 | Tba | W219 | F420 | Y512 | G660 | V661 | K755 |
| 37 | Tsi | W221 | L422 | Y514 | G662 | V663 | K744 |
| 38 | Mba | W200 | E409 | Y498 | G643 | A644 | Y729 |
| 39 | Mac | W200 | E409 | Y499 | G644 | A645 | F730 |
| 40 | Mmah | W196 | G405 | Y531 | G678 | A679 | N747 |
| 41 | Mmaz | W200 | E409 | Y499 | G644 | A645 | Y730 |
| 42 | Mth | W203 | M404 | Y491 | G629 | A630 | A693 |
| 43 | Mzh | W200 | N409 | Y505 | G651 | I652 | T739 |
| 44 | Mev | W200 | D409 | Y499 | G643 | V644 | F733 |
| 45 | Mma | W196 | G405 | Y531 | G678 | A679 | N747 |
| 46 | Nma | W201 | W413 | Y541 | G688 | V689 | F799 |
| 47 | Mbo | W197 | E402 | Y493 | G637 | I638 | G723 |
| 48 | Fac | F197 | T390 | Y480 | G613 | V614 | R681 |
| 49 | Mfe | W199 | Q408 | Y494 | G629 | A630 | F696 |
| 50 | Mja | W197 | Q406 | Y492 | G627 | A628 | F694 |
| 51 | Min | W189 | Q390 | Y476 | G604 | A605 | I670 |
| 52 | Mhu | W198 | D402 | Y493 | G637 | V638 | C799 |
| 53 | Afu | W201 | F399 | Y487 | G626 | V627 | F696 |
| 54 | Htu | W201 | W413 | Y533 | G680 | V681 | F791 |
| 55 | Hpa | W201 | W412 | Y502 | G657 | V658 | E752 |
| 58 | Hsp (ski2-like helicase) | W210 | Y421 | Y512 | G687 | V688 | S783 |

The Hel308 helicase preferably comprises the sequence of Hel308 Mbu (i.e. SEQ ID NO: 10) or a variant thereof. In Hel308 Mbu, the polynucleotide domain and opening can be found between domain 2 (one of the ATPase domains) and domain 4 (the ratchet domain) and domain 2 and domain 5 (the molecular brake). The two or more parts of Hel308 Mbu connected are preferably (a) any amino acid in domain 2 and any amino acid in domain 4 or (b) any amino acid in domain 2 and any amino acid in domain 5. The amino acid residues which define domains 2, 4 and 5 for Hel308 Mbu are listed in Table 2 above. The two or more parts of Hel308 Mbu connected are preferably amino acids 284 and 615 in SEQ ID NO: 10. These amino acids are preferably substituted with cysteine (i.e. E284C and S615C) such that they can be connected by cysteine linkage.

The invention may use a mutant Hel308 Mbu protein which comprises a variant of SEQ ID NO: 10 in which E284 and S615 are modified. E284 and S615 are preferably substituted. E284 and S615 are more preferably substituted with cysteine (i.e. E284C and 5615C). The variant may differ from SEQ ID NO: 10 at positions other than E284 and S615 as long as E284 and S615 are modified. The variant will preferably be at least 30% homologous to SEQ ID NO: 10 based on amino acid identity as discussed in more detail below. E284 and S615 do not have to be connected. Alternatively, E284 and S615 may be connected.

The Hel308 helicase more preferably comprises (a) the sequence of Hel308 Tga (i.e. SEQ ID NO: 33) or a variant thereof, (b) the sequence of Hel308 Csy (i.e. SEQ ID NO: 22) or a variant thereof or (c) the sequence of Hel308 Mhu (i.e. SEQ ID NO: 52) or a variant thereof.

SEQ ID NO: 10 (Hel308 Mbu) contains five natural cysteine residues. However, all of these residues are located within or around the DNA binding grove of the enzyme. Once a DNA strand is bound within the enzyme, these natural cysteine residues become less accessible for external modifications. This allows specific cysteine mutants of SEQ ID NO: 10 to be designed and attached to the moiety using cysteine linkage as discussed above. Preferred variants of SEQ ID NO: 10 have one or more of the following substitutions: A29C, Q221C, Q442C, T569C, A577C, A700C and S708C. The introduction of a cysteine residue at one or more of these positions facilitates cysteine linkage as discussed above. Other preferred variants of SEQ ID NO: 10 have one or more of the following substitutions: M2Faz, R10Faz, F15Faz, A29Faz, R185Faz, A268Faz, E284Faz, Y387Faz, F400Faz, Y455Faz, E464Faz, E573Faz, A577Faz, E649Faz, A700Faz, Y720Faz, Q442Faz and S708Faz. The introduction of a Faz residue at one or more of these positions facilitates Faz linkage as discussed above.

The Hel308 helicase is modified by the introduction of one or more cysteine residues and/or one or more non-natural amino acids at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10), wherein the helicase retains its ability to control the movement of a polynucleotide. The one or more cysteine residues and/or one or more non-natural amino acids are preferably introduced by substitution.

These modifications do not prevent the helicase from binding to a polynucleotide. For instance, the helicase may bind to a polynucleotide via internal nucleotides or at one of its termini. These modifications decrease the ability of the polynucleotide to unbind or disengage from the helicase, particularly from internal nucleotides of the polynucleotide. In other words, the one or more modifications increase the processivity of the Hel308 helicase by preventing dissociation from the polynucleotide strand. The thermal stability of the enzyme is also increased by the one or more modifications giving it an improved structural stability that is beneficial in Strand Sequencing. The modified Hel308 helicases of the invention have all of the advantages and uses discussed above.

The modified Hel308 helicase has the ability to control the movement of a polynucleotide. This can be measured as discussed above. The modified Hel308 helicase is artificial or non-natural.

The Hel308 helicase preferably comprises a variant of one of the helicases shown in Table 1 above which comprises one or more cysteine residues and/or one or more non-natural amino acids at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10). The Hel308 helicase preferably comprises a variant of one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 which comprises one or more cysteine residues and/or one or more non-natural amino acids at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10).

The Hel308 helicase preferably comprises a variant of one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 which comprises one or more cysteine residues and/or one or more non-natural amino acids at one or more of the positions which correspond to D274, E284, E285, E287, S288, T289, G290, E291, N316, K319, S615, K717 or Y720 in Hel308 Mbu (SEQ ID NO: 10).

Table 3a and 3b below show the positions in other Hel308 helicases which correspond to D274, E284, E285, S288, S615, K717, Y720, E287, T289, G290, E291, N316 and K319 in Hel308 Mbu (SEQ ID NO: 10). For instance, in Hel308 Hvo (SEQ ID NO:16), E283 corresponds to D274 in Hel308 Mbu, E293 corresponds to E284 in Hel308 Mbu, I294 corresponds to E285 in Hel308 Mbu, V297 corresponds to S288 in Hel308 Mbu, D671 corresponds to S615 in Hel308 Mbu, K775 corresponds to K717 in Hel308 Mbu and E778 corresponds to Y720 in Hel308 Mbu. The lack of a corresponding position in another Hel308 helicase is marked as a "-".

TABLE 3a

Positions which correspond to D274, E284, E285, S288, S615, K717 and Y720 in Hel308 Mbu (SEQ ID NO: 10).

| SEQ ID NO: | Hel308 homologue | A | B | C | D | E | F | G |
|---|---|---|---|---|---|---|---|---|
| 10 | Mbu | D274 | E284 | E285 | S288 | S615 | K717 | Y720 |
| 13 | Pfu | L265 | E275 | L276 | S279 | P585 | K690 | E693 |
| 16 | Hvo | E283 | E293 | I294 | V297 | D671 | K775 | E778 |
| 19 | Hla | E283 | E293 | I294 | G297 | D668 | R775 | E778 |
| 22 | Csy | D280 | K290 | I291 | S294 | P589 | T694 | N697 |
| 25 | Sso | L281 | K291 | Q292 | D295 | D596 | K702 | Q705 |
| 28 | Mfr | H264 | E272 | K273 | A276 | G576 | K678 | E681 |
| 29 | Mok | S279 | L289 | S290 | D293 | P649 | K753 | R756 |
| 32 | Mig | Y276 | L286 | S287 | D290 | P579 | K679 | K682 |
| 33 | Tga | L266 | S276 | L277 | Q280 | P583 | K689 | D692 |
| 34 | Tba | L287 | E297 | L298 | S301 | S604 | K710 | E713 |
| 37 | Tsi | L289 | Q299 | L300 | G303 | N606 | G712 | E715 |
| 38 | Mba | E274 | D284 | E285 | E288 | S589 | K691 | D694 |
| 39 | Mac | E274 | D284 | E285 | E288 | P590 | K692 | E695 |
| 40 | Mmah | H272 | L282 | S283 | D286 | P621 | K725 | K728 |
| 41 | Mmaz | E274 | D284 | E285 | E288 | P590 | K692 | E698 |
| 42 | Mth | A269 | L279 | A280 | L283 | H575 | K677 | E680 |
| 43 | Mzh | H274 | Q284 | E285 | E288 | P596 | K699 | Q702 |
| 44 | Mev | G274 | E284 | E285 | E288 | T590 | K691 | Y694 |
| 45 | Mma | H272 | L282 | S283 | D286 | P621 | K725 | K728 |
| 46 | Nma | G277 | T287 | E288 | E291 | D634 | K737 | E740 |
| 47 | Mbo | A270 | E277 | R278 | E281 | S583 | G685 | E688 |
| 48 | Fac | Q264 | F267 | E268 | E271 | P559 | K663 | K666 |
| 49 | Mfe | R275 | L285 | S286 | E289 | P576 | K676 | K679 |
| 50 | Mja | I273 | L283 | S284 | E287 | P574 | K674 | K677 |
| 51 | Min | R257 | L267 | S268 | D271 | P554 | K651 | K654 |
| 52 | Mhu | S269 | Q277 | E278 | R281 | S583 | G685 | R688 |
| 53 | Afu | K268 | K277 | A278 | E281 | D575 | R677 | E680 |
| 54 | Htu | D277 | D287 | D288 | D291 | D626 | K729 | E732 |
| 55 | Hpa | D276 | D286 | Q287 | D290 | D595 | K707 | E710 |
| 58 | Hsp (ski2-like helicase) | E286 | E296 | I297 | V300 | D633 | A737 | E740 |

TABLE 3b

Positions which correspond to E287, T289, G290, E291, N316 and K319 in Hel308 Mbu (SEQ ID NO: 10).

| SEQ ID NO: | Hel308 homologue | H | I | J | K | L | M |
|---|---|---|---|---|---|---|---|
| 10 | Mbu | E287 | T289 | G290 | E291 | N316 | K319 |
| 13 | Pfu | D278 | L280 | E281 | E282 | D307 | V310 |
| 16 | Hvo | D296 | S298 | D299 | T300 | E324 | T327 |
| 19 | Hla | S296 | S298 | D299 | T300 | E324 | A327 |
| 22 | Csy | S293 | G295 | G296 | E297 | D322 | S325 |
| 25 | Sso | D294 | I296 | E297 | E298 | A325 | D328 |
| 28 | Mfr | E275 | A277 | A278 | E279 | M304 | T307 |
| 29 | Mok | L292 | N294 | P295 | T296 | E320 | K323 |
| 32 | Mig | L289 | P291 | P292 | T293 | E317 | K320 |
| 33 | Tga | S279 | L281 | E282 | D283 | V308 | T311 |
| 34 | Tba | E300 | L302 | E303 | S304 | A329 | T332 |
| 37 | Tsi | D302 | L304 | D305 | T306 | T331 | S334 |
| 38 | Mba | L287 | N289 | S290 | E291 | P316 | E319 |
| 39 | Mac | L287 | N289 | S290 | E291 | P316 | E319 |
| 40 | Mmah | L285 | R287 | P288 | V289 | K313 | K316 |
| 41 | Mmaz | I287 | N289 | S290 | E291 | P316 | E319 |
| 42 | Mth | R282 | S284 | G285 | E286 | E311 | R314 |
| 43 | Mzh | G287 | A289 | G290 | E291 | E316 | K319 |
| 44 | Mev | L287 | T289 | S290 | D291 | A316 | K319 |
| 45 | Mma | L285 | R287 | P288 | V289 | K313 | K316 |
| 46 | Nma | R290 | D292 | S293 | D294 | T319 | S322 |
| 47 | Mbo | L280 | G282 | T283 | P284 | K309 | S312 |
| 48 | Fac | L270 | I272 | P273 | P274 | D299 | T302 |
| 49 | Mfe | L288 | P290 | P291 | T292 | Q316 | K319 |
| 50 | Mja | L286 | P288 | P289 | T290 | Q314 | K317 |
| 51 | Min | F270 | P272 | P273 | T274 | E298 | K301 |
| 52 | Mhu | R280 | L282 | R283 | D284 | Q309 | T312 |
| 53 | Afu | L280 | E282 | N283 | E284 | G309 | R312 |
| 54 | Htu | R290 | D292 | S293 | D294 | T319 | S322 |
| 55 | Hpa | R289 | V291 | S292 | D293 | D318 | S321 |
| 58 | Hsp (ski2-like helicase) | G299 | S301 | D302 | T303 | E327 | E330 |

The Hel308 helicase more preferably comprises a variant of one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 which comprises one or more cysteine residues and/or one or more non-natural amino acids at one or more of the positions which correspond to D274, E284, E285, S288, S615, K717 and Y720 in Hel308 Mbu (SEQ ID NO: 10). The relevant positions are shown in columns A to G in Table 3a above.

The helicase may comprise a cysteine residue at one, two, three, four, five, six or seven of the positions which correspond to D274, E284, E285, S288, S615, K717 and Y720 in Hel308 Mbu (SEQ ID NO: 10). Any combination of these positions may be substituted with cysteine. For instance, for each row of Table 3a above, the helicase of the invention may comprise a cysteine at any of the following combinations of the positions labelled A to G in that row: {A}, {B}, {C}, {D}, {G}, {E}, {F}, {A and B}, {A and C}, {A and D}, {A and G}, {A and E}, {A and F}, {B and C}, {B and D}, {B and G}, {B and E}, {B and F}, {C and D}, {C and G}, {C and E}, {C and F}, {D and G}, {D and E}, {D and F}, {G and E}, {G and F}, {E and F}, {A, B and C}, {A, B and D}, {A, B and G}, {A, B and E}, {A, B and F}, {A, C and D}, {A, C and G}, {A, C and E}, {A, C and F}, {A, D and G}, {A, D and E}, {A, D and F}, {A, G and E}, {A, G and F}, {A, E and F}, {B, C and D}, {B, C and G}, {B, C and E}, {B, C and F}, {B, D and G}, {B, D and E}, {B, D and F}, {B, G and E}, {B, G and F}, {B, E and F}, {C, D and G}, {C, D and E}, {C, D and F}, {C, G and E}, {C, G and F}, {C, E and F}, {D, G and E}, {D, G and F}, {D, E and F}, {G, E and F}, {A, B, C and D}, {A, B, C and G}, {A, B, C and E}, {A, B, C and F}, {A, B, D and G}, {A, B, D and E}, {A, B, D and F}, {A, B, G and E}, {A, B, G and F}, {A, B, E and F}, {A, C, D and G}, {A, C, D and E}, {A, C, D and F}, {A, C, G and E}, {A, C, G and F}, {A, C, E and F}, {A, D, G and E}, {A, D, G and F}, {A, D, E and F}, {A, G, E and F}, {B, C, D and G}, {B, C, D and E}, {B, C, D and F}, {B, C, G and E}, {B, C, G and F}, {B, C, E and F}, {B, D, G and E}, {B, D, G and F}, {B, D, E and F}, {B, G, E and F}, {C, D, G and E}, {C, D, G and F}, {C, D, E and F}, {C, G, E and F}, {D, G, E and F}, {A, B, C, D and G}, {A, B, C, D and E}, {A, B, C, D and F}, {A, B, C, G and E}, {A, B, C, G and F}, {A, B, C, E and F}, {A, B, D, G and E}, {A, B, D, G and F}, {A, B, D, E and F}, {A, B, G, E and F}, {A, C, D, G and E}, {A, C, D, G and F}, {A, C, D, E and F}, {A, C, G, E and F}, {A, D, G, E and F}, {B, C, D, G and E}, {B, C, D, G and F}, {B, C, D, E and F}, {B, C, G, E and F}, {B, D, G, E and F}, {C, D, G, E and F}, {A, B, C, D, G and E}, {A, B, C, D, G and F}, {A, B, C, D, E and F}, {A, B, C, G, E and F}, {A, B, D, G, E and F}, {A, C, D, G, E and F}, {B, C, D, G, E and F}, or {A, B, C, D, G, E and F}.

The helicase may comprises a non-natural amino acid, such as Faz, at one, two, three, four, five, six or seven of the positions which correspond to D274, E284, E285, S288, S615, K717 and Y720 in Hel308 Mbu (SEQ ID NO: 10). Any combination of these positions may be substituted with a non-natural amino acid, such as Faz. For instance, for each row of Table 3a above, the helicase of the invention may comprise a non-natural amino acid, such as Faz, at any of the combinations of the positions labelled A to G above.

The helicase may comprise a combination of one or more cysteines and one or more non-natural amino acids, such as Faz, at two or more of the positions which correspond to D274, E284, E285, S288, S615, K717 and Y720 in Hel308 Mbu (SEQ ID NO: 10). Any combination of one or more cysteine residues and one or more non-natural amino acids, such as Faz, may be present at the relevant positions. For instance, for each row of Table 3a and 3b above, the helicase of the invention may comprise one or more cysteines and one or more non-natural amino acids, such as Faz, at any of the combinations of the positions labelled A to G above.

The Hel308 helicase more preferably comprises a variant of one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 which comprises one or more cysteine residues and/or one or more non-natural amino acids at one or more of the positions which correspond to D274, E284, E285, S288 and S615 in Hel308 Mbu (SEQ ID NO: 10). The relevant positions are shown in columns A to E in Table 3a above.

The helicase may comprise a cysteine residue at one, two, three, four or five, six or seven of the positions which correspond to D274, E284, E285, S288, S615, K717 and Y720 in Hel308 Mbu (SEQ ID NO: 10). Any combination of these positions may be substituted with cysteine. For instance, for each row of Table 3a above, the helicase of the invention may comprise a cysteine at any of the following combinations of the positions labelled A to E in that row: {A}, {B}, {C}, {D}, {E}, {A and B}, {A and C}, {A and D}, {A and E}, {B and C}, {B and D}, {B and E}, {C and D}, {C and E}, {D and E}, {A, B and C}, {A, B and D}, {A, B and E}, {A, C and D}, {A, C and E}, {A, D and E}, {B, C and D}, {B, C and E}, {B, D and E}, {C, D and E}, {A, B, C and D}, {A, B, C and E}, {A, B, D and E}, {A, C, D and E}, {B, C, D and E} or {A, B, C, D and E}.

The helicase may comprises a non-natural amino acid, such as Faz, at one, two, three, four or five of the positions which correspond to D274, E284, E285, S288, S615, K717 and Y720 in Hel308 Mbu (SEQ ID NO: 10). Any combination of these positions may be substituted with a non-natural amino acid, such as Faz. For instance, for each row of Table 3a above, the helicase of the invention may comprise a non-natural amino acid, such as Faz, at any of the combinations of the positions labelled A to E above.

The helicase may comprise a combination of one or more cysteines and one or more non-natural amino acids, such as Faz, at two or more of the positions which correspond to D274, E284, E285, S288 and S615 in Hel308 Mbu (SEQ ID NO: 10). Any combination of one or more cysteine residues and one or more non-natural amino acids, such as Faz, may be present at the relevant positions. For instance, for each row of Table 3a above, the helicase of the invention may comprise one or more cysteines and one or more non-natural amino acids, such as Faz, at any of the combinations of the positions labelled A to E above.

The Hel308 helicase preferably comprises a variant of the sequence of Hel308 Mbu (i.e. SEQ ID NO: 10) which comprises one or more cysteine residues and/or one or more non-natural amino acids at D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724. The variant preferably comprises D272C, N273C, D274C, G281C, E284C, E285C, E287C, S288C, T289C, G290C, E291C, D293C, T294C, N300C, R303C, K304C, N314C, S315C, N316C, H317C, R318C, K319C, L320C, E322C, R326C, N328C, S615C, K717C, Y720C, N721C or S724C. The variant preferably comprises D272Faz, N273Faz, D274Faz, G281Faz, E284Faz, E285Faz, E287Faz, S288Faz, T289Faz, G290Faz, E291Faz, D293Faz, T294Faz, N300Faz, R303Faz, K304Faz, N314Faz, S315Faz, N316Faz, H317 Faz, R318Faz, K319Faz, L320Faz, E322Faz, R326Faz, N328Faz, S615Faz, K717Faz, Y720Faz, N721Faz or S724Faz.

The Hel308 helicase preferably comprises a variant of the sequence of Hel308 Mbu (i.e. SEQ ID NO: 10) which comprises one or more cysteine residues and/or one or more non-natural amino acids at D274, E284, E285, S288, S615, K717 and Y720. The helicase of the invention may comprise one or more cysteines, one or more non-natural amino acids, such as Faz, or a combination thereof at any of the combinations of the positions labelled A to G above.

The Hel308 helicase preferably comprises a variant of the sequence of Hel308 Mbu (i.e. SEQ ID NO: 10) which comprises one or more cysteine residues and/or one or more non-natural amino acids at one or more of D274, E284, E285, S288 and S615. For instance, for Hel308 Mbu (SEQ ID NO: 10), the helicase of the invention may comprise a cysteine or a non-natural amino acid, such as Faz, at any of the following combinations of positions: {D274}, {E284}, {E285}, {S288}, {S615}, {D274 and E284}, {D274 and E285}, {D274 and S288}, {D274 and S615}, {E284 and E285}, {E284 and S288}, {E284 and S615}, {E285 and S288}, {E285 and S615}, {S288 and S615}, {D274, E284 and E285}, {D274, E284 and S288}, {D274, E284 and S615}, {D274, E285 and S288}, {D274, E285 and S615}, {D274, S288 and S615}, {E284, E285 and S288}, {E284, E285 and S615}, {E284, S288 and S615}, {E285, S288 and S615}, {D274, E284, E285 and S288}, {D274, E284, E285 and S615}, {D274, E284, S288 and S615}, {D274, E285, S288 and S615}, {E284, E285, S288 and S615} or {D274, E284, E285, S288 and S615}.

The helicase preferably comprises a variant of SEQ ID NO: 10 which comprises (a) E284C and S615C, (b), E284Faz and S615Faz, (c) E284C and S615Faz or (d) E284Faz and S615C.

The helicase more preferably comprises the sequence shown in SEQ ID NO: 10 with E284C and S615C.

Preferred non-natural amino acids for use in the invention include, but are not limited, to 4-Azido-L-phenylalanine (Faz), 4-Acetyl-L-phenylalanine, 3-Acetyl-L-phenylalanine, 4-Acetoacetyl-L-phenylalanine, O-Allyl-L-tyrosine, 3-(Phenylselanyl)-L-alanine, O-2-Propyn-1-yl-L-tyrosine, 4-(Dihydroxyboryl)-L-phenylalanine, 4-[(Ethylsulfanyl)carbonyl]-L-phenylalanine, (2S)-2-amino-3-{4-[(propan-2-ylsulfanyl)carbonyl]phenyl}propanoic acid, (2S)-2-amino-3-{4-[(2-amino-3-sulfanylpropanoyl)amino]phenyl}propanoic acid, O-Methyl-L-tyrosine, 4-Amino-L-phenylalanine, 4-Cyano-L-phenylalanine, 3-Cyano-L-phenylalanine, 4-Fluoro-L-phenylalanine, 4-Iodo-L-phenylalanine, 4-Bromo-L-phenylalanine, O-(Trifluoromethyl)tyrosine, 4-Nitro-L-phenylalanine, 3-Hydroxy-L-tyrosine, 3-Amino-L-tyrosine, 3-Iodo-L-tyrosine, 4-Isopropyl-L-phenylalanine, 3-(2-Naphthyl)-L-alanine, 4-Phenyl-L-phenylalanine, (2S)-2-amino-3-(naphthalen-2-ylamino)propanoic acid, 6-(Methylsulfanyl)norleucine, 6-Oxo-L-lysine, D-tyrosine, (2R)-2-Hydroxy-3-(4-hydroxyphenyl)propanoic acid, (2R)-2-Ammoniooctanoate3-(2,2'-Bipyridin-5-yl)-D-alanine, 2-amino-3-(8-hydroxy-3-quinolyl)propanoic acid, 4-Benzoyl-L-phenylalanine, S-(2-Nitrobenzyl)cysteine, (2R)-2-amino-3-[(2-nitrobenzyl)sulfanyl]propanoic acid, (2S)-2-amino-3-[(2-nitrobenzyl)oxy]propanoic acid, O-(4,5-Dimethoxy-2-nitrobenzyl)-L-serine, (2S)-2-amino-6-({[(2-nitrobenzyl)oxy]carbonyl}amino)hexanoic acid, O-(2-Nitrobenzyl)-L-tyrosine, 2-Nitrophenylalanine, 4-[(E)-Phenyldiazenyl]-L-phenylalanine, 4-[3-(Trifluoromethyl)-3H-diaziren-3-yl]-D-phenylalanine, 2-amino-3-[[5-(dimethylamino)-1-naphthyl]sulfonylamino]propanoic acid, (2S)-2-amino-4-(7-hydroxy-2-oxo-2H-chromen-4-yl)butanoic acid, (2S)-3-[(6-acetylnaphthalen-2-yl)amino]-2-aminopropanoic acid, 4-(Carboxymethyl)phenylalanine, 3-Nitro-L-tyrosine, O-Sulfo-L-tyrosine, (2R)-6-Acetamido-2-ammoniohexanoate, 1-Methylhistidine, 2-Aminononanoic acid, 2-Aminodecanoic acid, L-Homocysteine, 5-Sulfanylnorvaline, 6-Sulfanyl-L-norleucine, 5-(Methylsulfanyl)-L-norvaline, $N^6$-{[(2R,3R)-3-Methyl-3,4-dihydro-2H-pyrrol-2-yl]carbonyl}-L-lysine, $N^6$-[(Benzyloxy)carbonyl]lysine, (2S)-2-amino-6-[(cyclopentylcarbonyl)amino]hexanoic acid, $N^6$-[(Cyclopentyloxy)carbonyl]-L-lysine, (2S)-2-amino-6-{[(2R)-tetrahydrofuran-2-ylcarbonyl]amino}hexanoic acid, (2S)-2-amino-8-[(2R,3S)-3-ethynyltetrahydrofuran-2-yl]-8-oxooctanoic acid, $N^6$-(tert-Butoxycarbonyl)-L-lysine, (2S)-2-Hydroxy-6-({[(2-methyl-2-propanyl)oxy]carbonyl}amino)hexanoic acid, $N^6$-[(Allyloxy)carbonyl]lysine, (2S)-2-amino-6-({[(2-azidobenzyl)oxy]carbonyl}amino)hexanoic acid, $N^6$-L-Prolyl-L-lysine, (2S)-2-amino-6-{[(prop-2-yn-1-yloxy)carbonyl]amino}hexanoic acid and $N^6$-[(2-Azidoethoxy)carbonyl]-L-lysine.

The most preferred non-natural amino acid is 4-azido-L-phenylalanine (Faz).

As discussed above, variant of a Hel308 helicase is an enzyme that has an amino acid sequence which varies from that of the wild-type helicase and which retains polynucleotide binding activity. A variant of one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 may comprise additional modifications as long as it comprises one or more cysteine residues and/or one or more non-natural amino acids at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10). Suitable modifications and variants are discussed above with reference to the embodiments with two or more parts connected.

A variant may comprise the mutations in domain 5 disclosed in Woodman et al. (J. Mol. Biol. (2007)374, 1139-1144). These mutations correspond to R685A, R687A and R689A in SEQ ID NO: 10.

The two or more parts may be connected in any way. The connection can be transient, for example non-covalent. Even transient connection will reduce the size of the opening and reduce unbinding of the polynucleotide from the helicase through the opening.

The two or more parts are preferably connected by affinity molecules. Suitable affinity molecules are known in the art. The affinity molecules are preferably (a) complementary polynucleotides (International Application No. PCT/GB10/000132 (published as WO 2010/086602), (b) an antibody or a fragment thereof and the complementary epitope (Biochemistry 6th Ed, W.H. Freeman and co (2007) pp 953-954), (c) peptide zippers (O'Shea et al., Science 254 (5031): 539-544), (d) capable of interacting by β-sheet augmentation (Remaut and Waksman Trends Biochem. Sci. (2006) 31 436-444), (e) capable of hydrogen bonding, pi-stacking or forming a salt bridge, (f) rotaxanes (Xiang Ma and He Tian Chem. Soc. Rev., 2010, 39, 70-80), (g) an aptamer and the complementary protein (James, W. in Encyclopedia of Analytical Chemistry, R. A. Meyers (Ed.) pp. 4848-4871 John Wiley & Sons Ltd, Chichester, 2000) or (h) half-chelators (Hammerstein et al. J Biol Chem. 2011 Apr. 22; 286(16): 14324-14334). For (e), hydrogen bonding occurs between a proton bound to an electronegative atom and another electronegative atom. Pi-stacking requires two aromatic rings that can stack together where the planes of the rings are parallel. Salt bridges are between groups that can delocalize their electrons over several atoms, e. g. between aspartate and arginine.

The two or more parts may be transiently connected by a hexa-his tag or Ni-NTA. The two or more parts may also be modified such that they transiently connect to each other.

The two or more parts are preferably permanently connected. In the context of the invention, a connection is permanent if it is not broken while the helicase is used or cannot be broken without intervention on the part of the user, such as using reduction to open—S—S— bonds.

The two or more parts are preferably covalently-attached. The two or more parts may be covalently attached using any method known in the art.

Figure 1:
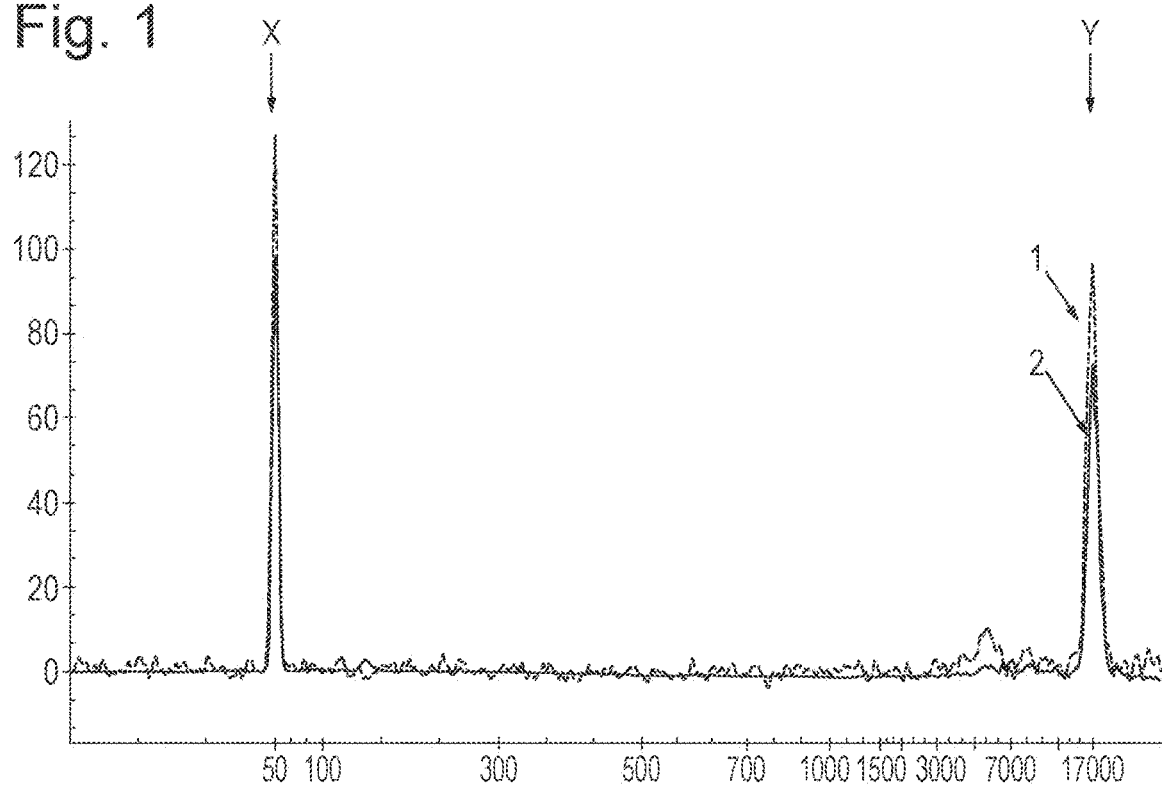
FIG. 1 shows an Agilent 2100 Bioanalyser trace. The lower marker is labelled X and the upper marker is labelled Y. No PhiX peak was observed between the upper and lower markers for transpososome 1 (labelled 1) or transpososome 2 (labelled 2) when incubated at room temp in the absence of an enzyme.

The two or more parts may be covalently attached via their naturally occurring amino acids, such as cysteines, threonines, serines, aspartates, asparagines, glutamates and glutamines. Naturally occurring amino acids may be modified to facilitate attachment. For instance, the naturally occurring amino acids may be modified by acylation, phosphorylation, glycosylation or farnesylation. Other suitable modifications are known in the art. Modifications to naturally occurring amino acids may be post-translation modifications. The two or more parts may be attached via amino acids that have been introduced into their sequences. Such amino acids are preferably introduced by substitution. The introduced amino acid may be cysteine or a non-natural amino acid that facilitates attachment. Suitable non-natural amino acids include, but are not limited to, 4-azido-L-phenylalanine (Faz), any one of the amino acids numbered 1-71 included in FIG. 1 of Liu C. C. and Schultz P. G., Annu. Rev. Biochem., 2010, 79, 413-444 or any one of the amino acids listed below. The introduced amino acids may be modified as discussed above.

In a preferred embodiment, the two or more parts are connected using linkers. Linker molecules are discussed in more detail below. One suitable method of connection is cysteine linkage. This is discussed in more detail below. The two or more parts are preferably connected using one or more, such as two or three, linkers. The one or more linkers may be designed to reduce the size of, or close, the opening as discussed above. If one or more linkers are being used to close the opening as discussed above, at least a part of the one or more linkers is preferably oriented such that it is not parallel to the polynucleotide when it is bound by the helicase. More preferably, all of the linkers are oriented in this manner. If one or more linkers are being used to close the opening as discussed above, at least a part of the one or more linkers preferably crosses the opening in an orientation that is not parallel to the polynucleotide when it bound by the helicase. More preferably, all of the linkers cross the opening in this manner. In these embodiments, at least a part of the one or more linkers may be perpendicular to the polynucleotide. Such orientations effectively close the opening such that the polynucleotide cannot unbind from the helicase through the opening.

Each linker may have two or more functional ends, such as two, three or four functional ends. Suitable configurations of ends in linkers are well known in the art.

One or more ends of the one or more linkers are preferably covalently attached to the helicase. If one end is covalently attached, the one or more linkers may transiently connect the two or more parts as discussed above. If both or all ends are covalently attached, the one or more linkers permanently connect the two or more parts.

At least one of the two or more parts is preferably modified to facilitate the attachment of the one or more linkers. Any modification may be made. The linkers may be attached to one or more reactive cysteine residues, reactive lysine residues or non-natural amino acids in the two or more parts. The non-natural amino acid may be any of those discussed above. The non-natural amino acid is preferably 4-azido-L-phenylalanine (Faz). At least one amino acid in the two or more parts is preferably substituted with cysteine or a non-natural amino acid, such as Faz.

The one or more linkers are preferably amino acid sequences and/or chemical crosslinkers.

Suitable amino acid linkers, such as peptide linkers, are known in the art. The length, flexibility and hydrophilicity of the amino acid or peptide linker are typically designed such that it reduces the size of the opening, but does not to disturb the functions of the helicase. Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$, $(SG)_8$, $(SG)_{10}$, $(SG)_{15}$ or $(SG)_{20}$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline. The amino acid sequence of a linker preferably comprises a polynucleotide binding moiety. Such moieties and the advantages associated with their use are discussed below.

Suitable chemical crosslinkers are well-known in the art. Suitable chemical crosslinkers include, but are not limited to, those including the following functional groups: maleimide, active esters, succinimide, azide, alkyne (such as dibenzocyclooctynol (DIBO or DBCO), difluoro cycloalkynes and linear alkynes), phosphine (such as those used in traceless and non-traceless Staudinger ligations), haloacetyl (such as iodoacetamide), phosgene type reagents, sulfonyl chloride reagents, isothiocyanates, acyl halides, hydrazines, disulphides, vinyl sulfones, aziridines and photoreactive reagents (such as aryl azides, diaziridines).

Reactions between amino acids and functional groups may be spontaneous, such as cysteine/maleimide, or may require external reagents, such as Cu(I) for linking azide and linear alkynes.

Linkers can comprise any molecule that stretches across the distance required. Linkers can vary in length from one carbon (phosgene-type linkers) to many Angstroms. Examples of linear molecules, include but are not limited to, are polyethyleneglycols (PEGs), polypeptides, polysaccharides, deoxyribonucleic acid (DNA), peptide nucleic acid (PNA), threose nucleic acid (TNA), glycerol nucleic acid (GNA), saturated and unsaturated hydrocarbons, polyamides. These linkers may be inert or reactive, in particular they may be chemically cleavable at a defined position, or may be themselves modified with a fluorophore or ligand. The linker is preferably resistant to dithiothreitol (DTT).

Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate, di-maleimide PEG 1k, di-maleimide PEG 3.4k, di-maleimide PEG 5k, di-maleimide PEG 10k, bis(maleimido)ethane (BMOE), bis-maleimidohexane (BMH), 1,4-bis-maleimidobutane (BMB), 1,4 bis-maleimidyl-2,3-dihydroxybutane (BMDB), BM[PEO]2 (1,8-bis-maleimidodiethyleneglycol), BM[PEO]3 (1,11-bis-maleimidotriethylene glycol), tris[2-maleimidoethyl]amine (TMEA), DTME dithiobismaleimidoethane, bis-maleimide PEG3, bis-maleimide PEG11, DBCO-maleimide, DBCO-PEG4-maleimide, DBCO-PEG4-NH2, DBCO-PEG4-NHS, DBCO-NHS, DBCO-PEG-DBCO 2.8 kDa, DBCO-PEG-DBCO 4.0 kDa, DBCO-15 atoms-DBCO, DBCO-26 atoms-DBCO, DBCO-35 atoms-DBCO, DBCO-PEG4-S-S-PEG3-biotin, DBCO-S-S-PEG3-biotin, DBCO-S-S-PEG11-biotin, (succinimidyl 3-(2-pyridyldithio)propionate (SPDP) and maleimide-PEG(2 kDa)-maleimide (ALPHA,OMEGA-BIS-MALEIMIDO POLY(ETHYLENE GLYCOL)). The most preferred crosslinker is maleimide-propyl-SRDFWRS-(1,2-diaminoethane)-propyl-maleimide as used in the Examples.

The one or more linkers may be cleavable. This is discussed in more detail below.

The two or more parts may be connected using two different linkers that are specific for each other. One of the linkers is attached to one part and the other is attached to another part. The linkers should react to form a modified helicase of the invention. The two or more parts may be connected using the hybridization linkers described in International Application No. PCT/GB10/000132 (published as WO 2010/086602). In particular, the two or more parts may be connected using two or more linkers each comprising a hybridizable region and a group capable of forming a covalent bond. The hybridizable regions in the linkers hybridize and link the two or more parts. The linked parts are then coupled via the formation of covalent bonds between the groups. Any of the specific linkers disclosed in International Application No. PCT/GB10/000132 (published as WO 2010/086602) may be used in accordance with the invention.

The two or more parts may be modified and then attached using a chemical crosslinker that is specific for the two modifications. Any of the crosslinkers discussed above may be used.

The linkers may be labeled. Suitable labels include, but are not limited to, fluorescent molecules (such as Cy3 or AlexaFluor®555), radioisotopes, e.g. $^{125}I$, $^{35}S$, enzymes, antibodies, antigens, polynucleotides and ligands such as biotin. Such labels allow the amount of linker to be quantified. The label could also be a cleavable purification tag, such as biotin, or a specific sequence to show up in an identification method, such as a peptide that is not present in the protein itself, but that is released by trypsin digestion.

A preferred method of connecting the two or more parts is via cysteine linkage. This can be mediated by a bi-functional chemical crosslinker or by an amino acid linker with a terminal presented cysteine residue. Linkage can occur via natural cysteines in the helicase. Alternatively, cysteines can be introduced into the two or more parts of the helicase. If the two or more parts are connected via cysteine linkage, the one or more cysteines have preferably been introduced to the two or more parts by substitution.

The length, reactivity, specificity, rigidity and solubility of any bi-functional linker may be designed to ensure that the size of the opening is reduced sufficiently and the function of the helicase is retained. Suitable linkers include bismaleimide crosslinkers, such as 1,4-bis(maleimido)butane (BMB) or bis(maleimido)hexane. One draw back of bi-functional linkers is the requirement of the helicase to contain no further surface accessible cysteine residues if attachment at specific sites is preferred, as binding of the bi-functional linker to surface accessible cysteine residues may be difficult to control and may affect substrate binding or activity. If the helicase does contain several accessible cysteine residues, modification of the helicase may be required to remove them while ensuring the modifications do not affect the folding or activity of the helicase. This is discussed in International Application No. PCT/GB10/000133 (published as WO 2010/086603). The reactivity of cysteine residues may be enhanced by modification of the adjacent residues, for example on a peptide linker. For instance, the basic groups of flanking arginine, histidine or lysine residues will change the pKa of the cysteines thiol group to that of the more reactive S⁻ group. The reactivity of cysteine residues may be protected by thiol protective groups such as 5,5'-dithiobis-(2-nitrobenzoic acid) (dTNB). These may be reacted with one or more cysteine residues of the helicase before a linker is attached. Selective deprotection of surface accessible cysteines may be possible using reducing reagents immobilized on beads (for example immobilized tris(2-carboxyethyl) phosphine, TCEP). Cysteine linkage of the two or more parts is discussed in more detail below.

Another preferred method of attaching the two or more parts is via 4-azido-L-phenylalanine (Faz) linkage. This can be mediated by a bi-functional chemical linker or by a polypeptide linker with a terminal presented Faz residue. The one or more Faz residues have preferably been introduced to the helicase by substitution. Faz linkage of two or more helicases is discussed in more detail below.

The helicase is preferably a RecD helicase. Any RecD helicase may be used in accordance with the invention. The structures of RecD helicases are known in the art (FEBS J. 2008 April; 275(8):1835-51. Epub 2008 Mar. 9. ATPase activity of RecD is essential for growth of the Antarctic *Pseudomonas syringae* Lz4W at low temperature. Satapathy A K, Pavankumar T L, Bhattacharjya S, Sankaranarayanan R, Ray MK; EMS Microbiol Rev. 2009 May; 33(3):657-87. The diversity of conjugative relaxases and its application in plasmid classification. Garcillan-Barcia M P, Francia M V, de la Cruz F; J Biol Chem. 2011 Apr. 8; 286(14):12670-82. Epub 2011 Feb. 2. Functional characterization of the multidomain F plasmid TraI relaxase-helicase. Cheng Y, McNamara D E, Miley M J, Nash R P, Redinbo M R).

The RecD helicase typically comprises the amino acid motif X1-X2-X3-G-X4-X5-X6-X7 (hereinafter called the RecD-like motif I; SEQ ID NO: 59), wherein X1 is G, S or A, X2 is any amino acid, X3 is P, A, S or G, X4 is T, A, V, S or C, X5 is G or A, X6 is K or R and X7 is T or S. X1 is preferably G. X2 is preferably G, I, Y or A. X2 is more preferably G. X3 is preferably P or A. X4 is preferably T, A, V or C. X4 is preferably T, V or C. X5 is preferably G. X6 is preferably K. X7 is preferably T or S. The RecD helicase preferably comprises Q-(X8)$_{16-18}$-X1-X2-X3-G-X4-X5-X6-X7 (hereinafter called the extended RecD-like motif I; SEQ ID NOs: 60, 61 and 62), wherein X1 to X7 are as defined above and X8 is any amino acid. There are preferably 16 X8 residues (i.e. (X8)$_{16}$) in the extended RecD-like motif I (SEQ ID NO: 60). Suitable sequences for (X8)$_{16}$ can be identified in SEQ ID NOs: 14, 17, 20, 23, 26, 29, 32, 35, 38, 41, 44, 47 and 50 of U.S. Patent Application No. 61/581,332 and SEQ ID NOs: 18, 21, 24, 25, 28, 30, 32, 35, 37, 39, 41, 42 and 44 of International Application No. PCT/GB2012/053274 (published as WO 2012/098562).

The RecD helicase preferably comprises the amino acid motif G-G-P-G-Xa-G-K-Xb (hereinafter called the RecD motif I; SEQ ID NO: 63) wherein Xa is T, V or C and Xb is T or S. Xa is preferably T. Xb is preferably T. The Rec-D helicase preferably comprises the sequence G-G-P-G-T-G-K-T (SEQ ID NO: 64). The RecD helicase more preferably comprises the amino acid motif Q-(X8)$_{16-18}$-G-G-P-G-Xa-G-K-Xb (hereinafter called the extended RecD motif I; SEQ ID NO: 65, 66 and 67), wherein Xa and Xb are as defined above and X8 is any amino acid. There are preferably 16 X8 residues (i.e. (X8)$_{16}$) in the extended RecD motif I (SEQ ID NO: 65). Suitable sequences for (X8)$_{16}$ can be identified in SEQ ID NOs: 14, 17, 20, 23, 26, 29, 32, 35, 38, 41, 44, 47 and 50 of U.S. Patent Application No. 61/581,332 and SEQ ID NOs: 18, 21, 24, 25, 28, 30, 32, 35, 37, 39, 41, 42 and 44 of International Application No. PCT/GB2012/053274 (published as WO 2012/098562).

The RecD helicase typically comprises the amino acid motif X1-X2-X3-X4-X5-(X6)$_3$-Q-X7 (hereinafter called the RecD-like motif V; SEQ ID NO: 68), wherein X1 is Y, W or F, X2 is A, T, S, M, C or V, X3 is any amino acid, X4 is T, N or S, X5 is A, T, G, S, V or I, X6 is any amino acid and X7 is G or S. X1 is preferably Y. X2 is preferably A, M, C or V. X2 is more preferably A. X3 is preferably I, M or L. X3 is more preferably I or L. X4 is preferably T or S. X4 is more preferably T. X5 is preferably A, V or I. X5 is more preferably V or I. X5 is most preferably V. (X6)$_3$ is preferably H-K-S, H-M-A, H-G-A or H-R-S. (X6)$_3$ is more preferably H-K-S. X7 is preferably G. The RecD helicase preferably comprises the amino acid motif Xa-Xb-Xc-Xd-Xe-H-K-S-Q-G (hereinafter called the RecD motif V; SEQ ID NO: 69), wherein Xa is Y, W or F, Xb is A, M, C or V, Xc is I, M or L, Xd is T or S and Xe is V or I. Xa is preferably Y. Xb is preferably A. Xd is preferably T. Xd is preferably V. Preferred RecD motifs I are shown in Table 5 of U.S. Patent Application No. 61/581,332. Preferred RecD-like motifs I are shown in Table 7 of U.S. Patent Application No. 61/581,332 and International Application No. PCT/GB2012/053274 (published as WO 2012/098562). Preferred RecD-like motifs V are shown in Tables 5 and 7 of U.S. Patent Application No. 61/581,332 and International Application No. PCT/GB2012/053274 (published as WO 2012/098562).

The RecD helicase is preferably one of the helicases shown in Table 4 or 5 of U.S. Patent Application No. 61/581,332 and International Application No. PCT/GB2012/053274 (published as WO 2012/098562) or a variant thereof. Variants are described in U.S. Patent Application No. 61/581,332 and International Application No. PCT/GB2012/053274 (published as WO 2012/098562).

The RecD helicase is preferably a TraI helicase or a TraI subgroup helicase. TraI helicases and TraI subgroup helicases may contain two RecD helicase domains, a relaxase domain and a C-terminal domain. The TraI subgroup helicase is preferably a TrwC helicase. The TraI helicase or TraI subgroup helicase is preferably one of the helicases shown in Table 6 of U.S. Patent Application No. 61/581,332 and International Application No. PCT/GB2012/053274 (published as WO 2012/098562) or a variant thereof. Variants are described in U.S. Patent Application No. 61/581,332 and International Application No. PCT/GB2012/053274 (published as WO 2012/098562).

The TraI helicase or a TraI subgroup helicase typically comprises a RecD-like motif I as defined above (SEQ ID NO: 59) and/or a RecD-like motif V as defined above (SEQ ID NO: 68). The TraI helicase or a TraI subgroup helicase preferably comprises both a RecD-like motif I (SEQ ID NO: 59) and a RecD-like motif V (SEQ ID NO: 68). The TraI helicase or a TraI subgroup helicase typically further comprises one of the following two motifs:

The amino acid motif H-(X1)$_2$-X2-R-(X3)$_{5-12}$-H-X4-H (hereinafter called the MobF motif III; SEQ ID NOs: 70 to 77), wherein X1 and X2 are any amino acid and X2 and X4 are independently selected from any amino acid except D, E, K and R. (X1)$_2$ is of course X1a-X1b. X1a and X1b can be the same of different amino acid. X1a is preferably D or E. X1b is preferably T or D. (X1)$_2$ is preferably DT or ED. (X1)$_2$ is most preferably DT. The 5 to 12 amino acids in (X3)$_{5-12}$ can be the same or different. X2 and X4 are independently selected from G, P, A, V, L, I, M, C, F, Y, W, H, Q, N, S and T. X2 and X4 are preferably not charged. X2 and X4 are preferably not H. X2 is more preferably N, S or A. X2 is most preferably N. X4 is most preferably F or T. (X3)$_{5-12}$ is preferably 6 or 10 residues in length. Suitable embodiments of (X3)$_{5-12}$ can be derived from SEQ ID NOs: 58, 62, 66 and 70 shown in Table 7 of U.S. Patent Application No. 61/581,332 and SEQ ID NOs: 61, 65, 69, 73, 74, 82, 86, 90, 94, 98, 102, 110, 112, 113, 114, 117, 121, 124, 125, 129, 133, 136, 140, 144, 147, 151, 152, 156, 160, 164 and 168 of International Application No. PCT/GB2012/053274 (published as WO 2012/098562).

The amino acid motif G-X1-X2-X3-X4-X5-X6-X7-H-(X8)$_{6-12}$-H-X9 (hereinafter called the MobQ motif III; SEQ ID NOs: 78 to 84), wherein X1, X2, X3, X5, X6, X7 and X9 are independently selected from any amino acid except D, E, K and R, X4 is D or E and X8 is any amino acid. X1, X2, X3, X5, X6, X7 and X9 are independently selected from G, P, A, V, L, I, M, C, F, Y, W, H, Q, N, S and T. X1, X2, X3, X5, X6, X7 and X9 are preferably not charged. X1, X2, X3, X5, X6, X7 and X9 are preferably not H. The 6 to 12 amino acids in (X8)$_{6-12}$ can be the same or different. Preferred MobF motifs III are shown in Table 7 of U.S. Patent Application No. 61/581,332 and International Application No. PCT/GB2012/053274 (published as WO 2012/098562).

The TraI helicase or TraI subgroup helicase is more preferably one of the helicases shown in Table 6 or 7 of U.S. Patent Application No. 61/581,332 and International Application No. PCT/GB2012/053274 (published as WO 2012/098562) or a variant thereof. The TraI helicase most preferably comprises the sequence shown in SEQ ID NO: 85 or a variant thereof. SEQ ID NO: 85 is TraI Eco (NCBI Reference Sequence: NP_061483.1; Genbank AAQ98619.1; SEQ ID NO: 85). TraI Eco comprises the following motifs: RecD-like motif I (GYAGVGKT; SEQ ID NO: 86), RecD-like motif V (YAITAHGAQG; SEQ ID NO: 87) and Mob F motif III (HDTSRDQEPQLHTH; SEQ ID NO: 88).

The TraI helicase or TraI subgroup helicase more preferably comprises the sequence of one of the helicases shown in Table 4 below, i.e. one of SEQ ID NOs: 85, 126, 134 and 138, or a variant thereof.

TABLE 4

| | | | | | RecD-like motif I (SEQ ID NO:) | RecD-like motif V (SEQ ID NO:) | Mob F motif III (SEQ ID NO:) |
|---|---|---|---|---|---|---|---|
| SEQ ID NO | Name | Strain | NCBI ref | % Identity to TraI Eco | | | |
| 85 | TraI Eco | *Escherichia coli* | NCBI Reference Sequence: NP_061483.1 Genbank AAQ98619.1 | — | GYAGVGKT (86) | YAITAHGAQG (87) | HDTSRDQEPQLHTH 88) |

More preferred TraI helicase and TraI subgroup helicases

TABLE 4-continued

More preferred TraI helicase and TraI subgroup helicases

| SEQ ID NO | Name | Strain | NCBI ref | % Identity to TraI Eco | RecD-like motif I (SEQ ID NO:) | RecD-like motif V (SEQ ID NO:) | Mob F motif III (SEQ ID NO:) |
|---|---|---|---|---|---|---|---|
| 126 | TrwC Cba | Citromicrobium bathyomarinum JL354 | NCBI Reference Sequence: ZP_06861556.1 | 15% | GIAGA GKS (131) | YALNV HMAQG (132) | HDTNR NQEPN LHFH (133) |
| 134 | TrwC Hne | Halothiobacillus neapolitanus c2 | NCBI Reference Sequence: YP_003262832.1 | 11.5% | GAAGA GKT (135) | YCITIH RSQG (136) | HEDAR TVDDI ADPQL HTH (137) |
| 138 | TrwC Eli | Erythrobacter litoralis HTCC259 | NCBI Reference Sequence: YP_457045.14 | 16% | GIAGA GKS (131) | YALNA HMAQG (139) | HDTNR NQEPN LHFH (133) |

As discussed above for Hel308 helicases, two or more parts on the RecD helicase, TraI helicase or TraI subgroup helicase may be connected to reduce the size of the opening in the polynucleotide domain through which a polynucleotide can unbind from the helicase and wherein the helicase retains its ability to control the movement of the polynucleotide. Any of the embodiments discussed above for Hel308 helicases equally apply to RecD helicases, TraI helicases or TraI subgroup helicases. The two or more parts of TrwC Cba that are connected are preferably (a) amino acids 691 and 346 in SEQ ID NO: 126; (b) amino acids 657 and 339 in SEQ ID NO: 126; (c) amino acids 691 and 350 in SEQ ID NO: 126; or (d) amino acids 690 and 350 in SEQ ID NO: 126. These amino acids are preferably substituted with cysteine such that they can be connected by cysteine linkage.

The invention may use a mutant TrwC Cba protein which comprises a variant of SEQ ID NO: 126 in which amino acids 691 and 346; 657 and 339; 691 and 350; or 690 and 350 are modified. The amino acids are preferably substituted. The amino acids are more preferably substituted with cysteine. The variant may differ from SEQ ID NO: 126 at positions other than 691 and 346; 657 and 339; 691 and 350; or 690 and 350 as long as the relevant amino acids are modified. The variant will preferably be at least 10% homologous to SEQ ID NO: 126 based on amino acid identity as discussed in more detail below. Amino acid 691 and 346; 657 and 339; 691 and 350; or 690 and 350 are not connected. These mutant TrwC Cba proteins may be used to form a modified helicase in which the modified amino acids are connected.

A variant of a RecD helicase, TraI helicase or TraI subgroup helicase is an enzyme that has an amino acid sequence which varies from that of the wild-type helicase and which retains polynucleotide binding activity. This can be measured as described above. In particular, a variant of SEQ ID NO: 85, 126, 134 or 138 is an enzyme that has an amino acid sequence which varies from that of SEQ ID NO: 85, 126, 134 or 138 and which retains polynucleotide binding activity. The variant retains helicase activity. The variant must work in at least one of the two modes discussed below. Preferably, the variant works in both modes. The variant may include modifications that facilitate handling of the polynucleotide encoding the helicase and/or facilitate its activity at high salt concentrations and/or room temperature. Variants typically differ from the wild-type helicase in regions outside of the motifs discussed above. However, variants may include modifications within these motif(s).

Over the entire length of the amino acid sequence of any one of SEQ ID NO: 85, 126, 134 and 138, a variant will preferably be at least 10% homologous to that sequence based on amino acid identity. More preferably, the variant polypeptide may be at least 20%, at least 25%, at least 30%, at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of any one of SEQ ID NOs: 85, 126, 134 and 138 over the entire sequence. There may be at least 70%, for example at least 80%, at least 85%, at least 90% or at least 95%, amino acid identity over a stretch of 150 or more, for example 200, 300, 400, 500, 600, 700, 800, 900 or 1000 or more, contiguous amino acids ("hard homology"). Homology is determined as described below. The variant may differ from the wild-type sequence in any of the ways discussed above with reference to SEQ ID NOs: 2 and 4.

A variant of any one of SEQ ID NOs: 85, 126, 134 and 138 preferably comprises the RecD-like motif I and/or RecD-like motif V of the wild-type sequence. However, a variant of SEQ ID NO: 85, 126, 134 or 138 may comprise the RecD-like motif I and/or extended RecD-like motif V from a different wild-type sequence. For instance, a variant may comprise any one of the preferred motifs shown in Tables 5 and 7 of U.S. Patent Application No. 61/581,332 and International Application No. PCT/GB2012/053274 (published as WO 2012/098562). Variants of SEQ ID NOs: 85, 126, 134 and 138 may also include modifications within the RecD-like motifs I and V of the wild-type sequence. A variant of SEQ ID NO: 85, 126, 134 or 138 preferably comprises one or more substituted cysteine residues and/or one or more substituted Faz residues to facilitate attachment as discussed above.

The helicase is preferably an XPD helicase. Any XPD helicase may be used in accordance with the invention. XPD helicases are also known as Rad3 helicases and the two terms can be used interchangeably.

The structures of XPD helicases are known in the art (Cell. 2008 May 30; 133(5):801-12. Structure of the DNA repair helicase XPD. Liu H, Rudolf J, Johnson K A, McMahon S A, Oke M, Carter L, McRobbie A M, Brown S E, Naismith J H, White M F). The XPD helicase typically comprises the amino acid motif X1-X2-X3-G-X4-X5-X6-E-G (hereinafter called XPD motif V; SEQ ID NO: 89). X1, X2, X5 and X6 are independently selected from any amino acid except D, E, K and R. X1, X2, X5 and X6 are independently selected from G, P, A, V, L, I, M, C, F, Y, W, H, Q, N, S and T. X1, X2, X5 and X6 are preferably not charged. X1, X2, X5 and X6 are preferably not H. X1 is more preferably V, L, I, S or Y. X5 is more preferably V, L, I, N or F. X6 is more preferably S or A. X3 and X4 may be any amino acid residue. X4 is preferably K, R or T.

The XPD helicase typically comprises the amino acid motif Q-Xa-Xb-G-R-Xc-Xd-R-(Xe)$_3$-Xf-(Xg)$_7$-D-Xh-R (hereinafter called XPD motif VI; SEQ ID NO: 90). Xa, Xe and Xg may be any amino acid residue. Xb, Xc and Xd are independently selected from any amino acid except D, E, K and R. Xb, Xc and Xd are typically independently selected from G, P, A, V, L, I, M, C, F, Y, W, H, Q, N, S and T. Xb, Xc and Xd are preferably not charged. Xb, Xc and Xd are preferably not H. Xb is more preferably V, A, L, I or M. Xc is more preferably V, A, L, I, M or C. Xd is more preferably I, H, L, F, M or V. Xf may be D or E. (Xg)$_7$ is $X_{g1}$, $X_{g2}$, $X_{g3}$, $X_{g4}$, $X_{g5}$, $X_{g6}$ and $X_{g7}$. $X_{g2}$ is preferably G, A, S or C. $X_{g5}$ is preferably F, V, L, I, M, A, W or Y. $X_{g6}$ is preferably L, F, Y, M, I or V. $X_{g7}$ is preferably A, C, V, L, I, M or S.

The XPD helicase preferably comprises XPD motifs V and VI. The most preferred XPD motifs V and VI are shown in Table 5 of U.S. Patent Application No. 61/581,340 and International Application No. PCT/GB2012/053273 (published as WO 2012/098561).

The XPD helicase preferably further comprises an iron sulphide (FeS) core between two Walker A and B motifs (motifs I and II). An FeS core typically comprises an iron atom coordinated between the sulphide groups of cysteine residues. The FeS core is typically tetrahedral.

The XPD helicase is preferably one of the helicases shown in Table 4 or 5 of International Application No. PCT/GB2012/053273 (published as WO 2012/098561) or a variant thereof. The XPD helicase most preferably comprises the sequence shown in SEQ ID NO: 91 or a variant thereof. SEQ ID NO: 91 is XPD Mbu (*Methanococcoides burtonii*; YP_566221.1; GI:91773529). XPD Mbu comprises YLWGTLSEG (Motif V; SEQ ID NO: 92) and QAMGRVVRSPTDYGARILLDGR (Motif VI; SEQ ID NO: 93).

A variant of a XPD helicase is an enzyme that has an amino acid sequence which varies from that of the wild-type helicase and which retains polynucleotide binding activity. This can be measured as described above. In particular, a variant of SEQ ID NO: 91 is an enzyme that has an amino acid sequence which varies from that of SEQ ID NO: 91 and which retains polynucleotide binding activity. The variant retains helicase activity. The variant must work in at least one of the two modes discussed below. Preferably, the variant works in both modes. The variant may include modifications that facilitate handling of the polynucleotide encoding the helicase and/or facilitate its activity at high salt concentrations and/or room temperature. Variants typically differ from the wild-type helicase in regions outside of XPD motifs V and VI discussed above. However, variants may include modifications within one or both of these motifs.

Over the entire length of the amino acid sequence of SEQ ID NO: 91, such as SEQ ID NO: 10, a variant will preferably be at least 10%, preferably 30% homologous to that sequence based on amino acid identity. More preferably, the variant polypeptide may be at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 91 over the entire sequence. There may be at least 70%, for example at least 80%, at least 85%, at least 90% or at least 95%, amino acid identity over a stretch of 150 or more, for example 200, 300, 400, 500, 600, 700, 800, 900 or 1000 or more, contiguous amino acids ("hard homology"). Homology is determined as described below. The variant may differ from the wild-type sequence in any of the ways discussed above with reference to SEQ ID NOs: 2 and 4.

A variant of SEQ ID NO: 91 preferably comprises the XPD motif V and/or the XPD motif VI of the wild-type sequence. A variant of SEQ ID NO: 91 more preferably comprises both XPD motifs V and VI of SEQ ID NO: 91. However, a variant of SEQ ID NO: 91 may comprise XPD motifs V and/or VI from a different wild-type sequence. For instance, a variant of SEQ ID NO: 91 may comprise any one of the preferred motifs shown in Table 5 of U.S. Patent Application No. 61/581,340 and International Application No. PCT/GB2012/053273 (published as WO 2012/098561). Variants of SEQ ID NO: 91 may also include modifications within XPD motif V and/or XPD motif VI of the wild-type sequence. Suitable modifications to these motifs are discussed above when defining the two motifs. As discussed above for Hel308 helicases, two or more parts on the XPD helicase may be connected to reduce the size of the opening in the polynucleotide domain through which a polynucleotide can unbind from the helicase and wherein the helicase retains its ability to control the movement of the polynucleotide. Any of the embodiments discussed above for Hel308 helicases equally apply to XPD helicases. A variant of SEQ ID NO: 91 preferably comprises one or more substituted cysteine residues and/or one or more substituted Faz residues to facilitate attachment as discussed above.

The helicase is preferably a UvrD helicase. Any UvrD helicase may be used in the invention. The UvrD helicase preferably comprises the sequence shown in SEQ ID NO: 122 or a variant thereof. Variants are defined above. Over the entire length of the amino acid sequence of any one of SEQ ID NO: 122, a variant will preferably be at least 20% homologous to that sequence based on amino acid similarity or identity. More preferably, the variant polypeptide may be at least 30%, at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of any one of SEQ ID Ns: 122 over the entire sequence. There may be at least 70%, for example at least 80%, at least 85%, at least 90% or at least 95%, amino acid identity over a stretch of 100 or more, for example 150, 200, 300, 400 or 500 or more, contiguous amino acids ("hard homology"). Homology or similarity is determined as described below.

The helicase is preferably a Dda helicase. Any Dda helicase may be used in the invention. Dda helicases typically comprises the following five domains: 1A (RecA-like motor) domain, 2A (RecA-like motor) domain, tower domain, pin domain and hook domain (Xiaoping He et al., 2012, Structure; 20: 1189-1200). The domains may be identified using protein modelling, x-ray diffraction measurement of the protein in a crystalline state (Rupp B (2009).

Biomolecular Crystallography: Principles, Practice and Application to Structural Biology. New York: Garland Science), nuclear magnetic resonance (NMR) spectroscopy of the protein in solution (Mark Rance; Cavanagh, John; Wayne J. Fairbrother; Arthur W. Hunt III; Skelton, NNicholas J. (2007). Protein NMR spectroscopy: principles and practice (2nd ed.). Boston: Academic Press.) or cryo-electron microscopy of the protein in a frozen-hydrated state (van Heel M, Gowen B, Matadeen R, Orlova E V, Finn R, Pape T, Cohen D, Stark H, Schmidt R, Schatz M, Patwardhan A (2000). "Single-particle electron cryo-microscopy: towards atomic resolution.". Q Rev Biophys. 33: 307-69). Structural information of proteins determined by above mentioned methods are publicly available from the protein bank (PDB) database.

Preferred Dda helicases are shown in Table 5 below.

will preferably be at least 20% homologous to that sequence based on amino acid similarity or identity. More preferably, the variant polypeptide may be at least 30%, at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of any one of SEQ ID NOs: 97 to 112 over the entire sequence. There may be at least 70%, for example at least 80%, at least 85%, at least 90% or at least 95%, amino acid identity over a stretch of 100 or more, for example 150, 200, 300, 400 or 500 or more, contiguous amino acids ("hard homology"). Homology or similarity is determined as described below.

Preferred variants of any one of SEQ ID NOs: 97 to 112 have a non-natural amino acid, such as Faz, at the amino-

| Dda Homologue (SEQ ID NO:) | | Habitat | Uniprot | Length | Sequence Identity to 1993/% | Number of D/E vs. K/R amino acids | # C |
|---|---|---|---|---|---|---|---|
| Rma-DSM (SEQ ID NO: 98) | *Rhodothermus marinus* | Mild halophile, moderate thermophile >65° C. | D0MKQ2 | 678 | 21 | −84/+85 | 2 |
| Csp (SEQ ID NO: 99) | *Cyanothece* sp. (strain ATCC 51142) | Marine bacterium | B1X365 | 496 | 24 | −76/+76 | 5 |
| Sru (SEQ ID NO: 100) | *Salinibacter ruber* | Extremely halophilic, 35-45° C. | Q2S429 | 421 | 26 | −78/+54 | 3 |
| Sgo (SEQ ID NO: 101) | *Sulfurimonas gotlandica* GD1 | Habitat: hydrothermal vents, coastal sediments | B6BJ43 | 500 | 27 | −72/+64 | 2 |
| Vph12B8 (SEQ ID NO: 102) | *Vibrio* phage henriette 12B8 | Host found in saltwater, stomach bug | M4MBC3 | 450 | 27 | −62/+47 | 6 |
| Vph (SEQ ID NO: 103) | *Vibrio* phage phi-pp2 | Host found in saltwater, stomach bug | I6XGX8 | 421 | 39 | −55/+45 | 5 |
| Aph65 (SEQ ID NO: 104) | *Aeromonas* phage 65 | Host found in fresh/brackish water, stomach bug | E5DRP6 | 434 | 40 | −57/+48 | 4 |
| AphCC2 (SEQ ID NO: 105) | *Aeromonas* phage CC2 | Host found in fresh/brackish water, stomach bug | I6XH64 | 420 | 41 | −53/+44 | 4 |
| Cph (SEQ ID NO: 106) | *Cronobacter* phage vB CsaM GAP161 | Host member of enterobacteriaceae | K4FBD0 | 443 | 42 | −59/+57 | 4 |
| Kph (SEQ ID NO: 107) | *Klebsiella* phage KP15 | Host member of enterobacteriaceae | D5JF67 | 442 | 44 | −59/+58 | 5 |
| SphlME13 (SEQ ID NO: 108) | *Stenotrophomonas* phage IME13 | Host found in soil | J7HXT5 | 438 | 51 | −58/+59 | 7 |
| AphAc42 (SEQ ID NO: 109) | *Acinetobacter* phage Ac42 | Host found in soil | E5EYE6 | 442 | 59 | −53/+49 | 9 |
| SphSP18 (SEQ ID NO: 110) | *Shigella* phage SP18 | Host member of enterobacteriaceae | E3SFA5 | 442 | 59 | −55/+55 | 9 |
| Yph (SEQ ID NO: 111) | *Yersinia* phage phiR1-RT | Host member of enterobacteriaceae | I7J3V8 | 439 | 64 | −52/+52 | 7 |
| SphS16 (SEQ ID NO: 112) | *Salmonella* phage S16 | Host member of enterobacteriaceae | M1EA88 | 441 | 72 | −56/+55 | 5 |
| 1993 (SEQ ID NO: 97) | *Enterobateria* phage T4 | Host member of enterobacteriaceae | P32270 | 439 | 100 | −57/+58 | 5 |

The Dda helicase more preferably comprises the sequence of one of the helicases shown in the Table 5 above, i.e. one of SEQ ID NOs: 97 to 112, or a variant thereof. Variants are defined above. Over the entire length of the amino acid sequence of any one of SEQ ID NOs: 97 to 112, a variant (N—) terminus and/or carboxy (C—) terminus. Preferred variants of any one of SEQ ID NOs: 8 to 23 have a cysteine residue at the amino-(N—) terminus and/or carboxy (C—) terminus. Preferred variants of any one of SEQ ID NOs: 8 to 23 have a cysteine residue at the amino-(N—) terminus and a non-natural amino acid, such as Faz, at the carboxy (C—) terminus or vice versa. Preferred variants of SEQ ID NO: 8 contain one or more of, such as all of, the following modifications E54G, D151E, I196N and G357A.

The Dda helicase preferably comprises any of the modifications disclosed in International Application Nos. PCT/GB2014/052736 and PCT/GB2015/052916 (published as WO/2015/055981 and WO 2016/055777).

A preferred variant of SEQ ID NO: 97 comprises (a) E94C and A360C or (b) E94C, A360C, C109A and C136A and then optionally (ΔM1)G1 (i.e. deletion of M1 and then addition G1). It may also be termed M1G. Any of the variants discussed above may further comprise M1G.

As discussed above for Hel308 helicases, two or more parts on the Dda helicase may be connected to reduce the size of the opening in the polynucleotide domain through which a polynucleotide can unbind from the helicase and wherein the helicase retains its ability to control the movement of the polynucleotide. Any of the embodiments discussed above for Hel308 helicases equally apply to Dda helicases.

The translocase is preferably a strippase. The strippase is preferably the INO80 chromatin remodeling complex or a FtsK/SpoIIIE transporter.

In one embodiment, the translocase is contacted with the constructs after they are created by the MuA transposase. In another embodiment, the translocase is bound to the substrates before the substrates are contacted with the template polynucleotide.

Hairpin Loops

After fragmentation of the template polynucleotide and ligation of the MuA substrate to the fragments of the template polynucleotide (tagmentation), constructs comprising a fragment of the template polynucleotide and one or more MuA substrates are formed. The two strands of each construct are preferably linked at one end by a hairpin loop. In this embodiment, a hairpin loop is added to each of the fragments of the template polynucleotide generated by the MuA transposase. Suitable hairpin loops can be designed using methods known in the art. The hairpin loop may be any length. The hairpin loop is typically 110 or fewer nucleotides, such as 100 or fewer nucleotides, 90 or fewer nucleotides, 80 or fewer nucleotides, 70 or fewer nucleotides, 60 or fewer nucleotides, 50 or fewer nucleotides, 40 or fewer nucleotides, 30 or fewer nucleotides, 20 or fewer nucleotides or 10 or fewer nucleotides, in length. The hairpin loop is preferably from about 1 to 110, from 2 to 100, from 5 to 80 or from 6 to 50 nucleotides in length. Longer lengths of the hairpin loop, such as from 50 to 110 nucleotides, are preferred if the loop is involved in the differential selectability of the adaptor. Similarly, shorter lengths of the hairpin loop, such as from 1 to 5 nucleotides, are preferred if the loop is not involved in the selectable binding as discussed below.

The hairpin loop preferably comprises a selectable binding moiety. This allows the constructs to be purified or isolated. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the invention. In preferred embodiments, the moiety binds to a surface to which no other moiety used in the invention binds.

Suitable selective binding moieties are known in the art. Preferred selective binding moieties include, but are not limited to, biotin, a polynucleotide sequence, antibodies, antibody fragments, such as Fab and ScSv, antigens, polynucleotide binding proteins, poly histidine tails and GST tags. The most preferred selective binding moieties are biotin and a selectable polynucleotide sequence. Biotin specifically binds to a surface coated with avidins. Selectable polynucleotide sequences specifically bind (i.e. hybridise) to a surface coated with homologus sequences. Alternatively, selectable polynucleotide sequences specifically bind to a surface coated with polynucleotide binding proteins.

The hairpin loop and/or the selectable binding moiety may comprise a region that can be cut, nicked, cleaved or hydrolysed. Such a region can be designed to allow the constructs to be removed from the surface to which it is bound following purification or isolation. Suitable regions are known in the art. Suitable regions include, but are not limited to, an RNA region, a region comprising desthiobiotin and streptavidin, a disulphide bond and a photocleavable region.

The hairpin loop may be provided at either end of the polynucleotide, i.e. the 5' or the 3' end. The hairpin loop may be ligated to the polynucleotide using any method known in the art. The hairpin loop may be ligated using a ligase, such as T4 DNA ligase, E. coli DNA ligase, Taq DNA ligase, Tma DNA ligase and 9°N DNA ligase. The hairpin loop may be added to the constructs as described in International Application No. PCT/GB2014/052505 (published as WO 2015/022544).

Molecular Brakes The method preferably further comprises attaching one or more molecular brakes to a non-substrate strand. A non-substrate strand is a strand of a MuA double stranded substrate that does not comprise an overhang. The molecular brakes may be attached to the non-substrate strands in the substrates before they are contacted with the template polynucleotide and the MuA transposase. The molecular brakes may be attached to the other strands from the substrates remaining in the constructs after they are created by the MuA transposase.

The molecular brakes are preferably bound to Y adaptors comprising a leader sequence and/or one or more anchors capable of coupling the adaptor to a membrane and the Y adaptors are attached to the other strands in step (c).

The Y adaptors are typically polynucleotide adaptors. They may be formed from any of the polynucleotides discussed above.

The Y adaptor typically comprises (a) a double stranded region and (b) a single stranded region or a region that is not complementary at the other end. The Y adaptor may be described as having an overhang if it comprises a single stranded region. The presence of a non-complementary region in the Y adaptor gives the adaptor its Y shape since the two strands typically do not hybridise to each other unlike the double stranded portion. The Y adaptor may comprise one or more anchors.

The Y adaptor and/or the hairpin loop may be ligated to the polynucleotide using any method known in the art. One or both of the adaptors may be ligated using a ligase, such as T4 DNA ligase, E. coli DNA ligase, Taq DNA ligase, Tma DNA ligase and 9°N DNA ligase. Alternatively, the adaptors may be added to the constructs as described in International Application No. PCT/GB2014/052505 (published as WO 2015/022544).

The Y adaptor may be provided with a leader sequence which preferentially threads into the pore. The leader sequence facilitates the method of the invention. The leader sequence is designed to preferentially thread into the transmembrane pore and thereby facilitate the movement of polynucleotide through the pore. The leader sequence can also be used to link the polynucleotide to the one or more anchors as discussed below.

The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises the one or more spacers.

The leader sequence can be any length, but is typically 10 to 150 nucleotides in length, such as from 20 to 150 nucleotides in length. The length of the leader typically depends on the transmembrane pore used in the method.

The Y adaptor preferably comprises a selectable binding moiety as discussed above. The Y adaptor and/or the selectable binding moiety may comprise a region that can be cut, nicked, cleaved or hydrolysed as discussed above.

The method comprises contacting the target polynucleotide with a molecular brake which controls the movement of the target polynucleotide through the pore. Any molecular brake may be used including any of those disclosed in International Application No. PCT/GB2014/052737 (published as WO 2015/110777).

The molecular brake is preferably a polynucleotide binding protein. The polynucleotide binding protein may be any protein that is capable of binding to the polynucleotide and controlling its movement through a transmembrane pore as discussed in more detail below. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably derived from a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases, translocases and topoisomerases, such as gyrases. Suitable enzymes include, but are not limited to, exonuclease I from E. coli (SEQ ID NO: 11), exonuclease III enzyme from E. coli (SEQ ID NO: 13), RecJ from T. thermophilus (SEQ ID NO: 15) and bacteriophage lambda exonuclease (SEQ ID NO: 17), TatD exonuclease and variants thereof. Three subunits comprising the sequence shown in SEQ ID NO: 15 or a variant thereof interact to form a trimer exonuclease. The polymerase may be PyroPhage® 3173 DNA Polymerase (which is commercially available from Lucigen® Corporation), SD Polymerase (commercially available from Bioron®) or variants thereof. The enzyme is preferably Phi29 DNA polymerase (SEQ ID NO: 9) or a variant thereof. The topoisomerase is preferably a member of any of the Moiety Classification (EC) groups 5.99.1.2 and 5.99.1.3.

The enzyme is most preferably derived from a helicase. The helicase may be or be derived from a Hel308 helicase, a RecD helicase, such as TraI helicase or a TrwC helicase, a XPD helicase or a Dda helicase. The helicase may be or be derived from Hel308 Mbu (SEQ ID NO: 18), Hel308 Csy (SEQ ID NO: 19), Hel308 Tga (SEQ ID NO: 20), Hel308 Mhu (SEQ ID NO: 21), TraI Eco (SEQ ID NO: 22), XPD Mbu (SEQ ID NO: 23) or a variant thereof.

The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925 (published as WO 2014/013260); PCT/GB2013/051924 (published as WO 2014/013259); PCT/GB2013/051928 (published as WO 2014/013262) and PCT/GB2014/052736 (published as WO/2015/055981).

The helicase preferably comprises the sequence shown in SEQ ID NO: 25 (Trwc Cba) or as variant thereof, the sequence shown in SEQ ID NO: 18 (Hel308 Mbu) or a variant thereof or the sequence shown in SEQ ID NO: 24 (Dda) or a variant thereof. Variants may differ from the native sequences in any of the ways discussed below for transmembrane pores. A preferred variant of SEQ ID NO: 24 comprises (a) E94C and A360C or (b) E94C, A360C, C109A and C136A and then optionally (ΔM1)G1 (i.e. deletion of M1 and then addition G1). It may also be termed M1G. Any of the variants discussed above may further comprise M1G.

The Dda helicase preferably comprises any of the modifications disclosed in International Application Nos. PCT/GB2014/052736 and PCT/GB2015/052916 (published as WO/2015/055981 and WO 2016/055777).

Any number of helicases may be used in accordance with the invention. For instance, 1, 2, 3, 4, 5, 6, 7, 8, 9, 10 or more helicases may be used. In some embodiments, different numbers of helicases may be used.

The method of the invention preferably comprises attaching two or more helicases to the other strands. The two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs for use in the invention are described in International Application Nos. PCT/GB2013/051925 (published as WO 2014/013260); PCT/GB2013/051924 (published as WO 2014/013259); PCT/GB2013/051928 (published as WO 2014/013262) and PCT/GB2014/052736.

A variant of SEQ ID NO: 9, 11, 13, 15, 17, 18, 19, 20, 21, 22, 23, 24 or 25 is an enzyme that has an amino acid sequence which varies from that of SEQ ID NO: 9, 11, 13, 15, 17, 18, 19, 20, 21, 22, 23, 24 or 25 and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature. Variants may be modified such that they bind polynucleotides (i.e. retain polynucleotide binding ability) but do not function as a helicase (i.e. do not move along polynucleotides when provided with all the necessary components to facilitate movement, e.g. ATP and $Mg^{2+}$). Such modifications are known in the art. For instance, modification of the $Mg^{2+}$ binding domain in helicases typically results in variants which do not function as helicases. These types of variants may act as molecular brakes (see below).

Over the entire length of the amino acid sequence of SEQ ID NO: 9, 11, 13, 15, 17, 18, 19, 20, 21, 22, 23, 24 or 25, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 9, 11, 13, 15, 17, 18, 19, 20, 21, 22, 23, 24 or 25 over the entire sequence. There may be at least 80%, for example at least 85%, 90% or 95%, amino acid identity over a stretch of 200 or more, for example 230, 250, 270, 280, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NO: 2 and 4 above. The enzyme may be covalently attached to the pore. Any method may be used to covalently attach the enzyme to the pore.

A preferred molecular brake is TrwC Cba-Q594A (SEQ ID NO: 25 with the mutation Q594A). This variant does not function as a helicase (i.e. binds polynucleotides but does not move along them when provided with all the necessary components to facilitate movement, e.g. ATP and $Mg^{2+}$).

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Any helicase may be used in the method. Helicases may work in two modes with respect to the pore. First, the method is preferably carried out using a helicase such that it moves the polynucleotide through the pore with the field resulting from the applied voltage. In this mode the 5' end of the polynucleotide is first captured in the pore, and the helicase moves the polynucleotide into the pore such that it is passed through the pore with the field until it finally translocates through to the trans side of the membrane. Alternatively, the method is preferably carried out such that a helicase moves the polynucleotide through the pore against the field resulting from the applied voltage. In this mode the 3' end of the polynucleotide is first captured in the pore, and the helicase moves the polynucleotide through the pore such that it is pulled out of the pore against the applied field until finally ejected back to the cis side of the membrane.

The method may also be carried out in the opposite direction. The 3' end of the polynucleotide may be first captured in the pore and the helicase may move the polynucleotide into the pore such that it is passed through the pore with the field until it finally translocates through to the trans side of the membrane.

When the helicase is not provided with the necessary components to facilitate movement or is modified to hinder or prevent its movement, it can bind to the polynucleotide and act as a brake slowing the movement of the polynucleotide when it is pulled into the pore by the applied field. In the inactive mode, it does not matter whether the polynucleotide is captured either 3' or 5' down, it is the applied field which pulls the polynucleotide into the pore towards the trans side with the enzyme acting as a brake. When in the inactive mode, the movement control of the polynucleotide by the helicase can be described in a number of ways including ratcheting, sliding and braking. Helicase variants which lack helicase activity can also be used in this way.

The molecular brake may function as the translocase that removes the MuA transposase. Preferably, the molecular brake is used in addition to a translocase. The molecular brake and translocase may be the same enzyme or different enzymes. Where the molecule brake and translcase are the same enzyme, one molecule of the enzyme may act as a molecular brake and another molecule of the enzyme may act as a translocase to remove the MuA transposase.

The polynucleotide may be contacted with the molecular brake and the pore in any order. It is preferred that, when the polynucleotide is contacted with the molecular brake, such as a helicase, and the pore, the polynucleotide firstly forms a complex with the protein. When the voltage is applied across the pore, the polynucleotide/protein complex then forms a complex with the pore and controls the movement of the polynucleotide through the pore.

Any steps in the method using a polynucleotide binding protein are typically carried out in the presence of free nucleotides or free nucleotide analogues and an enzyme cofactor that facilitates the action of the polynucleotide binding protein. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

The molecular brakes may be any compound or molecule which binds to the polynucleotide and slows the movement of the polynucleotide through the pore. The molecular brake may be any of those discussed above. The molecular brake preferably comprises a compound which binds to the polynucleotide. The compound is preferably a macrocycle. Suitable macrocycles include, but are not limited to, cyclodextrins, calixarenes, cyclic peptides, crown ethers, cucurbiturils, pillararenes, derivatives thereof or a combination thereof. The cyclodextrin or derivative thereof may be any of those disclosed in Eliseev, A. V., and Schneider, H-J. (1994) *J. Am. Chem. Soc.* 116, 6081-6088. The cyclodextrin is more preferably heptakis-6-amino-β-cyclodextrin ($am_7$-βCD), 6-monodeoxy-6-monoamino-β-cyclodextrin ($am_1$-βCD) or heptakis-(6-deoxy-6-guanidino)-cyclodextrin ($gu_7$-βCD).

Lack of Heating

The method of the invention preferably does not comprise heat inactivating the MuA transposase. Heat inactivation may also inactivate any other enzymes or proteins being used in the preparation or characterisation of the modified polynucleotides. Removing the heat inactivation step also dispenses with the need for additional equipment required for heating, such as a thermal cycler, hot block, or water bath, used for heating up the sample. The method of the invention can therefore be used in a variety of different settings including those without an electricity supply.

Products of the Invention

The invention also provides a population of double stranded MuA substrates for modifying a template polynucleotide, wherein each substrate comprises an overhang at one or both ends and a translocases bound to an overhang. Any of the embodiments discussed above equally apply to the population of the invention.

The invention also provides a plurality of polynucleotides modified using the method of the invention. The plurality of polynucleotides may be in any of the forms discussed above.

The population or plurality may be isolated, substantially isolated, purified or substantially purified. A population or plurality is isolated or purified if it is completely free of any other components, such as the template polynucleotide, lipids or pores. A population or plurality is substantially isolated if it is mixed with carriers or diluents which will not interfere with its intended use. For instance, a population or plurality is substantially isolated or substantially purified if it is present in a form that comprises less than 10%, less than 5%, less than 2% or less than 1% of other components, such as lipids or pores.

Characterisation Method of the Invention

The invention also comprises a method of characterising at least one polynucleotide modified using a method of the invention. The modified polynucleotide is contacted with a transmembrane pore such that at least one strand of the polynucleotide moves through the pore. One or more measurements which are indicative of one or more characteristics of the polynucleotide are taken as the at least one strand moves with respect to the pore.

The invention also provides a method of characterising a template polynucleotide. The template polynucleotide is modified using the method of the invention to produce a plurality of modified polynucleotides. Each modified polynucleotide is contacted with a transmembrane pore such that at least one strand of each polynucleotide moves through the pore. One or more measurements which are indicative of one or more characteristics of the polynucleotide are taken as the at least one strand of each polynucleotide moves with respect to the pore.

If the/each modified polynucleotide comprises a hairpin loop, the method preferably comprises contacting the/each modified polynucleotide with a transmembrane pore such that both strands of the polynucleotide move through the pore. If molecular brakes are present on the/each modified polynucleotides, the molecular brakes may control the movement of the/each modified polynucleotide through the pore and/or separate the two strands of the/each modified polynucleotide.

Membrane

The transmembrane pore is typically in a membrane. Any membrane may be used in accordance with the invention. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units are polymerised together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer.

It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviours from vesicles through to laminar membranes. Membranes formed from these triblock copolymers hold several advantages over biological lipid membranes. Because the triblock copolymer is synthesised, the exact construction can be carefully controlled to provide the correct chain lengths and properties required to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customise polymer based membranes for a wide range of applications.

The membrane is most preferably one of the membranes disclosed in International Application No. PCT/GB2013/052766 or PCT/GB2013/052767.

The amphiphilic molecules may be chemically-modified or functionalised to facilitate coupling of the polynucleotide.

The amphiphilic layer may be a monolayer or a bilayer. The amphiphilic layer is typically planar. The amphiphilic layer may be curved. The amphiphilic layer may be supported. The amphiphilic layer may be concave. The amphiphilic layer may be suspended from raised pillars such that the peripheral region of the amphiphilic layer is higher than the amphiphilic layer region in the centre. This may allow the microparticle to travel, move, slide or roll along the membrane as described above.

Amphiphilic membranes are typically naturally mobile, essentially acting as two dimensional fluids with lipid diffusion rates of approximately $10^{-8}$ cm s−1. This means that the pore and coupled polynucleotide can typically move within an amphiphilic membrane.

The membrane may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has evaporated, the solution/air interfaces on either side of the aperture are physically moved up and down past the aperture until a bilayer is formed. Planar lipid bilayers may be formed across an aperture in a membrane or across an opening into a recess.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

Tip-dipping bilayer formation entails touching the aperture surface (for example, a pipette tip) onto the surface of a test solution that is carrying a monolayer of lipid. Again, the lipid monolayer is first generated at the solution/air interface by allowing a drop of lipid dissolved in organic solvent to evaporate at the solution surface. The bilayer is then formed by the Langmuir-Schaefer process and requires mechanical automation to move the aperture relative to the solution surface.

For painted bilayers, a drop of lipid dissolved in organic solvent is applied directly to the aperture, which is submerged in an aqueous test solution. The lipid solution is spread thinly over the aperture using a paintbrush or an equivalent. Thinning of the solvent results in formation of a lipid bilayer. However, complete removal of the solvent from the bilayer is difficult and consequently the bilayer formed by this method is less stable and more prone to noise during electrochemical measurement.

Patch-clamping is commonly used in the study of biological cell membranes. The cell membrane is clamped to the end of a pipette by suction and a patch of the membrane becomes attached over the aperture. The method has been adapted for producing lipid bilayers by clamping liposomes which then burst to leave a lipid bilayer sealing over the aperture of the pipette. The method requires stable, giant and unilamellar liposomes and the fabrication of small apertures in materials having a glass surface.

Liposomes can be formed by sonication, extrusion or the Mozafari method (Colas et al. (2007) Micron 38:841-847).

In a preferred embodiment, the lipid bilayer is formed as described in International Application No. PCT/GB08/004127 (published as WO 2009/077734). Advantageously in this method, the lipid bilayer is formed from dried lipids. In a most preferred embodiment, the lipid bilayer is formed across an opening as described in WO2009/077734 (PCT/GB08/004127).

A lipid bilayer is formed from two opposing layers of lipids. The two layers of lipids are arranged such that their hydrophobic tail groups face towards each other to form a hydrophobic interior. The hydrophilic head groups of the lipids face outwards towards the aqueous environment on each side of the bilayer. The bilayer may be present in a number of lipid phases including, but not limited to, the liquid disordered phase (fluid lamellar), liquid ordered phase, solid ordered phase (lamellar gel phase, interdigitated gel phase) and planar bilayer crystals (lamellar sub-gel phase, lamellar crystalline phase).

Any lipid composition that forms a lipid bilayer may be used. The lipid composition is chosen such that a lipid bilayer having the required properties, such as surface charge, ability to support membrane proteins, packing density or mechanical properties, is formed. The lipid composition can comprise one or more different lipids. For instance, the lipid composition can contain up to 100 lipids. The lipid composition preferably contains 1 to 10 lipids. The lipid composition may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradeconic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester. The lipids may be mycolic acid.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine. The lipids may be chemically-modified or functionalised to facilitate coupling of the polynucleotide.

The amphiphilic layer, for example the lipid composition, typically comprises one or more additives that will affect the properties of the layer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lysophospholipids, such as 1-Acyl-2-Hydroxy-sn-Glycero-3-Phosphocholine; and ceramides.

In another preferred embodiment, the membrane is a solid state layer. Solid state layers can be formed from both organic and inorganic materials including, but not limited to, microelectronic materials, insulating materials such as $HfO_2$, $Si_3N_4$, $Al_2O_3$, and $SiO$, organic and inorganic polymers such as polyamide, plastics such as Teflon® or elastomers such as two-component addition-cure silicone rubber, and glasses. The solid state layer may be by atomic layer deposition (ALD). The ALD solid state layer may comprise alternating layers of $HfO_2$ and $Al_2O_3$. The solid state layer may be formed from monatomic layers, such as graphene, or layers that are only a few atoms thick. Suitable graphene layers are disclosed in International Application No. PCT/US2008/010637 (published as WO 2009/035647). Yusko et al., Nature Nanotechnology, 2011; 6: 253-260 and US Patent Application No. 2013/0048499 describe the delivery of proteins to transmembrane pores in solid state layers without the use of microparticles. The method of the invention may be used to improve the delivery in the methods disclosed in these documents.

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial triblock copolymer layer. The layer may comprise other transmembrane and/or intramembrane proteins as well as other molecules in addition to the pore. Suitable apparatus and conditions are discussed below. The method of the invention is typically carried out in vitro.

Transmembrane Pore

A transmembrane pore is a structure that crosses the membrane to some degree. Typically, a transmembrane pore comprises a first opening and a second opening with a lumen extending between the first opening and the second opening. The transmembrane pore permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

Any transmembrane pore may be used in the invention. The pore may be biological or artificial. Suitable pores include, but are not limited to, protein pores, polynucleotide pores and solid state pores. The pore may be a DNA origami pore (Langecker et al., Science, 2012; 338: 932-936).

The transmembrane pore is preferably a transmembrane protein pore. A transmembrane protein pore is a polypeptide or a collection of polypeptides that permits hydrated ions, such as polynucleotide, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits polynucleotides to flow from one side of the membrane, such as a triblock copolymer membrane, to the other. The transmembrane protein pore allows a polynucleotide, such as DNA or RNA, to be moved through the pore.

The transmembrane protein pore may be a monomer or an oligomer. The pore is preferably made up of several repeating subunits, such as at least 6, at least 7, at least 8, at least 9, at least 10, at least 11, at least 12, at least 13, at least 14, at least 15, or at least 16 subunits. The pore is preferably a hexameric, heptameric, octameric or nonameric pore. The pore may be a homo-oligomer or a hetero-oligomer.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with s, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, CsgG, outer membrane porin F (OmpF), outer membrane porin G (OmpG), outer membrane phospholipase A and *Neisseria* autotransporter lipoprotein (NalP) and other pores, such as lysenin. α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from lysenin. Suitable pores derived from CsgG are disclosed in International Application No. PCT/EP2015/069965. Suitable pores derived from lysenin are disclosed in International Application No. PCT/GB2013/050667 (published as WO 2013/153359). The transmembrane pore may be derived from or based on Msp, α-hemolysin (α-HL), lysenin, CsgG, ClyA, SpI and haemolytic protein fragaceatoxin C (FraC). The wild type α-hemolysin pore is formed of 7 identical monomers or sub-units (i.e., it is heptameric). The sequence of one monomer or sub-unit of α-hemolysin-NN is shown in SEQ ID NO: 4.

The transmembrane protein pore is preferably derived from Msp, more preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a triblock copolymer membrane such that it diffuses to the membrane and is inserted by binding to the membrane and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid similarity or identity. More preferably, the variant may be at least 55%, at least 60%, at least 65%, at least 70%, at least 75%, at least 80%, at least 85%, at least 90% and more preferably at least 95%, 97% or 99% homologous based on amino acid similarity or identity to the amino acid sequence of SEQ ID NO: 2 over the entire sequence. There may be at least 80%, for example at least 85%, 90% or 95%, amino acid similarity or identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (ncbi.nlm.nih.gov). Similarity can be measured using pairwise identity or by applying a scoring matrix such as BLOSUM62 and converting to an equivalent identity. Since they represent functional rather than evolved changes, deliberately mutated positions would be masked when determining homology. Similarity may be determined more sensitively by the application of position-specific scoring matrices using, for example, PSIBLAST on a comprehensive database of protein sequences. A different scoring matrix could be used that reflect amino acid chemico-physical properties rather than frequency of substitution over evolutionary time scales (e.g. charge).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-B1 and is called MS-(B2)8. The pore used in the invention is preferably MS-(B2)8. The variant of SEQ ID NO: 2 preferably comprises one or more of D56N, D56F, E59R, G75S, G77S, A96D and Q126R. A variant of SEQ ID NO: 2 has the mutations G75S/G77S/L88N/Q126R in addition to all the mutations of MS-B1 and is called MS-B2C. The pore used in the invention is preferably MS-(B2)8 or MS-(B2C)8. The variant of SEQ ID NO: 2 preferably comprises N93D. The variant more preferably comprises the mutations G75S/G77S/L88N/N93D/Q126R.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid.

The transmembrane protein pore is preferably derived from CsgG, more preferably from CsgG from *E. coli* Str. K-12 substr. MC4100. Such a pore will be oligomeric and typically comprises 7, 8, 9 or 10 monomers derived from CsgG. The pore may be a homo-oligomeric pore derived from CsgG comprising identical monomers. Alternatively, the pore may be a hetero-oligomeric pore derived from CsgG comprising at least one monomer that differs from the others.

A monomer derived from CsgG typically comprises the sequence shown in SEQ ID NO: 114 or a variant thereof. A variant of SEQ ID NO: 114 is a polypeptide that has an amino acid sequence which varies from that of SEQ ID NO: 114 and which retains its ability to form a pore. The ability of a variant to form a pore can be assayed using any method known in the art as discussed above.

Over the entire length of the amino acid sequence of any one of SEQ ID NO: 114, a variant will preferably be at least 50% homologous to that sequence based on amino acid similarity or identity. More preferably, the variant may be at least 55%, at least 60%, at least 65%, at least 70%, at least 75%, at least 80%, at least 85%, at least 90% and more preferably at least 95%, 97% or 99% homologous based on amino acid similarity or identity to the amino acid sequence of SEQ ID NO: 114 over the entire sequence. There may be at least 80%, for example at least 85%, 90% or 95%, amino acid similarity or identity over a stretch of 100 or more, for example 125, 150, 175 or 200 or more, contiguous amino acids ("hard homology"). Homology can be measured as discussed above.

The variant of SEQ ID NO: 114 may comprise any of the mutations disclosed in International Application No. PCT/GB2015/069965 (published as WO 2016/034591). The variant of SEQ ID NO: 114 preferably comprises one or more of the following (i) one or more mutations at the following positions (i.e. mutations at one or more of the following positions) N40, D43, E44, S54, S57, Q62, R97, E101, E124, E131, R142, T150 and R192, such as one or more mutations at the following positions (i.e. mutations at one or more of the following positions) N40, D43, E44, S54, S57, Q62, E101, E131 and T150 or N40, D43, E44, E101 and E131; (ii) mutations at Y51/N55, Y51/F56, N55/F56 or Y51/N55/F56; (iii) Q42R or Q42K; (iv) K49R; (v) N102R, N102F, N102Y or N102W; (vi) D149N, D149Q or D149R; (vii) E185N, E185Q or E185R; (viii) D195N, D195Q or D195R; (ix) E201N, E201Q or E201R; (x) E203N, E203Q or E203R; and (xi) deletion of one or more of the following positions F48, K49, P50, Y51, P52, A53, S54, N55, F56 and S57. The variant may comprise any combination of (i) to (xi). If the variant comprises any one of (i) and (iii) to (xi), it may further comprise a mutation at one or more of Y51, N55 and F56, such as at Y51, N55, F56, Y51/N55, Y51/F56, N55/F56 or Y51/N55/F56.

Preferred variants of SEQ ID NO: 114 which form pores in which fewer nucleotides contribute to the current as the polynucleotide moves through the pore comprise Y51A/F56A, Y51A/F56N, Y51I/F56A, Y51L/F56A, Y51T/F56A, Y51I/F56N, Y51L/F56N or Y51T/F56N or more preferably Y51I/F56A, Y51L/F56A or Y51T/F56A.

Preferred variants of SEQ ID NO: 114 which form pores displaying an increased range comprise mutations at the following positions:
 Y51, F56, D149, E185, E201 and E203;
 N55 and F56;
 Y51 and F56;
 Y51, N55 and F56; or
 F56 and N102.

Preferred variants of SEQ ID NO: 114 which form pores displaying an increased range comprise:
 Y51N, F56A, D149N, E185R, E201N and E203N;
 N55S and F56Q;
 Y51A and F56A;
 Y51A and F56N;
 Y51I and F56A;
 Y51L and F56A;
 Y51T and F56A;
 Y51I and F56N;
 Y51L and F56N;
 Y51T and F56N;
 Y51T and F56Q;
 Y51A, N55S and F56A;
 Y51A, N55S and F56N;
 Y51T, N55S and F56Q; or
 F56Q and N102R.

Preferred variants of SEQ ID NO: 114 which form pores in which fewer nucleotides contribute to the current as the polynucleotide moves through the pore comprise mutations at the following positions:
 N55 and F56, such as N55X and F56Q, wherein X is any amino acid; or
 Y51 and F56, such as Y51X and F56Q, wherein X is any amino acid.

Preferred variants of SEQ ID NO: 114 which form pores displaying an increased throughput comprise mutations at the following positions:
 D149, E185 and E203;
 D149, E185, E201 and E203; or
 D149, E185, D195, E201 and E203.

Preferred variants which form pores displaying an increased throughput comprise:
 D149N, E185N and E203N;
 D149N, E185N, E201N and E203N;
 D149N, E185R, D195N, E201N and E203N; or
 D149N, E185R, D195N, E201R and E203N.

Preferred variants of SEQ ID NO: 7 which form pores in which capture of the polynucleotide is increased comprise the following mutations:
 D43N/Y51T/F56Q;
 E44N/Y51T/F56Q;
 D43N/E44N/Y51T/F56Q;
 Y51T/F56Q/Q62R;
 D43N/Y51T/F56Q/Q62R;
 E44N/Y51T/F56Q/Q62R; or
 D43N/E44N/Y51T/F56Q/Q62R.

Preferred variants of SEQ ID NO: 114 comprise the following mutations:
 D149R/E185R/E201R/E203R or Y51T/F56Q/D149R/E185R/E201R/E203R;
 D149N/E185N/E201N/E203N or Y51T/F56Q/D149N/E185N/E201N/E203N;
 E201R/E203R or Y51T/F56Q/E201R/E203R
 E201N/E203R or Y51T/F56Q/E201N/E203R;

E203R or Y51T/F56Q/E203R;
E203N or Y51T/F56Q/E203N;
E201R or Y51T/F56Q/E201R;
E201N or Y51T/F56Q/E201N;
E185R or Y51T/F56Q/E185R;
E185N or Y51T/F56Q/E185N;
D149R or Y51T/F56Q/D149R;
D149N or Y51T/F56Q/D149N;
R142E or Y51T/F56Q/R142E;
R142N or Y51T/F56Q/R142N;
R192E or Y51T/F56Q/R192E; or
R192N or Y51T/F56Q/R192N.

Preferred variants of SEQ ID NO: 114 comprise the following mutations:
Y51A/F56Q/E101N/N102R;
Y51A/F56Q/R97N/N102G;
Y51A/F56Q/R97N/N102R;
Y51A/F56Q/R97N;
Y51A/F56Q/R97G;
Y51A/F56Q/R97L;
Y51A/F56Q/N102R;
Y51A/F56Q/N102F;
Y51A/F56Q/N102G;
Y51A/F56Q/E101R;
Y51A/F56Q/E101F;
Y51A/F56Q/E101N; or
Y51A/F56Q/E101G The variant of SEQ ID NO: 114 may comprise any of the substitutions present in another CsgG homologue. Preferred CsgG homologues are shown in SEQ ID NOs: 3 to 7 and 26 to 41 of International Application No. PCT/GB2015/069965 (published as WO 2016/034591).

Any of the proteins described herein, such as the transmembrane protein pores, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the pore or construct. An example of this would be to react a gel-shift reagent to a cysteine engineered on the outside of the pore. This has been demonstrated as a method for separating hemolysin hetero-oligomers (Chem Biol. 1997 July; 4(7):497-505).

The pore may be labelled with a revealing label. The revealing label may be any suitable label which allows the pore to be detected. Suitable labels include, but are not limited to, fluorescent molecules, radioisotopes, e.g. $^{125}$I, $^{35}$S, enzymes, antibodies, antigens, polynucleotides and ligands such as biotin.

Any of the proteins described herein, such as the transmembrane protein pores, may be made synthetically or by recombinant means. For example, the pore may be synthesised by in vitro translation and transcription (IVTT). The amino acid sequence of the pore may be modified to include non-naturally occurring amino acids or to increase the stability of the protein. When a protein is produced by synthetic means, such amino acids may be introduced during production. The pore may also be altered following either synthetic or recombinant production.

Any of the proteins described herein, such as the transmembrane protein pores, can be produced using standard methods known in the art. Polynucleotide sequences encoding a pore or construct may be derived and replicated using standard methods in the art. Polynucleotide sequences encoding a pore or construct may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Coupling

The/each modified polynucleotide preferably comprises one or more anchors which are capable of coupling to the membrane. The method preferably further comprises coupling the target polynucleotide to the membrane using the one or more anchors.

The anchor comprises a group which couples (or binds) to the polynucleotide and a group which couples (or binds) to the membrane. Each anchor may covalently couple (or bind) to the polynucleotide and/or the membrane. The group may be a chemical group and/or a functional group.

The polynucleotide may be coupled to the membrane using any number of anchors, such as 2, 3, 4 or more anchors. For instance, the polynucleotide may be coupled to the membrane using two anchors each of which separately couples (or binds) to both the polynucleotide and membrane.

The one or more anchors may comprise one or more molecular brakes or polynucleotide binding proteins. Each anchor may comprise one or more molecular brakes or polynucleotide binding proteins. The molecular brake(s) or polynucleotide binding protein(s) may be any of those discussed below.

If the membrane is an amphiphilic layer, such as a triblock copolymer membrane, the one or more anchors preferably comprise a polypeptide anchor present in the membrane and/or a hydrophobic anchor present in the membrane. The hydrophobic anchor is preferably a lipid, fatty acid, sterol, carbon nanotube, polypeptide, protein or amino acid, for example cholesterol, palmitate or tocopherol. In preferred embodiments, the one or more anchors are not the pore.

The components of the membrane, such as the amphiphilic molecules, copolymer or lipids, may be chemically-modified or functionalised to form the one or more anchors. Examples of suitable chemical modifications and suitable ways of functionalising the components of the membrane are discussed in more detail below. Any proportion of the membrane components may be functionalised, for example at least 0.01%, at least 0.1%, at least 1%, at least 10%, at least 25%, at least 50% or 100%.

The polynucleotide may be coupled directly to the membrane. The one or more anchors used to couple the polynucleotide to the membrane preferably comprise a linker. The one or more anchors may comprise one or more, such as 2, 3, 4 or more, linkers. One linker may be used to couple more than one, such as 2, 3, 4 or more, polynucleotides to the membrane.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The polynucleotide may hybridise to a complementary sequence on the circular polynucleotide linker.

The one or more anchors or one or more linkers may comprise a component that can be cut or broken down, such as a restriction site or a photolabile group.

Functionalised linkers and the ways in which they can couple molecules are known in the art. For instance, linkers functionalised with maleimide groups will react with and attach to cysteine residues in proteins. In the context of this invention, the protein may be present in the membrane, may be the polynucleotide itself or may be used to couple (or bind) to the polynucleotide. This is discussed in more detail below.

Crosslinkage of polynucleotides can be avoided using a "lock and key" arrangement. Only one end of each linker may react together to form a longer linker and the other ends of the linker each react with the polynucleotide or membrane respectively. Such linkers are described in International Application No. PCT/GB10/000132 (published as WO 2010/086602).

The use of a linker is preferred in the sequencing embodiments discussed below. If a polynucleotide is permanently coupled directly to the membrane in the sense that it does not uncouple when interacting with the pore, then some sequence data will be lost as the sequencing run cannot continue to the end of the polynucleotide due to the distance between the membrane and the pore. If a linker is used, then the polynucleotide can be processed to completion.

The coupling may be permanent or stable. In other words, the coupling may be such that the polynucleotide remains coupled to the membrane when interacting with the pore.

The coupling may be transient. In other words, the coupling may be such that the polynucleotide may decouple from the membrane when interacting with the pore. For certain applications, such as aptamer detection and polynucleotide sequencing, the transient nature of the coupling is preferred. If a permanent or stable linker is attached directly to either the 5' or 3' end of a polynucleotide and the linker is shorter than the distance between the membrane and the transmembrane pore's channel, then some sequence data will be lost as the sequencing run cannot continue to the end of the polynucleotide. If the coupling is transient, then when the coupled end randomly becomes free of the membrane, then the polynucleotide can be processed to completion. Chemical groups that form permanent/stable or transient links are discussed in more detail below. The polynucleotide may be transiently coupled to an amphiphilic layer or triblock copolymer membrane using cholesterol or a fatty acyl chain. Any fatty acyl chain having a length of from 6 to 30 carbon atom, such as hexadecanoic acid, may be used.

In preferred embodiments, a polynucleotide, such as a nucleic acid, is coupled to an amphiphilic layer such as a triblock copolymer membrane or lipid bilayer. Coupling of nucleic acids to synthetic lipid bilayers has been carried out previously with various different tethering strategies. These are summarised in Table 3 below.

TABLE 3

| Anchor comprising | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucletides to lipid membrane assemblies." *J Am Chem Soc* 126(33): 10224-5 |
| Surfactant (e.g. Lipid, Palmitate, etc) | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Synthetic polynucleotides and/or linkers may be functionalised using a modified phosphoramidite in the synthesis reaction, which is easily compatible for the direct addition of suitable anchoring groups, such as cholesterol, tocopherol, palmitate, thiol, lipid and biotin groups. These different attachment chemistries give a suite of options for attachment to polynucleotides. Each different modification group couples the polynucleotide in a slightly different way and coupling is not always permanent so giving different dwell times for the polynucleotide to the membrane. The advantages of transient coupling are discussed above.

Coupling of polynucleotides to a linker or to a functionalised membrane can also be achieved by a number of other means provided that a complementary reactive group or an anchoring group can be added to the polynucleotide. The addition of reactive groups to either end of a polynucleotide has been reported previously. A thiol group can be added to the 5' of ssDNA or dsDNA using T4 polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). An azide group can be added to the 5'-phosphate of ssDNA or dsDNA using T4 polynucleotide kinase and γ-[2-Azidoethyl]-ATP or γ-[6-Azidohexyl]-ATP. Using thiol or Click chemistry a tether, containing either a thiol, iodoacetamide OPSS or maleimide group (reactive to thiols) or a DIBO (dibenzocyclooctyne) or alkyne group (reactive to azides), can be covalently attached to the polynucleotide. A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82). Streptavidin/biotin and/or streptavidin/desthiobiotin coupling may be used for any other polynucleotide. A polynucleotide can be coupled to a membrane using streptavidin/biotin and streptavidin/desthiobiotin. It may also be possible that anchors may be directly added to polynucleotides using terminal transferase with suitably modified nucleotides (e.g. cholesterol or palmitate).

The one or more anchors preferably couple the polynucleotide to the membrane via hybridisation. The hybridisation may be present in any part of the one or more anchors, such as between the one or more anchors and the polynucleotide, within the one or more anchors or between the one or more anchors and the membrane. Hybridisation in the one or more anchors allows coupling in a transient manner as discussed above. For instance, a linker may comprise two or more polynucleotides, such as 3, 4 or 5 polynucleotides, hybridised together. The one or more anchors may hybridise to the polynucleotide. The one or more anchors may hybridise directly to the polynucleotide, directly to a Y adaptor and/or leader sequence attached to the polynucleotide or directly to a hairpin loop adaptor attached to the polynucleotide (as discussed in more detail below). Alternatively, the one or more anchors may be hybridised to one or more, such as 2 or 3, intermediate polynucleotides (or "splints") which are hybridised to the polynucleotide, to a Y adaptor and/or leader sequence attached to the polynucleotide or to a hairpin loop adaptor attached to the polynucleotide (as discussed in more detail below).

The one or more anchors may comprise a single stranded or double stranded polynucleotide. One part of the anchor may be ligated to a single stranded or double stranded polynucleotide analyte. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci USA 89(20): 9823-5). Alternatively, either a single stranded or double stranded polynucleotide can be ligated to a double stranded polynucleotide and then the two strands separated by thermal or chemical denaturation. To a double stranded polynucleotide, it is possible to add either a piece of single stranded polynucleotide to one or both of the ends of the duplex, or a double stranded polynucleotide to one or both ends. For addition of single stranded polynucleotides to the double stranded polynucleotide, this can be achieved using T4 RNA ligase I as for ligation to other regions of single stranded polynucleotides. For addition of double stranded polynucleotides to a double stranded polynucleotide then ligation can be "blunt-ended", with complementary 3' dA/dT tails on the polynucleotide and added polynucleotide respectively (as is routinely done for many sample prep applications to prevent concatemer or dimer formation) or using "sticky-ends" generated by restriction digestion of the polynucleotide and ligation of compatible adapters. Then, when the duplex is melted, each single strand will have either a 5' or 3' modification if a single stranded polynucleotide was used for ligation or a modification at the 5' end, the 3' end or both if a double stranded polynucleotide was used for ligation.

If the polynucleotide is a synthetic strand, the one or more anchors can be incorporated during the chemical synthesis of the polynucleotide. For instance, the polynucleotide can be synthesised using a primer having a reactive group attached to it.

Adenylated polynucleotides are intermediates in ligation reactions, where an adenosine-monophosphate is attached to the 5'-phosphate of the polynucleotide. Various kits are available for generation of this intermediate, such as the 5' DNA Adenylation Kit from NEB. By substituting ATP in the reaction for a modified nucleotide triphosphate, then addition of reactive groups (such as thiols, amines, biotin, azides, etc) to the 5' of a polynucleotide can be possible. It may also be possible that anchors could be directly added to polynucleotides using a 5' DNA adenylation kit with suitably modified nucleotides (e.g. cholesterol or palmitate).

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. Single or multiple nucleotides can be added to 3' end of single or double stranded DNA by employing a polymerase. Examples of polymerases which could be used include, but are not limited to, Terminal Transferase, Klenow and *E. coli* Poly(A) polymerase). By substituting ATP in the reaction for a modified nucleotide triphosphate then anchors, such as cholesterol, thiol, amine, azide, biotin or lipid, can be incorporated into double stranded polynucleotides. Therefore, each copy of the amplified polynucleotide will contain an anchor.

Ideally, the polynucleotide is coupled to the membrane without having to functionalise the polynucleotide. This can be achieved by coupling the one or more anchors, such as a polynucleotide binding protein or a chemical group, to the membrane and allowing the one or more anchors to interact with the polynucleotide or by functionalizing the membrane. The one or more anchors may be coupled to the membrane by any of the methods described herein. In particular, the one or more anchors may comprise one or more linkers, such as maleimide functionalised linkers.

In this embodiment, the polynucleotide is typically RNA, DNA, PNA, TNA or LNA and may be double or single stranded. This embodiment is particularly suited to genomic DNA polynucleotides.

The one or more anchors can comprise any group that couples to, binds to or interacts with single or double stranded polynucleotides, specific nucleotide sequences within the polynucleotide or patterns of modified nucleotides within the polynucleotide, or any other ligand that is present on the polynucleotide.

Suitable binding proteins for use in anchors include, but are not limited to, *E. coli* single stranded binding protein, P5 single stranded binding protein, T4 gp32 single stranded binding protein, the TOPO V dsDNA binding region, human histone proteins, *E. coli* HU DNA binding protein and other archaeal, prokaryotic or eukaryotic single stranded or double stranded polynucleotide (or nucleic acid) binding proteins, including those listed below.

The specific nucleotide sequences could be sequences recognised by transcription factors, ribosomes, endonucleases, topoisomerases or replication initiation factors. The patterns of modified nucleotides could be patterns of methylation or damage.

The one or more anchors can comprise any group which couples to, binds to, intercalates with or interacts with a polynucleotide. The group may intercalate or interact with the polynucleotide via electrostatic, hydrogen bonding or Van der Waals interactions. Such groups include a lysine monomer, poly-lysine (which will interact with ssDNA or dsDNA), ethidium bromide (which will intercalate with dsDNA), universal bases or universal nucleotides (which can hybridise with any polynucleotide) and osmium complexes (which can react to methylated bases). A polynucleotide may therefore be coupled to the membrane using one or more universal nucleotides attached to the membrane. Each universal nucleotide may be coupled to the membrane using one or more linkers. The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 2-O'-methyl-inosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2, 6-diaminopurine monophosphate).

The one or more anchors may couple to (or bind to) the polynucleotide via Hoogsteen hydrogen bonds (where two nucleobases are held together by hydrogen bonds) or reversed Hoogsteen hydrogen bonds (where one nucleobase is rotated through 180° with respect to the other nucleobase). For instance, the one or more anchors may comprise one or more nucleotides, one or more oligonucleotides or one or more polynucleotides which form Hoogsteen hydrogen bonds or reversed Hoogsteen hydrogen bonds with the polynucleotide. These types of hydrogen bonds allow a third polynucleotide strand to wind around a double stranded helix and form a triplex. The one or more anchors may couple to (or bind to) a double stranded polynucleotide by forming a triplex with the double stranded duplex.

In this embodiment at least 1%, at least 10%, at least 25%, at least 50% or 100% of the membrane components may be functionalised.

Where the one or more anchors comprise a protein, they may be able to anchor directly into the membrane without further functonalisation, for example if it already has an external hydrophobic region which is compatible with the membrane. Examples of such proteins include, but are not limited to, transmembrane proteins, intramembrane proteins and membrane proteins. Alternatively the protein may be expressed with a genetically fused hydrophobic region which is compatible with the membrane. Such hydrophobic protein regions are known in the art.

The one or more anchors are preferably mixed with the polynucleotide before delivery to the membrane, but the one or more anchors may be contacted with the membrane and subsequently contacted with the polynucleotide.

In another aspect the polynucleotide may be functionalised, using methods described above, so that it can be recognised by a specific binding group. Specifically the polynucleotide may be functionalised with a ligand such as biotin (for binding to streptavidin), amylose (for binding to maltose binding protein or a fusion protein), Ni-NTA (for binding to poly-histidine or poly-histidine tagged proteins) or peptides (such as an antigen).

According to a preferred embodiment, the one or more anchors may be used to couple a polynucleotide to the membrane when the polynucleotide is attached to a leader sequence which preferentially threads into the pore. Leader sequences are discussed in more detail below. Preferably, the polynucleotide is attached (such as ligated) to a leader sequence which preferentially threads into the pore. Such a leader sequence may comprise a homopolymeric polynucleotide or an abasic region. The leader sequence is typically designed to hybridise to the one or more anchors either directly or via one or more intermediate polynucleotides (or splints). In such instances, the one or more anchors typically comprise a polynucleotide sequence which is complementary to a sequence in the leader sequence or a sequence in the one or more intermediate polynucleotides (or splints). In such instances, the one or more splints typically comprise a polynucleotide sequence which is complementary to a sequence in the leader sequence.

Any of the methods discussed above for coupling polynucleotides to membranes, such as amphiphilic layers, can of course be applied to other polynucleotide and membrane combinations. In some embodiments, an amino acid, peptide, polypeptide or protein is coupled to an amphiphilic layer, such as a triblock copolymer layer or lipid bilayer. Various methodologies for the chemical attachment of such polynucleotides are available. An example of a molecule used in chemical attachment is EDC (1-ethyl-3-[3-dimethylaminopropyl]carbodiimide hydrochloride). Reactive groups can also be added to the 5' of polynucleotides using commercially available kits (Thermo Pierce, Part No. 22980). Suitable methods include, but are not limited to, transient affinity attachment using histidine residues and Ni-NTA, as well as more robust covalent attachment by reactive cysteines, lysines or non natural amino acids.

Polynucleotide Characterisation

Any number of polynucleotides can be investigated. For instance, the method of the invention may concern characterising two or more polynucleotides, such as 3 or more, 4 or more, 5 or more, 6 or more, 7 or more, 8 or more, 9 or more, 10 or more, 20 or more, 30 or more, 50 or more, 100 or more, 500 or more, 1,000 or more, 5,000 or more, 10,000 or more, 100,000 or more, 1000,000 or more or 5000,000 or more, polynucleotides. The two or more polynucleotides may be delivered using the same microparticle or different microparticles.

A microparticle is a microscopic particle whose size is typically measured in micrometres (μm). Microparticles may also known as microspheres or microbeads. The microparticle may be a nanoparticle. A nanoparticle is a microscopic particle whose size is typically measured in nanometres (nm).

A microparticle typically has a particle size of from about 0.001 μm to about 500 μm. For instance, a nanoparticle may have a particle size of from about 0.01 μm to about 200 μm or about 0.1 μm to about 100 μm. More often, a microparticle has a particle size of from about 0.5 μm to about 100 μm, or for instance from about 1 μm to about 50 μm. The microparticle may have a particle size of from about 1 nm to about 1000 nm, such as from about 10 nm to about 500 nm, about 20 nm to about 200 nm or from about 30 nm to about 100 nm.

If two or more polynucleotides are characterised, they may be different from one another. The two or more polynucleotides may be two or more instances of the same polynucleotide. This allows proof reading.

The polynucleotides can be naturally occurring or artificial. For instance, the method may be used to verify the sequence of two or more manufactured oligonucleotides. The methods are typically carried out in vitro.

The method may involve measuring two, three, four or five or more characteristics of each polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the invention, such as {i}, {ii}, {iii}, {iv}, {v}, {i, ii}, {i,iii}, {i, iv}, {i,v}, {ii, iii}, {ii, iv}, {ii, v}, {iii, iv}, {iii, v}, {iv, v}, {i, ii, iii}, {i, ii, iv}, {i, ii, v}, {i, iii, iv}, {i, iii, v}, {i, iv, v}, {ii, iii, iv}, {ii, iii, v}, {ii, iv, v}, {iii, iv, v}, {i, ii, iii, iv}, {i, ii, iii, v}, {i, ii, iv, v}, {i, iii, iv, v}, {ii, iii, iv, v} or {i, ii, iii, iv, v}.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcyotsine may be distinguished from cytosine on the basis of the current flowing through the pore during its interaction with each nucleotide.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

A variety of different types of measurements may be made. This includes without limitation: electrical measurements and optical measurements. A suitable optical method involving the measurement of fluorescence is disclosed by J. Am. Chem. Soc. 2009, 131 1652-1653. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Application WO 2009/077734 and International Application WO 2011/067559.

The method is preferably carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129(27):8650-5. In some instances, the current passing through the pore as a polynucleotide moves with respect to the pore is used to estimate or determine the sequence of the polynucleotide. This is strand sequencing.

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

In a preferred embodiment, the method comprises:
(a) contacting the/each modified polynucleotide with a transmembrane pore such that at least one strand of the/each polynucleotide moves through the pore; and
(b) measuring the current passing through the pore as at least one strand of the/each polynucleotide moves with respect to the pore wherein the current is indicative of one or more characteristics of the at least one strand of the/each polynucleotide and thereby characterising the modified/template polynucleotide.

The methods of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Kits

The present invention also provides a kit for modifying a template polynucleotide. The kit comprises (a) a population of MuA substrates as defined above, (b) a MuA transposase and (c) a translocase. Any of the embodiments discussed above with reference to the methods and products of the invention equally apply to the kits.

The kit may further comprise the components of a membrane, such as the components of an amphiphilic layer or a lipid bilayer. The kit may further comprise the components of a transmembrane pore. The kit may further comprise a molecular brake. Suitable membranes, pores and molecular brakes are discussed above.

The kit may further comprise a Y adaptor comprising a leader sequence and/or one or more anchors capable of coupling the adaptor to a membrane. Suitable Y adaptors, leader sequences and anchors are discussed above.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

The following Example illustrates the invention.

Example 1

MuA binds to the transposon as a tetramer and is extremely stable; remaining tightly bound after strand transfer of the transposon. If the MuA is not removed from the DNA, this can inhibit characterisation using a nanopore system. MuA can be removed by heating to 75° C. However, this relies on the use of a thermal cycler or water bath and could damage other components in the solution. Here we describe an alternative technique for removing MuA without needing to heat the reaction, using a helicase. Hel308Mbu-E284C/S615C-STrEP(C) (SEQ ID NO: 10 with mutations E284C/S615C with a streptavidin tag attached at its C terminus) is a processive helicase which binds to single stranded DNA and moves in a 3' to 5' direction. When the transposon has a 3' overhang on the bottom strand, Hel308Mbu-E284C/S615C-STrEP(C) (SEQ ID NO: 10 with mutations E284C/S615C with a streptavidin tag attached at its C terminus) can bind and, upon moving along the DNA, force the MuA complex to dissociate from the DNA.

Materials and Method

Enzyme Preparation:

Hel308Mbu-E284C/S615C-STrEP(C) (20 uM, SEQ ID NO: 10 with mutations E284C/S615C with a streptavidin tag attached at its C terminus) was reduced using 10 mM DTT in a 2 ml protein low bind Eppendorf and rotated on a Hula shaker (ThermoFisher Scientific) for 1 h, at 10 rpm with no vibration. The enzyme was then buffer exchanged, into 100 mM sodium phosphate, 500 mM NaCl, 5 mM EDTA and 0.1% Tween-20 pH8.0, using Zeba spin desalting columns 7K MWCO, 0.5 ml (ThermoFisher Scientific) according to the manufacturers protocol. The sample was diluted to 10 uM and 50 uM 1,11-bis(maleimido)triethylene glycol was added. The sample was then rotated on a Hula shaker for further 2 hours. This resulted in a closed complex helicase which was able to load onto DNA at the 3' end.

Adapter Annealing

The sequence for the transposon top strand was (SEQ ID NO: 115). This was annealed with either SEQ ID NO: 116 to form transposon 1 or annealed with SEQ ID NO: 117 to form transposon 2 which has a 3' overhang on the bottom strand.

The transposon top strand was also annealed with the transposon leader (30 iSpC3 spacers attached at the 3' end to the 5' of SEQ ID NO: 118, which is attached at its 3' end to the 5' end of four iSp18 spacers which are attached at the 3' end to the 5' end of SEQ ID NO: 119).

Transposons (10 uM) were annealed in 50 mM NaCl, 10 mM Tris.HCl pH8.0. The transposon sequences were heated to 95 C for 2 minutes and then slow cooled (6 seconds for every 0.1° C. decrease) to 4° C.

Transpososome Formation

Transposon 1, transposon 2 and leader transposon were each mixed to 2 uM in 40 ul, with concentrated MuA transposase (20 ul, 1.1 mg/ml, ThermoFisher Scientific) in 25 mM Tris.HCl pH8, 110 mM NaCl, 0.5 mM EDTA, 10% glycerol and 0.05% Triton-X100. These were then incubated at 30° C. for 90 minutes to form transpososome 1, transpososome 2 and leader transpososome respectively, at 2 uM.

Transposition

Transpososome 1 and transpososome 2 were each mixed to 50 nM with 1.5 ug of PhiX174 RFI DNA (New England Biolabs) in 25 mM Tris.HCl pH8, 110 mM NaCl and 10 mM $MgCl_2$ in a 30 ul reaction in a 0.2 ml PCR tube. Each reaction was incubated at room temperature for 2 minutes before being split in half to form 3 tubes of 10 uls for each. 1 tube of each transpososome was incubated at 75° C. for 5 minutes, 1 tube of each transpososome was left at room temperature for 5 minutes with nothing added. Hel308Mbu-E284C/S615C-STrEP(C) (1 uM) was added to the final tubes along with 10 mM of ATP (Sigma-Aldrich) and incubated at room temperature for 5 minutes. 1 ul of each reaction was then analysed on the Agilent 2100 Bioanalyser 12,000 bp setting, along with 1 ul of unmodified PhiX.

Electrophysiology

A 60 ul sample was made with 1.5 ug of lambda DNA (New England Biolabs) and 120 nM of leader transpososome in 25 mM Tris.HCl pH8, 110 mM NaCl and 10 mM $MgCl_2$ and the sample mixed by inversion. The sample was incubated at room temperature for 10 minutes. The sample was then split into 3 sets of 20 ul reactions. nH2O (4 ul, ThermoFisher Scientific) was added to sample 1 and the sample was heated at 75° C. for 10 minutes. Hel308Mbu-E284C/S615C-STrEP(C) (2 ul, 10 uM) and ATP (2 ul, 100 mM, Sigma-Aldrich) were added to sample 2 and it was incubated at room temperature for 10 minutes. nH20 (4 ul, ThermoFisher Scientific) was added to sample 3 and the sample was incubated at room temperature for 10 minutes. Agencourt AMPure XP SPRI beads (24 ul) were added to each sample (1-3) and the samples were incubated at room temperature for 5 minutes. The samples were then transferred to a magnetic rack and incubated for 2 minutes at room temperature. The supernatant was then removed and discarded from each sample. Buffer was added to each sample (50 ul, 750 mM NaCl, 10% PEG8000 and 50 mM Tris.HCl pH8). The wash buffer was then removed and discarded from each sample. Buffer 1 (6 ul, 10 mM Tris.HCl, 20 mM NaCl) was then to each sample and each samples was then mixed in order to resuspend the beads. Each sample was then spun down and returned to the magnetic rack. 6 ul of each sample was then removed and 1.5 ul of buffer 2 (1 uM of SEQ ID NO: 20 (which has 6 iSp18 spacers attached at its 3' end), 750 mM KCl, 5 mM EDTA, 125 mM Kpi pH8) was added to each sample. The samples were then incubated at room temperature for 10 minutes. T4 Dda-(E94C/C109A/C136A/A360C) (SEQ ID NO: 97 with mutations E94C/C109A/C136A/A360C and then (ΔM1) G1G2 (where (ΔM1)G1G2=deletion of M1 and then addition G1 and G2), 1.25 ul, 5 uM), 25 mM Potassium phosphate, 150 mM KCl, 5% glycerol, 1 mM EDTA, pH7) was then added to each sample and then each sample was incubated at room temperature for 5 minutes. Buffer (1.25 ul, 800 uM TMAD) was then added to each sample and then each was incubated at room temperature for 5 minutes. Finally, 6 ul of fuel mix (75 mM ATP, 75 mM $MgCl_2$) and 284 ul of buffer (25 mM Potassium phosphate, 500 mM potassium chloride, pH8) was added to each sample.

Electrical measurements were acquired from single MspA nanopores inserted in block copolymer in buffer (25 mM K Phosphate buffer, 150 mM Potassium Ferrocyanide (II), 150 mM Potassium Ferricyanide (III), pH 8.0). After achieving a single pore inserted in the block copolymer, then buffer (2 mL, 25 mM K Phosphate buffer, 150 mM Potassium Ferrocyanide (II), 150 mM Potassium Ferricyanide (III), pH 8.0) was flowed through the system to remove any excess MspA nanopores. 150 uL of 500 mM KCl, 25 mM K Phosphate, pH8.0 was then flowed through the system. After 10 minutes a further 150 uL of the sample described above was then flowed into the single nanopore experimental system. The experiment was run at −140 mV and helicase-controlled DNA movement was monitored.

Results

Agilent Analysis

When the MuA transpososome is not removed from transpososome 1 (FIG. 1 line labelled 1) or tranpososome 2 (FIG. 1, line labelled 2) e.g. the control where both transposomes are incubated at room temperature (sample 3), no peak was seen on the trace between the upper marker (labelled Y) and the lower marker (labelled X). This was because the MuA was still bound to the DNA, which prevented both transposomes (1 and 2) from moving into the gel matrix of the Agilent 2100 Bioanalyser system.

Figure 2:
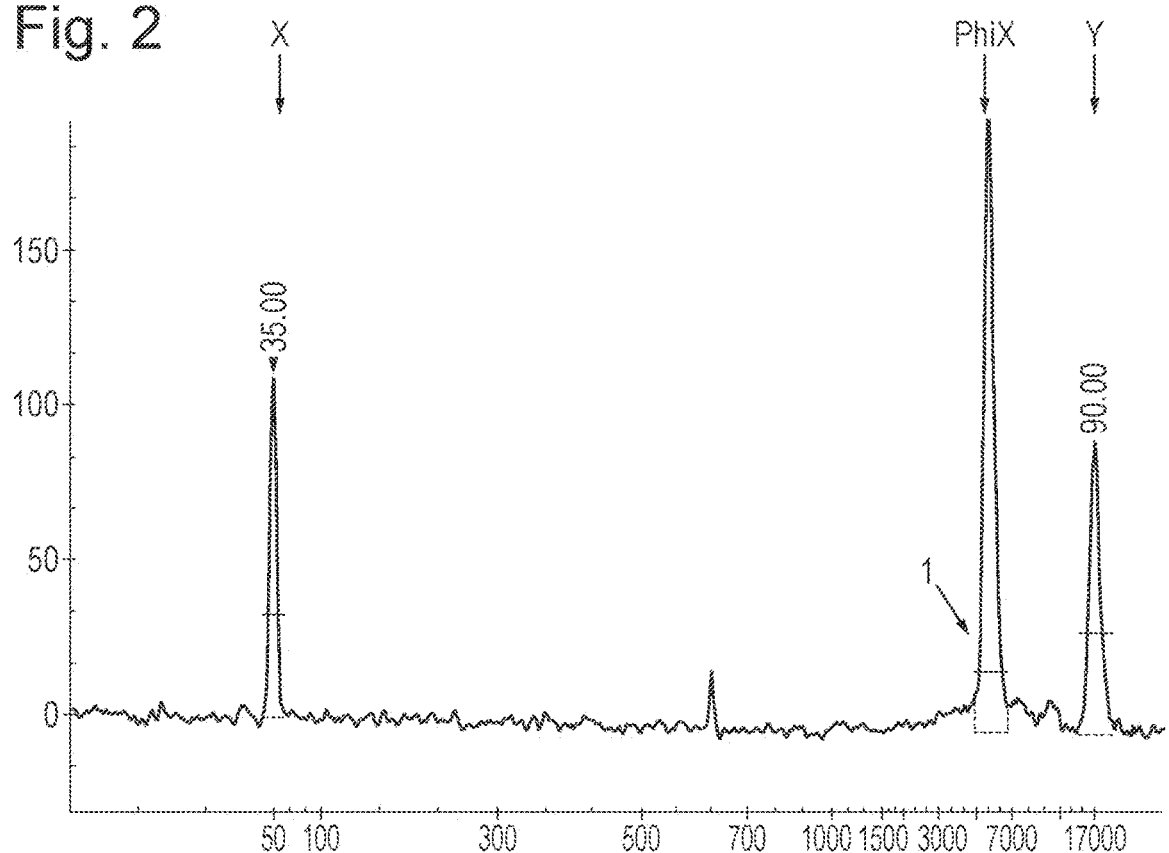
FIG. 2 shows an Agilent 2100 Bioanalyser trace. The lower marker is labelled X and the upper marker is labelled Y. A PhiX peak was observed between the upper and lower markers for transpososome 1 (labelled 1) when incubated at 75° C. for 10 minutes.
Figure 3:
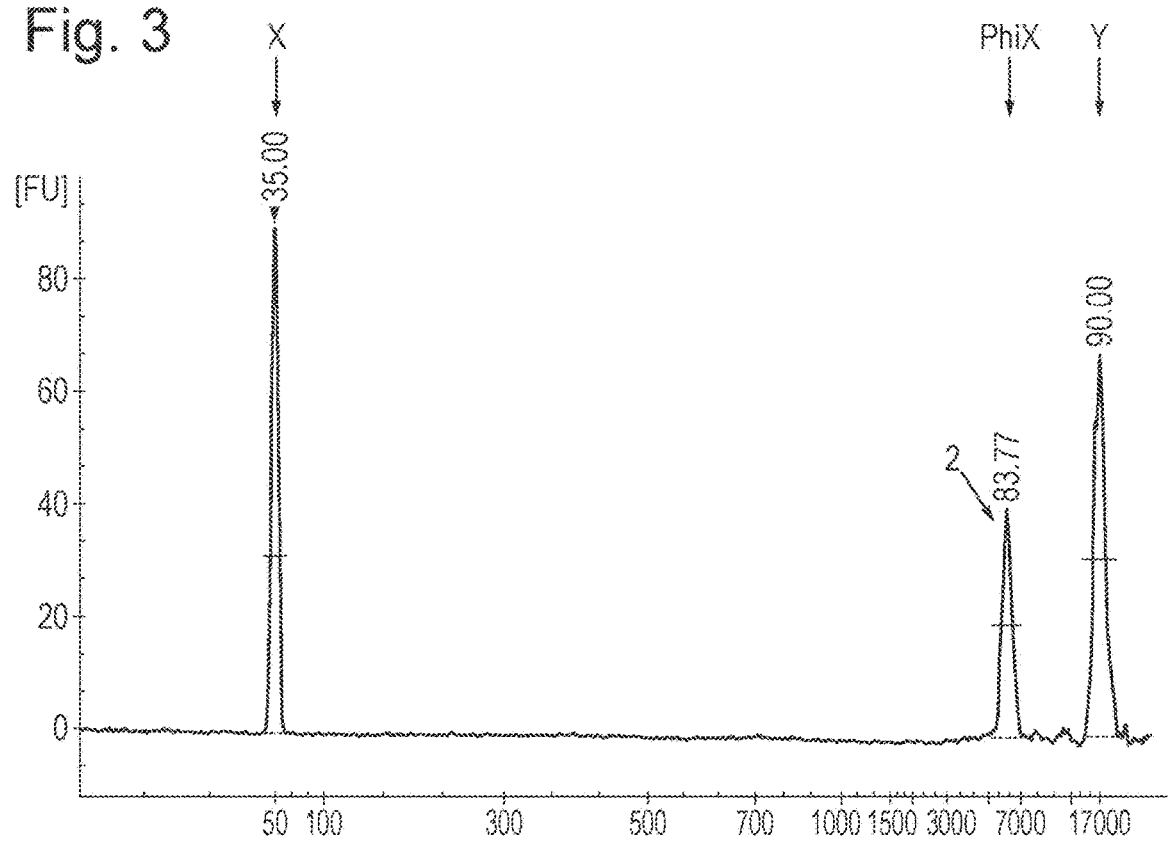
FIG. 3 shows an Agilent 2100 Bioanalyser trace. The lower marker is labelled X and the upper marker is labelled Y. A PhiX peak was observed between the upper and lower markers for transpososome 2 (labelled 1) when incubated at 75° C. for 10 minutes.

When the sample was heated to 75° C. for 10 minutes, a peak can be seen for both transposomes (FIG. 2 (transpososome 1) and FIG. 3 (transpososome 2)) between the upper (Y) and lower (X) markers. This represents linearised PhiX with no MuA transposase bound to it.

Figure 4:
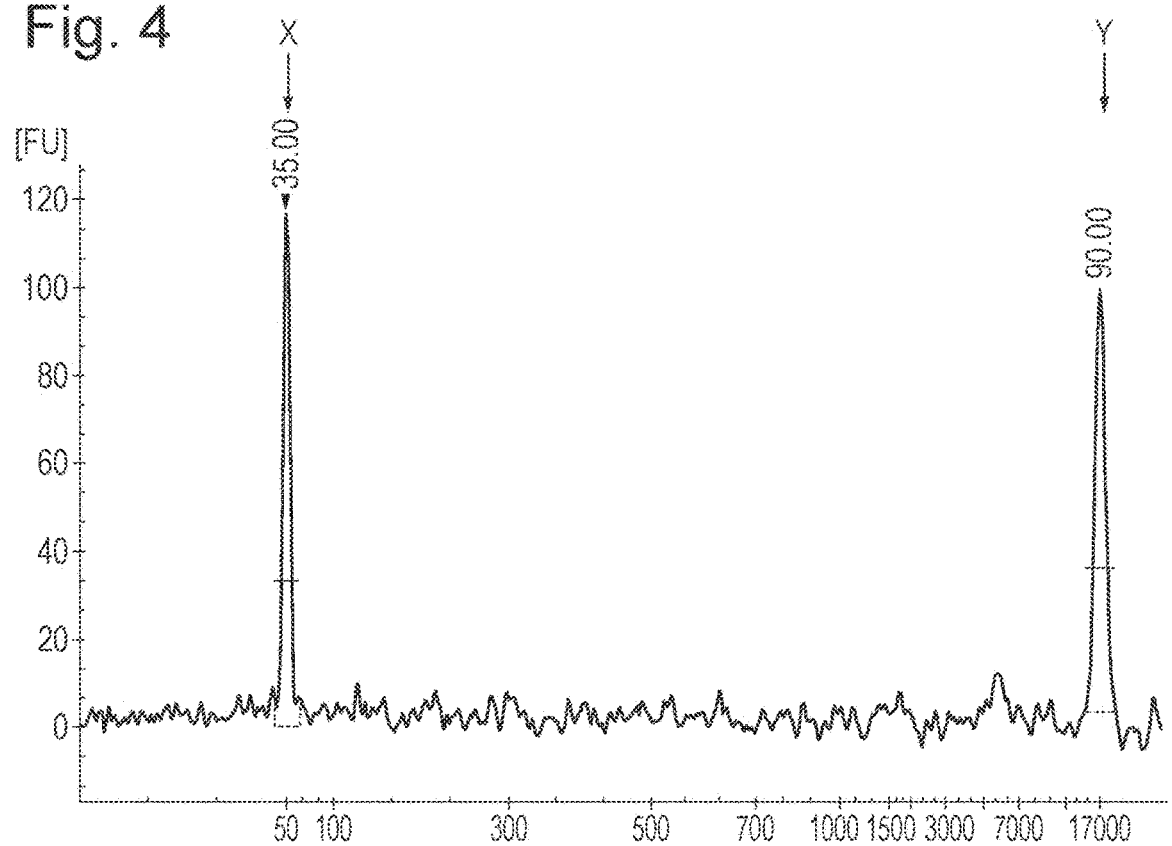
FIG. 4 shows an Agilent 2100 Bioanalyser trace. The lower marker is labelled X and the upper marker is labelled Y. A PhiX peak was not observed between the upper and lower markers for transpososome 1 (labelled 1) when incubated with Hel308Mbu-E284C/S615C-STrEP(C) (SEQ ID NO: 10 with mutations E284C/S615C with a streptavidin tag attached at its C terminus).

Treatment with Hel308Mbu-E284C/S615C-STrEP(C) does not result in a PhiX peak for transpososome 1, as there was no 3' overhang for the enzyme to load onto, so the MuA remained bound (See FIG. 4). For transpososome 2, a PhiX peak was seen after addition of Hel308Mbu-E284C/S615C-STrEP(C) because transpososome 2 had a 3' overhang for the enzyme to load onto (See FIG. 5). This indicated the fact that Hel308 was able to successfully remove MuA transposase from transposons.

FIG. 6 shows transpososome 2 after treatment with Hel308Mbu-E284C/S615C-STrEP(C) and heat treatment. The two PhiX peaks are of a similar height, indicating that Hel308 was just as efficient as heat at removing MuA transposase.

Electrophysiology Analysis

Electrophysiology experiments were carried out as described above and the throughput of the experiments were compared (kilobases/per nanopore/hour) for sample 3 (incubation at room temp in absence of Hel308Mbu-E284C/S615C-STrEP(C)), sample 2 (incubation at 75° C. for 10 minutes) and sample 1 (incubation at room temperature with Hel308Mbu-E284C/S615C-STrEP(C) using transpososome with 3' overhang). FIG. 11 shows a graph of throughput for samples 1-3. Sample 3 shows a throughput of around 20 kb/nanopore/hr which is significantly lower than samples 1 and 2 showing that by not removing the MuA transposase characterisation using a nanopore system was inhibited. Sample 2 (heat treatment) and sample 3 produce much higher throughput values around 80 kb/nanopore/hr for sample 2 and 85 kb/nanopore/hr for sample 3. This shows that removal of MuA transposase using Hel308Mbu-E284C/S615C-STrEP(C) was as efficient as heat treatment. Removal of MuA transposase using Hel308Mbu-E284C/S615C-STrEP(C) resulted in improved characterisation using a nanopore system.

Example 2

This example describes using a number of different translocases to remove MuA transposase.

Materials and Methods

Adapter Annealing

A MuA adapter consisting of SEQ ID NO: 117 and 121 were annealed to 10 uM in 10 mM Tris-HCl (pH 7.5), 50 mM NaCl, from 95° C. to 22° C. at 2° C. per minute. This adapter contained the minimal MuA recognition sequence, with the pre-formed 5' bottom strand flap, as well as a 12 nt 5' tail on the top strand and a 10 nt 3' tail on the bottom strand.

Transpososome Formation

A transposome complex was formed but addition of 1 ul of the MuA adapter, 4.5 ul of nuclease free water, 2 ul of 5× transposome buffer (125 mM Tris pH 8, 550 mM NaCl, 2.5 mM EDTA, 50% glycerol, 0.25% Triton-X100) and 2.5 ul of concentrated MuA transposase (Thermofisher). The mixture was then incubated at 30° C. for 1.5 hours.

Transposition

A transposition reaction, containing 10 ul of 5× transposase buffer (125 mM Tris pH 8, 550 mM NaCl, 50 mM MgCl2), 5 ul transposome, 2.5 ug PhiX RFI (NEB) and nuclease free water to 50 ul, was then carried out at room temperature for 10 minutes. After 10 mins 6.25 ul of 100 mM rATP was added and the reaction was split into 5×11.25 ul. To sample (i) and (ii) 1.25 ul of nuclease free water was added; to sample (iii) 1.25 ul of Hel308Mbu-E284C-STrEP (C) (SEQ ID NO: 10 with mutation E284C with a streptavidin tag attached at its C terminus) was added; to sample (iv) 1.25 ul of T4 Dda-(E94C/F98W/C109A/C136A/A360C) (SEQ ID NO: 97 with mutations E94C/F98W/C109A/C136A/A360C and then (ΔM1)G1G2 (where (ΔM1) G1G2=deletion of M1 and then addition G1 and G2), was added; to sample (v) 1.25 ul of UvrD Eco-(E117C/M380C)-STrEP (SEQ ID NO: 122 with mutations E177C/M380C with a streptavidin tag attached at the C terminus). Samples (i), (iii), (iv) and (v) were then left at room temperature for 10 mins while sample (ii) was left at 75° C. for 10 mins. All samples were then loaded onto a 12000 Agilent DNA chip to look for Tagmentation products.

Results

Figure 7:
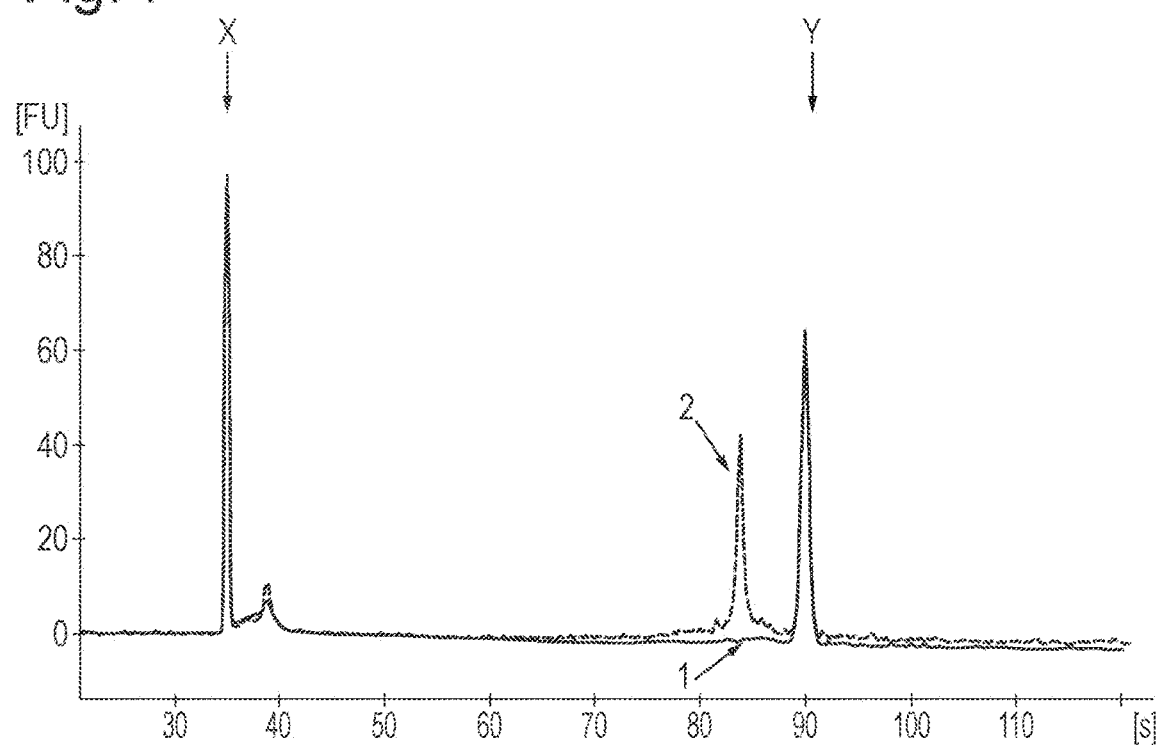
FIG. 7 shows an Agilent 2100 Bioanalyser trace. The lower marker is labelled X and the upper marker is labelled Y. Line 1 corresponds to control sample (i) which has been incubated at room temperature in the absence of a translocase. No tragmentation peak was observed for sample (i).

FIGS. 7 to 10 show a number of Agilent traces for samples (i)-(v). Sample (i) was a control where no translocase was added and the sample was no heated. FIGS. 7 to 10 all illustrate the control showing no tagmentation peak was observed for this sample this was because the MuA was still bound to the DNA, which prevented the transpososome from moving into the gel matrix of the Agilent 2100 Bioanalyser system. FIG. 7 also shows sample (ii) (line 2) which shows a clear tagmentation peak when the sample was heated to 75° C. in order to remove the MuA transposase.

FIG. 8 shows sample (iii, line 3) and the control sample (i, line 1). Sample (iii) shows a clear tagmentation peak when the sample was heated with Hel308Mbu-E284C-STrEP(C) in order to remove the MuA transposase. This indicated the fact that Hel308Mbu-E284C-STrEP(C) was able to successfully remove MuA transposase from transposons.

FIG. 9 shows sample (iv, line 4) and the control sample (i, line 1). Sample (iv) shows a clear tagmentation peak when the sample was heated with T4 Dda-(E94C/F98W/C109A/C136A/A360C) in order to remove the MuA transposase. This indicated the fact that T4 Dda-(E94C/F98W/C109A/C136A/A360C) was able to successfully remove MuA transposase from transposons.

FIG. 10 shows sample (v, line 5) and the control sample (i, line 1). Sample (v) shows a clear tagmentation peak when the sample was heated with UvrD Eco-(E117C/M380C)-STrEP in order to remove the MuA transposase. This indicated the fact that UvrD Eco-(E117C/M380C)-STrEP was able to successfully remove MuA transposase from transposons.

The invention claimed is:

1. A method for modifying a template double stranded polynucleotide, comprising:
   (a) contacting the template polynucleotide with a MuA transposase and a population of double stranded MuA substrates each comprising an overhang at one or both ends of one strand such that the transposase fragments the template polynucleotide and ligates a substrate to one or both ends of the double stranded fragments and thereby producing a plurality of fragment/substrate constructs; and
   (b) using a translocase to remove the MuA transposases from the constructs and thereby producing a plurality of modified double stranded polynucleotides.

2. The method according to claim 1, wherein the translocase is contacted with the constructs after they are created by the MuA transposase.

3. The method according to claim 1, wherein the translocase is bound to the substrates before the substrates are contacted with the template polynucleotide.

4. The method according to claim 1, wherein the translocase is a helicase.

5. The method according to claim 1, wherein the translocase is a helicase is from superfamily 1 or superfamily 2.

6. The method according to claim 5, wherein the helicase is a member of one of the following families: Pif1-like, Upf1-like, UvrD/Rep, Ski-like, Rad3/XPD, NS3/NPH-II, DEAD, DEAH/RHA, RecG-like, REcQ-like, T1R-like, Swi/Snf-like, and Rig-I-like.

7. The method according to claim 5, wherein the helicase is a UvrD helicase, a Hel308 helicase, a TraI helicase, a TraI subgroup helicase, an XPD helicase, or a Dda helicase.

8. The method according to claim 1, wherein the translocase is a Hel308 helicase.

9. The method according to claim 1, wherein the translocase is a Hel308 helicase and is Hel308 Mbu (E284C/S615C)-bismaleimidePEG11 (SEQ ID NO: 10 with mutations E284C/S615C connected by a bismaleimidePEG11 linker).

10. The method according to claim 1, wherein the translocase is a strippase.

11. The method according to claim 10, wherein the strippase is the INO80 chromatin remodeling complex or a FtsK/SpoIIIE transporter.

12. The method according to claim 1, wherein the method further comprises attaching molecular brakes to the other strands in the substrates.

13. The method according to claim 1, wherein the method further comprises attaching molecular brakes to the other strands in the substrates and wherein the molecular brakes are attached to the other strands in the substrates before they are contacted with the template polynucleotide and the MuA transposase.

14. The method according to claim 1, wherein the method further comprises attaching molecular brakes to the other strands in the substrates and wherein the molecular brakes are attached to the other strands from the substrates remaining in the constructs after they are created by the MuA transposase.

15. The method according to claim 1, wherein the method further comprises attaching molecular brakes to the other strands in the substrates and wherein the molecular brakes are bound to Y adaptors comprising a leader sequence and/or one or more anchors capable of coupling the adaptor to a membrane and the Y adaptors are attached to the other strands in step (c).

16. The method according to claim 1, wherein the method further comprises attaching molecular brakes to the other strands in the substrates and wherein the molecular brakes are derived from a polymerase, a helicase or an exonuclease.

17. The method according to claim 1, wherein the method does not comprise heat inactivating the MuA transposase.

18. A plurality of polynucleotides modified using the method according to claim 1.

19. The method of characterising at least one polynucleotide modified using a method according to claim 1, comprising:
   a) contacting the modified polynucleotide with a transmembrane pore such that at least one strand of the polynucleotide moves through the pore; and
   b) taking one or more measurements which are indicative of one or more characteristics of the polynucleotide as the at least one strand moves with respect to the pore and thereby characterising the modified polynucleotide.

20. A method of characterising a template polynucleotide, comprising:
   a) modifying the template polynucleotide using the method according to claim 1 to produce a plurality of modified polynucleotides;
   b) contacting each modified polynucleotide with a transmembrane pore such that at least one strand of each polynucleotide moves through the pore; and
   c) taking one or more measurements which are indicative of one or more characteristics of the polynucleotide as the at least one strand of each polynucleotide moves with respect to the pore and thereby characterising the template polynucleotide.

* * * * *

SEQUENCE LISTING

<160> NUMBER OF SEQ ID NOS: 122

<210> SEQ ID NO 1
<211> LENGTH: 558
<212> TYPE: DNA
<213> ORGANISM: Artificial sequence
<220> FEATURE:
<223> OTHER INFORMATION: Mycobacterium smegmatis porin A mutant
      (D90N/D91N/D93N/D118R/D134R/E139K)

<400> SEQUENCE: 1

```
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactggggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                    558
```

<210> SEQ ID NO 2
<211> LENGTH: 184
<212> TYPE: PRT
<213> ORGANISM: Artificial sequence
<220> FEATURE:
<223> OTHER INFORMATION: Mycobacterium smegmatis porin A mutant
(D90N/D91N/D93N/D118R/D134R/E139K)

<400> SEQUENCE: 2

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 3
<211> LENGTH: 885
<212> TYPE: DNA
<213> ORGANISM: Artificial sequence
<220> FEATURE:
<223> OTHER INFORMATION: alpha-hemolysin mutant E111N/K147N

<400> SEQUENCE: 3

```
atggcagatt ctgatattaa tattaaaacc ggtactacag atattggaag caatactaca     60
gtaaaaacag gtgatttagt cacttatgat aaagaaaatg gcatgcacaa aaaagtattt    120
tatagtttta tcgatgataa aaatcacaat aaaaaactgc tagttattag aacaaaaggt    180
accattgctg gtcaatatag agtttatagc gaagaaggtg ctaacaaaag tggtttagcc    240
tggccttcag cctttaaggt acagttgcaa ctacctgata atgaagtagc tcaaatatct    300
gattactatc caagaaattc gattgataca aaaaactata tgagtacttt aacttatgga    360
ttcaacggta atgttactgg tgatgataca ggaaaaattg gcggccttat tggtgcaaat    420
gtttcgattg gtcatacact gaactatgtt caacctgatt tcaaaacaat tttagagagc    480
ccaactgata aaaaagtagg ctggaaagtg atatttaaca atatggtgaa tcaaaattgg    540
ggaccatacg atcgagattc ttggaacccg gtatatggca atcaactttt catgaaaact    600
agaaatggtt ctatgaaagc agcagataac ttccttgatc ctaacaaagc aagttctcta    660
```

```
ttatcttcag ggttttcacc agacttcgct acagttatta ctatggatag aaaagcatcc    720
aaacaacaaa caaatataga tgtaatatac gaacgagttc gtgatgatta ccaattgcat    780
tggacttcaa caaattggaa aggtaccaat actaaagata atggacaga tcgttcttca    840 gaaagatata aaatcgattg ggaaaaagaa gaaatgacaa attaa                    885
```

<210> SEQ ID NO 4
<211> LENGTH: 293
<212> TYPE: PRT
<213> ORGANISM: Artificial sequence
<220> FEATURE:
<223> OTHER INFORMATION: alpha-hemolysin mutant E111N/K147N

<400> SEQUENCE: 4

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 5
<211> LENGTH: 184

<212> TYPE: PRT
<213> ORGANISM: Mycobacterium smegmatis

<400> SEQUENCE: 5

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 6
<211> LENGTH: 184
<212> TYPE: PRT
<213> ORGANISM: Mycobacterium smegmatis

<400> SEQUENCE: 6

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Val Ala Val
    130                 135                 140

Ser Asn Ala His Gly Thr Val Thr Gly Ala Ala Gly Gly Val Leu Leu
145                 150                 155                 160
```

```
Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 7
<211> LENGTH: 183
<212> TYPE: PRT
<213> ORGANISM: Mycobacterium smegmatis

<400> SEQUENCE: 7

```
Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180
```

<210> SEQ ID NO 8
<211> LENGTH: 8
<212> TYPE: PRT
<213> ORGANISM: Artificial sequence
<220> FEATURE:
<223> OTHER INFORMATION: Amino acid sequence of the Hel308 motif
<220> FEATURE:
<221> NAME/KEY: MISC_FEATURE
<222> LOCATION: (2)..(2)
<223> OTHER INFORMATION: Xaa = C, M or L
<220> FEATURE:
<221> NAME/KEY: MISC_FEATURE
<222> LOCATION: (3)..(3)
<223> OTHER INFORMATION: Xaa = any amino acid

<400> SEQUENCE: 8

```
Gln Xaa Xaa Gly Arg Ala Gly Arg
1               5
```

<210> SEQ ID NO 9
<211> LENGTH: 9
<212> TYPE: PRT
<213> ORGANISM: Artificial sequence
<220> FEATURE:
<223> OTHER INFORMATION: Amino acid sequence of the extended Hel308
      motif

```
<220> FEATURE:
<221> NAME/KEY: MISC_FEATURE
<222> LOCATION: (2)..(2)
<223> OTHER INFORMATION: Xaa = C, M or L
<220> FEATURE:
<221> NAME/KEY: MISC_FEATURE
<222> LOCATION: (3)..(3)
<223> OTHER INFORMATION: Xaa = any amino acid

<400> SEQUENCE: 9

Gln Xaa Xaa Gly Arg Ala Gly Arg Pro
1               5

<210> SEQ ID NO 10
<211> LENGTH: 760
<212> TYPE: PRT
<213> ORGANISM: Methanococcoides burtonii

<400> SEQUENCE: 10

Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
            20                  25                  30

Glu Met Gly Leu Leu Glu Lys Lys Asn Leu Leu Ala Ala Ile Pro Thr
        35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
            100                 105                 110

Val Asn Asp Ile Ile Val Ala Thr Ser Glu Lys Thr Asp Ser Leu Leu
        115                 120                 125

Arg Asn Gly Thr Ser Trp Met Asp Glu Ile Thr Thr Val Val Val Asp
    130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
            180                 185                 190

Ala Ala Leu Val Leu Ser Glu Trp Arg Pro Thr Asp Leu His Glu Gly
        195                 200                 205

Val Leu Phe Gly Asp Ala Ile Asn Phe Pro Gly Ser Gln Lys Lys Ile
    210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser
        275                 280                 285

Thr Gly Glu Thr Asp Thr Ala Ile Val Leu Ala Asn Cys Ile Arg Lys
    290                 295                 300
```

```
Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
                340                 345                 350

Arg Ser Tyr Arg Arg Phe Asp Ser Asn Phe Gly Met Gln Pro Ile Pro
                355                 360                 365

Val Leu Glu Tyr Lys Gln Met Ala Gly Arg Ala Gly Arg Pro His Leu
            370                 375                 380

Asp Pro Tyr Gly Glu Ser Val Leu Leu Ala Lys Thr Tyr Asp Glu Phe
385                 390                 395                 400

Ala Gln Leu Met Glu Asn Tyr Val Glu Ala Asp Ala Glu Asp Ile Trp
                405                 410                 415

Ser Lys Leu Gly Thr Glu Asn Ala Leu Arg Thr His Val Leu Ser Thr
                420                 425                 430

Ile Val Asn Gly Phe Ala Ser Thr Arg Gln Glu Leu Phe Asp Phe Phe
            435                 440                 445

Gly Ala Thr Phe Phe Ala Tyr Gln Gln Asp Lys Trp Met Leu Glu Glu
450                 455                 460

Val Ile Asn Asp Cys Leu Glu Phe Leu Ile Asp Lys Ala Met Val Ser
465                 470                 475                 480

Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
            500                 505                 510

Ser Lys Ile Val Asp Gly Phe Lys Asp Ile Gly Lys Ser Thr Gly Gly
    515                 520                 525

Asn Met Gly Ser Leu Glu Asp Asp Lys Gly Asp Asp Ile Thr Val Thr
    530                 535                 540

Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575

Ala His Ser Asp Glu Phe His Glu Ile Pro Asp Lys Leu Lys Glu Thr
                580                 585                 590

Asp Tyr Glu Trp Phe Met Gly Glu Val Lys Thr Ala Met Leu Leu Glu
            595                 600                 605

Glu Trp Val Thr Glu Val Ser Ala Glu Asp Ile Thr Arg His Phe Asn
            610                 615                 620

Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
                660                 665                 670

Asp Leu Met Glu Leu Val Gly Ile Arg Gly Val Gly Arg Val Arg Ala
            675                 680                 685

Arg Lys Leu Tyr Asn Ala Gly Phe Val Ser Val Ala Lys Leu Lys Gly
            690                 695                 700

Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
```

```
                    725                 730                 735
Ser Ala Pro Ile Ser Ser Asn Thr Leu Asp Thr Leu Asp Lys Asn
                740                 745                 750

Gln Lys Thr Phe Asn Asp Phe Gln
        755                 760
```

<210> SEQ ID NO 11
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 11

```
Gln Met Ala Gly Arg Ala Gly Arg
1               5
```

<210> SEQ ID NO 12
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 12

```
Gln Met Ala Gly Arg Ala Gly Arg Pro
1               5
```

<210> SEQ ID NO 13
<211> LENGTH: 720
<212> TYPE: PRT
<213> ORGANISM: Pyrococcus furiosus

<400> SEQUENCE: 13

```
Met Arg Val Asp Glu Leu Arg Val Asp Glu Arg Ile Lys Ser Thr Leu
1               5                   10                  15

Lys Glu Arg Gly Ile Glu Ser Phe Tyr Pro Pro Gln Ala Glu Ala Leu
                20                  25                  30

Lys Ser Gly Ile Leu Glu Gly Lys Asn Ala Leu Ile Ser Ile Pro Thr
            35                  40                  45

Ala Ser Gly Lys Thr Leu Ile Ala Glu Ile Ala Met Val His Arg Ile
    50                  55                  60

Leu Thr Gln Gly Gly Lys Ala Val Tyr Ile Val Pro Leu Lys Ala Leu
65                  70                  75                  80

Ala Glu Glu Lys Phe Gln Glu Phe Gln Asp Trp Glu Lys Ile Gly Leu
                85                  90                  95

Arg Val Ala Met Ala Thr Gly Asp Tyr Asp Ser Lys Asp Glu Trp Leu
            100                 105                 110

Gly Lys Tyr Asp Ile Ile Ile Ala Thr Ala Glu Lys Phe Asp Ser Leu
        115                 120                 125

Leu Arg His Gly Ser Ser Trp Ile Lys Asp Val Lys Ile Leu Val Ala
    130                 135                 140

Asp Glu Ile His Leu Ile Gly Ser Arg Asp Arg Gly Ala Thr Leu Glu
145                 150                 155                 160

Val Ile Leu Ala His Met Leu Gly Lys Ala Gln Ile Ile Gly Leu Ser
                165                 170                 175

Ala Thr Ile Gly Asn Pro Glu Glu Leu Ala Glu Trp Leu Asn Ala Glu
            180                 185                 190

Leu Ile Val Ser Asp Trp Arg Pro Val Lys Leu Arg Arg Gly Val Phe
```

```
                195                 200                 205
Tyr Gln Gly Phe Val Thr Trp Glu Asp Gly Ser Ile Asp Arg Phe Ser
        210                 215                 220
Ser Trp Glu Glu Leu Val Tyr Asp Ala Ile Arg Lys Lys Gly Ala
225                 230                 235                 240
Leu Ile Phe Val Asn Met Arg Arg Lys Ala Glu Arg Val Ala Leu Glu
                245                 250                 255
Leu Ser Lys Lys Val Lys Ser Leu Leu Thr Lys Pro Glu Ile Arg Ala
        260                 265                 270
Leu Asn Glu Leu Ala Asp Ser Leu Glu Glu Asn Pro Thr Asn Glu Lys
        275                 280                 285
Leu Ala Lys Ala Ile Arg Gly Val Ala Phe His His Ala Gly Leu
        290                 295                 300
Gly Arg Asp Glu Arg Val Leu Val Glu Glu Asn Phe Lys Gly Ile
305                 310                 315                 320
Ile Lys Ala Val Val Ala Thr Pro Thr Leu Ser Ala Gly Ile Asn Thr
                325                 330                 335
Pro Ala Phe Arg Val Ile Arg Asp Ile Trp Arg Tyr Ser Asp Phe
        340                 345                 350
Gly Met Glu Arg Ile Pro Ile Glu Val His Gln Met Leu Gly Arg
        355                 360                 365
Ala Gly Arg Pro Lys Tyr Asp Glu Val Gly Glu Gly Ile Ile Val Ser
        370                 375                 380
Thr Ser Asp Asp Pro Arg Glu Val Met Asn His Tyr Ile Phe Gly Lys
385                 390                 395                 400
Pro Glu Lys Leu Phe Ser Gln Leu Ser Asn Glu Ser Asn Leu Arg Ser
                405                 410                 415
Gln Val Leu Ala Leu Ile Ala Thr Phe Gly Tyr Ser Thr Val Glu Glu
                420                 425                 430
Ile Leu Lys Phe Ile Ser Asn Thr Phe Tyr Ala Tyr Gln Arg Lys Asp
                435                 440                 445
Thr Tyr Ser Leu Glu Glu Lys Ile Arg Asn Ile Leu Tyr Phe Leu Leu
        450                 455                 460
Glu Asn Glu Phe Ile Glu Ile Ser Leu Glu Asp Lys Ile Arg Pro Leu
465                 470                 475                 480
Ser Leu Gly Ile Arg Thr Ala Lys Leu Tyr Ile Asp Pro Tyr Thr Ala
                485                 490                 495
Lys Met Phe Lys Asp Lys Met Glu Glu Val Val Lys Asp Pro Asn Pro
                500                 505                 510
Ile Gly Ile Phe His Leu Ile Ser Leu Thr Pro Asp Ile Thr Pro Phe
        515                 520                 525
Asn Tyr Ser Lys Arg Glu Phe Glu Arg Leu Glu Glu Tyr Tyr Glu
        530                 535                 540
Phe Lys Asp Arg Leu Tyr Phe Asp Asp Pro Tyr Ile Ser Gly Tyr Asp
545                 550                 555                 560
Pro Tyr Leu Glu Arg Lys Phe Arg Ala Phe Lys Thr Ala Leu Val
                565                 570                 575
Leu Leu Ala Trp Ile Asn Glu Val Pro Glu Gly Glu Ile Val Glu Lys
        580                 585                 590
Tyr Ser Val Glu Pro Gly Asp Ile Tyr Arg Ile Val Glu Thr Ala Glu
        595                 600                 605
Trp Leu Val Tyr Ser Leu Lys Glu Ile Ala Lys Val Leu Gly Ala Tyr
        610                 615                 620
```

```
Glu Ile Val Asp Tyr Leu Glu Thr Leu Arg Val Arg Val Lys Tyr Gly
625                 630                 635                 640

Ile Arg Glu Glu Leu Ile Pro Leu Met Gln Leu Pro Leu Val Gly Arg
            645                 650                 655

Arg Arg Ala Arg Ala Leu Tyr Asn Ser Gly Phe Arg Ser Ile Glu Asp
        660                 665                 670

Ile Ser Gln Ala Arg Pro Glu Glu Leu Leu Lys Ile Glu Gly Ile Gly
    675                 680                 685

Val Lys Thr Val Glu Ala Ile Phe Lys Phe Leu Gly Lys Asn Val Lys
690                 695                 700

Ile Ser Glu Lys Pro Arg Lys Ser Thr Leu Asp Tyr Phe Leu Lys Ser
705                 710                 715                 720

<210> SEQ ID NO 14
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 14

Gln Met Leu Gly Arg Ala Gly Arg
1               5

<210> SEQ ID NO 15
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 15

Gln Met Leu Gly Arg Ala Gly Arg Pro
1               5

<210> SEQ ID NO 16
<211> LENGTH: 829
<212> TYPE: PRT
<213> ORGANISM: Haloferax volcanii

<400> SEQUENCE: 16

Met Arg Thr Ala Asp Leu Thr Gly Leu Pro Thr Gly Ile Pro Glu Ala
1               5                   10                  15

Leu Arg Asp Glu Gly Ile Glu Glu Leu Tyr Pro Pro Gln Ala Glu Ala
            20                  25                  30

Val Glu Ala Gly Leu Thr Asp Gly Glu Ser Leu Val Ala Ala Val Pro
        35                  40                  45

Thr Ala Ser Gly Lys Thr Leu Ile Ala Glu Leu Ala Met Leu Ser Ser
    50                  55                  60

Val Ala Arg Gly Gly Lys Ala Leu Tyr Ile Val Pro Leu Arg Ala Leu
65                  70                  75                  80

Ala Ser Glu Lys Lys Ala Glu Phe Glu Arg Trp Glu Tyr Gly Ile
            85                  90                  95

Asp Val Gly Val Ser Thr Gly Asn Tyr Glu Ser Asp Gly Glu Trp Leu
            100                 105                 110

Ser Ser Arg Asp Ile Ile Val Ala Thr Ser Glu Lys Val Asp Ser Leu
        115                 120                 125

Val Arg Asn Asn Ala Ala Trp Met Asp Gln Leu Thr Cys Val Val Ala
    130                 135                 140
```

```
Asp Glu Val His Leu Val Asp Arg His Arg Gly Pro Thr Leu Glu
145                 150                 155                 160

Val Thr Leu Ala Lys Leu Arg Arg Leu Asn Thr Asn Leu Gln Val Val
            165                 170                 175

Ala Leu Ser Ala Thr Val Gly Asn Ala Gly Val Val Ser Asp Trp Leu
            180                 185                 190

Asp Ala Glu Leu Val Lys Ser Asp Trp Arg Pro Ile Asp Leu Lys Met
            195                 200                 205

Gly Val His Tyr Gly Asn Ala Val Ser Phe Ala Asp Gly Ser Gln Arg
            210                 215                 220

Glu Val Pro Val Gly Arg Gly Glu Arg Gln Thr Pro Ala Leu Val Ala
225                 230                 235                 240

Asp Ala Leu Glu Gly Asp Gly Glu Gly Asp Gln Gly Ser Ser Leu Val
            245                 250                 255

Phe Val Asn Ser Arg Arg Asn Ala Glu Ser Ala Ala Arg Arg Met Ala
            260                 265                 270

Asp Val Thr Glu Arg Tyr Val Thr Gly Asp Glu Arg Ser Asp Leu Ala
            275                 280                 285

Glu Leu Ala Ala Glu Ile Arg Asp Val Ser Asp Thr Glu Thr Ser Asp
290                 295                 300

Asp Leu Ala Asn Ala Val Ala Lys Gly Ala Ala Phe His His Ala Gly
305                 310                 315                 320

Leu Ala Ala Glu His Arg Thr Leu Val Glu Asp Ala Phe Arg Asp Arg
            325                 330                 335

Leu Ile Lys Cys Ile Cys Ala Thr Pro Thr Leu Ala Ala Gly Val Asn
            340                 345                 350

Thr Pro Ser Arg Arg Val Val Arg Asp Trp Gln Arg Tyr Asp Gly
            355                 360                 365

Asp Tyr Gly Gly Met Lys Pro Leu Asp Val Leu Glu Val His Gln Met
            370                 375                 380

Met Gly Arg Ala Gly Arg Pro Gly Leu Asp Pro Tyr Gly Glu Ala Val
385                 390                 395                 400

Leu Leu Ala Lys Asp Ala Asp Ala Arg Asp Glu Leu Phe Glu Arg Tyr
            405                 410                 415

Ile Trp Ala Asp Ala Glu Asp Val Arg Ser Lys Leu Ala Ala Glu Pro
            420                 425                 430

Ala Leu Arg Thr His Leu Leu Ala Thr Val Ala Ser Gly Phe Ala His
            435                 440                 445

Thr Arg Glu Gly Leu Leu Glu Phe Leu Asp Gln Thr Leu Tyr Ala Thr
450                 455                 460

Gln Thr Asp Asp Pro Glu Arg Leu Gly Gln Val Thr Asp Arg Val Leu
465                 470                 475                 480

Asp Tyr Leu Glu Val Asn Gly Phe Val Glu Phe Glu Gly Glu Thr Ile
            485                 490                 495

Gln Ala Thr Pro Val Gly His Thr Val Ser Arg Leu Tyr Leu Asp Pro
            500                 505                 510

Met Ser Ala Ala Glu Ile Ile Asp Gly Leu Glu Trp Ala Ala Asp His
            515                 520                 525

Arg Thr Glu Lys Leu Arg Ala Leu Ala Gly Glu Thr Pro Glu Lys Pro
530                 535                 540

Thr Arg Asp Arg Ser Glu Ser Asp Glu Ser Gly Gly Phe Gln Arg Ala
545                 550                 555                 560
```

```
Ser Glu Met Val Ala Asp Asp Gly Asp Gly Gly Gly Glu Asp Gly
            565                 570                 575

Val Gly Ala Asn Gly Asp Gly Asp Ser Asp Asp Ala Asp Gly Val Glu
            580                 585                 590

Thr Asp Arg Thr Tyr Pro Thr Pro Leu Gly Leu Tyr His Leu Val Cys
        595                 600                 605

Arg Thr Pro Asp Met Tyr Gln Leu Tyr Leu Lys Ser Gly Asp Arg Glu
    610                 615                 620

Thr Tyr Thr Glu Leu Cys Tyr Glu Arg Glu Pro Glu Phe Leu Gly Arg
625                 630                 635                 640

Val Pro Ser Glu Tyr Glu Asp Val Ala Phe Glu Asp Trp Leu Ser Ala
            645                 650                 655

Leu Lys Thr Ala Lys Leu Leu Glu Asp Trp Val Gly Glu Val Asp Glu
            660                 665                 670

Asp Arg Ile Thr Glu Arg Tyr Gly Val Gly Pro Gly Asp Ile Arg Gly
        675                 680                 685

Lys Val Glu Thr Ser Glu Trp Leu Leu Gly Ala Ala Glu Arg Leu Ala
    690                 695                 700

Thr Glu Leu Asp Leu Asp Ser Val Tyr Ala Val Arg Glu Ala Lys Lys
705                 710                 715                 720

Arg Val Glu Tyr Gly Val Arg Glu Glu Leu Leu Asp Leu Ala Gly Val
            725                 730                 735

Arg Gly Val Gly Arg Lys Arg Ala Arg Leu Phe Glu Ala Gly Val
            740                 745                 750

Glu Thr Arg Ala Asp Leu Arg Glu Ala Asp Lys Pro Arg Val Leu Ala
            755                 760                 765

Ala Leu Arg Gly Arg Lys Thr Ala Glu Asn Ile Leu Glu Ala Ala
            770                 775                 780

Gly Arg Lys Asp Pro Ser Met Asp Ala Val Asp Glu Asp Ala Pro
785                 790                 795                 800

Asp Asp Ala Val Pro Asp Ala Gly Phe Glu Thr Ala Lys Glu Arg
            805                 810                 815

Ala Asp Gln Gln Ala Ser Leu Gly Asp Phe Glu Gly Ser
            820                 825

<210> SEQ ID NO 17
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 17

Gln Met Met Gly Arg Ala Gly Arg
1               5

<210> SEQ ID NO 18
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 18

Gln Met Met Gly Arg Ala Gly Arg Pro
1               5

<210> SEQ ID NO 19
```

<211> LENGTH: 824
<212> TYPE: PRT
<213> ORGANISM: Halorubrum lacusprofundi

<400> SEQUENCE: 19

```
Met Gln Pro Ser Ser Leu Ser Gly Leu Pro Ala Gly Val Gly Glu Ala
1               5                   10                  15
Leu Glu Ala Glu Gly Val Ala Glu Leu Tyr Pro Pro Gln Glu Ala Ala
            20                  25                  30
Val Glu Ala Gly Val Ala Asp Gly Glu Ser Leu Val Ala Ala Val Pro
        35                  40                  45
Thr Ala Ser Gly Lys Thr Leu Ile Ala Glu Leu Ala Met Leu Ser Ser
50                  55                  60
Ile Glu Arg Gly Gly Lys Ala Leu Tyr Ile Val Pro Leu Arg Ala Leu
65                  70                  75                  80
Ala Ser Glu Lys Lys Thr Glu Phe Glu Arg Trp Glu Glu Phe Gly Val
                85                  90                  95
Thr Val Gly Val Ser Thr Gly Asn Tyr Glu Ser Asp Gly Glu Trp Leu
            100                 105                 110
Ala Thr Arg Asp Ile Ile Val Ala Thr Ser Glu Lys Val Asp Ser Leu
        115                 120                 125
Ile Arg Asn Gly Ala Pro Trp Ile Asp Asp Leu Thr Cys Val Val Ser
130                 135                 140
Asp Glu Val His Leu Val Asp Asp Pro Asn Arg Gly Pro Thr Leu Glu
145                 150                 155                 160
Val Thr Leu Ala Lys Leu Arg Lys Val Asn Pro Gly Leu Gln Thr Val
                165                 170                 175
Ala Leu Ser Ala Thr Val Gly Asn Ala Asp Val Ile Ala Glu Trp Leu
            180                 185                 190
Asp Ala Glu Leu Val Glu Ser Asp Trp Arg Pro Ile Asp Leu Arg Met
        195                 200                 205
Gly Val His Phe Gly Asn Ala Ile Asp Phe Ala Asp Gly Ser Lys Arg
210                 215                 220
Glu Val Pro Val Glu Arg Gly Glu Asp Gln Thr Ala Arg Leu Val Ala
225                 230                 235                 240
Asp Ala Leu Asp Thr Glu Glu Asp Gly Gln Gly Gly Ser Ser Leu Val
                245                 250                 255
Phe Val Asn Ser Arg Arg Asn Ala Glu Ser Ser Ala Arg Lys Leu Thr
            260                 265                 270
Asp Val Thr Gly Pro Arg Leu Thr Asp Glu Arg Asp Gln Leu Arg
        275                 280                 285
Glu Leu Ala Asp Glu Ile Arg Ser Gly Ser Asp Thr Asp Thr Ala Ser
290                 295                 300
Asp Leu Ala Asp Ala Val Glu Gln Gly Ser Ala Phe His His Ala Gly
305                 310                 315                 320
Leu Arg Ser Glu Asp Arg Ala Arg Val Glu Asp Ala Phe Arg Asp
                325                 330                 335
Leu Ile Lys Cys Ile Ser Ala Thr Pro Thr Leu Ala Ala Gly Val Asn
            340                 345                 350
Thr Pro Ala Arg Arg Val Ile Val Arg Asp Trp Arg Tyr Asp Gly
        355                 360                 365
Glu Phe Gly Gly Met Lys Pro Leu Asp Val Leu Glu Val His Gln Met
370                 375                 380
Cys Gly Arg Ala Gly Arg Pro Gly Leu Asp Pro Tyr Gly Glu Ala Val
```

```
                385                 390                 395                 400
        Leu Leu Ala Asn Asp Ala Asp Thr Lys Glu Glu Leu Phe Glu Arg Tyr
                        405                 410                 415
        Leu Trp Ala Asp Pro Glu Pro Val Arg Ser Lys Leu Ala Ala Glu Pro
                        420                 425                 430
        Ala Leu Arg Thr His Val Leu Ala Thr Val Ala Ser Gly Phe Ala Ser
                        435                 440                 445
        Thr Arg Asp Gly Leu Leu Ser Phe Leu Asp Asn Thr Leu Tyr Ala Thr
                        450                 455                 460
        Gln Thr Asp Asp Glu Gly Arg Leu Ala Ala Val Thr Asp Thr Val Leu
        465                 470                 475                 480
        Asp Tyr Leu Ala Val Asn Asp Phe Ile Glu Arg Asp Arg Asp Gly Gly
                        485                 490                 495
        Ser Glu Ser Leu Thr Ala Thr Gly Ile Gly His Thr Val Ser Arg Leu
                        500                 505                 510
        Tyr Leu Asp Pro Met Ser Ala Ala Glu Met Ile Asp Gly Leu Arg Ser
                        515                 520                 525
        Val Ala Arg Asp Ala Ala Asp Thr Gly Ala Ser Ala Glu Ala Asp Asn
                        530                 535                 540
        Gly Glu Phe Val Arg Thr Gly Asp Ala Asp Ala Ser Gly Gly Asp
        545                 550                 555                 560
        Glu Pro Gly Phe Gly Thr Tyr Thr Arg Ala Gly Asp Asp Glu Ser Gly
                        565                 570                 575
        Glu Arg Glu Thr Glu Asn Glu Glu Thr Asp Glu Glu Thr Glu Ala
                        580                 585                 590
        Ser Glu Val Thr Pro Leu Gly Leu Tyr His Leu Ile Ser Arg Thr Pro
                        595                 600                 605
        Asp Met Tyr Glu Leu Tyr Leu Lys Ser Gly Asp Arg Glu Thr Tyr Thr
                        610                 615                 620
        Glu Leu Cys Tyr Glu Arg Glu Thr Glu Phe Leu Gly Asp Val Pro Ser
        625                 630                 635                 640
        Glu Tyr Glu Asp Val Arg Phe Glu Asp Trp Leu Ala Ser Leu Lys Thr
                        645                 650                 655
        Ala Arg Leu Leu Glu Asp Trp Val Asn Glu Val Asp Glu Arg Ile
                        660                 665                 670
        Thr Glu Arg Tyr Gly Val Gly Pro Gly Asp Ile Arg Gly Lys Val Asp
                        675                 680                 685
        Thr Ala Glu Trp Leu Leu Arg Ala Ala Glu Thr Leu Ala Arg Asp Val
                        690                 695                 700
        Glu Gly Val Asp Gly Asp Val Val Ala Val Arg Glu Ala Arg Lys
        705                 710                 715                 720
        Arg Ile Glu Tyr Gly Val Arg Glu Glu Leu Leu Asp Leu Ala Gly Val
                        725                 730                 735
        Arg Asn Val Gly Arg Lys Arg Ala Arg Arg Leu Phe Glu Ala Gly Ile
                        740                 745                 750
        Glu Thr Arg Ala Asp Leu Arg Glu Ala Asp Lys Ala Val Val Leu Gly
                        755                 760                 765
        Ala Leu Arg Gly Arg Glu Arg Thr Ala Glu Arg Ile Leu Glu His Ala
                        770                 775                 780
        Gly Arg Glu Asp Pro Ser Met Asp Asp Val Arg Pro Asp Lys Ser Ala
        785                 790                 795                 800
        Ser Ala Ala Ala Thr Ala Gly Ser Ala Ser Asp Glu Asp Gly Glu Gly
                        805                 810                 815
```

```
Gln Ala Ser Leu Gly Asp Phe Arg
            820

<210> SEQ ID NO 20
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 20

Gln Met Cys Gly Arg Ala Gly Arg
1               5

<210> SEQ ID NO 21
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 21

Gln Met Cys Gly Arg Ala Gly Arg Pro
1               5

<210> SEQ ID NO 22
<211> LENGTH: 707
<212> TYPE: PRT
<213> ORGANISM: Cenarchaeum symbiosum

<400> SEQUENCE: 22

Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
            20                  25                  30

Lys Ala Gly Leu Thr Asp Gly Lys Ser Val Leu Val Ser Ala Pro Thr
        35                  40                  45

Ala Ser Gly Lys Thr Leu Ile Ala Ala Ile Ala Met Ile Ser His Leu
    50                  55                  60

Ser Arg Asn Arg Gly Lys Ala Val Tyr Leu Ser Pro Leu Arg Ala Leu
65                  70                  75                  80

Ala Ala Glu Lys Phe Ala Glu Phe Gly Lys Ile Gly Gly Ile Pro Leu
                85                  90                  95

Gly Arg Pro Val Arg Val Gly Val Ser Thr Gly Asp Phe Glu Lys Ala
            100                 105                 110

Gly Arg Ser Leu Gly Asn Asn Asp Ile Leu Val Leu Thr Asn Glu Arg
        115                 120                 125

Met Asp Ser Leu Ile Arg Arg Pro Asp Trp Met Asp Glu Val Gly
    130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
            180                 185                 190

Ala Gly Trp Leu Asp Cys Thr Leu Val His Ser Thr Trp Arg Pro Val
        195                 200                 205

Pro Leu Ser Glu Gly Val Tyr Gln Asp Gly Glu Val Ala Met Gly Asp
        210                 215                 220
```

-continued

```
Gly Ser Arg His Glu Val Ala Thr Gly Gly Pro Ala Val Asp
225                 230                 235                 240

Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
                260                 265                 270

Ile Pro Glu Ala Lys Gly Ala Asp Ala Ala Lys Leu Ala Ala Ala
            275                 280                 285

Lys Lys Ile Ile Ser Ser Gly Gly Glu Thr Lys Leu Ala Lys Thr Leu
                290                 295                 300

Ala Glu Leu Val Glu Lys Gly Ala Ala Phe His His Ala Gly Leu Asn
305                 310                 315                 320

Gln Asp Cys Arg Ser Val Val Glu Glu Phe Arg Ser Gly Arg Ile
            325                 330                 335

Arg Leu Leu Ala Ser Thr Pro Thr Leu Ala Ala Gly Val Asn Leu Pro
                340                 345                 350

Ala Arg Arg Val Val Ile Ser Ser Val Met Arg Tyr Asn Ser Ser Ser
            355                 360                 365

Gly Met Ser Glu Pro Ile Ser Ile Leu Glu Tyr Lys Gln Leu Cys Gly
370                 375                 380

Arg Ala Gly Arg Pro Gln Tyr Asp Lys Ser Gly Glu Ala Ile Val Val
385                 390                 395                 400

Gly Gly Val Asn Ala Asp Glu Ile Phe Asp Arg Tyr Ile Gly Glu
                405                 410                 415

Pro Glu Pro Ile Arg Ser Ala Met Val Asp Asp Arg Ala Leu Arg Ile
                420                 425                 430

His Val Leu Ser Leu Val Thr Thr Ser Pro Gly Ile Lys Glu Asp Asp
            435                 440                 445

Val Thr Glu Phe Phe Leu Gly Thr Leu Gly Gly Gln Gln Ser Gly Glu
450                 455                 460

Ser Thr Val Lys Phe Ser Val Ala Val Ala Leu Arg Phe Leu Gln Glu
465                 470                 475                 480

Glu Gly Met Leu Gly Arg Arg Gly Gly Arg Leu Ala Ala Thr Lys Met
                485                 490                 495

Gly Arg Leu Val Ser Arg Leu Tyr Met Asp Pro Met Thr Ala Val Thr
                500                 505                 510

Leu Arg Asp Ala Val Gly Glu Ala Ser Pro Gly Arg Met His Thr Leu
            515                 520                 525

Gly Phe Leu His Leu Val Ser Glu Cys Ser Glu Phe Met Pro Arg Phe
530                 535                 540

Ala Leu Arg Gln Lys Asp His Glu Val Ala Glu Met Met Leu Glu Ala
545                 550                 555                 560

Gly Arg Gly Glu Leu Leu Arg Pro Val Tyr Ser Tyr Glu Cys Gly Arg
                565                 570                 575

Gly Leu Leu Ala Leu His Arg Trp Ile Gly Glu Ser Pro Glu Ala Lys
                580                 585                 590

Leu Ala Glu Asp Leu Lys Phe Glu Ser Gly Asp Val His Arg Met Val
            595                 600                 605

Glu Ser Ser Gly Trp Leu Leu Arg Cys Ile Trp Glu Ile Ser Lys His
            610                 615                 620

Gln Glu Arg Pro Asp Leu Leu Gly Glu Leu Asp Val Leu Arg Ser Arg
625                 630                 635                 640
```

```
Val Ala Tyr Gly Ile Lys Ala Glu Leu Val Pro Leu Val Ser Ile Lys
                645                 650                 655

Gly Ile Gly Arg Val Arg Ser Arg Arg Leu Phe Arg Gly Gly Ile Lys
            660                 665                 670

Gly Pro Gly Asp Leu Ala Ala Val Pro Val Glu Arg Leu Ser Arg Val
        675                 680                 685

Glu Gly Ile Gly Ala Thr Leu Ala Asn Asn Ile Lys Ser Gln Leu Arg
690                 695                 700

Lys Gly Gly
705

<210> SEQ ID NO 23
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 23

Gln Leu Cys Gly Arg Ala Gly Arg
1               5

<210> SEQ ID NO 24
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 24

Gln Leu Cys Gly Arg Ala Gly Arg Pro
1               5

<210> SEQ ID NO 25
<211> LENGTH: 715
<212> TYPE: PRT
<213> ORGANISM: Sulfolobus solfataricus

<400> SEQUENCE: 25

Met Ser Leu Glu Leu Glu Trp Met Pro Ile Glu Asp Leu Lys Leu Pro
1               5                   10                  15

Ser Asn Val Ile Glu Ile Ile Lys Lys Arg Gly Ile Lys Lys Leu Asn
            20                  25                  30

Pro Pro Gln Thr Glu Ala Val Lys Lys Gly Leu Leu Glu Gly Asn Arg
        35                  40                  45

Leu Leu Leu Thr Ser Pro Thr Gly Ser Gly Lys Thr Leu Ile Ala Glu
    50                  55                  60

Met Gly Ile Ile Ser Phe Leu Leu Lys Asn Gly Gly Lys Ala Ile Tyr
65                  70                  75                  80

Val Thr Pro Leu Arg Ala Leu Thr Asn Glu Lys Tyr Leu Thr Phe Lys
                85                  90                  95

Asp Trp Glu Leu Ile Gly Phe Lys Val Ala Met Thr Ser Gly Asp Tyr
            100                 105                 110

Asp Thr Asp Asp Ala Trp Leu Lys Asn Tyr Asp Ile Ile Ile Thr Thr
        115                 120                 125

Tyr Glu Lys Leu Asp Ser Leu Trp Arg His Arg Pro Glu Trp Leu Asn
    130                 135                 140

Glu Val Asn Tyr Phe Val Leu Asp Glu Leu His Tyr Leu Asn Asp Pro
145                 150                 155                 160
```

-continued

```
Glu Arg Gly Pro Val Val Glu Ser Val Thr Ile Arg Ala Lys Arg Arg
                165                 170                 175
Asn Leu Leu Ala Leu Ser Ala Thr Ile Ser Asn Tyr Lys Gln Ile Ala
            180                 185                 190
Lys Trp Leu Gly Ala Glu Pro Val Ala Thr Asn Trp Arg Pro Val Pro
        195                 200                 205
Leu Ile Glu Gly Val Ile Tyr Pro Glu Arg Lys Lys Lys Glu Tyr Asn
    210                 215                 220
Val Ile Phe Lys Asp Asn Thr Thr Lys Lys Val His Gly Asp Asp Ala
225                 230                 235                 240
Ile Ile Ala Tyr Thr Leu Asp Ser Leu Ser Lys Asn Gly Gln Val Leu
                245                 250                 255
Val Phe Arg Asn Ser Arg Lys Met Ala Glu Ser Thr Ala Leu Lys Ile
            260                 265                 270
Ala Asn Tyr Met Asn Phe Val Ser Leu Asp Glu Asn Ala Leu Ser Glu
        275                 280                 285
Ile Leu Lys Gln Leu Asp Asp Ile Glu Glu Gly Gly Ser Asp Glu Lys
    290                 295                 300
Glu Leu Leu Lys Ser Leu Ile Ser Lys Gly Val Ala Tyr His His Ala
305                 310                 315                 320
Gly Leu Ser Lys Ala Leu Arg Asp Leu Ile Glu Gly Phe Arg Gln
                325                 330                 335
Arg Lys Ile Lys Val Ile Val Ala Thr Pro Thr Leu Ala Ala Gly Val
                340                 345                 350
Asn Leu Pro Ala Arg Thr Val Ile Ile Gly Asp Ile Tyr Arg Phe Asn
            355                 360                 365
Lys Lys Ile Ala Gly Tyr Tyr Asp Glu Ile Pro Ile Met Glu Tyr Lys
        370                 375                 380
Gln Met Ser Gly Arg Ala Gly Arg Pro Gly Phe Asp Gln Ile Gly Glu
385                 390                 395                 400
Ser Ile Val Val Val Arg Asp Lys Glu Asp Val Asp Arg Val Phe Lys
                405                 410                 415
Lys Tyr Val Leu Ser Asp Val Glu Pro Ile Glu Ser Lys Leu Gly Ser
            420                 425                 430
Glu Arg Ala Phe Tyr Thr Phe Leu Leu Gly Ile Leu Ser Ala Glu Gly
        435                 440                 445
Asn Leu Ser Glu Lys Gln Leu Glu Asn Phe Ala Tyr Glu Ser Leu Leu
    450                 455                 460
Ala Lys Gln Leu Val Asp Val Tyr Phe Asp Arg Ala Ile Arg Trp Leu
465                 470                 475                 480
Leu Glu His Ser Phe Ile Lys Glu Gly Asn Thr Phe Ala Leu Thr
                485                 490                 495
Asn Phe Gly Lys Arg Val Ala Asp Leu Tyr Ile Asn Pro Phe Thr Ala
            500                 505                 510
Asp Ile Ile Arg Lys Gly Leu Glu Gly His Lys Ala Ser Cys Glu Leu
        515                 520                 525
Ala Tyr Leu His Leu Leu Ala Phe Thr Pro Asp Gly Pro Leu Val Ser
    530                 535                 540
Val Gly Arg Asn Glu Glu Glu Leu Ile Leu Leu Glu Asp Leu
545                 550                 555                 560
Asp Cys Glu Leu Leu Ile Glu Glu Pro Tyr Glu Glu Asp Glu Tyr Ser
                565                 570                 575
Leu Tyr Ile Asn Ala Leu Lys Val Ala Leu Ile Met Lys Asp Trp Met
```

-continued

```
                580                 585                 590
Asp Glu Val Asp Glu Asp Thr Ile Leu Ser Lys Tyr Asn Ile Gly Ser
            595                 600                 605

Gly Asp Leu Arg Asn Met Val Glu Thr Met Asp Trp Leu Thr Tyr Ser
610                 615                 620

Ala Tyr His Leu Ser Arg Glu Leu Lys Leu Asn Glu His Ala Asp Lys
625                 630                 635                 640

Leu Arg Ile Leu Asn Leu Arg Val Arg Asp Gly Ile Lys Glu Glu Leu
                645                 650                 655

Leu Glu Leu Val Gln Ile Ser Gly Val Gly Arg Lys Arg Ala Arg Leu
            660                 665                 670

Leu Tyr Asn Asn Gly Ile Lys Glu Leu Gly Asp Val Val Met Asn Pro
        675                 680                 685

Asp Lys Val Lys Asn Leu Leu Gly Gln Lys Leu Gly Glu Lys Val Val
    690                 695                 700

Gln Glu Ala Ala Arg Leu Leu Asn Arg Phe His
705                 710                 715

<210> SEQ ID NO 26
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 26

Gln Met Ser Gly Arg Ala Gly Arg
1               5

<210> SEQ ID NO 27
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 27

Gln Met Ser Gly Arg Ala Gly Arg Pro
1               5

<210> SEQ ID NO 28
<211> LENGTH: 685
<212> TYPE: PRT
<213> ORGANISM: Methanogenium frigidum

<400> SEQUENCE: 28

Met Asp Leu Ser Leu Pro Lys Ala Phe Ile Gln Tyr Tyr Lys Asp Lys
1               5                   10                  15

Gly Ile Glu Ser Leu Tyr Pro Pro Gln Ser Glu Cys Ile Glu Asn Gly
                20                  25                  30

Leu Leu Asp Gly Ala Asp Leu Leu Val Ala Ile Pro Thr Ala Ser Gly
            35                  40                  45

Lys Thr Leu Ile Ala Glu Met Ala Met His Ala Ala Ile Ala Arg Gly
        50                  55                  60

Gly Met Cys Leu Tyr Ile Val Pro Leu Lys Ala Leu Ala Thr Glu Lys
65                  70                  75                  80

Ala Gln Glu Phe Lys Gly Lys Gly Ala Glu Ile Gly Val Ala Thr Gly
                85                  90                  95

Asp Tyr Asp Gln Lys Glu Lys Arg Leu Gly Ser Asn Asp Ile Val Ile
```

```
            100                 105                 110
Ala Thr Ser Glu Lys Val Asp Ser Leu Leu Arg Asn Gly Val Pro Trp
            115                 120                 125

Leu Ser Gln Val Thr Cys Leu Val Val Asp Glu Val His Leu Ile Asp
            130                 135             140

Asp Glu Ser Arg Gly Pro Thr Leu Glu Met Val Ile Thr Lys Leu Arg
145                 150                 155                 160

His Ala Ser Pro Asp Met Gln Val Ile Gly Leu Ser Ala Thr Ile Gly
                    165                 170                 175

Asn Pro Lys Glu Leu Ala Gly Trp Leu Gly Ala Asp Leu Ile Thr Ser
                180                 185                 190

Asp Trp Arg Pro Val Asp Leu Arg Glu Gly Ile Cys Tyr His Asn Thr
            195                 200                 205

Ile Tyr Phe Asp Asn Glu Asp Lys Glu Ile Pro Ala Pro Ala Lys Thr
            210                 215                 220

Glu Asp Ile Asn Leu Leu Leu Asp Cys Val Ala Asp Gly Gly Gln Cys
225                 230                 235                 240

Leu Val Phe Val Ser Ser Arg Arg Asn Ala Glu Gly Tyr Ala Lys Arg
                    245                 250                 255

Ala Ala Thr Ala Leu Lys Cys Ser His Ala Ala Leu Asp Ser Ile Ala
                260                 265                 270

Glu Lys Leu Glu Ala Ala Ala Glu Thr Asp Met Gly Arg Val Leu Ala
            275                 280                 285

Thr Cys Val Lys Lys Gly Ala Ala Phe His His Ala Gly Met Asn Arg
            290                 295                 300

Met Gln Arg Thr Leu Val Glu Gly Gly Phe Arg Asp Gly Phe Ile Lys
305                 310                 315                 320

Ser Ile Ser Ser Thr Pro Thr Leu Ala Ala Gly Leu Asn Leu Pro Ala
                    325                 330                 335

Arg Arg Val Ile Ile Arg Asp Tyr Leu Arg Tyr Ser Gly Gly Glu Gly
                340                 345                 350

Met Arg Pro Ile Pro Val Arg Glu Tyr Arg Gln Met Ala Gly Arg Ala
            355                 360                 365

Gly Arg Pro His Leu Asp Pro Tyr Gly Glu Ala Ile Leu Ile Ala Lys
            370                 375                 380

Thr Glu Tyr Ala Val Asn Asp Leu His Glu Glu Tyr Val Glu Ala Pro
385                 390                 395                 400

Asp Glu Asp Val Thr Ser Arg Cys Gly Glu Lys Gly Val Leu Thr Ala
                    405                 410                 415

His Ile Leu Ser Leu Ile Ala Thr Gly Tyr Ala Arg Ser Tyr Asp Glu
                420                 425                 430

Leu Met Ala Phe Leu Glu Lys Thr Leu Tyr Ala Tyr Gln His Thr Gly
            435                 440                 445

Lys Lys Ala Leu Thr Arg Thr Leu Asp Asp Ala Leu Gly Phe Leu Thr
            450                 455                 460

Glu Ala Glu Met Val Thr Asp Leu Ser Gly Met Leu His Ala Thr Glu
465                 470                 475                 480

Tyr Gly Asp Leu Thr Ser Arg Leu Tyr Ile Asp Pro His Ser Ala Glu
                    485                 490                 495

Ile Ile Thr Thr Ala Leu Arg Glu Gly Glu Leu Thr Asp Leu Ala
                500                 505                 510

Leu Leu Gln Leu Leu Cys Met Thr Pro Asp Met Phe Thr Leu Tyr Val
            515                 520                 525
```

```
Lys Lys Asn Asp Leu Gly Thr Leu Glu Lys Phe Phe Glu His Glu
            530                 535                 540

Glu Glu Phe Arg Thr Glu Phe Ser Tyr Asp Glu Met Glu Asp Phe
545                 550                 555                 560

Arg Ser Leu Lys Thr Ala Met Leu Leu Ser Asp Trp Thr Asp Glu Ile
                565                 570                 575

Gly Asp Asp Thr Ile Cys Thr Arg Phe Gly Val Gly Pro Gly Asp Ile
                580                 585                 590

Phe Asn Ala Val Gln Gly Ile Ser Trp Leu Leu His Ala Ser Gly Arg
                595                 600                 605

Leu Ala Arg Leu Val Ala Pro Glu His Arg Asp Ala Val Glu Glu Thr
610                 615                 620

Thr Leu Arg Val Arg His Gly Ile Arg Arg Glu Leu Ile Pro Leu Val
625                 630                 635                 640

Arg Val Lys Gly Ile Gly Arg Val Arg Ala Arg Leu Phe Asn Asn
                645                 650                 655

Gly Ile Thr Gly Pro Glu Leu Leu Ala Ala Asp Pro Ser Val Val
                660                 665                 670

Gly His Ile Val Gly Gly Lys Thr Ala Glu Ser Ile Ile
                675                 680                 685

<210> SEQ ID NO 29
<211> LENGTH: 775
<212> TYPE: PRT
<213> ORGANISM: Methanothermococcus okinawensis

<400> SEQUENCE: 29

Met Leu Met Leu Met Glu Val Leu Lys Glu Asn Gly Ile Ala Glu Leu
1               5                   10                  15

Arg Pro Pro Gln Lys Lys Val Val Glu Gly Gly Leu Leu Asn Lys Asn
                20                  25                  30

Lys Asn Phe Leu Ile Cys Ile Pro Thr Ala Ser Gly Lys Thr Leu Ile
            35                  40                  45

Gly Glu Met Ala Phe Ile Asn His Leu Leu Asp Asn Asn Lys Thr Pro
50                  55                  60

Thr Asn Lys Lys Gly Leu Phe Ile Val Pro Leu Lys Ala Leu Ala Asn
65                  70                  75                  80

Glu Lys Tyr Glu Glu Phe Lys Gly Lys Tyr Glu Lys Tyr Gly Leu Lys
                85                  90                  95

Ile Ala Leu Ser Ile Gly Asp Phe Asp Glu Lys Glu Asp Leu Lys Gly
                100                 105                 110

Tyr Asp Leu Ile Ile Thr Thr Ala Glu Lys Leu Asp Ser Leu Ile Arg
                115                 120                 125

His Lys Val Glu Trp Ile Lys Asp Ile Ser Val Val Ile Asp Glu
            130                 135                 140

Ile His Leu Ile Gly Asp Glu Ser Arg Gly Gly Thr Leu Glu Val Leu
145                 150                 155                 160

Leu Thr Lys Leu Lys Thr Lys Lys Thr Ile Gln Ile Ile Gly Leu Ser
                165                 170                 175

Ala Thr Ile Gly Asn Pro Glu Glu Leu Ala Lys Trp Leu Asn Ala Glu
                180                 185                 190

Leu Ile Val Asp Glu Trp Arg Pro Val Lys Leu Lys Lys Gly Ile Gly
                195                 200                 205

Tyr Gly Asn Lys Ile Met Phe Ile Asp Asp Asn Gly Asn Thr Ile Asn
```

-continued

```
            210                 215                 220
Glu Val Ile Val Asp Glu Ile Ser Lys Asn Asn Met Phe Asn Leu Val
225                 230                 235                 240

Val Asp Ser Ile Leu Lys Asp Gly Ser Cys Ile Ile Phe Cys Asn Ser
                    245                 250                 255

Lys Arg Gly Ala Val Gly Glu Ala Lys Lys Leu Asn Leu Lys Lys Tyr
                260                 265                 270

Leu Ser Pro Asp Glu Ile Ser Glu Leu Arg His Leu Lys Glu Glu Val
            275                 280                 285

Leu Ser Val Leu Asp Asn Pro Thr Lys Thr Cys Lys Asp Leu Ala Glu
            290                 295                 300

Cys Ile Glu Lys Gly Val Ala Phe His His Ala Gly Leu Thr Tyr Glu
305                 310                 315                 320

Gln Arg Lys Ile Val Glu Glu Gly Phe Arg Lys Lys Leu Ile Lys Ala
                325                 330                 335

Ile Cys Cys Thr Pro Thr Leu Ser Ala Gly Ile Asn Met Pro Cys Arg
                340                 345                 350

Arg Ala Ile Ile Arg Asp Leu Lys Arg Phe Ser Ser Arg Gly Tyr Ile
            355                 360                 365

Pro Ile Pro Lys Met Glu Ile His Gln Cys Ile Gly Arg Ala Gly Arg
            370                 375                 380

Pro Asn Leu Asp Pro Tyr Gly Glu Gly Ile Ile Tyr Ile Asn Asn Thr
385                 390                 395                 400

Glu Asn Pro Glu Leu Ile Glu Asn Ala Lys Asn Tyr Leu Ile Gly Asn
                405                 410                 415

Val Glu Glu Ile Tyr Ser Lys Leu Ser Asn Gln Lys Val Leu Arg Thr
                420                 425                 430

His Met Leu Gly Leu Ile Thr Thr Gly Asp Ile Lys Asn Lys Asn Asp
            435                 440                 445

Leu Glu Glu Phe Ile Lys Asn Thr Phe Tyr Ala Tyr Gln Tyr Gln Asn
            450                 455                 460

Thr Lys Lys Ile Leu Glu Asn Ile Tyr Glu Ile Thr Asn Phe Leu Glu
465                 470                 475                 480

Lys Asn Gly Phe Ile Glu Leu Asn Tyr Arg Arg Asp Glu Asn Lys Asp
                485                 490                 495

Lys Ser Asn Asn Ser His Asn Asn Lys Lys Asn Ile Ser Asn Thr Asn
                500                 505                 510

Asn Ser Ile Lys Met Leu Val Leu Asp Asn Asn Ser Leu Thr Ile
            515                 520                 525

Lys Ser Arg His Glu Glu Asp Val Tyr Tyr Asn Ile Thr Pro Leu Gly
            530                 535                 540

Lys Lys Val Ser Glu Leu Tyr Ile Asp Pro Leu Ser Ala Glu Tyr Ile
545                 550                 555                 560

Ile Asp Gly Leu Lys Asn Leu His Lys Lys Thr Leu Ser Asn Pro Lys
                565                 570                 575

Asn Met Glu Cys Tyr Ile Leu His Ile Leu Tyr Ile Ile Ser Lys Thr
                580                 585                 590

Thr Glu Met Gln Pro Val Leu Arg Val Arg Arg Lys Glu Glu Asn Asp
            595                 600                 605

Leu Ile Asn Asp Met Ile Lys Leu Asp Ile Asp Val Asp Asp Val Ile
            610                 615                 620

Tyr Gly Ile Ser Ser Glu Asn Leu Glu Tyr Phe Lys Asn Ala Lys Leu
625                 630                 635                 640
```

-continued

```
Phe Tyr Asp Trp Ile Asn Glu Ile Pro Glu Glu Leu Leu Leu Gly
                645                 650                 655

Tyr Asn Ile Glu Pro Gly Ile Leu Arg Tyr Asn Val Glu Gln Ala Lys
            660                 665                 670

Trp Met Ile His Ser Ala Lys Glu Ile Phe Asn Leu Leu Asn Ile Asp
        675                 680                 685

Asn Lys Val Ile Lys Asp Cys Leu Asn Asp Leu Glu Ile Arg Met Glu
    690                 695                 700

Tyr Gly Ala Lys Gln Asp Ile Ile Glu Leu Leu Lys Ile Lys His Ile
705                 710                 715                 720

Gly Arg Ala Arg Ala Arg Ile Leu Tyr Asn Ala Gly Ile Lys Asn Ala
                725                 730                 735

Asn Asp Ile Ile Asn Asn Gln Lys Asn Ile Ile Asn Leu Leu Gly Glu
            740                 745                 750

Lys Ile Ala Arg Lys Ile Leu Ser Glu Leu Gly Val Asp Thr Lys Phe
        755                 760                 765

Gly Gln Met Arg Leu Ser Ile
    770                 775
```

<210> SEQ ID NO 30
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 30

```
Gln Cys Ile Gly Arg Ala Gly Arg
1               5
```

<210> SEQ ID NO 31
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 31

```
Gln Cys Ile Gly Arg Ala Gly Arg Pro
1               5
```

<210> SEQ ID NO 32
<211> LENGTH: 699
<212> TYPE: PRT
<213> ORGANISM: Methanotorris igneus

<400> SEQUENCE: 32

```
Met Gln Lys Tyr Ser His Val Phe Glu Val Leu Lys Glu Asn Gly Ile
1               5                   10                  15

Lys Glu Leu Arg Pro Pro Gln Lys Lys Val Ile Glu Lys Gly Leu Leu
            20                  25                  30

Asn Lys Glu Lys Asn Phe Leu Ile Cys Ile Pro Thr Ala Ser Gly Lys
        35                  40                  45

Thr Leu Ile Gly Glu Met Ala Leu Ile Asn His Leu Leu Asp Glu Asn
    50                  55                  60

Lys Thr Pro Thr Asn Lys Lys Gly Leu Phe Ile Val Pro Leu Lys Ala
65                  70                  75                  80

Leu Ala Ser Glu Lys Tyr Glu Glu Phe Lys Arg Lys Tyr Glu Lys Tyr
                85                  90                  95
```

```
Gly Leu Lys Val Ala Leu Ser Ile Gly Asp Tyr Asp Glu Lys Glu Asp
            100                 105                 110

Leu Ser Ser Tyr Asn Ile Ile Thr Thr Ala Glu Lys Leu Asp Ser
        115                 120                 125

Leu Met Arg His Glu Ile Asp Trp Leu Asn Tyr Val Ser Val Ala Ile
130                 135                 140

Val Asp Glu Ile His Met Ile Asn Asp Glu Lys Arg Gly Gly Thr Leu
145                 150                 155                 160

Glu Val Leu Leu Thr Lys Leu Lys Asn Leu Asp Val Gln Ile Ile Gly
                165                 170                 175

Leu Ser Ala Thr Ile Gly Asn Pro Glu Glu Leu Ala Glu Trp Leu Asn
            180                 185                 190

Ala Glu Leu Ile Ile Asp Asn Trp Arg Pro Val Lys Leu Arg Lys Gly
        195                 200                 205

Ile Phe Phe Gln Asn Lys Ile Met Tyr Leu Asn Gly Ala Cys Lys Glu
    210                 215                 220

Leu Pro Asn Phe Ser Asn Pro Met Leu Asn Leu Val Leu Asp Cys
225                 230                 235                 240

Val Lys Glu Gly Gly Cys Cys Leu Val Phe Cys Asn Ser Lys Asn Gly
                245                 250                 255

Ala Val Ser Glu Ala Lys Lys Leu Asn Leu Lys Lys Tyr Leu Ser Asn
            260                 265                 270

Ser Glu Lys Tyr Glu Leu Gln Lys Leu Lys Glu Ile Leu Ser Ile
        275                 280                 285

Leu Asp Pro Pro Thr Glu Thr Cys Lys Thr Leu Ala Glu Cys Leu Glu
290                 295                 300

Lys Gly Val Ala Phe His His Ala Gly Leu Thr Tyr Glu His Arg Lys
305                 310                 315                 320

Ile Val Glu Glu Gly Phe Arg Asn Lys Leu Ile Lys Val Ile Cys Cys
                325                 330                 335

Thr Pro Thr Leu Ser Ala Gly Ile Asn Ile Pro Cys Arg Arg Ala Ile
            340                 345                 350

Val Arg Asp Leu Met Arg Phe Ser Asn Gly Arg Met Lys Pro Ile Pro
        355                 360                 365

Ile Met Glu Ile His Gln Cys Ile Gly Arg Ala Gly Arg Pro Gly Leu
    370                 375                 380

Asp Pro Tyr Gly Glu Gly Ile Ile Phe Val Lys Asn Glu Arg Asp Leu
385                 390                 395                 400

Glu Arg Ala Glu Gln Tyr Leu Glu Gly Lys Pro Glu Tyr Ile Tyr Ser
                405                 410                 415

Lys Leu Ser Asn Gln Ala Val Leu Arg Thr Gln Leu Leu Gly Met Ile
            420                 425                 430

Ala Thr Arg Glu Ile Glu Asn Glu Phe Asp Leu Ile Ser Phe Ile Lys
        435                 440                 445

Asn Thr Phe Tyr Ala His Gln Tyr Gly Asn Leu Gly Val Leu Arg
    450                 455                 460

Asn Ile Lys Glu Val Ile Asn Phe Leu Glu Glu Asn Asp Phe Ile Ala
465                 470                 475                 480

Asp Tyr Phe Pro Thr Lys Leu Gly Lys Arg Val Ser Glu Leu Tyr Ile
                485                 490                 495

Asp Pro Leu Ser Ala Lys Ile Ile Ile Asp Gly Leu Lys Glu Met Gly
            500                 505                 510
```

```
Asn Val Asp Asn Glu Glu Leu Tyr Tyr Leu Tyr Leu Ile Ser Lys Thr
            515                 520                 525

Leu Glu Met Met Pro Leu Leu Arg Val Asn Ser Phe Glu Glu Leu Asp
        530                 535                 540

Leu Ile Leu Glu Met Glu Glu Ala Gly Ile Tyr Asp Arg Thr Tyr Asp
545                 550                 555                 560

Asp Leu Ala Ala Phe Lys Asn Ala Lys Met Leu Tyr Asp Trp Ile Asn
                565                 570                 575

Glu Val Pro Glu Asp Glu Ile Leu Lys Tyr Lys Ile Glu Pro Gly
            580                 585                 590

Ile Leu Arg Tyr Lys Val Glu Gln Ala Lys Trp Met Ile Tyr Ser Thr
        595                 600                 605

Lys Glu Ile Ala Lys Leu Leu Asn Arg Asn Ile Asp Thr Leu Ser Lys
    610                 615                 620

Leu Glu Ile Arg Leu Glu Tyr Gly Ala Lys Glu Asp Ile Ile Glu Leu
625                 630                 635                 640

Leu Lys Ile Lys Tyr Val Gly Arg Ala Arg Ala Arg Lys Leu Tyr Asp
                645                 650                 655

Ala Gly Ile Arg Ser Val Glu Asp Ile Ile Asn Asn Pro Lys Lys Val
            660                 665                 670

Ala Ser Leu Leu Gly Glu Lys Ile Ala Lys Lys Ile Leu Gly Glu Leu
        675                 680                 685

Gly Met Lys Phe Gly Gln Gln Thr Leu Gln Ile
    690                 695
```

<210> SEQ ID NO 33
<211> LENGTH: 720
<212> TYPE: PRT
<213> ORGANISM: Thermococcus gammatolerans

<400> SEQUENCE: 33

```
Met Lys Val Asp Glu Leu Pro Val Asp Glu Arg Leu Lys Ala Val Leu
1               5                   10                  15

Lys Glu Arg Gly Ile Glu Glu Leu Tyr Pro Pro Gln Ala Glu Ala Leu
            20                  25                  30

Lys Ser Gly Ala Leu Glu Gly Arg Asn Leu Val Leu Ala Ile Pro Thr
        35                  40                  45

Ala Ser Gly Lys Thr Leu Val Ser Glu Ile Val Met Val Asn Lys Leu
    50                  55                  60

Ile Gln Glu Gly Gly Lys Ala Val Tyr Leu Val Pro Leu Lys Ala Leu
65                  70                  75                  80

Ala Glu Glu Lys Tyr Arg Glu Phe Lys Glu Trp Lys Leu Gly Leu
                85                  90                  95

Lys Val Ala Ala Thr Thr Gly Asp Tyr Asp Ser Thr Asp Asp Trp Leu
            100                 105                 110

Gly Arg Tyr Asp Ile Ile Val Ala Thr Ala Glu Lys Phe Asp Ser Leu
        115                 120                 125

Leu Arg His Gly Ala Arg Trp Ile Asn Asp Val Lys Leu Val Val Ala
    130                 135                 140

Asp Glu Val His Leu Ile Gly Ser Tyr Asp Arg Gly Ala Thr Leu Glu
145                 150                 155                 160

Met Ile Leu Thr His Met Leu Gly Arg Ala Gln Ile Leu Ala Leu Ser
                165                 170                 175

Ala Thr Val Gly Asn Ala Glu Glu Leu Ala Glu Trp Leu Asp Ala Ser
            180                 185                 190
```

```
Leu Val Val Ser Asp Trp Arg Pro Val Gln Leu Arg Arg Gly Val Phe
        195                 200                 205

His Leu Gly Thr Leu Ile Trp Glu Asp Gly Lys Val Glu Ser Tyr Pro
        210                 215                 220

Glu Asn Trp Tyr Ser Leu Val Asp Ala Val Lys Arg Gly Lys Gly
225                 230                 235                 240

Ala Leu Val Phe Val Asn Thr Arg Arg Ser Ala Glu Lys Glu Ala Leu
                245                 250                 255

Ala Leu Ser Lys Leu Val Ser Ser His Leu Thr Lys Pro Glu Lys Arg
                260                 265                 270

Ala Leu Glu Ser Leu Ala Ser Gln Leu Glu Asp Asn Pro Thr Ser Glu
                275                 280                 285

Lys Leu Lys Arg Ala Leu Arg Gly Gly Val Ala Phe His His Ala Gly
        290                 295                 300

Leu Ser Arg Val Glu Arg Thr Leu Ile Glu Asp Ala Phe Arg Glu Gly
305                 310                 315                 320

Leu Ile Lys Val Ile Thr Ala Thr Pro Thr Leu Ser Ala Gly Val Asn
                325                 330                 335

Leu Pro Ser Phe Arg Val Ile Arg Asp Thr Lys Arg Tyr Ala Gly
        340                 345                 350

Phe Gly Trp Thr Asp Ile Pro Val Leu Glu Ile Gln Gln Met Met Gly
        355                 360                 365

Arg Ala Gly Arg Pro Arg Tyr Asp Lys Tyr Gly Glu Ala Ile Ile Val
        370                 375                 380

Ala Arg Thr Asp Glu Pro Gly Lys Leu Met Glu Arg Tyr Ile Arg Gly
385                 390                 395                 400

Lys Pro Glu Lys Leu Phe Ser Met Leu Ala Asn Glu Gln Ala Phe Arg
                405                 410                 415

Ser Gln Val Leu Ala Leu Ile Thr Asn Phe Gly Ile Arg Ser Phe Pro
                420                 425                 430

Glu Leu Val Arg Phe Leu Glu Arg Thr Phe Tyr Ala His Gln Arg Lys
        435                 440                 445

Asp Leu Ser Ser Leu Glu Tyr Lys Ala Lys Glu Val Val Tyr Phe Leu
        450                 455                 460

Ile Glu Asn Glu Phe Ile Asp Leu Asp Leu Glu Asp Arg Phe Ile Pro
465                 470                 475                 480

Leu Pro Phe Gly Lys Arg Thr Ser Gln Leu Tyr Ile Asp Pro Leu Thr
                485                 490                 495

Ala Lys Lys Phe Lys Asp Ala Phe Pro Ala Ile Glu Arg Asn Pro Asn
                500                 505                 510

Pro Phe Gly Ile Phe Gln Leu Ile Ala Ser Thr Pro Asp Met Ala Thr
        515                 520                 525

Leu Thr Ala Arg Arg Arg Glu Met Glu Asp Tyr Leu Asp Leu Ala Tyr
        530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                565                 570                 575

Asp Trp Ile Asn Glu Val Pro Glu Ala Arg Ile Tyr Glu Thr Tyr Ser
                580                 585                 590

Ile Asp Pro Gly Asp Leu Tyr Arg Leu Leu Glu Leu Ala Asp Trp Leu
        595                 600                 605
```

```
Met Tyr Ser Leu Ile Glu Leu Tyr Lys Leu Phe Glu Pro Lys Glu Glu
    610             615                 620

Ile Leu Asn Tyr Leu Arg Asp Leu His Leu Arg Leu Arg His Gly Val
625             630                 635                 640

Arg Glu Glu Leu Leu Glu Leu Val Arg Leu Pro Asn Ile Gly Arg Lys
            645                 650                 655

Arg Ala Arg Ala Leu Tyr Asn Ala Gly Phe Arg Ser Val Glu Ala Ile
            660                 665                 670

Ala Asn Ala Lys Pro Ala Glu Leu Leu Ala Val Glu Gly Ile Gly Ala
            675                 680                 685

Lys Ile Leu Asp Gly Ile Tyr Arg His Leu Gly Ile Glu Lys Arg Val
690             695                 700

Thr Glu Glu Lys Pro Lys Arg Lys Gly Thr Leu Glu Asp Phe Leu Arg
705             710                 715                 720

<210> SEQ ID NO 34
<211> LENGTH: 755
<212> TYPE: PRT
<213> ORGANISM: Thermococcus barophilus

<400> SEQUENCE: 34

Met Leu Ser Thr Lys Pro Lys Ala Tyr Lys Arg Phe Ser Pro Ile Gly
1               5                   10                  15

Tyr Ala Met Gln Val Asp Glu Leu Ser Lys Phe Gly Val Asp Glu Arg
            20                  25                  30

Ile Ile Arg Lys Ile Lys Glu Arg Gly Ile Ser Glu Phe Tyr Pro Pro
            35                  40                  45

Gln Ala Glu Ala Leu Arg Ser Gly Val Leu Asn Gly Glu Asn Leu Leu
50                  55                  60

Leu Ala Ile Pro Thr Ala Ser Gly Lys Thr Leu Val Ala Glu Ile Val
65                  70                  75                  80

Met Leu His Lys Leu Phe Thr Gly Gly Gly Lys Ala Val Tyr Leu Val
                85                  90                  95

Pro Leu Lys Ala Leu Ala Glu Glu Lys Tyr Arg Glu Phe Lys Thr Trp
            100                 105                 110

Glu Asp Leu Gly Val Arg Val Ala Val Thr Thr Gly Asp Tyr Asp Ser
            115                 120                 125

Ser Glu Glu Trp Leu Gly Lys Tyr Asp Ile Ile Ala Thr Ser Glu
            130                 135                 140

Lys Phe Asp Ser Leu Leu Arg His Lys Ser Arg Trp Ile Arg Asp Val
145                 150                 155                 160

Thr Leu Ile Val Ala Asp Glu Ile His Leu Leu Gly Ser Tyr Asp Arg
                165                 170                 175

Gly Ala Thr Leu Glu Met Ile Leu Ser His Met Leu Gly Lys Ala Gln
            180                 185                 190

Ile Leu Gly Leu Ser Ala Thr Val Gly Asn Ala Glu Glu Leu Ala Glu
            195                 200                 205

Trp Leu Asn Ala Lys Leu Val Val Ser Asp Trp Arg Pro Val Lys Leu
            210                 215                 220

Arg Lys Gly Val Phe Ala His Gly Gln Leu Ile Trp Glu Asp Gly Lys
225                 230                 235                 240

Val Asp Lys Phe Pro Pro Gln Trp Asp Ser Leu Val Ile Asp Ala Val
                245                 250                 255

Lys Lys Gly Lys Gln Ala Leu Val Phe Val Asn Thr Arg Arg Ser Ala
            260                 265                 270
```

```
Glu Lys Glu Ala Gly Met Leu Gly Lys Lys Val Arg Arg Leu Leu Thr
            275                 280                 285
Lys Pro Glu Ala Arg Arg Leu Lys Glu Leu Ala Glu Ser Leu Glu Ser
290                 295                 300
Asn Pro Thr Asn Asp Lys Leu Lys Glu Val Leu Val Asn Gly Ala Ala
305                 310                 315                 320
Phe His His Ala Gly Leu Gly Arg Ala Glu Arg Thr Leu Ile Glu Asp
                325                 330                 335
Ala Phe Arg Glu Gly Leu Ile Lys Val Leu Thr Ala Thr Pro Thr Leu
            340                 345                 350
Ala Met Gly Val Asn Leu Pro Ser Phe Arg Val Ile Arg Asp Thr
            355                 360                 365
Lys Arg Tyr Ser Thr Phe Gly Trp Ser Asp Ile Pro Val Leu Glu Ile
            370                 375                 380
Gln Gln Met Ile Gly Arg Ala Gly Arg Pro Lys Tyr Asp Lys Glu Gly
385                 390                 395                 400
Glu Ala Ile Ile Val Ala Lys Thr Glu Lys Pro Glu Glu Leu Met Glu
                405                 410                 415
Lys Tyr Ile Phe Gly Lys Pro Glu Lys Leu Phe Ser Met Leu Ser Asn
            420                 425                 430
Asp Ala Ala Phe Arg Ser Gln Val Leu Ala Leu Ile Thr Asn Phe Gly
            435                 440                 445
Val Glu Ser Phe Arg Glu Leu Ile Gly Phe Leu Glu Lys Thr Phe Tyr
            450                 455                 460
Tyr His Gln Arg Lys Asp Leu Glu Ile Leu Glu Gly Lys Ala Lys Ser
465                 470                 475                 480
Ile Val Tyr Phe Leu Leu Glu Asn Glu Phe Ile Asp Ile Asp Leu Asn
                485                 490                 495
Asp Ser Phe Ile Ala Leu Pro Phe Gly Ile Arg Thr Ser Gln Leu Tyr
            500                 505                 510
Leu Asp Pro Leu Thr Ala Lys Lys Phe Lys Asp Ala Leu Pro Gln Ile
            515                 520                 525
Glu Glu Asn Pro Asn Pro Leu Gly Ile Phe Gln Leu Leu Ala Ser Thr
530                 535                 540
Pro Asp Met Gly Thr Leu Ser Ile Lys Arg Lys Glu Gln Glu Ser Tyr
545                 550                 555                 560
Leu Asp Tyr Ala Tyr Glu Met Glu Asp Tyr Leu Tyr Arg Ser Ile Pro
                565                 570                 575
Tyr Trp Glu Asp Tyr Glu Phe Gln Lys Phe Leu Ser Glu Val Lys Thr
            580                 585                 590
Ala Lys Leu Leu Leu Asp Trp Ile Asn Glu Val Ser Gly Ala Lys Leu
            595                 600                 605
Ile Glu Ala Tyr Gly Ile Asp Thr Gly Asp Leu Tyr Arg Ile Ile Glu
            610                 615                 620
Leu Ala Asp Trp Leu Met Tyr Ser Leu Ile Glu Leu Ala Lys Val Leu
625                 630                 635                 640
Asn Ala Gly Gly Glu Thr Ile Lys Tyr Leu Arg Arg Leu His Leu Arg
                645                 650                 655
Leu Lys His Gly Val Arg Glu Glu Leu Leu Glu Leu Val Glu Leu Pro
            660                 665                 670
Met Ile Gly Arg Arg Arg Ala Arg Ala Leu Tyr Asn Ala Gly Phe Lys
            675                 680                 685
```

```
Asn Val Asn Asp Ile Val Lys Ala Lys Pro Ser Glu Leu Ala Val
    690             695                 700

Glu Gly Ile Gly Val Lys Val Leu Glu Arg Ile Tyr Arg His Phe Gly
705                 710                 715                 720

Val Glu Leu Pro Leu Leu Lys Asn Ile Lys Asp Pro Asp Lys Pro Glu
                725                 730                 735

Asp Lys Pro Lys Glu Lys Pro Lys Pro Lys Lys Gly Thr Leu Asp Tyr
            740                 745                 750

Phe Leu Lys
        755

<210> SEQ ID NO 35
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 35

Gln Met Ile Gly Arg Ala Gly Arg
1               5

<210> SEQ ID NO 36
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 36

Gln Met Ile Gly Arg Ala Gly Arg Pro
1               5

<210> SEQ ID NO 37
<211> LENGTH: 744
<212> TYPE: PRT
<213> ORGANISM: Thermococcus sibiricus

<400> SEQUENCE: 37

Met Lys Leu Asn Lys Leu Lys Ser Tyr Ile Asn Ala Phe Leu Leu Gly
1               5                   10                  15

Met Val Met Ser Met Lys Val Asp Glu Leu Lys Ser Leu Gly Val Asp
                20                  25                  30

Glu Arg Ile Leu Arg Leu Leu Arg Glu Arg Gly Ile Glu Glu Leu Tyr
            35                  40                  45

Pro Pro Gln Ala Asp Ala Leu Lys Thr Glu Val Leu Lys Gly Lys Asn
        50                  55                  60

Leu Val Leu Ala Ile Pro Thr Ala Ser Gly Lys Thr Leu Val Ala Glu
65                  70                  75                  80

Ile Val Met Ile Asn Lys Ile Leu Arg Glu Gly Gly Lys Thr Val Tyr
                85                  90                  95

Leu Val Pro Leu Lys Ala Leu Ala Glu Glu Lys Tyr Lys Glu Phe Lys
            100                 105                 110

Phe Trp Glu Lys Leu Gly Ile Arg Ile Ala Met Thr Thr Gly Asp Tyr
        115                 120                 125

Asp Ser Thr Glu Glu Trp Leu Gly Lys Tyr Asp Ile Ile Ala Thr
    130                 135                 140

Ser Glu Lys Phe Asp Ser Leu Leu Arg His Lys Ser Pro Trp Ile Lys
145                 150                 155                 160
```

-continued

```
Asp Ile Asn Leu Val Ile Ala Asp Glu Ile His Leu Leu Gly Ser Tyr
            165                 170                 175
Asp Arg Gly Ala Thr Leu Glu Met Ile Leu Ala His Leu Asp Asp Lys
        180                 185                 190
Ala Gln Ile Leu Gly Leu Ser Ala Thr Val Gly Asn Ala Glu Glu Val
    195                 200                 205
Ala Glu Trp Leu Asn Ala Asp Leu Val Met Ser Glu Trp Arg Pro Val
210                 215                 220
Ala Leu Arg Lys Gly Val Phe Tyr His Gly Glu Leu Phe Trp Glu Asp
225                 230                 235                 240
Gly Ser Ile Glu Arg Phe Pro Thr Gln Trp Asp Ser Leu Val Ile Asp
            245                 250                 255
Ala Leu Lys Lys Gly Lys Gln Ala Leu Val Phe Val Asn Thr Arg Arg
        260                 265                 270
Ser Ala Glu Lys Glu Ala Leu Leu Leu Ala Gly Lys Ile Gln Arg Phe
    275                 280                 285
Leu Thr Lys Pro Glu Glu Arg Lys Leu Lys Gln Leu Ala Asp Gly Leu
290                 295                 300
Asp Thr Thr Pro Thr Asn Gln Lys Leu Lys Glu Ala Leu Thr Lys Gly
305                 310                 315                 320
Val Ala Phe His His Ala Gly Leu Gly Arg Thr Glu Arg Ser Ile Ile
            325                 330                 335
Glu Asp Ala Phe Arg Glu Gly Leu Ile Lys Val Ile Thr Ala Thr Pro
        340                 345                 350
Thr Leu Ser Ala Gly Val Asn Leu Pro Ala Tyr Arg Val Ile Ile Arg
    355                 360                 365
Asp Thr Lys Arg Tyr Ser Asn Phe Gly Trp Val Asp Ile Pro Val Leu
370                 375                 380
Glu Ile Gln Gln Met Met Gly Arg Ala Gly Arg Pro Lys Tyr Asp Ile
385                 390                 395                 400
Glu Gly Gln Ala Ile Ile Ile Ala Lys Thr Glu Lys Pro Glu Asp Leu
            405                 410                 415
Met Lys Arg Tyr Val Leu Gly Lys Pro Glu Lys Leu Phe Ser Met Leu
        420                 425                 430
Ser Asn Glu Ala Ser Phe Arg Ser Gln Val Leu Ala Leu Ile Thr Asn
    435                 440                 445
Phe Gly Val Gly Asn Phe Lys Glu Leu Val Asn Phe Leu Glu Arg Thr
450                 455                 460
Phe Tyr Tyr His Gln Arg Lys Asn Leu Glu Ala Leu Glu Gly Lys Ala
465                 470                 475                 480
Lys Ser Ile Val Tyr Phe Leu Phe Glu Asn Glu Phe Ile Asp Ile Asp
            485                 490                 495
Leu Asn Asp Gln Phe Met Pro Leu Pro Leu Gly Ile Arg Thr Ser Gln
        500                 505                 510
Leu Tyr Leu Asp Pro Val Thr Ala Lys Lys Phe Lys Asp Ala Phe Glu
    515                 520                 525
Lys Leu Glu Lys Asn Pro Asn Pro Leu Gly Ile Phe Gln Leu Leu Ala
530                 535                 540
Ser Thr Pro Asp Met Ser Ser Leu Arg Val Lys Arg Lys Glu Gln Glu
545                 550                 555                 560
Asp Leu Leu Asp Tyr Ala Tyr Glu Met Glu Glu Tyr Leu Tyr Gln Asn
            565                 570                 575
Ile Pro Tyr Trp Glu Asp Tyr Lys Phe Glu Lys Phe Leu Gly Glu Thr
```

```
            580             585             590
Lys Thr Ala Lys Leu Leu Asp Trp Ile Asn Glu Val Asn Asp Val
            595             600             605

Lys Ile Leu Glu Thr Tyr Glu Ile Asp Thr Gly Asp Leu Tyr Arg Ile
610             615             620

Leu Glu Leu Val Asp Trp Leu Met Tyr Ser Leu Ile Glu Leu Tyr Lys
625             630             635             640

Leu Phe Asp Pro Lys Pro Glu Val Leu Asp Phe Leu Lys Lys Leu His
            645             650             655

Ile Arg Val Lys His Gly Val Arg Glu Glu Leu Leu Glu Leu Ile Thr
            660             665             670

Leu Pro Met Ile Gly Arg Lys Arg Ala Arg Ala Leu Tyr Asn Ala Gly
            675             680             685

Phe Lys Gly Ile Asp Asp Ile Val Arg Ala Lys Ala Ser Glu Leu Leu
            690             695             700

Lys Val Glu Gly Ile Gly Ile Gly Val Ile Glu Lys Ile Tyr Gln His
705             710             715             720

Phe Gly Val Glu Leu Pro Thr Asn Glu Lys Lys Lys Val Lys Lys
            725             730             735

Gly Thr Leu Asp Glu Phe Phe Lys
            740

<210> SEQ ID NO 38
<211> LENGTH: 729
<212> TYPE: PRT
<213> ORGANISM: Methanosarcina barkeri fusaro

<400> SEQUENCE: 38

Met Lys Ile Glu Ser Leu Asp Leu Pro Asp Glu Val Lys Gln Phe Tyr
1               5                   10                  15

Leu Asn Ser Gly Ile Met Glu Leu Tyr Pro Pro Gln Ala Glu Ala Val
            20                  25                  30

Glu Lys Gly Leu Leu Glu Gly Arg Asn Leu Leu Ala Ala Ile Pro Thr
        35                  40                  45

Ala Ser Gly Lys Thr Leu Leu Ala Glu Leu Ala Met Leu Lys Ser Ile
    50                  55                  60

Leu Ala Gly Gly Lys Ala Leu Tyr Ile Val Pro Leu Arg Ala Leu Ala
65                  70                  75                  80

Ser Glu Lys Phe Arg Arg Phe Arg Glu Phe Ser Glu Leu Gly Ile Arg
                85                  90                  95

Val Gly Ile Ser Thr Gly Asp Tyr Asp Leu Arg Asp Glu Gly Leu Gly
            100                 105                 110

Val Asn Asp Ile Ile Val Ala Thr Ser Glu Lys Thr Asp Ser Leu Leu
        115                 120                 125

Arg Asn Glu Thr Val Trp Met Gln Glu Ile Ser Val Val Ala Asp
    130                 135                 140

Glu Val His Leu Ile Asp Ser Pro Asp Arg Gly Pro Thr Leu Glu Val
145                 150                 155                 160

Thr Leu Ala Lys Leu Arg Lys Met Asn Pro Ser Cys Gln Ile Leu Ala
                165                 170                 175

Leu Ser Ala Thr Val Gly Asn Ala Asp Glu Leu Ala Val Trp Leu Glu
            180                 185                 190

Ala Glu Leu Val Val Ser Glu Trp Arg Pro Thr Glu Leu Leu Glu Gly
        195                 200                 205
```

```
Val Phe Phe Asn Gly Thr Phe Tyr Cys Lys Asp Arg Glu Lys Thr Val
210                 215                 220
Glu Gln Ser Thr Lys Asp Glu Ala Val Asn Leu Ala Leu Asp Thr Leu
225                 230                 235                 240
Lys Lys Asp Gly Gln Cys Leu Val Phe Glu Ser Ser Arg Lys Asn Cys
                245                 250                 255
Met Ala Phe Ala Lys Lys Ala Ala Ser Thr Val Lys Lys Thr Leu Ser
                260                 265                 270
Ala Glu Asp Arg Asn Ala Leu Ala Gly Ile Ala Asp Glu Ile Leu Glu
                275                 280                 285
Asn Ser Glu Thr Asp Thr Ser Thr Asn Leu Ala Val Cys Ile Arg Ser
290                 295                 300
Gly Thr Ala Phe His His Ala Gly Leu Thr Thr Pro Leu Arg Glu Leu
305                 310                 315                 320
Val Glu Asp Gly Phe Arg Ala Gly Arg Ile Lys Leu Ile Ser Ser Thr
                325                 330                 335
Pro Thr Leu Ala Ala Gly Leu Asn Leu Pro Ala Arg Arg Val Ile Ile
                340                 345                 350
Arg Asn Tyr Arg Arg Tyr Ser Ser Glu Asp Gly Met Gln Pro Ile Pro
                355                 360                 365
Val Leu Glu Tyr Lys Gln Met Ala Gly Arg Ala Gly Arg Pro Arg Leu
370                 375                 380
Asp Pro Tyr Gly Glu Ala Val Leu Val Ala Lys Ser Tyr Lys Glu Phe
385                 390                 395                 400
Val Phe Leu Phe Glu Asn Tyr Ile Glu Ala Asn Ala Glu Asp Ile Trp
                405                 410                 415
Ser Lys Leu Gly Thr Glu Asn Ala Leu Arg Thr His Val Leu Ser Thr
                420                 425                 430
Ile Ser Asn Gly Phe Ala Arg Thr Tyr Asp Glu Leu Met Asp Phe Leu
435                 440                 445
Glu Ala Thr Phe Phe Ala Phe Gln Tyr Ser Asn Phe Gly Leu Ser Thr
                450                 455                 460
Val Val Asn Glu Cys Leu Asn Phe Leu Arg Gln Glu Gly Met Leu Glu
465                 470                 475                 480
Lys Asp Asp Ala Leu Ile Pro Thr Ser Phe Gly Lys Leu Val Ser Arg
                485                 490                 495
Leu Tyr Ile Asp Pro Leu Ser Ala Ala Arg Ile Ala Lys Gly Leu Lys
                500                 505                 510
Gly Ala Lys Ser Leu Ser Glu Leu Thr Leu Leu His Leu Val Cys Ser
                515                 520                 525
Thr Pro Asp Met Arg Leu Leu Tyr Met Arg Ser His Asp Tyr Gln Asp
530                 535                 540
Ile Asn Asp Tyr Val Met Ala His Ala Ser Glu Phe Val Lys Val Pro
545                 550                 555                 560
Ser Pro Phe Asp Thr Thr Glu Tyr Glu Trp Phe Leu Gly Glu Val Lys
                565                 570                 575
Thr Ser Leu Leu Leu Leu Asp Trp Ile His Glu Lys Ser Glu Asn Glu
                580                 585                 590
Ile Cys Leu Lys Phe Gly Thr Gly Glu Gly Asp Ile His Ser Ile Ala
                595                 600                 605
Asp Ile Ala Glu Trp Ile Met His Val Thr Ser Gln Leu Ala Gly Leu
                610                 615                 620
Leu Asp Leu Lys Gly Ala Arg Glu Ala Ala Glu Leu Glu Lys Arg Ile
```

His Tyr Gly Ala Ala Pro Glu Leu Ile Asp Leu Leu Asn Ile Arg Gly
625                 630                 635                 640

Ile Gly Arg Val Arg Ala Arg Lys Leu Tyr Glu Ala Gly Phe Lys Ser
            645                 650                 655

Ser Ala Glu Leu Ala Glu Val Asp Pro Glu Lys Val Ala Ala Leu Leu
                660                 665                 670

Gly Pro Lys Ile Ala Asp Arg Ile Phe Lys Gln Ile Arg Gly Arg Gly
        675                 680                 685

Thr Ser Ser Gly Ile Ile Ala Ser Glu Pro Glu Lys Ser Pro Tyr
690                 695                 700

Ser Gly Gln Lys Thr Ile Ser Asp Tyr
705                 710                 715                 720

725

<210> SEQ ID NO 39
<211> LENGTH: 730
<212> TYPE: PRT
<213> ORGANISM: Methanosarcina acetivorans

<400> SEQUENCE: 39

Met Lys Ile Glu Ser Leu Asp Leu Pro Asp Glu Val Lys Arg Phe Tyr
1               5                   10                  15

Glu Asn Ser Gly Ile Pro Glu Leu Tyr Pro Pro Gln Ala Glu Ala Val
            20                  25                  30

Glu Lys Gly Leu Leu Glu Gly Lys Asn Leu Leu Ala Ala Ile Pro Thr
        35                  40                  45

Ala Ser Gly Lys Thr Leu Leu Ala Glu Leu Ala Met Leu Lys Ser Val
    50                  55                  60

Leu Ala Gly Gly Lys Ala Leu Tyr Ile Val Pro Leu Arg Ala Leu Ala
65                  70                  75                  80

Ser Glu Lys Phe Arg Arg Phe Gln Asp Phe Ser Glu Leu Gly Ile Arg
                85                  90                  95

Val Gly Ile Ser Thr Gly Asp Tyr Asp Arg Arg Asp Glu Gly Leu Gly
            100                 105                 110

Ile Asn Asp Ile Ile Val Ala Thr Ser Glu Lys Thr Asp Ser Leu Leu
        115                 120                 125

Arg Asn Glu Thr Ala Trp Met Gln Glu Ile Ser Val Val Val Val Asp
130                 135                 140

Glu Val His Leu Ile Asp Ser Ala Asp Arg Gly Pro Thr Leu Glu Val
145                 150                 155                 160

Thr Leu Ala Lys Leu Arg Lys Met Asn Pro Phe Cys Gln Ile Leu Ala
                165                 170                 175

Leu Ser Ala Thr Val Gly Asn Ala Asp Glu Leu Ala Ala Trp Leu Asp
            180                 185                 190

Ala Glu Leu Val Leu Ser Glu Trp Arg Pro Thr Asp Leu Met Glu Gly
        195                 200                 205

Val Phe Phe Asp Gly Thr Phe Phe Cys Lys Asp Lys Glu Lys Leu Ile
    210                 215                 220

Glu Gln Pro Thr Lys Asp Glu Ala Ile Asn Leu Val Leu Asp Thr Leu
225                 230                 235                 240

Arg Glu Gly Gly Gln Cys Leu Val Phe Glu Ser Ser Arg Lys Asn Cys
                245                 250                 255

Met Gly Phe Ala Lys Lys Ala Thr Ser Ala Val Lys Lys Thr Leu Ser
            260                 265                 270

```
Ala Glu Asp Lys Glu Lys Leu Ala Gly Ile Ala Asp Glu Ile Leu Glu
            275                 280                 285

Asn Ser Glu Thr Asp Thr Ala Ser Val Leu Ala Ser Cys Val Arg Ala
        290                 295                 300

Gly Thr Ala Phe His His Ala Gly Leu Thr Ser Pro Leu Arg Glu Leu
305                 310                 315                 320

Val Glu Thr Gly Phe Arg Gly Tyr Val Lys Leu Ile Ser Ser Thr
                325                 330                 335

Pro Thr Leu Ala Ala Gly Leu Asn Pro Ala Arg Arg Val Ile Ile
            340                 345                 350

Arg Ser Tyr Arg Arg Tyr Ser Ser Asp Ser Gly Met Gln Pro Ile Pro
        355                 360                 365

Val Leu Glu Tyr Lys Gln Met Ala Gly Arg Ala Gly Arg Pro Arg Leu
    370                 375                 380

Asp Pro Tyr Gly Glu Ala Val Leu Leu Ala Lys Ser Tyr Glu Glu Leu
385                 390                 395                 400

Leu Phe Leu Phe Glu Lys Tyr Ile Glu Ala Gly Ala Glu Asp Ile Trp
                405                 410                 415

Ser Lys Leu Gly Thr Glu Asn Ala Leu Arg Thr His Val Leu Ser Thr
            420                 425                 430

Ile Ser Asn Gly Phe Ala Arg Thr Lys Glu Glu Leu Met Asp Phe Leu
435                 440                 445

Glu Ala Thr Phe Phe Ala Tyr Gln Tyr Ser Asn Phe Gly Leu Ser Val
    450                 455                 460

Val Val Asp Glu Cys Leu Asn Phe Leu Arg Gln Glu Gly Met Leu Glu
465                 470                 475                 480

Gln Asp Ser Asp Ala Leu Ile Ser Thr Met Phe Gly Lys Leu Val Ser
                485                 490                 495

Arg Leu Tyr Ile Asp Pro Leu Ser Ala Ala Leu Ile Ala Lys Gly Leu
            500                 505                 510

Arg Glu Ala Gly Thr Leu Thr Glu Leu Thr Leu Leu His Leu Val Cys
        515                 520                 525

Ser Thr Pro Asp Met Arg Leu Met Tyr Met Arg Ser Gln Asp Tyr Gln
    530                 535                 540

Asp Ile Asn Asp Phe Val Met Ala His Ala Glu Glu Phe Ser Lys Val
545                 550                 555                 560

Pro Ser Pro Phe Asn Ile Val Glu Tyr Glu Trp Phe Leu Ser Glu Val
                565                 570                 575

Lys Thr Ser Leu Leu Leu Met Asp Trp Ile His Glu Lys Pro Glu Asn
            580                 585                 590

Glu Ile Cys Leu Lys Phe Gly Thr Gly Glu Gly Asp Ile His Thr Thr
        595                 600                 605

Ala Asp Ile Ala Glu Trp Ile Met His Val Ala Thr Gln Leu Ala Arg
    610                 615                 620

Leu Leu Asp Leu Lys Gly Ala Lys Glu Ala Ala Glu Leu Glu Lys Arg
625                 630                 635                 640

Ile His Tyr Gly Ala Gly Pro Glu Leu Met Asp Leu Leu Asp Ile Arg
                645                 650                 655

Gly Ile Gly Arg Val Arg Ala Arg Lys Leu Tyr Gly Ala Gly Phe Lys
            660                 665                 670

Ser Thr Ala Asp Leu Ala Gly Ala Thr Pro Glu Lys Val Ala Ala Leu
        675                 680                 685

Val Gly Pro Lys Ile Ala Glu Arg Ile Phe Arg Gln Ile Gly Arg Arg
```

-continued

```
                690                 695                 700
Glu Ala Val Ser Glu Ile Ser Asp Ser Glu Arg Leu Glu Lys Ser Ser
705                 710                 715                 720

Gln Asp Gly Gln Ser Thr Ile Ser Asp Phe
                725                 730

<210> SEQ ID NO 40
<211> LENGTH: 729
<212> TYPE: PRT
<213> ORGANISM: Methanohalophilus mahii

<400> SEQUENCE: 40

Met Lys Ile Glu Glu Leu Asp Leu Pro Ser Glu Ala Ile Glu Val Tyr
1               5                   10                  15

Leu Gln Ala Gly Ile Glu Glu Leu Tyr Pro Pro Gln Ala Asp Ala Val
                20                  25                  30

Glu Lys Gly Leu Leu Gln Gly Glu Asn Leu Leu Ala Ala Ile Pro Thr
            35                  40                  45

Ala Ser Gly Lys Thr Leu Leu Ala Glu Met Ala Met Leu Lys Ala Ile
        50                  55                  60

Lys Lys Gly Gly Lys Ala Leu Tyr Ile Val Pro Leu Arg Ala Leu Ala
65                  70                  75                  80

Ser Glu Lys Phe Arg Asp Phe Lys Arg Phe Glu Ser Leu Gly Ile Lys
                85                  90                  95

Thr Ala Ile Ser Thr Gly Asp Phe Asp Ser Arg Asp Glu Trp Leu Gly
            100                 105                 110

Ser Asn Asp Ile Ile Val Ala Thr Ser Glu Lys Thr Asp Ser Leu Leu
        115                 120                 125

Arg Asn Ser Thr Pro Trp Met Lys Asp Ile Thr Ala Val Ile Val Asp
130                 135                 140

Glu Val His Leu Leu Asp Ser Ala Asn Arg Gly Pro Thr Leu Glu Val
145                 150                 155                 160

Thr Leu Ala Lys Leu Lys Arg Leu Asn Pro Gly Ala Gln Val Val Ala
                165                 170                 175

Leu Ser Ala Thr Val Gly Asn Ala Met Glu Ile Ala Gln Trp Leu Glu
            180                 185                 190

Ala Lys Leu Val Leu Ser Glu Trp Arg Pro Thr Tyr Leu His Glu Gly
        195                 200                 205

Ile Phe Tyr Gly Asp Ala Ile Asn Phe Asp Glu Asp Gln Thr Phe Ile
210                 215                 220

Glu Arg Arg His Lys Glu Asp Ser Val Asn Leu Val Ile Asp Thr Val
225                 230                 235                 240

Ile Gln Gly Gly Gln Cys Leu Val Phe Asp Ser Ser Arg Arg Asn Cys
                245                 250                 255

Val Gly Phe Ala Lys Lys Cys Ala Pro Ala Val Gly Glu Leu Leu Asp
            260                 265                 270

Arg Gln Asn Arg Asn Glu Leu Glu Glu Val Ala Lys Glu Val Leu Glu
        275                 280                 285

Asn Gly Glu Thr Lys Leu Thr Glu Thr Leu Ala Tyr Cys Ile Lys Lys
        290                 295                 300

Gly Val Ala Phe His His Ala Gly Leu Asn Ser Ala His Arg Arg Ile
305                 310                 315                 320

Val Glu Asp Ala Phe Arg Asn Asn Leu Ile Lys Met Ile Cys Ser Thr
                325                 330                 335
```

```
Pro Thr Leu Ala Ala Gly Leu Asn Leu Pro Ala Arg Arg Val Ile Ile
            340                 345                 350
Arg Ser Tyr Lys Arg Tyr Asp Pro Asn Ala Gly Met Gln Pro Ile Pro
        355                 360                 365
Val Leu Asp Tyr Lys Gln Met Ala Gly Arg Ala Gly Arg Pro His Leu
    370                 375                 380
Asp Pro Tyr Gly Glu Ala Val Ile Val Lys Thr Tyr Glu Glu Phe
385                 390                 395                 400
Thr Asp Val Leu Glu Arg Tyr Ile Ser Ala Ser Ala Glu Asp Ile Trp
                405                 410                 415
Ser Lys Leu Gly Thr Glu Asn Ala Leu Arg Thr His Ile Leu Ser Thr
            420                 425                 430
Ile Ala Ser Gly Phe Ala Asn Cys His Arg Glu Ile Leu Thr Phe Leu
        435                 440                 445
Gly Ser Thr Phe Phe Ala His Gln Gln Gln Ser Trp Asn Phe Glu Glu
    450                 455                 460
Leu Leu Glu Asp Cys Leu Ile Phe Leu Lys Asn Glu Gly Met Leu Glu
465                 470                 475                 480
Gln Asp Asn Glu Thr Ile Arg Ala Thr Glu Leu Gly Lys Met Ile Ser
                485                 490                 495
Ser Leu Tyr Ile Asp Pro Leu Ser Ala Ser Lys Ile Ile Arg Gly Leu
            500                 505                 510
Glu Lys Thr Thr His Val Thr Asp Met Thr Leu Leu Gln Leu Ile Cys
        515                 520                 525
Ser Thr Pro Asp Met Arg Leu Leu Tyr Leu Arg Asn Arg Asp Tyr Glu
    530                 535                 540
Ile Ile Asn Asp Tyr Val Met Asn His Thr Glu Glu Phe Ile Glu Val
545                 550                 555                 560
Pro Ser Pro Phe Lys Gln Ile Glu Tyr Glu Trp Phe Leu Ser Glu Val
                565                 570                 575
Lys Thr Ala Leu Leu Leu Leu Glu Trp Ile Asn Glu Lys Ser Leu Glu
            580                 585                 590
Lys Ile Val Glu Asn Tyr Gln Val Gly Glu Gly Asp Ile Tyr Ala Ser
        595                 600                 605
Ser Asp Ile Ala Glu Trp Leu Met His Ala Thr Gln Arg Ile Ala Ser
    610                 615                 620
Arg Ile Asn Pro Gln Leu Glu Thr Glu Cys Ala Lys Leu Glu Lys Arg
625                 630                 635                 640
Ile His Tyr Gly Ala Gly Ser Glu Leu Ile Glu Leu Val Glu Ile Pro
                645                 650                 655
Asn Val Gly Arg Ala Arg Ala Arg Lys Leu Phe Lys Lys Gly Tyr Arg
            660                 665                 670
Ser Arg Gln Lys Leu Ala Thr Ala Asp Glu Lys Gln Leu Ala Gly Ile
        675                 680                 685
Val Gly Pro Lys Ile Ala Gln Lys Ile Leu Ser Tyr Leu Gly Arg Glu
    690                 695                 700
Thr Asp Ser Asn Gly Tyr Val Glu Pro Glu Thr Leu Glu Asn Lys Lys
705                 710                 715                 720
Gln Gln Lys Thr Phe Gln Asp Phe Ile
                725

<210> SEQ ID NO 41
<211> LENGTH: 730
<212> TYPE: PRT
```

<213> ORGANISM: Methanosarcina mazei

<400> SEQUENCE: 41

```
Met Lys Ile Glu Ser Leu Asp Leu Pro Asp Glu Ile Lys Arg Phe Tyr
1               5                   10                  15

Glu Asn Ser Gly Ile Leu Glu Leu Tyr Pro Pro Gln Ala Glu Ala Val
            20                  25                  30

Glu Lys Gly Leu Leu Glu Gly Lys Asn Leu Leu Ala Ala Ile Pro Thr
        35                  40                  45

Ala Ser Gly Lys Thr Leu Leu Ala Glu Leu Ala Met Leu Lys Ser Val
    50                  55                  60

Leu Asn Gly Gly Lys Ala Leu Tyr Ile Val Pro Leu Arg Ala Leu Ala
65                  70                  75                  80

Ser Glu Lys Phe Arg Arg Phe Gln Glu Phe Ser Val Leu Gly Met Arg
                85                  90                  95

Val Gly Ile Ser Thr Gly Asp Tyr Asp Arg Arg Asp Glu Gly Leu Gly
            100                 105                 110

Ile Asn Asp Ile Ile Val Ala Thr Ser Glu Lys Thr Asp Ser Leu Leu
        115                 120                 125

Arg Asn Glu Thr Ala Trp Met Gln Glu Ile Ser Val Val Val Ala Asp
130                 135                 140

Glu Val His Leu Ile Asp Ser Pro Asp Arg Gly Pro Thr Leu Glu Ile
145                 150                 155                 160

Thr Leu Ser Lys Leu Arg Arg Met Asn Pro Ser Cys Gln Val Leu Ala
                165                 170                 175

Leu Ser Ala Thr Val Gly Asn Ala Asp Glu Leu Ala Ala Trp Leu Asp
            180                 185                 190

Ala Glu Leu Val Leu Ser Glu Trp Arg Pro Thr Asp Leu Met Glu Gly
        195                 200                 205

Val Phe Tyr Asn Gly Ile Phe Tyr Cys Lys Asp Lys Glu Lys Pro Val
    210                 215                 220

Gly Gln Pro Thr Lys Asp Glu Ala Val Asn Leu Val Leu Asp Thr Ile
225                 230                 235                 240

Lys Glu Gly Gly Gln Cys Leu Val Phe Glu Ser Ser Arg Lys Asn Cys
                245                 250                 255

Met Gly Phe Ala Lys Lys Ala Val Ser Ala Val Lys Lys Thr Leu Ser
            260                 265                 270

Asn Glu Asp Arg Glu Thr Leu Ala Gly Ile Ala Asp Glu Ile Ile Glu
        275                 280                 285

Asn Ser Glu Thr Asp Val Ser Ser Val Leu Ala Thr Cys Val Arg Ser
    290                 295                 300

Gly Thr Ala Phe His His Ala Gly Leu Thr Thr Pro Leu Arg Glu Leu
305                 310                 315                 320

Val Glu Asn Gly Phe Arg Glu Gly Arg Ile Lys Ile Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Arg Arg Tyr Ser Ser Asp Ser Gly Met Gln Pro Ile Pro
        355                 360                 365

Val Leu Glu Tyr Lys Gln Met Ala Gly Arg Ala Gly Arg Pro Arg Leu
    370                 375                 380

Asp Pro Tyr Gly Glu Ala Val Leu Leu Ala Lys Ser Tyr Glu Glu Phe
385                 390                 395                 400
```

```
Val Phe Leu Phe Glu Lys Tyr Ile Glu Ala Gly Ala Glu Asp Ile Trp
            405                 410                 415

Ser Lys Leu Gly Thr Glu Asn Ala Leu Arg Thr His Ile Leu Ser Thr
        420                 425                 430

Ile Ser Asn Gly Phe Ala Arg Thr Arg Glu Glu Leu Met Asp Phe Leu
        435                 440                 445

Glu Ala Thr Phe Phe Ala Phe Gln Tyr Ser Asn Phe Gly Leu Ser Ala
    450                 455                 460

Val Val Asp Glu Cys Leu Asp Phe Leu Arg Arg Glu Gly Met Leu Glu
465                 470                 475                 480

Lys Asp Pro Asp Ala Leu Val Ser Thr Val Phe Gly Lys Leu Val Ser
                485                 490                 495

Arg Leu Tyr Ile Asp Pro Leu Ser Ala Ala Leu Ile Ala Lys Gly Leu
            500                 505                 510

Arg Glu Ala Gly Thr Leu Thr Glu Leu Thr Leu Leu His Leu Ile Cys
        515                 520                 525

Ser Thr Pro Asp Met Arg Leu Met Tyr Met Arg Ser Gln Asp Tyr Gln
    530                 535                 540

Glu Val Asn Asp Tyr Val Met Ala His Ala Gly Glu Phe Ser Lys Val
545                 550                 555                 560

Pro Asn Pro Phe Asn Ile Ala Glu Tyr Glu Trp Phe Leu Gly Glu Val
                565                 570                 575

Lys Thr Ser Leu Leu Met Asp Trp Ile His Glu Lys Pro Glu Asn
            580                 585                 590

Glu Ile Cys Leu Lys Phe Gly Ile Gly Glu Gly Asp Ile His Ala Thr
    595                 600                 605

Ala Asp Ile Ala Glu Trp Ile Met His Val Thr Ala Gln Leu Ala Gly
610                 615                 620

Leu Leu Asp Leu Lys Gly Ala Lys Glu Ala Ser Glu Leu Glu Lys Arg
625                 630                 635                 640

Ile Arg Tyr Gly Ala Ala Pro Glu Leu Met Asp Leu Leu Asp Ile Arg
                645                 650                 655

Ser Val Gly Arg Val Arg Ala Arg Lys Leu Tyr Glu Ala Gly Phe Lys
            660                 665                 670

Ser Thr Ala Glu Leu Ala Ala Ser Pro Glu His Ile Ala Val Leu
        675                 680                 685

Val Gly Pro Lys Ile Thr Glu Arg Ile Phe Lys Gln Ile Gly Arg Arg
    690                 695                 700

Glu Ala Val Ser Glu Phe Ser Asp Ile Glu Pro Leu Gly Lys Gly Ser
705                 710                 715                 720

Ser Asp Gly Gln Arg Thr Ile Ser Asp Tyr
                725                 730

<210> SEQ ID NO 42
<211> LENGTH: 693
<212> TYPE: PRT
<213> ORGANISM: Methanosaeta thermophila

<400> SEQUENCE: 42

Met Leu Thr Ile Arg Asp Leu Ile Arg Trp Leu Pro Glu Ser Val Ile
1               5                   10                  15

Glu Leu Tyr Glu Ala Leu Gly Ile Asp Glu Leu Tyr Pro Pro Gln Ala
            20                  25                  30

Glu Ala Ile Glu Arg Gly Leu Leu Asp Gly Arg Asn Met Ile Ile Ser
        35                  40                  45
```

-continued

```
Val Pro Thr Ala Ala Gly Lys Thr Leu Leu Ala Glu Leu Ala Met Leu
     50                  55                  60
Arg Gly Ala Leu Ser Gly Lys Arg Ser Leu Tyr Ile Val Pro Leu Arg
 65                  70                  75                  80
Ala Leu Ala Ser Glu Lys Phe Glu Ser Phe Ser Arg Phe Ser Lys Leu
                 85                  90                  95
Gly Leu Arg Val Gly Ile Ser Thr Gly Asp Phe Glu Lys Arg Asp Glu
                100                 105                 110
Arg Leu Gly Arg Asn Asp Ile Ile Ala Thr Ser Glu Lys Ala Asp
                115                 120                 125
Ser Leu Ile Arg Asn Gly Ala Ser Trp Val Arg Arg Ile Gly Val Leu
            130                 135                 140
Val Val Asp Glu Ile His Leu Leu Asp Ser Ala Asn Arg Gly Pro Thr
145                 150                 155                 160
Leu Glu Met Thr Met Thr Lys Leu Met His Leu Asn Pro Glu Met Gln
                    165                 170                 175
Val Ile Gly Leu Ser Ala Thr Ile Ala Asn Gly Arg Glu Ile Ala Asp
                180                 185                 190
Trp Ile Lys Gly Glu Ile Val Ser Ser Asp Trp Arg Pro Val Arg Leu
            195                 200                 205
Arg Glu Gly Val Leu Leu Glu Asp Arg Leu Val Phe Pro Asp Gly Glu
210                 215                 220
Ile Gln Leu Glu Asn Arg Asn Arg Asp Pro Val Leu Asn Leu Val Leu
225                 230                 235                 240
Asp Thr Val Asp Gln Gly Gly Gln Met Leu Ile Phe Glu Ser Thr Arg
                245                 250                 255
Arg Asn Ala Glu Ser Met Ala Lys Lys Val Ser Gly Ala Leu Gln Glu
                260                 265                 270
Ser Gly Glu Thr Ile Glu Leu Ala Glu Arg Leu Ser Gly Glu Gly Lys
            275                 280                 285
Thr Ala Lys Lys Leu Ala Met Cys Leu Arg His Gly Ala Ala Phe His
        290                 295                 300
His Ala Gly Leu Leu Pro Glu Gln Arg Leu Ile Glu Leu Gly Phe
305                 310                 315                 320
Arg Gln Asn Val Val Lys Val Ile Ala Cys Thr Pro Thr Leu Ala Ala
                325                 330                 335
Gly Leu Asn Leu Pro Ala Arg Arg Val Leu Ile Arg Ser Tyr Lys Arg
                340                 345                 350
Tyr Glu Ala Gly Leu Gly Thr Arg Pro Ile Pro Val Met Glu Tyr Arg
            355                 360                 365
Gln Met Ala Gly Arg Ala Gly Arg Pro Gly Leu Asp Pro Tyr Gly Glu
        370                 375                 380
Ser Leu Ile Met Ala Arg Ser Glu Ser Glu Leu Gln Lys Leu Met Asp
385                 390                 395                 400
His Tyr Val Met Gly Glu Pro Glu Asp Ile Trp Ser Lys Leu Ala Ser
                405                 410                 415
Glu Arg Ala Leu Arg Thr His Val Leu Ala Thr Ile Ala Ser Arg Phe
                420                 425                 430
Ala Asp Ser Val Asp Ser Leu Ser Arg Leu Met Ala Ser Thr Phe Tyr
            435                 440                 445
Ala Arg Gln Gln Asp Pro Ser Tyr Leu Gly Glu Thr Ile Ala Ser Val
        450                 455                 460
```

```
Leu Glu Phe Leu Val Arg Ser Asp Met Ile Asp Lys Asp Leu Thr Pro
465                 470                 475                 480

Thr Pro Leu Gly Ala Leu Val Ser Arg Leu Tyr Ile Asp Pro Leu Ser
            485                 490                 495

Ala Met Val Met Ile Gln Glu Ile Arg Gly Ile Arg Arg Pro Thr Val
            500                 505                 510

Leu Thr Leu Leu His Val Ile Thr Met Thr Pro Asp Met Glu Leu Leu
            515                 520                 525

Phe Val Gln Gln Ser Asp Asn Trp Leu Glu Asp Phe Ile Ser Glu His
            530                 535                 540

Ser Ser Glu Leu Gly Asn Glu Lys Asn Phe Asp Trp Leu Leu Arg Glu
545                 550                 555                 560

Val Lys Thr Ala Ser Met Leu Met Asp Trp Ile Asn Glu Val His Glu
            565                 570                 575

Asp Arg Ile Glu Asp Arg Tyr Ser Ile Ser Pro Gly Asp Leu Val Arg
            580                 585                 590

Ile Ala Glu Thr Ala Glu Trp Leu Met Ser Ala Leu His Arg Ile Ser
            595                 600                 605

Lys His Met Asp Leu Gly Val Thr Tyr Leu Ala Glu Arg Leu Ala Leu
            610                 615                 620

Arg Ile His Tyr Gly Ala Gly Asp Glu Leu Leu Gln Leu Leu Glu Leu
625                 630                 635                 640

Lys Gly Ile Gly Arg Val Arg Ala Arg Lys Leu Tyr Gln Ala Gly Tyr
            645                 650                 655

Arg Ser Leu Glu Asp Leu Lys Ala Ala Asp Lys Ser Thr Leu Ser Glu
            660                 665                 670

Ile Leu Gly Pro Lys Ile Ala Glu Gly Val Ile Ser Gln Leu Lys Glu
            675                 680                 685

Pro Gly Val Ser Ala
            690

<210> SEQ ID NO 43
<211> LENGTH: 739
<212> TYPE: PRT
<213> ORGANISM: Methanosalsum zhilinae

<400> SEQUENCE: 43

Met Asn Ile Asn Asn Leu Asn Leu Pro Glu Lys Val Lys Lys Tyr Tyr
1               5                   10                  15

Thr Asp Thr Gly Ile Val Asp Leu Tyr Pro Pro Gln Arg Glu Ala Val
            20                  25                  30

Asp Lys Gly Leu Leu Asp Gly Glu Asn Ile Val Ala Ala Ile Pro Thr
            35                  40                  45

Ala Ser Gly Lys Thr Leu Leu Ala Glu Leu Cys Met Leu Lys Ser Ile
            50                  55                  60

Gly Met Gly Gly Lys Cys Leu Tyr Ile Val Pro Leu Lys Ala Leu Ala
65                  70                  75                  80

Ser Glu Lys Tyr Ser Arg Phe Arg Glu Phe Glu Ser Leu Gly Ile Lys
            85                  90                  95

Val Gly Ile Ala Thr Gly Asp Leu Asp Ser Arg Glu Glu Trp Leu Gly
            100                 105                 110

Lys Asn Asp Ile Ile Ile Ala Thr Ser Glu Lys Val Asp Ser Leu Leu
            115                 120                 125

Arg Asn Glu Ser Ser Trp Met Lys Glu Ile Asn Thr Val Val Ala Asp
            130                 135                 140
```

```
Glu Val His Leu Leu Asn Ser Val Asn Arg Gly Pro Thr Leu Glu Ile
145                 150                 155                 160

Thr Leu Ala Lys Leu Ile His Leu Asn Pro Gly Ser Gln Ile Ile Ala
            165                 170                 175

Leu Ser Ala Thr Ile Gly Asn Pro Glu Asp Ile Ala Gly Trp Leu Gly
            180                 185                 190

Ala Arg Leu Val Val Ser Glu Trp Arg Pro Thr Asp Leu Tyr Glu Gly
            195                 200                 205

Ile Leu Leu Asp Gly Leu Leu His Ile Gly Asn Ile Lys Lys Asp Ile
210                 215                 220

Gln Asp Glu Ser Arg Asp Asp Ala Val Asn Leu Val Ile Asp Thr Val
225                 230                 235                 240

Lys Asp Lys Gly Gln Cys Leu Val Phe Glu Ser Ser Arg Arg Asn Cys
            245                 250                 255

Met Gly Phe Ala Lys Lys Ala Gly Lys Trp Val Ser Lys Ile Leu Asp
            260                 265                 270

Glu His Asp Thr Ile Gln Leu Lys Ser Leu Ser Gln Glu Ile Gly Glu
            275                 280                 285

Ala Gly Glu Thr Glu Ile Ala Asp Val Leu Ser Arg Cys Val Arg Gln
            290                 295                 300

Gly Val Ala Phe His His Ala Gly Leu Asn Ser Glu His Arg Arg Met
305                 310                 315                 320

Val Glu Glu Gly Phe Arg Lys Asn Leu Ile Lys Met Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Lys Arg Tyr Asp Pro Asn Phe Gly Met Lys Pro Ile Pro
            355                 360                 365

Val Leu Glu Tyr Lys Gln Met Ala Gly Arg Ala Gly Arg Pro His Leu
370                 375                 380

Asp Pro Tyr Gly Glu Ser Val Leu Ile Ala Arg Ser Tyr Asp Glu Phe
385                 390                 395                 400

Met Asp Ile Met Glu Asn Tyr Val Asn Ala Asp Pro Glu Asp Ile Trp
                405                 410                 415

Ser Lys Leu Gly Thr Glu Asn Ala Leu Arg Thr His Val Leu Ser Thr
            420                 425                 430

Ile Val Asn Gly Phe Ala Tyr Thr Tyr Arg Gly Leu Met Asp Phe Val
            435                 440                 445

Lys Met Thr Phe Phe Ala Tyr Gln Lys Glu Ala Ser Asp Leu His Asp
            450                 455                 460

Val Ile Glu Glu Cys Val Arg Phe Leu Ile Asp Asn Glu Met Ile Ile
465                 470                 475                 480

Ser Asp Ser Asn Asp Ile Leu Pro Glu Ser Ala Phe Arg Ser Thr Ala
                485                 490                 495

Thr Gly Lys Leu Ile Ser Met Leu Tyr Ile Asp Pro Leu Ser Gly Ser
            500                 505                 510

Leu Ile Met Asp Gly Ile Arg Lys Ala Asp Tyr Phe Glu Asp Ile Thr
            515                 520                 525

Met Met His Leu Ile Cys Ser Thr Pro Asp Met Lys Asn Leu Tyr Met
            530                 535                 540

Arg Ser Ser Asp Tyr Glu Asn Val Asn Met Tyr Val Leu Gln Asn Lys
545                 550                 555                 560
```

Asp Lys Phe Ile Ser Met Pro Ser Pro Phe Lys Met Ile Glu Tyr Glu
                565                 570                 575

Trp Phe Leu Gly Glu Val Lys Thr Ala Leu Leu Leu Leu Asp Trp Ile
            580                 585                 590

Asn Glu Val Pro Ala Asp Asp Ile Cys Lys Lys Tyr Gly Ile Gly Glu
        595                 600                 605

Gly Asp Ile Arg Met Phe Ser Glu Thr Ala Val Trp Leu Met His Ala
    610                 615                 620

Thr Ser Arg Leu Ser Gly Leu Leu Lys Val Ser Glu Ala Ser Glu Lys
625                 630                 635                 640

Ser Lys Glu Leu Glu Lys Arg Leu Ser Tyr Gly Ile Asn Ser Glu Leu
                645                 650                 655

Val Asn Ile Val Ala Leu Lys Gly Ile Gly Arg Val Arg Ala Arg Lys
            660                 665                 670

Ile Tyr Glu Asn Gly Tyr Arg Ser Ile Asp Asp Leu Lys Lys Ala Asp
        675                 680                 685

Pro Leu Lys Leu Ser Lys Ile Val Gly Ser Lys Ile Ser Gln Lys Ile
    690                 695                 700

Leu Lys Gln Leu Asp Ile Asp Val Asp Ile Ser Glu Ile Lys Glu Lys
705                 710                 715                 720

Asp Ser Asp Thr Val Pro Glu Pro Glu Ser Ser Gln Lys Thr Ile Ser
                725                 730                 735

Asp Phe Thr

<210> SEQ ID NO 44
<211> LENGTH: 733
<212> TYPE: PRT
<213> ORGANISM: Methanohalobium evestigatum

<400> SEQUENCE: 44

Met Glu Thr Gly Lys Leu Glu Leu Pro Glu Tyr Val Ile Gln Phe Tyr
1               5                   10                  15

Leu Asp Thr Gly Ile Glu Lys Leu Tyr Pro Pro Gln Ala Glu Ala Val
            20                  25                  30

Glu Lys Gly Leu Leu Asp Asn Lys Asn Leu Leu Ala Ala Ile Pro Thr
        35                  40                  45

Ala Ser Gly Lys Thr Leu Ile Ser Glu Leu Ala Met Leu Lys Ser Ile
50                  55                  60

Ser Asn Gly Gly Lys Cys Leu Tyr Ile Val Pro Leu Arg Ala Leu Ala
65                  70                  75                  80

Ser Glu Lys Phe Glu Arg Phe Lys Gln Phe Ser Ser Ile Gly Val Asn
                85                  90                  95

Ile Gly Ile Ser Thr Gly Asp Phe Asp Ser Thr Asp Glu Trp Leu Gly
            100                 105                 110

Ser Asn Asp Ile Ile Val Ala Thr Ser Glu Lys Ala Asp Ser Leu Leu
        115                 120                 125

Arg Asn Glu Thr Ser Trp Met Lys Asp Ile Thr Thr Ile Val Val Asp
    130                 135                 140

Glu Ile His Leu Leu Asp Ser Ala Asp Arg Gly Pro Thr Leu Glu Ile
145                 150                 155                 160

Thr Ile Ala Lys Leu Leu Arg Leu Asn Pro Asn Ser Gln Ile Ile Gly
                165                 170                 175

Leu Ser Ala Thr Ile Gly Asn Ala Glu Glu Ile Ala Gly Trp Leu Asp
            180                 185                 190

```
Ala Glu Leu Val Gln Ser Gln Trp Arg Pro Ile Glu Leu Tyr Glu Gly
            195                 200                 205
Val Phe Leu Glu Asp Asn Ile Asn Phe Lys Gln Ser Gln Lys Pro Ile
        210                 215                 220
Lys Asn Ile Val Lys Asp Thr Ala Val Asn Leu Val Leu Asp Thr Ile
225                 230                 235                 240
Asp Glu Asn Gly Gln Cys Leu Val Phe Glu Ser Ser Arg Arg Asn Cys
                245                 250                 255
Ala Gly Phe Ala Lys Lys Ala Lys Ser Lys Val Gly Lys Ser Leu Asp
            260                 265                 270
Lys Gly Leu Leu Ala Glu Leu Asn Asn Ile Ala Glu Glu Val Leu Glu
        275                 280                 285
Thr Ser Asp Thr Glu Thr Thr Lys Glu Leu Ala Ser Cys Ile Lys Arg
    290                 295                 300
Gly Thr Ala Phe His His Ala Gly Leu Asn Ser Ala Gln Arg Lys Ile
305                 310                 315                 320
Val Glu Asp Asn Phe Arg Asn Asn Lys Ile Lys Val Ile Ser Ser Thr
                325                 330                 335
Pro Thr Leu Ala Ala Gly Leu Asn Leu Pro Ala Arg Arg Val Ile Val
            340                 345                 350
Arg Asn Tyr Lys Arg Tyr Asp Pro Asn Phe Gly Met Gln Pro Ile Pro
        355                 360                 365
Val Leu Asp Tyr Lys Gln Met Ala Gly Arg Ala Gly Arg Pro Ser Leu
    370                 375                 380
Asp Pro Tyr Gly Glu Ser Val Leu Ile Ser His Thr Tyr Asn Glu Phe
385                 390                 395                 400
Thr Asp Leu Leu Asp Arg Tyr Ile Asp Ala Glu Pro Glu Asp Ile Leu
                405                 410                 415
Ser Lys Leu Gly Thr Glu Asn Ala Leu Arg Thr His Val Leu Ser Thr
            420                 425                 430
Ile Val Asn Gly Phe Ala Thr Thr Arg Gln Gly Met Val Asp Phe Met
        435                 440                 445
Gly Ser Ser Phe Phe Ala Tyr Gln Gln Gln Lys Trp Ser Leu Ile Asp
    450                 455                 460
Val Val Asp Asp Cys Ile Glu Phe Leu Gln Asp Asn Glu Met Ile Lys
465                 470                 475                 480
Asp Asp Gly Glu Arg Leu Tyr Ala Thr Arg Leu Gly Gln Val Ile Ser
                485                 490                 495
Thr Leu Tyr Ile Asp Pro Leu Ser Gly Ala Ile Ile Asp Lys Leu
            500                 505                 510
Lys Lys Ala Asp Lys Val Thr Asp Met Thr Met Leu His Ile Ile Cys
        515                 520                 525
Ser Thr Pro Asp Met Arg Gln Leu Tyr Leu Arg Ser Lys Glu Tyr Glu
    530                 535                 540
Lys Ile Asn Glu Tyr Val Met Thr His Ser Asp Glu Phe Val Glu Val
545                 550                 555                 560
Pro Asn Pro Phe Lys Ser Ile Glu Tyr Glu Trp Phe Leu Gly Glu Val
                565                 570                 575
Lys Thr Ala Leu Leu Ile Asn Glu Trp Ile Asp Glu Lys Thr Leu Asp
            580                 585                 590
Asp Ile Thr Ala Glu Phe Gly Val Gly Glu Gly Asp Ile Asn Ala Leu
        595                 600                 605
Ser Asp Ile Ser Glu Trp Leu Met His Ser Ala Val Asn Leu Ala Asn
```

-continued

```
                610                 615                 620
Leu Thr Asp Leu Asp Ala Asp Lys Ala Gln Glu Leu Glu Lys Arg Ile
625                 630                 635                 640

His His Gly Val Asn Lys Asp Leu Ile Gln Leu Val Ser Ile Ser Asn
                645                 650                 655

Ile Gly Arg Val Arg Ala Arg Lys Leu Tyr Glu Ala Gly Ile Gln Ser
                660                 665                 670

Val Ser Asp Ile Lys Asn Thr Lys Leu His Ile Leu Ser Asn Tyr Leu
                675                 680                 685

Gly Arg Lys Thr Ala Tyr Lys Val Leu Glu Gln Leu Gly Val Glu Pro
                690                 695                 700

Glu Asp Asn Gln Gln Ile Asp Glu Glu Pro Glu Ser Ile Lys Ser Tyr
705                 710                 715                 720

Ser Gly Asn Asp Gln Gly Gln Lys Thr Phe Asn Asp Phe
                725                 730
```

<210> SEQ ID NO 45
<211> LENGTH: 747
<212> TYPE: PRT
<213> ORGANISM: Methanococcus maripaludis

<400> SEQUENCE: 45

```
Met His Val Leu Asp Leu Leu Lys Glu Asn Lys Ile Thr Glu Leu Arg
1               5                   10                  15

Pro Pro Gln Lys Lys Val Ile Asp Glu Gly Leu Phe Asp Lys Thr Lys
                20                  25                  30

Asn Phe Leu Ile Cys Ile Pro Thr Ala Ser Gly Lys Thr Leu Ile Gly
            35                  40                  45

Glu Met Ala Leu Leu Asn His Ile Leu Asp Glu Asn Lys Asn Leu Thr
50                  55                  60

Gly Lys Lys Gly Leu Phe Ile Val Pro Leu Lys Ala Leu Ala Asn Glu
65                  70                  75                  80

Lys Phe Asp Glu Phe Arg Glu Lys Tyr Glu Lys Tyr Gly Ile Lys Val
                85                  90                  95

Gly Leu Ser Ile Gly Asp Phe Asp Thr Lys Glu Asn Leu Ser Lys Phe
            100                 105                 110

His Ile Ile Ile Thr Thr Ser Glu Lys Leu Asp Ser Leu Met Arg His
        115                 120                 125

Asn Val Glu Trp Ile Asn Asp Val Ser Leu Ala Val Ile Asp Glu Ile
    130                 135                 140

His Leu Ile Gly Asp Asn Glu Arg Gly Gly Thr Leu Glu Val Ile Leu
145                 150                 155                 160

Thr Lys Leu Lys Asn Leu Asn Ala Gln Ile Val Gly Leu Ser Ala Thr
                165                 170                 175

Ile Gly Asn Pro Glu Glu Leu Ser Asn Trp Leu Asn Ala Lys Leu Ile
            180                 185                 190

Val Asp Gly Trp Arg Pro Val Glu Leu Lys Lys Gly Ile Tyr Phe Glu
        195                 200                 205

Asn Glu Leu Glu Phe Leu Lys Asn Pro Ala Lys Lys Ile Lys Gln Val
    210                 215                 220

Ser Arg Asn Asn Leu Thr Asp Leu Ile Val Asp Ser Val Glu Glu Lys
225                 230                 235                 240

Gly Ser Cys Leu Ile Phe Cys Asn Ser Lys Arg Asn Ala Val Gly Glu
                245                 250                 255
```

```
Ala Lys Lys His Asn Leu Ala Lys Tyr Leu Thr Arg Thr Glu Gln His
            260                 265                 270

Glu Leu Asn Lys Leu Ser Glu Glu Ile Leu Ser Ile Leu Asp Arg Pro
        275                 280                 285

Val Glu Thr Cys Lys Ala Leu Ser Lys Cys Ile Gln Asn Gly Val Ala
    290                 295                 300

Phe His His Ala Gly Leu Thr Tyr Lys His Arg Lys Ile Val Glu Asp
305                 310                 315                 320

Gly Phe Arg Asn Arg Leu Ile Lys Val Ile Cys Cys Thr Pro Thr Leu
                325                 330                 335

Ser Ala Gly Leu Asn Leu Pro Cys Arg Arg Ala Ile Val Arg Asp Ile
            340                 345                 350

Lys Arg Tyr Ser Gln Asn Gly Leu Val Asp Ile Pro Arg Met Glu Ile
        355                 360                 365

Gln Gln Cys Ile Gly Arg Ala Gly Arg Pro Gly Leu Asp Pro Tyr Gly
    370                 375                 380

Glu Gly Ile Ile Tyr Ile Lys Asn Glu Arg Asp Ala Glu Lys Ala Tyr
385                 390                 395                 400

Glu Ile Leu Thr Gly Ser Val Glu Asn Ile Tyr Ser Lys Leu Ala Asn
                405                 410                 415

Gln Lys Val Leu Arg Ile His Ile Leu Gly Leu Ile Ser Thr Gly Glu
            420                 425                 430

Ile Lys Asp Gly Gln Asn Leu Val Asn Phe Met Lys Asn Thr Phe Tyr
        435                 440                 445

Ala His Gln Phe Gly Asn Ile Gly Ala Val Leu Leu Asn Val Ser Glu
    450                 455                 460

Val Val Glu Phe Leu Glu Lys Asn Lys Phe Leu Glu Thr Thr Ile His
465                 470                 475                 480

Lys Lys Thr Glu Asn Lys Val Arg Glu Leu Ser Phe Asp Ser Ser Asn
                485                 490                 495

Asn Leu Val Leu Asp Ser Lys Glu Thr Ser Phe Asp Leu Thr Asn Pro
            500                 505                 510

Asn Ser Asn Ile Glu Phe Arg Ser Thr Lys Leu Gly Lys Arg Ile Ser
        515                 520                 525

Glu Leu Tyr Ile Asp Pro Met Ser Ser Glu Ile Ile Glu Glu Leu
    530                 535                 540

His Glu Leu Lys Lys Lys Cys Asp Gln Leu Asp Arg Ser Lys Ile Asp
545                 550                 555                 560

Gln Tyr Leu Phe Tyr Leu Ile Ser Lys Thr Asn Glu Met Arg Pro Leu
                565                 570                 575

Leu Arg Ile Arg Pro Asn Glu Glu Leu Asp Leu Ile Leu Glu Met Asp
            580                 585                 590

Lys Met Gly Leu Lys Asp Tyr Ser Ile Glu Asn Ile Glu Ala Phe Lys
        595                 600                 605

Asn Ser Lys Met Phe Cys Asp Trp Val Ser Glu Ile Pro Glu Glu Ile
    610                 615                 620

Ile Leu Glu Lys Tyr Gly Val Glu Pro Gly Ile Leu Arg Tyr Lys Val
625                 630                 635                 640

Glu Gln Ala Lys Trp Met Ile Tyr Ser Thr Lys Glu Ile Ala Lys Leu
                645                 650                 655

Ile His Leu Asp Asn Ser Glu Ile Tyr Lys Ser Leu Leu Lys Met Glu
            660                 665                 670

Val Arg Ile Glu Tyr Gly Ala Lys Glu Glu Leu Ile Glu Leu Leu Asn
```

```
            675                 680                 685
Val Lys Asn Val Gly Arg Ile Arg Ser Arg Lys Leu Tyr Asp Ala Gly
            690                 695                 700

Ile Arg Ser Lys Ile Glu Ile Asn Lys Asn Pro Glu Lys Ile Leu Glu
705                 710                 715                 720

Leu Phe Gly Glu Lys Ile Gly Lys Lys Ile Leu Gly Glu His Gly Met
            725                 730                 735

Lys Tyr Gly Gln Gln Thr Leu Leu Asn Phe Asn
            740                 745

<210> SEQ ID NO 46
<211> LENGTH: 799
<212> TYPE: PRT
<213> ORGANISM: Natrialba magadii

<400> SEQUENCE: 46

Met Asn Val Glu Glu Leu Ser Gly Leu Pro Pro Gly Ala Arg Ser His
1               5                   10                  15

Phe Gln Glu Gln Gly Ile Glu Leu Tyr Pro Pro Gln Ala Glu Ala
            20                  25                  30

Val Glu Ala Gly Ala Thr Glu Gly Glu Asn Leu Val Ala Ala Val Pro
            35                  40                  45

Thr Ala Ser Gly Lys Thr Met Ile Ala Ala Leu Ser Met Leu Ser Ala
50                  55                  60

Val Gln Arg Gly Gly Lys Ala Leu Tyr Ile Val Pro Leu Arg Ala Leu
65                  70                  75                  80

Ala Ser Glu Lys Lys Ala Glu Phe Asp Ala Tyr Glu Glu Phe Gly Val
            85                  90                  95

Thr Thr Gly Val Ala Thr Gly Asn Tyr Glu Ser Thr Ser Glu Trp Leu
            100                 105                 110

Ala Thr Lys Asp Ile Ile Val Ala Thr Ser Glu Lys Val Asp Ser Leu
            115                 120                 125

Val Arg Asn Gly Ala Asp Trp Leu Ser Asp Leu Thr Cys Val Val Ser
            130                 135                 140

Asp Glu Val His Leu Ile Asp Asp Arg Asn Arg Gly Pro Thr Leu Glu
145                 150                 155                 160

Val Thr Leu Ala Lys Leu Arg Arg Leu Asn Pro Gln Leu Gln Val Val
            165                 170                 175

Ala Leu Ser Ala Thr Val Gly Asn Ala Asp Glu Leu Ala Asp Trp Leu
            180                 185                 190

Asp Ala Glu Leu Val Asp Thr Asp Trp Arg Pro Ile Asp Leu Gln Met
            195                 200                 205

Gly Val His Tyr Gly Asn Ala Leu Asn Phe Asp Gly Glu Thr Arg
            210                 215                 220

Glu Val Pro Val Glu Ala Gly Glu Lys Gln Glu Ala Ala Leu Val Arg
225                 230                 235                 240

Asp Ile Leu Gln Glu Gly Gly Ser Ser Leu Val Phe Val Asn Ser Arg
            245                 250                 255

Arg Asn Ala Glu Ala Ala Ala Arg Arg Leu Gly Gln Val Ser Ser Arg
            260                 265                 270

Glu Leu Thr Ala Gly Glu Gln Asn Asp Leu Ala Ala Leu Ala Thr Glu
            275                 280                 285

Ile Arg Glu Asp Ser Asp Thr Glu Thr Ser Gln Asp Leu Ala Asp Cys
            290                 295                 300
```

```
Val Glu Arg Gly Ala Ala Phe His His Ala Gly Leu Ser Ser Thr Gln
305                 310                 315                 320

Arg Ser Leu Val Glu Asp Ala Phe Arg Asp Arg Leu Leu Lys Val Ile
                325                 330                 335

Ser Ala Thr Pro Thr Leu Ala Ala Gly Val Asn Thr Pro Ala Arg Arg
            340                 345                 350

Val Ile Val Arg Asp Trp Arg Arg Phe Asp Pro Ser Ala Gly Gly Met
        355                 360                 365

Ala Pro Leu Asp Val Leu Glu Val His Gln Met Met Gly Arg Ala Gly
370                 375                 380

Arg Pro Gly Leu Asp Pro Tyr Gly Glu Ala Val Leu Leu Ala Lys Ser
385                 390                 395                 400

His Asp Glu Ser Gln Glu Leu Phe Asp Arg Tyr Val Trp Ala Asp Pro
                405                 410                 415

Glu Pro Val Arg Ser Lys Leu Ala Ala Glu Pro Ala Leu Arg Thr His
            420                 425                 430

Val Leu Ala Thr Ile Ala Ser Gly Phe Ala Arg Thr Arg Glu Gly Leu
        435                 440                 445

Leu Glu Phe Leu Glu Ala Thr Leu Tyr Ala Ser Gln Ser Ser Glu Gly
450                 455                 460

Gly Arg Leu Glu Arg Val Thr Asp Asp Val Leu Ser Tyr Leu Glu Arg
465                 470                 475                 480

Asn Asp Phe Ile Glu Arg Ser Gly Gly Pro Glu Asp Thr Leu Asn Ser
                485                 490                 495

Glu Ala Asp Ala Ala Ser Ala Phe Thr Ser Ala Ala Asp Leu Ala Asp
            500                 505                 510

Ser Asp Gly Gly Asp Ser Gly Gly Thr Thr Gly Gln Glu Glu Asp Leu
        515                 520                 525

Glu Ala Thr Ser Leu Gly His Thr Val Ser Arg Leu Tyr Leu Asp Pro
530                 535                 540

Met Ser Ala Ala Glu Ile Val His Gly Leu Glu Asp Ala Asp Glu Arg
545                 550                 555                 560

Pro Thr Ala Leu Gly Leu Tyr Gln Leu Val Ser Arg Thr Pro Asp Met
                565                 570                 575

Tyr Glu Leu Tyr Leu Arg Ser Gly Glu Asp Glu Lys Phe Gly Glu Leu
            580                 585                 590

Tyr Tyr Glu Arg Glu Arg Glu Leu Leu Gly Asp Ala Pro Ser Glu Phe
        595                 600                 605

Glu Glu Glu Arg Phe Glu Asp Trp Leu Ala Ala Leu Lys Thr Gly Lys
610                 615                 620

Leu Leu Glu Asp Trp Ala Thr Glu Asp Asp Glu Glu Gln Ile Thr Glu
625                 630                 635                 640

Arg Tyr Lys Ile Gly Pro Gly Asp Leu Arg Gly Lys Val Asp Thr Ala
                645                 650                 655

Glu Trp Leu Leu Gly Ala Ala Glu Ser Leu Ala Ser Glu Ile Asp Ser
            660                 665                 670

Glu Trp Ala Val Ala Val Arg Glu Ala Arg Ala Arg Val Glu His Gly
        675                 680                 685

Val Gly Glu Glu Leu Leu Glu Leu Val Ser Val Ser Gly Ile Gly Arg
690                 695                 700

Lys Arg Ala Arg Arg Leu Tyr Ala Ala Gly Ile Glu Glu Pro Ala Ala
705                 710                 715                 720

Leu Arg Ser Ala Asp Lys Gly Val Ile Leu His Val Leu Lys Gly Glu
```

-continued

```
                725                 730                 735
Lys Thr Ala Glu Asn Ile Leu Glu Asn Ala Gly Arg Glu Glu Pro Ser
                740                 745                 750

Met Asp Gly Val Glu Pro Ile Pro Val Glu Gly Ser Gly Ser Gly
                755                 760                 765

Ser Ser Asn Ser Ser Gly Ser Ser Glu Pro Asn Ala Asp Ala Asn Ala
                770                 775                 780

Thr Glu Asp Asp Ala Asp Asp Asn Gln Ser Ser Leu Gly Asp Phe
785                 790                 795

<210> SEQ ID NO 47
<211> LENGTH: 723
<212> TYPE: PRT
<213> ORGANISM: Methanoregula boonei

<400> SEQUENCE: 47

Met Gln Ile Gln Asp Leu Ala Ile Pro Glu Pro Leu Arg Gln Tyr
1               5                   10                  15

Leu Gly Leu Gly Ile Arg Glu Leu Tyr Pro Pro Gln Ala Ala Cys Val
                20                  25                  30

Glu Arg Gly Leu Leu Asp Gly Lys Asn Leu Leu Val Ala Ile Pro Thr
            35                  40                  45

Ala Ser Gly Lys Thr Leu Ile Ala Glu Met Ala Met His Arg His Ile
        50                  55                  60

Ala Asn Gly Gly Lys Cys Leu Tyr Ile Val Pro Leu Lys Ala Leu Ala
65                  70                  75                  80

Ser Glu Lys Tyr Glu Glu Phe Gly Asn Lys Gly Val Lys Val Gly Leu
                85                  90                  95

Ser Thr Gly Asp Leu Asp Arg Arg Asp Asp Ala Leu Gly Lys Asn Asp
                100                 105                 110

Ile Ile Val Ala Thr Ser Glu Lys Val Asp Ser Leu Leu Arg Asn Gly
            115                 120                 125

Ala Arg Trp Ile Pro Asp Ile Thr Leu Val Val Ile Asp Glu Ile His
        130                 135                 140

Leu Ile Asp Ser Pro Asp Arg Gly Pro Thr Leu Glu Met Val Ile Ala
145                 150                 155                 160

Lys Met Arg Ser Lys Asn Pro Gly Met Gln Leu Ile Gly Leu Ser Ala
                165                 170                 175

Thr Ile Gly Asn Pro Lys Val Leu Ala Gly Trp Leu Asp Ala Glu Leu
                180                 185                 190

Val Thr Ser Ser Trp Arg Pro Val Asp Leu Arg Gln Gly Val Phe Tyr
            195                 200                 205

Asp Asn Arg Ile Gln Phe Ala Glu Arg Met Arg Pro Val Lys Gln Val
210                 215                 220

Ser Lys Asn Tyr Asp Asp Leu Asn Leu Cys Leu Asp Thr Ile Ala Glu
225                 230                 235                 240

Gly Gly Gln Cys Leu Val Phe Val Ser Ser Arg Arg Asn Ala Glu Ala
                245                 250                 255

Phe Ala Lys Arg Ala Ala Gly Ala Ile Lys Ser Glu Asp Ala Ala Leu
                260                 265                 270

Ala Ala Cys Ala Glu Arg Leu Leu Glu Gly Thr Pro Thr Glu Met Val
            275                 280                 285

Lys Thr Leu Ala Ala Cys Val Ala Lys Gly Ala Ala Phe His His Ala
        290                 295                 300
```

```
Gly Leu Ser Arg Lys Glu Arg Ser Ile Val Glu Ala Phe Arg Lys
305                 310                 315                 320

Asn Leu Leu Lys Cys Ile Ser Ser Thr Pro Thr Leu Ala Ala Gly Leu
            325                 330                 335

Asn Leu Pro Ala Arg Arg Val Ile Ile Arg Asp Tyr Leu Arg Phe Ser
            340                 345                 350

Ala Gly Glu Gly Met Gln Pro Ile Pro Val Ser Glu Tyr Arg Gln Met
        355                 360                 365

Ala Gly Arg Ala Gly Arg Pro Arg Leu Asp Pro Tyr Gly Glu Ala Val
    370                 375                 380

Leu Ile Ala Lys Glu Ala Glu Gln Val Pro Glu Leu Phe Glu Val Tyr
385                 390                 395                 400

Ile Glu Ala Glu Ala Glu Asp Val His Ser Arg Ile Ala Glu Pro Thr
                405                 410                 415

Ala Leu Tyr Thr His Val Leu Ser Leu Val Ala Ser Gly Phe Ala Gly
            420                 425                 430

Thr Arg Gly Glu Leu Thr Glu Phe Met Asn Arg Ser Phe Tyr Val His
        435                 440                 445

Glu His Lys Gln Gly Arg Leu Ile His Arg Ala Ile Asp Glu Ala Leu
    450                 455                 460

Gln Phe Leu Ile Thr Ala Glu Met Val Val Glu Val Gly Glu His Ile
465                 470                 475                 480

Gly Ala Thr Glu Leu Gly Thr Leu Val Ser Arg Met Tyr Ile Asp Pro
                485                 490                 495

Arg Ser Ala Phe Ala Ile Val Thr Thr Leu Arg Glu Gln Glu Lys Tyr
            500                 505                 510

Ala Asp Leu Gly Leu Ile Gln Leu Ile Cys Thr Thr Pro Asp Met Pro
        515                 520                 525

Thr Leu Tyr Ala Lys Asn Ala Asp Leu Pro Ala Leu Ser Arg Met Leu
    530                 535                 540

Glu Val Arg Gly Ala Asp Ile Trp Leu Pro Pro Leu Asp Asp Asp
545                 550                 555                 560

Ala Ala Glu Thr Tyr Tyr Arg Ala Val Lys Thr Ala Met Leu Leu Ser
                565                 570                 575

Asp Trp Thr Asp Glu Leu Ser Glu Glu Lys Ile Cys Glu Arg Tyr Gly
            580                 585                 590

Val Gly Pro Gly Asp Val Phe Gly Met Val Glu Asn Ile Asn Trp Leu
        595                 600                 605

Leu His Ala Thr Ser Gln Leu Ala Arg Met Phe Val Pro Lys Phe Tyr
    610                 615                 620

Gly Gln Ile Ala Asp Cys Glu Ile Cys Met Lys Asn Gly Ile Arg Arg
625                 630                 635                 640

Glu Leu Leu Pro Leu Val Arg Leu Arg Gly Ile Gly Arg Val Arg Ala
                645                 650                 655

Arg Arg Leu Phe Asn Asn Gly Ile Thr Ser Pro Glu Glu Leu Ser Arg
            660                 665                 670

His Lys Lys Glu Asp Leu Val Lys Ile Leu Gly Ser Gly Ile Ala Glu
        675                 680                 685

Gln Val Leu Glu Gln Leu His Pro Ser Lys Asp Thr Gly Lys Lys Glu
    690                 695                 700

Pro Pro Ser Gly Asp Lys Asn Thr Asn Pro Gly Gln Ser Thr Leu Phe
705                 710                 715                 720

His Phe Gly
```

<210> SEQ ID NO 48
<211> LENGTH: 681
<212> TYPE: PRT
<213> ORGANISM: Ferroplasma acidarmanus

<400> SEQUENCE: 48

```
Met Lys Leu Ser Glu Ile Thr Pro Ser Glu Phe Leu Lys Val Thr Asp
1               5                   10                  15

Asn Asn Asp Phe Thr Leu Tyr Glu His Gln Glu Ala Val Ala Lys
            20                  25                  30

Leu Arg Glu Asn Lys Asn Val Ile Val Ser Val Pro Thr Ala Ser Gly
        35                  40                  45

Lys Thr Leu Ile Gly Tyr Ile Ser Ile Tyr Asp Thr Tyr Leu Lys Gly
    50                  55                  60

Lys Lys Ser Met Tyr Ile Val Pro Leu Arg Ser Leu Ala Met Glu Lys
65                  70                  75                  80

Phe Ser Glu Leu Leu Ser Leu Arg Asn Leu Gly Val Lys Val Thr Met
                85                  90                  95

Ser Ile Gly Asp Tyr Asp Val Pro Pro Ser Phe Val Lys Asn Tyr Asp
            100                 105                 110

Val Ile Ile Ala Thr Ser Glu Arg Ala Asp Ser Met Leu His Arg Asp
        115                 120                 125

Pro Asp Ile Leu Asn Tyr Phe Gly Leu Val Ile Ile Asp Glu Ile His
    130                 135                 140

Met Ile Ser Asp Pro Ser Arg Gly Pro Arg Leu Glu Thr Val Ile Ser
145                 150                 155                 160

Ser Leu Leu Tyr Leu Asn Pro Glu Ile Leu Leu Gly Leu Ser Ala
                165                 170                 175

Thr Val Ser Asn Ile Gln Glu Ile Ala Glu Trp Met Asn Ala Glu Thr
            180                 185                 190

Val Val Ser Asn Phe Arg Ala Val Pro Leu Glu Thr Gly Ile Ile Phe
        195                 200                 205

Lys Gly Asn Leu Ile Thr Asp Gly Glu Lys Lys His Leu Gly Arg Asp
    210                 215                 220

Asp Glu Val Ser Leu Ile Lys Glu Ser Ile Glu Ser Gly Gly Gln Ala
225                 230                 235                 240

Leu Val Phe Arg Asn Ser Arg Arg Asn Ala Glu Lys Tyr Ala Gln Ser
                245                 250                 255

Met Val Asn Phe Phe Asp Phe Gln Asn Asp Phe Glu Lys Leu Glu Ile
            260                 265                 270

Pro Pro Asp Leu Phe Asn Glu Ala Gln Ala Asn Met Val Ala His Gly
        275                 280                 285

Val Met Phe His His Ala Gly Leu Ser Asn Asp Gln Arg Thr Met Ile
    290                 295                 300

Glu Lys Leu Phe Lys Gln Gly Tyr Ile Lys Ile Leu Thr Ala Thr Pro
305                 310                 315                 320

Thr Leu Ala Ala Gly Val Asn Leu Pro Ala Arg Thr Val Ile Arg
                325                 330                 335

Asp Ile Thr Arg Phe Ser Asp Gly Tyr Ser Lys Pro Ile Ser Gly Ile
            340                 345                 350

Glu Ile Gln Gln Met Ile Gly Arg Ala Gly Arg Pro Lys Tyr Asp Lys
        355                 360                 365

Lys Gly Tyr Gly Tyr Ile Tyr Ala Ala Ser Pro Gly Met Leu Arg Val
```

```
      370                 375                 380
Ala Glu Gly Tyr Leu Thr Gly Glu Leu Glu Pro Val Ile Ser Arg Met
385                 390                 395                 400

Asp Ser Asn Ser Leu Ile Arg Phe Asn Val Leu Ala Leu Ile Ser Ser
                405                 410                 415

Gly Ile Ala Thr Asp Leu Lys Gly Ile Gln Asp Phe Tyr Gly Lys Thr
                420                 425                 430

Leu Leu Ala Ala Gln Asn Asp Ile Asp Gly Tyr Glu Leu Ala Phe Glu
                435                 440                 445

Ser Ala Leu Tyr Phe Leu Lys Asp Asn Asp Phe Ile Thr Glu Glu Asn
            450                 455                 460

Asp Ile Tyr Ser Ala Thr Lys Phe Gly Arg Leu Thr Ser Asp Leu Tyr
465                 470                 475                 480

Ile Asp Pro Val Ser Ser Leu Ile Leu Lys Lys Cys Leu Asp Leu Glu
                485                 490                 495

Phe Ser Glu Glu Leu Tyr Leu Tyr Tyr Ile Ser Lys Thr Pro Asp Met
                500                 505                 510

Leu Thr Phe Asn Tyr Arg Ala Ser Asp Tyr Glu Tyr Leu Glu Glu Phe
            515                 520                 525

Leu Asp Arg His Asn Ile Ser Asp Phe Ser Glu Glu Ser Met Gly Ala
        530                 535                 540

Ala Lys Thr Ala Ile Ile Leu Asn Glu Trp Ile Asn Glu Val Pro Ile
545                 550                 555                 560

Asn Thr Ile Ala Glu Thr Phe Gly Ile Gly Pro Gly Asp Ile Gln Ala
                565                 570                 575

Lys Ala Ser Ser Ala Asp Trp Ile Ser Tyr Ser Leu Tyr Arg Leu Gly
                580                 585                 590

Ser Met Phe Asp Lys Glu Asn Glu Asn Asn Leu Leu His Leu Asn Ile
            595                 600                 605

Arg Ile Lys Glu Gly Val Lys Glu Glu Ile Ile Arg Ile Ile Glu Ile
        610                 615                 620

Pro Gln Val Gly Arg Val Arg Gly Arg Arg Leu Tyr Asn Asn Gly Phe
625                 630                 635                 640

Lys Ser Ile Asp Asp Ile Ala Asn Ala Arg Val Glu Asp Ile Ser Arg
                645                 650                 655

Ile Phe Gly Phe Ser Thr Lys Leu Ala Lys Asp Ile Ile Glu Asn Ala
                660                 665                 670

Gly Lys Leu Asn Asn Arg Tyr Tyr Arg
            675                 680

<210> SEQ ID NO 49
<211> LENGTH: 696
<212> TYPE: PRT
<213> ORGANISM: Methanocaldococcus fervens

<400> SEQUENCE: 49

Met Pro Thr Asn Lys Ile Leu Glu Ile Leu Lys Asp Phe Gly Ile Glu
1               5                   10                  15

Glu Leu Arg Pro Pro Gln Lys Lys Ala Leu Glu Lys Gly Leu Leu Asp
                20                  25                  30

Lys Asn Lys Asn Phe Leu Ile Ser Ile Pro Thr Ala Ser Gly Lys Thr
            35                  40                  45

Leu Ile Gly Glu Met Ala Leu Ile Asn His Leu Leu Asp Glu Asn Lys
        50                  55                  60
```

```
Asn Pro Thr Asn Lys Lys Gly Ile Phe Ile Val Pro Leu Lys Ala Leu
 65                  70                  75                  80

Ala Ser Glu Lys Tyr Glu Glu Phe Lys Asn Lys Tyr Glu Arg Tyr Gly
                 85                  90                  95

Leu Arg Val Ala Leu Ser Ile Gly Asp Tyr Asp Glu Asp Glu Asp Leu
            100                 105                 110

Ser Arg Tyr His Leu Ile Ile Thr Ala Glu Lys Leu Asp Ser Leu
            115                 120                 125

Trp Arg His Lys Ile Asp Trp Ile Asp Asp Val Ser Val Val Val
130                 135                 140

Asp Glu Ile His Leu Ile Asn Asp Gly Ser Arg Gly Gly Thr Leu Glu
145                 150                 155                 160

Ile Leu Leu Thr Lys Leu Lys Lys Phe Asn Ile Gln Ile Ile Gly Leu
                165                 170                 175

Ser Ala Thr Ile Gly Asn Pro Glu Glu Leu Ala Asn Trp Leu Asn Ala
            180                 185                 190

Glu Leu Ile Val Asp Asp Trp Arg Pro Val Glu Leu Lys Lys Gly Ile
            195                 200                 205

Tyr Lys Asn Gly Ile Ile Glu Phe Ile Asn Gly Glu Asn Arg Glu Ile
210                 215                 220

Lys Ala Ile Asn Asn Asn Asp Ile Tyr Asn Leu Val Val Asp Cys Val
225                 230                 235                 240

Lys Asp Gly Gly Cys Cys Ile Val Phe Cys Asn Thr Lys Arg Gly Ala
            245                 250                 255

Val Asn Glu Ala Lys Lys Leu Asn Leu Lys Lys Phe Leu Thr Asn Glu
            260                 265                 270

Glu Lys Arg Lys Leu Lys Glu Val Ala Glu Glu Ile Leu Ser Ile Leu
            275                 280                 285

Glu Pro Pro Thr Glu Met Cys Lys Thr Leu Ala Glu Cys Ile Leu Asn
            290                 295                 300

Gly Ser Ala Phe His His Ala Gly Leu Thr Tyr Gln His Arg Lys Ile
305                 310                 315                 320

Val Glu Asp Ala Phe Arg Asn Lys Leu Ile Lys Val Ile Cys Cys Thr
                325                 330                 335

Pro Thr Leu Ser Val Gly Leu Asn Leu Pro Cys Arg Arg Ala Ile Val
            340                 345                 350

Lys Asp Leu Thr Arg Tyr Thr Asn Arg Gly Met Arg Tyr Ile Pro Ile
            355                 360                 365

Met Glu Ile Gln Gln Cys Ile Gly Arg Ala Gly Arg Leu Gly Leu Asp
            370                 375                 380

Pro Tyr Gly Glu Gly Ile Ile Val Ala Lys Asn Asp Arg Asp Tyr Leu
385                 390                 395                 400

Arg Ser Tyr Gln Val Leu Thr Gln Lys Pro Glu Pro Ile Tyr Ser Lys
                405                 410                 415

Leu Ser Asn Gln Ala Val Leu Arg Thr Gln Leu Leu Gly Leu Ile Ala
            420                 425                 430

Thr Ile Glu Ile Arg Asp Glu Tyr Asp Leu Glu Trp Phe Ile Arg Asn
            435                 440                 445

Thr Phe Tyr Ala Tyr Gln Tyr Gly Asn Leu Arg Glu Val Ala Lys Asn
            450                 455                 460

Ile Asn Glu Val Ile Arg Phe Leu Glu Glu Lys Glu Phe Met Ile Asp
465                 470                 475                 480

Phe Ile Pro Thr Glu Leu Gly Lys Arg Val Ala Glu Leu Tyr Ile Asp
```

```
                485                 490                 495
Pro Leu Ser Ala Lys Tyr Met Ile Asp Gly Leu Asn Glu Met Glu Asn
            500                 505                 510

Glu Asp Asp Ile Tyr Tyr Leu Tyr Leu Ile Ser Lys Thr Leu Glu Met
        515                 520                 525

Met Pro Asn Leu Arg Val Tyr Lys Ser Glu Glu Leu Asn Leu Ile Asp
    530                 535                 540

Glu Met Glu Asn Leu Gly Ile Lys Ser Phe Glu Ile Glu Asp Leu Glu
545                 550                 555                 560

Ala Phe Lys Thr Ala Lys Met Leu Tyr Asp Trp Ile Ser Glu Val Pro
                565                 570                 575

Glu Asp Glu Ile Leu Lys Lys Tyr Lys Ile Glu Pro Gly Ile Leu Arg
            580                 585                 590

Tyr Lys Val Glu Asn Ala Val Trp Leu Met His Ala Leu Lys Glu Met
        595                 600                 605

Ala Lys Ile Ile Gly Lys Asn Ser Glu Ile Pro Glu Lys Leu Glu Ile
    610                 615                 620

Arg Leu Glu Tyr Gly Ala Lys Glu Asp Ile Ile Glu Leu Leu Asn Val
625                 630                 635                 640

Lys Tyr Ile Gly Arg Val Arg Ala Arg Lys Leu Tyr Asn Ala Gly Ile
                645                 650                 655

Arg Asn Val Glu Asp Ile Asn Asn Pro Ser Lys Val Ala Ser Ile
            660                 665                 670

Ile Gly Glu Lys Ile Thr Lys Lys Ile Leu Glu Asp Leu Gly Ile Lys
                675                 680                 685

Phe Gly Gln Gln Lys Leu Ile Phe
            690                 695

<210> SEQ ID NO 50
<211> LENGTH: 729
<212> TYPE: PRT
<213> ORGANISM: Methanocaldococcus jannaschii

<400> SEQUENCE: 50

Met Asp Lys Ile Leu Glu Ile Leu Lys Asp Phe Gly Ile Val Glu Leu
1               5                   10                  15

Arg Pro Pro Gln Lys Lys Ala Leu Glu Arg Gly Leu Leu Asp Lys Asn
            20                  25                  30

Lys Asn Phe Leu Ile Ser Ile Pro Thr Ala Ser Gly Lys Thr Leu Ile
        35                  40                  45

Gly Glu Met Ala Leu Ile Asn His Leu Leu Asp Gly Asn Lys Asn Pro
    50                  55                  60

Thr Asn Lys Lys Gly Ile Phe Ile Val Pro Leu Lys Ala Leu Ala Ser
65                  70                  75                  80

Glu Lys Tyr Glu Glu Phe Lys Ser Lys Tyr Glu Arg Tyr Gly Leu Arg
                85                  90                  95

Ile Ala Leu Ser Ile Gly Asp Tyr Asp Glu Asp Glu Asp Leu Ser Lys
            100                 105                 110

Tyr His Leu Ile Ile Thr Thr Ala Glu Lys Leu Asp Ser Leu Trp Arg
        115                 120                 125

His Lys Ile Asp Trp Ile Asn Asp Val Ser Val Val Val Val Asp Glu
    130                 135                 140

Ile His Leu Ile Asn Asp Glu Thr Arg Gly Gly Thr Leu Glu Ile Leu
145                 150                 155                 160
```

-continued

```
Leu Thr Lys Leu Lys Glu Phe Asn Val Gln Ile Ile Gly Leu Ser Ala
            165                 170                 175
Thr Ile Gly Asn Pro Asp Glu Leu Ala Glu Trp Leu Asn Ala Glu Leu
        180                 185                 190
Ile Val Asp Asp Trp Arg Pro Val Glu Leu Lys Lys Gly Ile Tyr Lys
    195                 200                 205
Asn Glu Ala Ile Glu Phe Ile Asn Gly Glu Ile Arg Glu Ile Lys Ala
210                 215                 220
Val Asp Asn Asn Asp Ile Tyr Asn Leu Val Val Asp Cys Val Lys Glu
225                 230                 235                 240
Gly Gly Cys Cys Leu Val Phe Cys Asn Thr Lys Arg Asn Ala Val Asn
                245                 250                 255
Glu Ala Lys Lys Leu Asn Leu Lys Lys Phe Leu Thr Glu Glu Glu Lys
            260                 265                 270
Ile Arg Leu Lys Glu Ile Ala Glu Glu Ile Leu Ser Ile Leu Glu Pro
        275                 280                 285
Pro Thr Glu Met Cys Lys Thr Leu Ala Glu Cys Ile Leu Asn Gly Ser
    290                 295                 300
Ala Phe His His Ala Gly Leu Thr Tyr Gln His Arg Lys Ile Val Glu
305                 310                 315                 320
Asp Ala Phe Arg Lys Arg Leu Ile Lys Val Ile Cys Cys Thr Pro Thr
                325                 330                 335
Leu Ser Ala Gly Leu Asn Leu Pro Cys Arg Arg Ala Ile Val Lys Asp
            340                 345                 350
Leu Thr Arg Phe Thr Asn Lys Gly Met Arg Tyr Ile Pro Ile Met Glu
        355                 360                 365
Ile Gln Gln Cys Ile Gly Arg Ala Gly Arg Pro Gly Leu Asp Pro Tyr
    370                 375                 380
Gly Glu Gly Ile Ile Val Ala Lys Asn Asp Arg Asp Tyr Leu Arg Ala
385                 390                 395                 400
Tyr Gln Ala Leu Thr Gln Lys Pro Glu Pro Ile Tyr Ser Lys Leu Ser
                405                 410                 415
Asn Gln Ala Val Leu Arg Thr Gln Leu Leu Gly Leu Ile Ala Thr Gly
            420                 425                 430
Glu Ile Arg Asp Glu Tyr Asp Leu Glu Trp Phe Ile Arg Asn Thr Phe
        435                 440                 445
Tyr Ala His Gln Tyr Gly Asn Leu Arg Glu Val Ala Lys Asn Ile Asn
    450                 455                 460
Glu Val Ile Arg Phe Leu Glu Glu Asn Glu Phe Ile Ile Asp Phe Met
465                 470                 475                 480
Pro Thr Glu Leu Gly Lys Arg Val Ser Glu Leu Tyr Ile Asp Pro Leu
                485                 490                 495
Ser Ala Lys Phe Ile Ile Asp Gly Leu Glu Glu Met Glu Asn Glu Glu
            500                 505                 510
Glu Ile Tyr Tyr Leu Tyr Leu Ile Ser Lys Thr Leu Glu Met Met Pro
        515                 520                 525
Asn Leu Arg Val Tyr Asn Ser Glu Glu Leu Asn Leu Ile Asp Glu Met
    530                 535                 540
Asp Ser Leu Gly Ile Lys Ser Phe Glu Ile Glu Asp Leu Glu Ala Phe
545                 550                 555                 560
Lys Thr Ala Lys Met Leu Tyr Asp Trp Ile Asn Glu Val Pro Glu Asp
                565                 570                 575
Glu Ile Leu Lys Arg Tyr Lys Ile Glu Pro Gly Ile Leu Arg Tyr Lys
```

```
                     580                 585                 590
Val Glu Asn Ala Val Trp Ile Met His Ala Leu Lys Glu Ile Ala Lys
                595                 600                 605

Leu Ile Gly Lys Ser Ser Asp Ile Pro Glu Lys Leu Glu Ile Arg Leu
            610                 615                 620

Glu Tyr Gly Ala Lys Glu Asp Ile Ile Glu Leu Leu Ser Ile Lys Tyr
625                 630                 635                 640

Ile Gly Arg Val Arg Ala Arg Lys Leu Tyr Asn Ala Gly Ile Arg Ser
                645                 650                 655

Ile Glu Asp Ile Ile Asn Asn Pro Ser Lys Val Ala Ser Ile Ile Gly
            660                 665                 670

Glu Lys Ile Ala Lys Lys Ile Leu Asp Glu Leu Gly Val Lys Phe Gly
                675                 680                 685

Gln Gln Lys Leu Ser Phe Ser Gly Gly Ser Ala Trp Ser His Pro Gln
            690                 695                 700

Phe Glu Lys Gly Gly Gly Ser Gly Gly Gly Ser Gly Gly Ser Ala Trp
705                 710                 715                 720

Ser His Pro Gln Phe Glu Lys Lys Leu
                725

<210> SEQ ID NO 51
<211> LENGTH: 670
<212> TYPE: PRT
<213> ORGANISM: Methanocaldococcus infernus

<400> SEQUENCE: 51

Met Asp Glu Ile Leu Lys Phe Leu Gly Ile Lys Glu Leu Arg Pro Pro
1               5                   10                  15

Gln Lys Lys Ala Leu Glu Leu Gly Ile Leu Asp Lys Lys Lys Asn Phe
            20                  25                  30

Leu Ile Ser Ile Pro Thr Gly Ala Gly Lys Thr Val Ile Ala Glu Met
        35                  40                  45

Ala Leu Ile Asn His Leu Leu Leu Asp Lys Gly Lys Lys Gly Val Tyr
    50                  55                  60

Ile Val Pro Leu Lys Ala Leu Ala Ser Glu Lys Tyr Glu Glu Phe Lys
65                  70                  75                  80

Lys Lys Tyr Glu Lys Phe Gly Val Arg Val Ala Leu Ser Ile Gly Asp
                85                  90                  95

Tyr Asp Glu Asp Glu Asp Leu Glu Asn Tyr Asp Leu Ile Ile Thr Thr
            100                 105                 110

Ala Glu Lys Phe Asp Ser Leu Trp Arg His Gly Ile Lys Leu Ser Asp
        115                 120                 125

Ile Ser Val Val Val Asp Glu Ile His Val Ile Gly Asp Ser Glu
    130                 135                 140

Arg Gly Gly Thr Leu Glu Val Leu Leu Thr Lys Leu Lys Glu Leu Asp
145                 150                 155                 160

Val Gln Ile Ile Gly Leu Ser Ala Thr Ile Gly Asn Pro Glu Glu Leu
                165                 170                 175

Ser Glu Trp Leu Asn Ala Glu Leu Leu Leu Asp Asn Trp Arg Pro Val
            180                 185                 190

Glu Leu Arg Lys Gly Ile Tyr Arg Glu Gly Val Ile Glu Tyr Leu Asp
        195                 200                 205

Gly Glu Val Lys Glu Cys Gln Asp Ile Val Lys Glu Val Val Lys Asp
    210                 215                 220
```

-continued

Asn Gly Ser Val Ile Ile Phe Cys Pro Thr Lys Lys Ala Glu Asn
225                 230                 235                 240

Arg Ala Leu Ser Leu Asp Leu Ser Asp Leu Leu Lys Lys Ser Glu Lys
                245                 250                 255

Arg Lys Leu Glu Glu Ile Ser Glu Glu Leu Leu Ser Leu Phe Asp Pro
                260                 265                 270

Pro Thr Glu Leu Cys Lys Lys Leu Ala Ser Cys Val Arg Lys Gly Ile
            275                 280                 285

Ala Phe His His Ser Gly Leu Thr Tyr Glu His Arg Lys Ile Ile Glu
        290                 295                 300

Lys Ala Phe Arg Glu Arg Ile Leu Lys Val Ile Cys Ser Thr Thr Thr
305                 310                 315                 320

Leu Ala Phe Gly Leu Asn Leu Pro Cys Arg Arg Val Ile Ile Ser Glu
                325                 330                 335

Leu Lys Arg Tyr Thr Arg Arg Gly Leu Thr Tyr Ile Pro Ile Met Glu
                340                 345                 350

Val Gln Gln Cys Ile Gly Arg Ala Gly Arg Pro Gly Leu Asp Glu Tyr
                355                 360                 365

Gly Glu Gly Ile Leu Val Ala Lys Asp Glu Arg Asp Tyr Leu Arg Ala
370                 375                 380

Leu Gln Cys Leu Thr Gln Lys Pro Glu Pro Ile Tyr Ser Lys Leu Ser
385                 390                 395                 400

Asn Asp Ser Val Leu Arg Thr Gln Ile Leu Gly Leu Ile Ala Thr Arg
                405                 410                 415

Tyr Val Leu Asp Glu Tyr Asp Leu Glu Glu Phe Ile Lys Asn Thr Phe
                420                 425                 430

Tyr Ala Tyr Gln Tyr Lys Asn Leu Asp Glu Ile Lys Lys Lys Ile Lys
                435                 440                 445

Glu Ile Ile Glu Phe Leu Glu Asp Cys Asn Phe Ile Lys Asn Phe Glu
450                 455                 460

Val Thr Pro Leu Gly Lys Lys Val Ser Asn Leu Tyr Leu Asp Pro Leu
465                 470                 475                 480

Ser Ala Lys Ile Met Ile Asp Asn Ile Glu Val Lys Asp Asp Leu His
                485                 490                 495

Leu Leu Tyr Ile Leu Cys Lys Cys Ile Glu Met Lys Pro Leu Leu Arg
                500                 505                 510

Val Tyr Arg Lys Glu Glu Glu Glu Leu Ala Glu Glu Leu Leu Asn Tyr
                515                 520                 525

Glu Ile Phe Ile Ser Tyr Glu Asn Leu Glu Glu Phe Lys Thr Ala Lys
                530                 535                 540

Met Leu Tyr Asp Trp Ile Asn Glu Val Pro Glu Asp Glu Ile Leu Lys
545                 550                 555                 560

Thr Tyr Lys Val Glu Pro Gly Ile Leu Arg Tyr Lys Val Glu Val Ala
                565                 570                 575

Lys Trp Leu Ser Tyr Ser Leu Lys Glu Ile Ala Lys Ile Leu Asn Lys
                580                 585                 590

Glu Val Pro Asn Leu Glu Leu Arg Leu Glu Tyr Gly Ala Lys Glu Glu
                595                 600                 605

Leu Leu Glu Leu Leu Lys Ile Lys Tyr Ile Gly Arg Val Arg Ala Arg
                610                 615                 620

Lys Leu Tyr Ser Ala Gly Ile Arg Asn Arg Glu Asp Ile Ile Lys Asn
625                 630                 635                 640

Pro Lys Lys Val Ala Asn Ile Leu Gly Glu Lys Ile Ser Lys Lys Ile

-continued

```
                    645                 650                 655

Phe Glu Glu Leu Gly Val Arg Tyr Gly Gln Gln Arg Leu Ile
            660                 665                 670

<210> SEQ ID NO 52
<211> LENGTH: 799
<212> TYPE: PRT
<213> ORGANISM: Methanospirillum hungatei

<400> SEQUENCE: 52

Met Glu Ile Ala Ser Leu Pro Leu Pro Asp Ser Phe Ile Arg Ala Cys
1               5                   10                  15

His Ala Lys Gly Ile Arg Ser Leu Tyr Pro Pro Gln Ala Glu Cys Ile
            20                  25                  30

Glu Lys Gly Leu Leu Glu Gly Lys Asn Leu Leu Ile Ser Ile Pro Thr
        35                  40                  45

Ala Ser Gly Lys Thr Leu Leu Ala Glu Met Ala Met Trp Ser Arg Ile
    50                  55                  60

Ala Ala Gly Gly Lys Cys Leu Tyr Ile Val Pro Leu Arg Ala Leu Ala
65                  70                  75                  80

Ser Glu Lys Tyr Asp Glu Phe Ser Lys Lys Gly Val Ile Arg Val Gly
                85                  90                  95

Ile Ala Thr Gly Asp Leu Asp Arg Thr Asp Ala Tyr Leu Gly Glu Asn
            100                 105                 110

Asp Ile Ile Val Ala Thr Ser Glu Lys Thr Asp Ser Leu Leu Arg Asn
        115                 120                 125

Arg Thr Pro Trp Leu Ser Gln Ile Thr Cys Ile Val Leu Asp Glu Val
    130                 135                 140

His Leu Ile Gly Ser Glu Asn Arg Gly Ala Thr Leu Glu Met Val Ile
145                 150                 155                 160

Thr Lys Leu Arg Tyr Thr Asn Pro Val Met Gln Ile Ile Gly Leu Ser
                165                 170                 175

Ala Thr Ile Gly Asn Pro Ala Gln Leu Ala Glu Trp Leu Asp Ala Thr
            180                 185                 190

Leu Ile Thr Ser Thr Trp Arg Pro Val Asp Leu Arg Gln Gly Val Tyr
        195                 200                 205

Tyr Asn Gly Lys Ile Arg Phe Ser Asp Ser Glu Arg Pro Ile Gln Gly
    210                 215                 220

Lys Thr Lys His Asp Asp Leu Asn Leu Cys Leu Asp Thr Ile Glu Glu
225                 230                 235                 240

Gly Gly Gln Cys Leu Val Phe Val Ser Ser Arg Arg Asn Ala Glu Gly
                245                 250                 255

Phe Ala Lys Lys Ala Gly Ala Leu Lys Ala Gly Ser Pro Asp Ser
            260                 265                 270

Lys Ala Leu Ala Gln Glu Leu Arg Arg Leu Arg Asp Arg Asp Glu Gly
        275                 280                 285

Asn Val Leu Ala Asp Cys Val Glu Arg Gly Ala Ala Phe His His Ala
    290                 295                 300

Gly Leu Ile Arg Gln Glu Arg Thr Ile Ile Glu Glu Gly Phe Arg Asn
305                 310                 315                 320

Gly Tyr Ile Glu Val Ile Ala Ala Thr Pro Thr Leu Ala Ala Gly Leu
                325                 330                 335

Asn Leu Pro Ala Arg Arg Val Ile Ile Arg Asp Tyr Asn Arg Phe Ala
            340                 345                 350
```

-continued

Ser Gly Leu Gly Met Val Pro Ile Pro Val Gly Tyr His Gln Met
         355                 360                 365
Ala Gly Arg Ala Gly Arg Pro His Leu Asp Pro Tyr Gly Glu Ala Val
370                 375                 380
Leu Leu Ala Lys Asp Ala Pro Ser Val Glu Arg Leu Phe Glu Thr Phe
385                 390                 395                 400
Ile Asp Ala Glu Ala Glu Arg Val Asp Ser Gln Cys Val Asp Asp Ala
             405                 410                 415
Ser Leu Cys Ala His Ile Leu Ser Leu Ile Ala Thr Gly Phe Ala His
             420                 425                 430
Asp Gln Glu Ala Leu Ser Ser Phe Met Glu Arg Thr Phe Tyr Phe Phe
         435                 440                 445
Gln His Pro Lys Thr Arg Ser Leu Pro Arg Leu Val Ala Asp Ala Ile
         450                 455                 460
Arg Phe Leu Thr Thr Ala Gly Met Val Glu Glu Arg Glu Asn Thr Leu
465                 470                 475                 480
Ser Ala Thr Arg Leu Gly Ser Leu Val Ser Arg Leu Tyr Leu Asn Pro
             485                 490                 495
Cys Thr Ala Arg Leu Ile Leu Asp Ser Leu Lys Ser Cys Lys Thr Pro
             500                 505                 510
Thr Leu Ile Gly Leu Leu His Val Ile Cys Val Ser Pro Asp Met Gln
         515                 520                 525
Arg Leu Tyr Leu Lys Ala Ala Asp Thr Gln Leu Leu Arg Thr Phe Leu
         530                 535                 540
Phe Lys His Lys Asp Asp Leu Ile Leu Pro Leu Pro Phe Glu Gln Glu
545                 550                 555                 560
Glu Glu Glu Leu Trp Leu Ser Gly Leu Lys Thr Ala Leu Val Leu Thr
             565                 570                 575
Asp Trp Ala Asp Glu Phe Ser Glu Gly Met Ile Glu Arg Tyr Gly
             580                 585                 590
Ile Gly Ala Gly Asp Leu Tyr Asn Ile Val Asp Ser Gly Lys Trp Leu
         595                 600                 605
Leu His Gly Thr Glu Arg Leu Val Ser Val Glu Met Pro Glu Met Ser
     610                 615                 620
Gln Val Val Lys Thr Leu Ser Val Arg Val His His Gly Val Lys Ser
625                 630                 635                 640
Glu Leu Leu Pro Leu Val Ala Leu Arg Asn Ile Gly Arg Val Arg Ala
             645                 650                 655
Arg Thr Leu Tyr Asn Ala Gly Tyr Pro Asp Pro Glu Ala Val Ala Arg
             660                 665                 670
Ala Gly Leu Ser Thr Ile Ala Arg Ile Ile Gly Glu Gly Ile Ala Arg
         675                 680                 685
Gln Val Ile Asp Glu Ile Thr Gly Val Lys Arg Ser Gly Ile His Ser
     690                 695                 700
Ser Asp Asp Asp Tyr Gln Gln Lys Thr Pro Glu Leu Leu Thr Asp Ile
705                 710                 715                 720
Pro Gly Ile Gly Lys Lys Met Ala Glu Lys Leu Gln Asn Ala Gly Ile
             725                 730                 735
Ile Thr Val Ser Asp Leu Leu Thr Ala Asp Glu Val Leu Leu Ser Asp
             740                 745                 750
Val Leu Gly Ala Ala Arg Ala Arg Lys Val Leu Ala Phe Leu Ser Asn
         755                 760                 765
Ser Glu Lys Glu Asn Ser Ser Ser Asp Lys Thr Glu Glu Ile Pro Asp

```
                  770                 775                 780
Thr Gln Lys Ile Arg Gly Gln Ser Ser Trp Glu Asp Phe Gly Cys
785                 790                 795

<210> SEQ ID NO 53
<211> LENGTH: 702
<212> TYPE: PRT
<213> ORGANISM: Archaeoglobus fulgidus

<400> SEQUENCE: 53

Met Lys Val Glu Glu Leu Ala Glu Ser Ile Ser Ser Tyr Ala Val Gly
1               5                   10                  15

Ile Leu Lys Glu Glu Gly Ile Glu Glu Leu Phe Pro Pro Gln Ala Glu
                20                  25                  30

Ala Val Glu Lys Val Phe Ser Gly Lys Asn Leu Leu Leu Ala Met Pro
            35                  40                  45

Thr Ala Ala Gly Lys Thr Leu Leu Ala Glu Met Ala Met Val Arg Glu
50                  55                  60

Ala Ile Lys Gly Gly Lys Ser Leu Tyr Val Val Pro Leu Arg Ala Leu
65                  70                  75                  80

Ala Gly Glu Lys Tyr Glu Ser Phe Lys Lys Trp Glu Lys Ile Gly Leu
                85                  90                  95

Arg Ile Gly Ile Ser Thr Gly Asp Tyr Glu Ser Arg Asp Glu His Leu
            100                 105                 110

Gly Asp Cys Asp Ile Ile Val Thr Thr Ser Glu Lys Ala Asp Ser Leu
        115                 120                 125

Ile Arg Asn Arg Ala Ser Trp Ile Lys Ala Val Ser Cys Leu Val Val
    130                 135                 140

Asp Glu Ile His Leu Leu Asp Ser Glu Lys Arg Gly Ala Thr Leu Glu
145                 150                 155                 160

Ile Leu Val Thr Lys Met Arg Arg Met Asn Lys Ala Leu Arg Val Ile
                165                 170                 175

Gly Leu Ser Ala Thr Ala Pro Asn Val Thr Glu Ile Ala Glu Trp Leu
            180                 185                 190

Asp Ala Asp Tyr Tyr Val Ser Asp Trp Arg Pro Val Pro Leu Val Glu
        195                 200                 205

Gly Val Leu Cys Glu Gly Thr Leu Glu Leu Phe Asp Gly Ala Phe Ser
    210                 215                 220

Thr Ser Arg Arg Val Lys Phe Glu Glu Leu Val Glu Glu Cys Val Ala
225                 230                 235                 240

Glu Asn Gly Gly Val Leu Val Phe Glu Ser Thr Arg Arg Gly Ala Glu
                245                 250                 255

Lys Thr Ala Val Lys Leu Ser Ala Ile Thr Ala Lys Tyr Val Glu Asn
            260                 265                 270

Glu Gly Leu Glu Lys Ala Ile Leu Glu Glu Asn Glu Gly Glu Met Ser
        275                 280                 285

Arg Lys Leu Ala Glu Cys Val Arg Lys Gly Ala Ala Phe His His Ala
    290                 295                 300

Gly Leu Leu Asn Gly Gln Arg Arg Val Val Glu Asp Ala Phe Arg Arg
305                 310                 315                 320

Gly Asn Ile Lys Val Val Val Ala Thr Pro Thr Leu Ala Ala Gly Val
                325                 330                 335

Asn Leu Pro Ala Arg Arg Val Ile Val Arg Ser Leu Tyr Arg Phe Asp
            340                 345                 350
```

```
Gly Tyr Ser Lys Arg Ile Lys Val Ser Glu Tyr Lys Gln Met Ala Gly
            355                 360                 365

Arg Ala Gly Arg Pro Gly Met Asp Glu Arg Gly Glu Ala Ile Ile Ile
        370                 375                 380

Val Gly Lys Arg Asp Arg Glu Ile Ala Val Lys Arg Tyr Ile Phe Gly
385                 390                 395                 400

Glu Pro Glu Arg Ile Thr Ser Lys Leu Gly Val Glu Thr His Leu Arg
                405                 410                 415

Phe His Ser Leu Ser Ile Ile Cys Asp Gly Tyr Ala Lys Thr Leu Glu
            420                 425                 430

Glu Leu Glu Asp Phe Phe Ala Asp Thr Phe Phe Phe Lys Gln Asn Glu
        435                 440                 445

Ile Ser Leu Ser Tyr Glu Leu Glu Arg Val Val Arg Gln Leu Glu Asn
    450                 455                 460

Trp Gly Met Val Val Glu Asp His His Leu Ala Pro Thr Lys Leu Gly
465                 470                 475                 480

Ser Leu Val Ser Arg Leu Tyr Ile Asp Pro Leu Thr Gly Phe Ile Phe
                485                 490                 495

His Asp Val Leu Ser Arg Met Glu Leu Ser Asp Ile Gly Ala Leu His
            500                 505                 510

Leu Ile Cys Arg Thr Pro Asp Met Glu Arg Leu Thr Val Arg Lys Thr
        515                 520                 525

Asp Ser Trp Val Glu Glu Ala Phe Arg Leu Arg Lys Glu Leu Ser
    530                 535                 540

Tyr Tyr Pro Ser Asp Phe Ser Val Glu Tyr Asp Trp Phe Leu Ser Glu
545                 550                 555                 560

Val Lys Thr Ala Leu Cys Leu Lys Asp Trp Ile Glu Lys Asp Glu
                565                 570                 575

Asp Glu Ile Cys Ala Lys Tyr Gly Ile Ala Pro Gly Asp Leu Arg Arg
            580                 585                 590

Ile Val Glu Thr Ala Glu Trp Leu Ser Asn Ala Met Asn Arg Ile Ala
        595                 600                 605

Glu Glu Val Gly Asn Thr Ser Val Ser Gly Leu Thr Glu Arg Ile Lys
    610                 615                 620

His Gly Val Lys Glu Glu Leu Leu Glu Leu Val Arg Ile Arg His Ile
625                 630                 635                 640

Gly Arg Val Arg Ala Arg Lys Leu Tyr Asn Ala Gly Ile Arg Asn Ala
                645                 650                 655

Glu Asp Ile Val Arg His Arg Glu Lys Val Ala Ser Leu Ile Gly Arg
            660                 665                 670

Gly Ile Ala Glu Arg Val Val Glu Gly Ile Ser Val Lys Ser Leu Asn
        675                 680                 685

Pro Glu Ser Ala Ala Ala Leu Glu His His His His His
    690                 695                 700

<210> SEQ ID NO 54
<211> LENGTH: 791
<212> TYPE: PRT
<213> ORGANISM: Haloterrigena turkmenica

<400> SEQUENCE: 54

Met Asn Leu Glu Glu Leu Thr Gly Leu Pro Pro Gly Ala Thr Asp His
1               5                   10                  15

Phe Arg Gly Glu Gly Ile Glu Glu Leu Tyr Pro Pro Gln Ala Asp Ala
            20                  25                  30
```

-continued

```
Val Glu Ala Gly Ala Thr Asp Gly Glu Asn Leu Val Ala Ala Val Pro
         35                  40                  45
Thr Ala Ser Gly Lys Thr Met Ile Ala Ala Leu Ser Met Leu Ser Ala
 50                  55                  60
Val Gln Arg Gly Gly Lys Ala Leu Tyr Ile Val Pro Leu Arg Ala Leu
 65                  70                  75                  80
Ala Ser Glu Lys Lys Glu Glu Phe Glu Ala Tyr Glu Glu Phe Gly Val
                 85                  90                  95
Thr Thr Gly Val Thr Thr Gly Asn Tyr Glu Ser Thr Asp Asp Trp Leu
                100                 105                 110
Ala Thr Lys Asp Ile Ile Val Ala Thr Ser Glu Lys Val Asp Ser Leu
                115                 120                 125
Val Arg Asn Gly Ala Asp Trp Leu Ser Glu Leu Thr Cys Val Val Ser
        130                 135                 140
Asp Glu Val His Leu Ile Asp Asp Arg Asn Arg Gly Pro Thr Leu Glu
145                 150                 155                 160
Val Thr Leu Ala Lys Leu Arg Arg Leu Asn Pro Gly Met Gln Val Val
                165                 170                 175
Ala Leu Ser Ala Thr Val Gly Asn Ala Asp Glu Ile Ala Asp Trp Leu
                180                 185                 190
Asp Ala Ser Leu Val Asp Thr Asp Trp Arg Pro Ile Asp Leu Gln Met
        195                 200                 205
Gly Val His Tyr Gly Asn Ala Leu Asn Phe Asp Gly Ser Thr Arg
        210                 215                 220
Glu Val Pro Val Glu Gly Ser Glu Lys Gln Glu Ala Ala Leu Val Arg
225                 230                 235                 240
Asp Ile Leu Arg Glu Gly Gly Ser Ser Leu Val Phe Val Asn Ser Arg
                245                 250                 255
Arg Asn Ala Glu Gly Ala Ala Lys Arg Leu Gly Gln Val Ser Ser Arg
                260                 265                 270
Glu Ile Thr Glu Asp Glu Arg Ala Glu Leu Ala Glu Leu Ala Asp Asp
        275                 280                 285
Ile Arg Asp Asp Ser Asp Thr Glu Thr Ser Ala Asp Leu Ala Asp Cys
        290                 295                 300
Val Glu Arg Gly Ala Ala Phe His His Ala Gly Leu Ser Ser Thr Gln
305                 310                 315                 320
Arg Ser Leu Val Glu Asp Ala Phe Arg Asp Arg Leu Leu Lys Val Ile
                325                 330                 335
Ser Ala Thr Pro Thr Leu Ala Ala Gly Val Asn Thr Pro Ala Arg Arg
                340                 345                 350
Val Ile Val Arg Asp Trp Arg Arg Phe Asp Pro Ser Ala Gly Gly Met
        355                 360                 365
Ala Pro Leu Asp Val Leu Glu Val His Gln Met Met Gly Arg Ala Gly
        370                 375                 380
Arg Pro Gly Leu Asp Pro Tyr Gly Glu Ala Val Leu Leu Ala Lys Ser
385                 390                 395                 400
His Asp Glu Ser Glu Glu Leu Phe Asp Arg Tyr Ile Trp Ala Asp Pro
                405                 410                 415
Glu Pro Val Arg Ser Lys Leu Ala Ala Glu Pro Ala Leu Arg Thr His
                420                 425                 430
Val Leu Ala Thr Ile Ala Ser Gly Phe Ala Arg Thr Arg Gly Gly Leu
        435                 440                 445
```

```
Leu Glu Phe Leu Glu Ala Thr Leu Tyr Ala Ser Gln Ser Ser Glu Ala
    450                 455                 460

Gly Arg Leu Glu Ser Val Thr Asp Asp Val Leu Asp Tyr Leu Glu Arg
465                 470                 475                 480

Asn Asp Phe Ile Glu Arg Ser Arg Asp Asp Glu Ala Glu Asp Ser Gly
                485                 490                 495

Glu Asp Asp Gly Pro Phe Thr Ser Ala Ala Asp Leu Ala Glu Gln Gln
            500                 505                 510

Ala Ala Lys Arg Glu Glu Thr Leu Glu Ala Thr Ser Leu Gly His Thr
        515                 520                 525

Val Ser Arg Leu Tyr Leu Asp Pro Met Ser Ala Glu Ile Val His
    530                 535                 540

Gly Leu Glu Arg Ala Asp Glu Arg Pro Thr Ala Leu Gly Leu Tyr Gln
545                 550                 555                 560

Leu Val Ser Arg Thr Pro Asp Met Tyr Glu Leu Tyr Leu Arg Ser Gly
                565                 570                 575

Glu Asp Glu Lys Phe Gly Glu Leu Phe Tyr Glu Arg Glu Thr Glu Leu
            580                 585                 590

Leu Gly Asp Ala Pro Ser Glu Tyr Glu Glu Asp Arg Phe Glu Asp Trp
        595                 600                 605

Leu Ala Ala Leu Lys Thr Gly Lys Leu Leu Glu Asp Trp Ala Asp Glu
    610                 615                 620

Thr Asp Glu Glu Thr Ile Thr Asp Arg Tyr Lys Ile Gly Pro Gly Asp
625                 630                 635                 640

Leu Arg Gly Lys Val Asp Thr Ala Glu Trp Leu Leu Gly Ala Ala Glu
                645                 650                 655

Ser Leu Ala Ala Glu Ile Asp Ser Glu Trp Thr Val Ala Val Arg Glu
            660                 665                 670

Ala Arg Ala Arg Val Glu His Gly Val Gly Glu Glu Leu Leu Glu Leu
        675                 680                 685

Val Ser Val Gly Gly Val Gly Arg Lys Arg Ala Arg Leu Tyr Asp
    690                 695                 700

Ala Gly Ile Glu Glu Pro Ala Asp Leu Arg Ser Ala Asp Lys Gly Ile
705                 710                 715                 720

Val Leu Ser Val Leu Lys Gly Glu Lys Thr Ala Glu Asn Ile Leu Glu
                725                 730                 735

Asn Ala Gly Arg Glu Asp Pro Ser Met Asp Gly Val Glu Pro Ala Asp
            740                 745                 750

Gly Gly Pro Ala Val Gly Ala Thr Asn Gly Ser Ser Gly Gly Ser
        755                 760                 765

Glu Thr Asp Glu Thr Gly Arg Ala Asp Ala Ala Glu Ser Asp Ser
    770                 775                 780

Gln Ser Ser Leu Gly Asp Phe
785                 790

<210> SEQ ID NO 55
<211> LENGTH: 752
<212> TYPE: PRT
<213> ORGANISM: Haladaptatus paucihalophilus

<400> SEQUENCE: 55

Met Asn Val Ala Asp Leu Thr Gly Leu Pro Asp Gly Val Pro Glu His
1               5                   10                  15

Phe His Ala Gln Gly Ile Glu Glu Leu Tyr Pro Pro Gln Ala Glu Ala
                20                  25                  30
```

```
Val Glu Ala Gly Ile Thr Glu Gly Glu Ser Val Val Ala Ser Ile Pro
        35                  40                  45
Thr Ala Ser Gly Lys Thr Phe Ile Ala Glu Leu Ala Met Leu Ser Ser
 50                  55                  60
Val Ala Arg Gly Gly Lys Ala Leu Tyr Ile Val Pro Leu Arg Ala Leu
 65                  70                  75                  80
Ala Ser Glu Lys Lys Glu Glu Phe Glu Phe Glu Gln Tyr Gly Val
                85                  90                  95
Ser Ile Gly Val Ser Thr Gly Asn Tyr Glu Ser Asp Gly Asp Trp Leu
                100                 105                 110
Ala Ser Arg Asp Ile Ile Val Ala Thr Ser Glu Lys Val Asp Ser Leu
                115                 120                 125
Val Arg Asn Gly Ala Lys Trp Ile Asp Asp Leu Ser Cys Val Val Ala
        130                 135                 140
Asp Glu Val His Leu Val Asn Asp Ala His Arg Gly Pro Thr Leu Glu
145                 150                 155                 160
Val Thr Leu Ala Lys Leu Arg Arg Val Asn Pro Asp Leu Gln Thr Val
                165                 170                 175
Ala Leu Ser Ala Thr Val Gly Asn Ala Gly Glu Met Ala Asp Trp Leu
                180                 185                 190
Asp Ala Thr Leu Val Asp Ser Thr Trp Arg Pro Ile Asp Leu Arg Lys
                195                 200                 205
Gly Val Leu Tyr Gly Gln Ala Leu His Phe Asp Gly Thr Gln Gln
        210                 215                 220
Glu Leu Ala Arg Gly Asn Glu Lys Glu Thr Ala Ala Leu Val Arg Asp
225                 230                 235                 240
Thr Leu Glu Asp Gly Gly Ser Ser Leu Val Phe Val Asn Ser Arg Arg
                245                 250                 255
Asn Ala Glu Ala Ala Lys Arg Leu Ala Asp Val Thr Lys Thr His
        260                 265                 270
Leu Thr Asp Asp Glu Arg Arg Asp Leu Leu Asp Ile Ala Asp Gln Ile
        275                 280                 285
Arg Asp Val Ser Asp Thr Glu Thr Ser Asp Asp Leu Ala Thr Ile
        290                 295                 300
Glu Lys Gly Ala Ala Phe His His Ala Gly Leu Ala Ser Asp His Arg
305                 310                 315                 320
Ser Leu Val Glu Asp Ala Phe Arg Asp Lys Leu Ile Lys Val Ile Ser
                325                 330                 335
Ala Thr Pro Thr Leu Ala Ala Gly Val Asn Thr Pro Ser Arg Arg Val
                340                 345                 350
Ile Val Arg Asp Trp Arg Arg Tyr Asp Gly Asp Ile Gly Gly Met Gln
        355                 360                 365
Pro Leu Asp Val Leu Glu Val His Gln Met Phe Gly Arg Ala Gly Arg
        370                 375                 380
Pro Gly Leu Asp Pro His Gly Glu Ala Val Leu Ile Ala Lys Ser His
385                 390                 395                 400
Asp Glu Leu Gln Glu Leu Phe Asp Gln Tyr Val Trp Ala Asp Pro Glu
                405                 410                 415
Pro Val His Ser Lys Leu Ala Ala Glu Pro Ala Leu Arg Thr His Ile
                420                 425                 430
Leu Ala Thr Val Ala Ser Gly Phe Ala Gly Thr Glu Glu Glu Leu Leu
        435                 440                 445
```

-continued

```
Asp Phe Leu Glu Arg Thr Leu Tyr Ala Thr Gln Thr Asp Glu Thr Gly
    450                 455                 460

Arg Leu Glu Thr Val Thr Gln His Val Leu Asp Tyr Leu Asp Arg Asn
465                 470                 475                 480

Gly Phe Leu Glu Arg Asp Asp Arg Leu Arg Ala Thr Gly Leu Gly His
                485                 490                 495

Arg Val Ser Gln Leu Tyr Leu Asp Pro Met Ser Ala Ala Glu Ile Ile
                500                 505                 510

Asp Gly Leu Arg Asp Ala Asp Gly Lys Pro Thr Ala Leu Gly Leu Tyr
                515                 520                 525

His Leu Val Ser Arg Thr Pro Asp Met Tyr Gln Leu Tyr Leu Arg Ser
    530                 535                 540

Gly Asp Arg Glu Arg Tyr Thr Glu Ile Ala Tyr Glu Arg Glu Pro Glu
545                 550                 555                 560

Phe Leu Gly His Met Pro Ser Glu Phe Glu Asp Asn Ala Phe Glu Asp
                565                 570                 575

Trp Leu Ser Ala Leu Lys Thr Ala Arg Leu Leu Glu Asp Trp Ala Ser
                580                 585                 590

Glu Leu Asp Glu Asp Arg Ile Thr Glu Arg Tyr Ala Ile Gly Pro Gly
                595                 600                 605

Asp Ile Arg Gly Lys Val Glu Thr Ala Gln Trp Leu Leu Asn Ala Ala
                610                 615                 620

Glu Arg Leu Ala Ala Glu Leu Gln Arg Asp Asp Ala Glu Gly Ile Pro
625                 630                 635                 640

Ser Ala Thr Thr Thr Ala Val Arg Glu Ala Arg Lys Arg Val Glu Tyr
                645                 650                 655

Gly Val Glu Glu Glu Leu Leu Asp Leu Ala Gly Val Arg Asn Val Gly
                660                 665                 670

Arg Lys Arg Ala Arg Arg Leu Tyr Glu Ala Gly Ile Glu Ser Arg Ala
                675                 680                 685

Asp Leu Arg Glu Ala Asp Lys Ser Val Val Leu Gly Ala Leu Arg Gly
                690                 695                 700

Arg Lys Lys Thr Ala Glu Asn Ile Leu Glu Asn Val Gly Arg Gln Asp
705                 710                 715                 720

Pro Ser Leu Asp Asp Val Glu Ala Asp Ala Glu Thr Ala Ala Thr Ser
                725                 730                 735

Ala Arg Ala Thr Asn Asp Gly Gly Gln Gln Ser Leu Gly Asp Phe Glu
                740                 745                 750

<210> SEQ ID NO 56
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 56

Gln Met Phe Gly Arg Ala Gly Arg
1               5

<210> SEQ ID NO 57
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 57
```

```
Gln Met Phe Gly Arg Ala Gly Arg Pro
1               5
```

<210> SEQ ID NO 58
<211> LENGTH: 783
<212> TYPE: PRT
<213> ORGANISM: Halobacterium sp. NRC-1

<400> SEQUENCE: 58

```
Met Arg Val Ala Asp Val Pro Gly Leu Pro Gly Gly Val Ala Asp His
1               5                   10                  15

Phe Glu Gly Glu Gly Val Glu Glu Leu Tyr Pro Pro Gln Ala Glu Ala
                20                  25                  30

Val Glu Arg Gly Val Thr Glu Gly Ala Asn Leu Val Ala Ser Val Pro
            35                  40                  45

Thr Ala Ser Gly Lys Thr Leu Ile Ala Gln Leu Ala Met Leu Ser Ala
        50                  55                  60

Ile Ala Glu Gly Gly Asp Ser Pro Thr Phe Ser Gly Asp Gly Thr Ala
65                  70                  75                  80

Leu Tyr Ile Val Pro Leu Arg Ala Leu Ala Gly Glu Lys Ala Gln Glu
                85                  90                  95

Phe Glu Ala Phe Glu Arg Phe Gly Leu Ser Val Gly Val Ser Thr Gly
                100                 105                 110

Asn Tyr Glu Arg Asp Gly Ala Arg Leu Ala Asp Asn Asp Ile Val Val
            115                 120                 125

Ala Thr Ser Glu Lys Val Asp Ser Leu Val Arg Asn Gly Ala Gly Trp
        130                 135                 140

Ile Asp Asp Leu Ser Cys Val Ala Asp Glu Val His Leu Val Asp
145                 150                 155                 160

Asp Asp His Arg Gly Pro Thr Leu Glu Val Thr Leu Ala Lys Leu Arg
                165                 170                 175

Gln Gln Val Ala Asp Leu Gln Val Ala Leu Ser Ala Thr Val Gly
                180                 185                 190

Asn Ala Gly Glu Leu Ala Ala Trp Leu Asp Ala Glu Leu Val Asp Ser
            195                 200                 205

Asp Trp Arg Pro Ile Glu Leu Arg Thr Gly Val His Tyr Gly Gln Ser
        210                 215                 220

Leu His Tyr Asp Asp Gly Thr Gln Ala Glu Leu Ser Val Gly Ser Gly
225                 230                 235                 240

Ser Gln Thr Ala Ala Val Val Ala Asp Thr Leu Ala Asp Gly Ser
                245                 250                 255

Thr Leu Val Phe Val Asn Ser Arg Arg Asn Ala Glu Ala Ser Ala Arg
                260                 265                 270

Arg Leu Ala Asp Val Thr Gly Asn Ala Leu Ser Ser Ala Glu Arg Glu
            275                 280                 285

Arg Leu Ala Asp Ile Ala Ala Glu Ile Arg Gly Val Ser Asp Thr Glu
        290                 295                 300

Thr Ser Asp Glu Leu Ala Asp Ala Val Ala Ser Gly Ala Ala Phe His
305                 310                 315                 320

His Ala Gly Leu Ala Arg Glu His Arg Glu Leu Val Glu Glu Ala Phe
                325                 330                 335

Arg Asp Arg Leu Val Lys Ala Val Ser Ala Thr Pro Thr Leu Ala Ala
                340                 345                 350

Gly Val Asn Thr Pro Ala Arg Arg Val Val Val Arg Asp Trp Gln Arg
```

```
            355                 360                 365
Tyr Asp Gly Thr Ala Gly Gly Met Gln Pro Leu Asp Val Leu Glu Val
    370                 375                 380

His Gln Met Phe Gly Arg Ala Gly Arg Pro Gly Leu Asp Pro Tyr Gly
385                 390                 395                 400

Glu Ala Val Leu Leu Ala Asn Ser His Asp Glu Leu Glu Glu Leu Phe
                405                 410                 415

Asp Arg Tyr Val Tyr Ala Asp Pro Glu Pro Val Arg Ser Lys Leu Ala
            420                 425                 430

Ala Glu Pro Ala Leu Arg Thr His Val Leu Ala Ala Ile Ala Thr Gly
            435                 440                 445

Phe Thr Thr Thr Glu Asp Gly Leu His Glu Phe Leu Gly Gly Thr Leu
    450                 455                 460

Tyr Ala Thr Gln Thr Asp Asp Thr Gly Arg Leu Arg Ser Val Thr Gly
465                 470                 475                 480

Asp Val Leu Arg Tyr Leu Asp Arg Asn Gly Phe Val Glu Arg Asp Gly
                485                 490                 495

Ala Ala Leu Arg Ala Thr Ala Thr Gly Gln Leu Val Ser Arg Leu Tyr
            500                 505                 510

Val Asp Pro Met Ser Ala Ala Thr Ile Ile Asp Gly Leu Arg Asp Ala
            515                 520                 525

Ala Arg Asp Ala Thr Glu Thr Asp Asp Glu Gly Ala Phe Arg Pro Ala
    530                 535                 540

Ser Glu Leu Gly Asp Asp Ala Ala Leu Pro Ala Asp Ala Ser Val Glu
545                 550                 555                 560

Pro Thr Pro Leu Gly Leu Tyr His Leu Val Ser Arg Thr Pro Asp Met
                565                 570                 575

Tyr Glu Leu Tyr Leu Arg Ser Gly Asp Arg Glu Gln Tyr Thr Glu Val
            580                 585                 590

Ala Tyr Glu His Glu Asp Glu Leu Leu Gly Ala Thr Pro Arg Glu Glu
            595                 600                 605

Gln Ala Glu Phe Glu Asp Trp Leu Ser Ala Leu Lys Thr Ala Arg Leu
    610                 615                 620

Met Ala Asp Trp Ala Ser Glu Leu Asp Glu Glu Arg Ile Ala Glu Arg
625                 630                 635                 640

Tyr Asp Val Gly Pro Gly Asp Ile Arg Gly Lys Val Glu Thr Ala Glu
                645                 650                 655

Trp Leu Leu Asn Ala Ala Glu Arg Leu Ala Gly Glu Leu Asp Val Glu
            660                 665                 670

Cys Gly Pro Ala Val Arg Glu Ala Arg Lys Arg Val Gln Tyr Gly Val
            675                 680                 685

Arg Glu Glu Leu Leu Gly Leu Ala Gly Val Arg Asn Val Gly Arg Lys
    690                 695                 700

Arg Ala Arg Arg Leu Tyr Asn Ala Gly Val Glu Ser Arg Ala Asp Leu
705                 710                 715                 720

Arg Asn Ala Asp Lys Gly Val Val Leu Gly Ala Val Arg Gly Arg Ala
                725                 730                 735

Ala Thr Ala Glu Arg Ile Leu Glu Thr Val Gly His Pro Asp Pro Gly
            740                 745                 750

Met Asp Gly Val Ala Ala Asp Thr Asp Ala Ala Pro Glu Ser Gly Gly
            755                 760                 765

Glu Ala Gly Gly Asp Glu Gly Gln Ala Ser Leu Gly Asp Phe Ser
    770                 775                 780
```

```
<210> SEQ ID NO 59
<211> LENGTH: 8
<212> TYPE: PRT
<213> ORGANISM: Artificial sequence
<220> FEATURE:
<223> OTHER INFORMATION: RecD-like motif I
<220> FEATURE:
<221> NAME/KEY: MISC_FEATURE
<222> LOCATION: (1)..(1)
<223> OTHER INFORMATION: Xaa = G, S or A
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = P, A, S or G
<220> FEATURE:
<221> NAME/KEY: MISC_FEATURE
<222> LOCATION: (5)..(5)
<223> OTHER INFORMATION: Xaa = T, A, V, S or C
<220> FEATURE:
<221> NAME/KEY: MISC_FEATURE
<222> LOCATION: (6)..(6)
<223> OTHER INFORMATION: Xaa = G or A
<220> FEATURE:
<221> NAME/KEY: MISC_FEATURE
<222> LOCATION: (7)..(7)
<223> OTHER INFORMATION: Xaa = K or R
<220> FEATURE:
<221> NAME/KEY: MISC_FEATURE
<222> LOCATION: (8)..(8)
<223> OTHER INFORMATION: Xaa = T or S

<400> SEQUENCE: 59

Xaa Xaa Xaa Gly Xaa Xaa Xaa Xaa
1               5

<210> SEQ ID NO 60
<211> LENGTH: 25
<212> TYPE: PRT
<213> ORGANISM: Artificial sequence
<220> FEATURE:
<223> OTHER INFORMATION: Extended RecD-like motif I
<220> FEATURE:
<221> NAME/KEY: MISC_FEATURE
<222> LOCATION: (2)..(17)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = G, S or A
<220> FEATURE:
<221> NAME/KEY: MISC_FEATURE
<222> LOCATION: (19)..(19)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = P, A, S or G
<220> FEATURE:
<221> NAME/KEY: MISC_FEATURE
<222> LOCATION: (22)..(22)
<223> OTHER INFORMATION: Xaa = T, A, V, S or C
<220> FEATURE:
<221> NAME/KEY: MISC_FEATURE
<222> LOCATION: (23)..(23)
<223> OTHER INFORMATION: Xaa = G or A
<220> FEATURE:
<221> NAME/KEY: MISC_FEATURE
<222> LOCATION: (24)..(24)
<223> OTHER INFORMATION: Xaa = K or R
<220> FEATURE:
<221> NAME/KEY: MISC_FEATURE
```

```
<222> LOCATION: (25)..(25)
<223> OTHER INFORMATION: Xaa = T or S

<400> SEQUENCE: 60

Gln Xaa Xaa Xaa Xaa Xaa Xaa Xaa Xaa Xaa Xaa Xaa Xaa Xaa Xaa
1               5                   10                  15

Xaa Xaa Xaa Xaa Gly Xaa Xaa Xaa Xaa
            20              25

<210> SEQ ID NO 61
<211> LENGTH: 26
<212> TYPE: PRT
<213> ORGANISM: Artificial sequence
<220> FEATURE:
<223> OTHER INFORMATION: Extended RecD-like motif I
<220> FEATURE:
<221> NAME/KEY: MISC_FEATURE
<222> LOCATION: (2)..(18)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = G, S or A
<220> FEATURE:
<221> NAME/KEY: MISC_FEATURE
<222> LOCATION: (20)..(20)
<223> OTHER INFORMATION: Xaa = any amino acid
<220> FEATURE:
<221> NAME/KEY: MISC_FEATURE
<222> LOCATION: (21)..(21)
<223> OTHER INFORMATION: Xaa = P, A, S or G
<220> FEATURE:
<221> NAME/KEY: MISC_FEATURE
<222> LOCATION: (23)..(23)
<223> OTHER INFORMATION: Xaa = T, A, V, S or C
<220> FEATURE:
<221> NAME/KEY: MISC_FEATURE
<222> LOCATION: (24)..(24)
<223> OTHER INFORMATION: Xaa = G or A
<220> FEATURE:
<221> NAME/KEY: MISC_FEATURE
<222> LOCATION: (25)..(25)
<223> OTHER INFORMATION: Xaa = K or A
<220> FEATURE:
<221> NAME/KEY: MISC_FEATURE
<222> LOCATION: (26)..(26)
<223> OTHER INFORMATION: Xaa = T or S

<400> SEQUENCE: 61

Gln Xaa Xaa Xaa Xaa Xaa Xaa Xaa Xaa Xaa Xaa Xaa Xaa Xaa Xaa
1               5                   10                  15

Xaa Xaa Xaa Xaa Gly Xaa Xaa Xaa Xaa
            20              25

<210> SEQ ID NO 62
<211> LENGTH: 27
<212> TYPE: PRT
<213> ORGANISM: Artificial sequence
<220> FEATURE:
<223> OTHER INFORMATION: Extended RecD-like motif I
<220> FEATURE:
<221> NAME/KEY: MISC_FEATURE
<222> LOCATION: (2)..(19)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = G, S or A
<220> FEATURE:
<221> NAME/KEY: MISC_FEATURE
<222> LOCATION: (21)..(21)
<223> OTHER INFORMATION: Xaa = any amino acid
<220> FEATURE:
```

```
<221> NAME/KEY: MISC_FEATURE
<222> LOCATION: (22)..(22)
<223> OTHER INFORMATION: Xaa = P, A, S or G
<220> FEATURE:
<221> NAME/KEY: MISC_FEATURE
<222> LOCATION: (24)..(24)
<223> OTHER INFORMATION: Xaa = T, A, V, S or C
<220> FEATURE:
<221> NAME/KEY: MISC_FEATURE
<222> LOCATION: (25)..(25)
<223> OTHER INFORMATION: Xaa = G or A
<220> FEATURE:
<221> NAME/KEY: MISC_FEATURE
<222> LOCATION: (26)..(26)
<223> OTHER INFORMATION: Xaa = K or R
<220> FEATURE:
<221> NAME/KEY: MISC_FEATURE
<222> LOCATION: (27)..(27)
<223> OTHER INFORMATION: Xaa = T or S

<400> SEQUENCE: 62

Gln Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Gly Xaa Xaa Xaa Xaa
            20                  25

<210> SEQ ID NO 63
<211> LENGTH: 8
<212> TYPE: PRT
<213> ORGANISM: Artificial sequence
<220> FEATURE:
<223> OTHER INFORMATION: RecD motif I
<220> FEATURE:
<221> NAME/KEY: MISC_FEATURE
<222> LOCATION: (5)..(5)
<223> OTHER INFORMATION: Xaa = T, V or C
<220> FEATURE:
<221> NAME/KEY: MISC_FEATURE
<222> LOCATION: (8)..(8)
<223> OTHER INFORMATION: Xaa = T or S

<400> SEQUENCE: 63

Gly Gly Pro Gly Xaa Gly Lys Xaa
1               5

<210> SEQ ID NO 64
<211> LENGTH: 8
<212> TYPE: PRT
<213> ORGANISM: Artificial sequence
<220> FEATURE:
<223> OTHER INFORMATION: Preferred RecD motif I

<400> SEQUENCE: 64

Gly Gly Pro Gly Thr Gly Lys Thr
1               5

<210> SEQ ID NO 65
<211> LENGTH: 25
<212> TYPE: PRT
<213> ORGANISM: Artificial sequence
<220> FEATURE:
<223> OTHER INFORMATION: Extended RecD motif I
<220> FEATURE:
<221> NAME/KEY: MISC_FEATURE
<222> LOCATION: (2)..(17)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = T, V or C
<220> FEATURE:
<221> NAME/KEY: MISC_FEATURE
```

```
<222> LOCATION: (25)..(25)
<223> OTHER INFORMATION: Xaa = T or S

<400> SEQUENCE: 65

Gln Xaa Xaa Xaa Xaa Xaa Xaa Xaa Xaa Xaa Xaa Xaa Xaa Xaa Xaa
1               5                   10                  15

Xaa Gly Gly Pro Gly Xaa Gly Lys Xaa
            20                  25

<210> SEQ ID NO 66
<211> LENGTH: 26
<212> TYPE: PRT
<213> ORGANISM: Artificial sequence
<220> FEATURE:
<223> OTHER INFORMATION: Extended RecD motif I
<220> FEATURE:
<221> NAME/KEY: MISC_FEATURE
<222> LOCATION: (2)..(18)
<223> OTHER INFORMATION: Xaa = any amino acid
<220> FEATURE:
<221> NAME/KEY: MISC_FEATURE
<222> LOCATION: (23)..(23)
<223> OTHER INFORMATION: Xaa = T, V or C
<220> FEATURE:
<221> NAME/KEY: MISC_FEATURE
<222> LOCATION: (26)..(26)
<223> OTHER INFORMATION: Xaa = T or S

<400> SEQUENCE: 66

Gln Xaa Xaa Xaa Xaa Xaa Xaa Xaa Xaa Xaa Xaa Xaa Xaa Xaa Xaa
1               5                   10                  15

Xaa Xaa Gly Gly Pro Gly Xaa Gly Lys Xaa
            20                  25

<210> SEQ ID NO 67
<211> LENGTH: 27
<212> TYPE: PRT
<213> ORGANISM: Artificial sequence
<220> FEATURE:
<223> OTHER INFORMATION: Extended RecD motif I
<220> FEATURE:
<221> NAME/KEY: MISC_FEATURE
<222> LOCATION: (2)..(19)
<223> OTHER INFORMATION: Xaa = any amino acid
<220> FEATURE:
<221> NAME/KEY: MISC_FEATURE
<222> LOCATION: (24)..(24)
<223> OTHER INFORMATION: Xaa = T, V or C
<220> FEATURE:
<221> NAME/KEY: MISC_FEATURE
<222> LOCATION: (27)..(27)
<223> OTHER INFORMATION: Xaa = T or S

<400> SEQUENCE: 67

Gln Xaa Xaa Xaa Xaa Xaa Xaa Xaa Xaa Xaa Xaa Xaa Xaa Xaa Xaa
1               5                   10                  15

Xaa Xaa Xaa Gly Gly Pro Gly Xaa Gly Lys Xaa
            20                  25

<210> SEQ ID NO 68
<211> LENGTH: 10
<212> TYPE: PRT
<213> ORGANISM: Artificial sequence
<220> FEATURE:
<223> OTHER INFORMATION: RecD-like motif V
<220> FEATURE:
<221> NAME/KEY: MISC_FEATURE
<222> LOCATION: (1)..(1)
<223> OTHER INFORMATION: Xaa = Y, W or F
<220> FEATURE:
```

```
<221> NAME/KEY: MISC_FEATURE
<222> LOCATION: (2)..(2)
<223> OTHER INFORMATION: Xaa = A, T, S, M, C or V
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = T, N or S
<220> FEATURE:
<221> NAME/KEY: MISC_FEATURE
<222> LOCATION: (5)..(5)
<223> OTHER INFORMATION: Xaa = A, T, G, S, V or I
<220> FEATURE:
<221> NAME/KEY: MISC_FEATURE
<222> LOCATION: (6)..(8)
<223> OTHER INFORMATION: Xaa = any amino acid
<220> FEATURE:
<221> NAME/KEY: MISC_FEATURE
<222> LOCATION: (10)..(10)
<223> OTHER INFORMATION: Xaa = G or S

<400> SEQUENCE: 68

Xaa Xaa Xaa Xaa Xaa Xaa Xaa Xaa Gln Xaa
1               5                   10

<210> SEQ ID NO 69
<211> LENGTH: 10
<212> TYPE: PRT
<213> ORGANISM: Artificial sequence
<220> FEATURE:
<223> OTHER INFORMATION: RecD motif V
<220> FEATURE:
<221> NAME/KEY: MISC_FEATURE
<222> LOCATION: (1)..(1)
<223> OTHER INFORMATION: Xaa = Y, W or F
<220> FEATURE:
<221> NAME/KEY: MISC_FEATURE
<222> LOCATION: (2)..(2)
<223> OTHER INFORMATION: Xaa = A, M, C or V
<220> FEATURE:
<221> NAME/KEY: MISC_FEATURE
<222> LOCATION: (3)..(3)
<223> OTHER INFORMATION: Xaa = I, M or L
<220> FEATURE:
<221> NAME/KEY: MISC_FEATURE
<222> LOCATION: (4)..(4)
<223> OTHER INFORMATION: Xaa = T or S
<220> FEATURE:
<221> NAME/KEY: MISC_FEATURE
<222> LOCATION: (5)..(5)
<223> OTHER INFORMATION: Xaa = V or I

<400> SEQUENCE: 69

Xaa Xaa Xaa Xaa Xaa His Lys Ser Gln Gly
1               5                   10

<210> SEQ ID NO 70
<211> LENGTH: 13
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
```

```
<222> LOCATION: (6)..(10)
<223> OTHER INFORMATION: Xaa = any amino acid
<220> FEATURE:
<221> NAME/KEY: MISC_FEATURE
<222> LOCATION: (12)..(12)
<223> OTHER INFORMATION: Xaa = any amino acid except D, E, R and K

<400> SEQUENCE: 70

His Xaa Xaa Xaa Arg Xaa Xaa Xaa Xaa Xaa His Xaa His
1               5                   10

<210> SEQ ID NO 71
<211> LENGTH: 14
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(11)
<223> OTHER INFORMATION: Xaa = any amino acid
<220> FEATURE:
<221> NAME/KEY: MISC_FEATURE
<222> LOCATION: (13)..(13)
<223> OTHER INFORMATION: Xaa = any amino acid except D, E, R and K

<400> SEQUENCE: 71

His Xaa Xaa Xaa Arg Xaa Xaa Xaa Xaa Xaa Xaa His Xaa His
1               5                   10

<210> SEQ ID NO 72
<211> LENGTH: 15
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(12)
<223> OTHER INFORMATION: Xaa = any amino acid
<220> FEATURE:
<221> NAME/KEY: MISC_FEATURE
<222> LOCATION: (14)..(14)
<223> OTHER INFORMATION: Xaa = any amino acid except D, E, R and K

<400> SEQUENCE: 72

His Xaa Xaa Xaa Arg Xaa Xaa Xaa Xaa Xaa Xaa Xaa His Xaa His
1               5                   10                  15

<210> SEQ ID NO 73
<211> LENGTH: 16
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
```

```
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(13)
<223> OTHER INFORMATION: Xaa = any amino acid
<220> FEATURE:
<221> NAME/KEY: MISC_FEATURE
<222> LOCATION: (15)..(15)
<223> OTHER INFORMATION: Xaa = any amino acid except D, E, R and K

<400> SEQUENCE: 73

His Xaa Xaa Xaa Arg Xaa Xaa Xaa Xaa Xaa Xaa Xaa Xaa His Xaa His
1               5                   10                  15

<210> SEQ ID NO 74
<211> LENGTH: 17
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(14)
<223> OTHER INFORMATION: Xaa = any amino acid
<220> FEATURE:
<221> NAME/KEY: MISC_FEATURE
<222> LOCATION: (16)..(16)
<223> OTHER INFORMATION: Xaa = any amino acid except D, E, R and K

<400> SEQUENCE: 74

His Xaa Xaa Xaa Arg Xaa Xaa Xaa Xaa Xaa Xaa Xaa Xaa Xaa His Xaa
1               5                   10                  15

His

<210> SEQ ID NO 75
<211> LENGTH: 18
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(15)
<223> OTHER INFORMATION: Xaa = any amino acid
<220> FEATURE:
<221> NAME/KEY: MISC_FEATURE
<222> LOCATION: (17)..(17)
<223> OTHER INFORMATION: Xaa = any amino acid except D, E, R and K

<400> SEQUENCE: 75

His Xaa Xaa Xaa Arg Xaa Xaa Xaa Xaa Xaa Xaa Xaa Xaa Xaa Xaa His
1               5                   10                  15
```

Xaa His

```
<210> SEQ ID NO 76
<211> LENGTH: 19
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(16)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = any amino acid except D, E, R and K
```

<400> SEQUENCE: 76

His Xaa Xaa Xaa Arg Xaa Xaa Xaa Xaa Xaa Xaa Xaa Xaa Xaa Xaa
1               5                   10                  15

His Xaa His

```
<210> SEQ ID NO 77
<211> LENGTH: 20
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(17)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = any amino acid
```

<400> SEQUENCE: 77

His Xaa Xaa Xaa Arg Xaa Xaa Xaa Xaa Xaa Xaa Xaa Xaa Xaa Xaa Xaa
1               5                   10                  15

Xaa His Xaa His
            20

```
<210> SEQ ID NO 78
<211> LENGTH: 17
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
```

-continued

```
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(15)
<223> OTHER INFORMATION: Xaa = any amino acid
<220> FEATURE:
<221> NAME/KEY: MISC_FEATURE
<222> LOCATION: (17)..(17)
<223> OTHER INFORMATION: Xaa = any amino acid except D, E, K and R

<400> SEQUENCE: 78

Gly Xaa Xaa Xaa Xaa Xaa Xaa Xaa His Xaa Xaa Xaa Xaa Xaa Xaa His
1               5                   10                  15

Xaa

<210> SEQ ID NO 79
<211> LENGTH: 18
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(16)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = any amino acid except D, E, K and R

<400> SEQUENCE: 79

Gly Xaa Xaa Xaa Xaa Xaa Xaa Xaa His Xaa Xaa Xaa Xaa Xaa Xaa Xaa
1               5                   10                  15

His Xaa

<210> SEQ ID NO 80
<211> LENGTH: 19
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(17)
```

```
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = any amino acid except D, E, K and R

<400> SEQUENCE: 80

Gly Xaa Xaa Xaa Xaa Xaa Xaa Xaa His Xaa Xaa Xaa Xaa Xaa Xaa Xaa
1               5                   10                  15

Xaa His Xaa

<210> SEQ ID NO 81
<211> LENGTH: 20
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(18)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = any amino acid except D, E, K and R

<400> SEQUENCE: 81

Gly Xaa Xaa Xaa Xaa Xaa Xaa Xaa His Xaa Xaa Xaa Xaa Xaa Xaa Xaa
1               5                   10                  15

Xaa Xaa His Xaa
            20

<210> SEQ ID NO 82
<211> LENGTH: 21
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(19)
<223> OTHER INFORMATION: Xaa = any amino acid
<220> FEATURE:
<221> NAME/KEY: MISC_FEATURE
<222> LOCATION: (21)..(21)
<223> OTHER INFORMATION: Xaa = any amino acid

<400> SEQUENCE: 82
```

Gly Xaa Xaa Xaa Xaa Xaa Xaa Xaa His Xaa Xaa Xaa Xaa Xaa Xaa Xaa
1               5                   10                  15

Xaa Xaa Xaa His Xaa
            20

<210> SEQ ID NO 83
<211> LENGTH: 22
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(20)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid except D, E, K and R

<400> SEQUENCE: 83

Gly Xaa Xaa Xaa Xaa Xaa Xaa Xaa His Xaa Xaa Xaa Xaa Xaa Xaa Xaa
1               5                   10                  15

Xaa Xaa Xaa Xaa His Xaa
            20

<210> SEQ ID NO 84
<211> LENGTH: 23
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (23)..(23)
<223> OTHER INFORMATION: Xaa = any amino acid except D, E, K and R

<400> SEQUENCE: 84

Gly Xaa Xaa Xaa Xaa Xaa Xaa Xaa His Xaa Xaa Xaa Xaa Xaa Xaa Xaa
1               5                   10                  15

Xaa Xaa Xaa Xaa Xaa His Xaa
            20

```
<210> SEQ ID NO 85
<211> LENGTH: 1756
<212> TYPE: PRT
<213> ORGANISM: Escherichia coli

<400> SEQUENCE: 85
```

| | | | | | | | | | | | | | | | |
|---|---|---|---|---|---|---|---|---|---|---|---|---|---|---|---|
| Met | Met | Ser | Ile | Ala | Gln | Val | Arg | Ser | Ala | Gly | Ser | Ala | Gly | Asn | Tyr |
| 1 | | | | 5 | | | | | 10 | | | | | 15 | |
| Tyr | Thr | Asp | Lys | Asp | Asn | Tyr | Tyr | Val | Leu | Gly | Ser | Met | Gly | Glu | Arg |
| | | | 20 | | | | | 25 | | | | | 30 | | |
| Trp | Ala | Gly | Lys | Gly | Ala | Glu | Gln | Leu | Gly | Leu | Gln | Gly | Ser | Val | Asp |
| | | 35 | | | | | 40 | | | | | 45 | | | |
| Lys | Asp | Val | Phe | Thr | Arg | Leu | Leu | Glu | Gly | Arg | Leu | Pro | Asp | Gly | Ala |
| | 50 | | | | | 55 | | | | | 60 | | | | |
| Asp | Leu | Ser | Arg | Met | Gln | Asp | Gly | Ser | Asn | Lys | His | Arg | Pro | Gly | Tyr |
| 65 | | | | | 70 | | | | | 75 | | | | | 80 |
| Asp | Leu | Thr | Phe | Ser | Ala | Pro | Lys | Ser | Val | Ser | Met | Met | Ala | Met | Leu |
| | | | | 85 | | | | | 90 | | | | | 95 | |
| Gly | Gly | Asp | Lys | Arg | Leu | Ile | Asp | Ala | His | Asn | Gln | Ala | Val | Asp | Phe |
| | | | 100 | | | | | 105 | | | | | 110 | | |
| Ala | Val | Arg | Gln | Val | Glu | Ala | Leu | Ala | Ser | Thr | Arg | Val | Met | Thr | Asp |
| | | 115 | | | | | 120 | | | | | 125 | | | |
| Gly | Gln | Ser | Glu | Thr | Val | Leu | Thr | Gly | Asn | Leu | Val | Met | Ala | Leu | Phe |
| | 130 | | | | | 135 | | | | | 140 | | | | |
| Asn | His | Asp | Thr | Ser | Arg | Asp | Gln | Glu | Pro | Gln | Leu | His | Thr | His | Ala |
| 145 | | | | | 150 | | | | | 155 | | | | | 160 |
| Val | Val | Ala | Asn | Val | Thr | Gln | His | Asn | Gly | Glu | Trp | Lys | Thr | Leu | Ser |
| | | | | 165 | | | | | 170 | | | | | 175 | |
| Ser | Asp | Lys | Val | Gly | Lys | Thr | Gly | Phe | Ile | Glu | Asn | Val | Tyr | Ala | Asn |
| | | | 180 | | | | | 185 | | | | | 190 | | |
| Gln | Ile | Ala | Phe | Gly | Arg | Leu | Tyr | Arg | Glu | Lys | Leu | Lys | Glu | Gln | Val |
| | | 195 | | | | | 200 | | | | | 205 | | | |
| Glu | Ala | Leu | Gly | Tyr | Glu | Thr | Glu | Val | Val | Gly | Lys | His | Gly | Met | Trp |
| | 210 | | | | | 215 | | | | | 220 | | | | |
| Glu | Met | Pro | Gly | Val | Pro | Val | Glu | Ala | Phe | Ser | Gly | Arg | Ser | Gln | Ala |
| 225 | | | | | 230 | | | | | 235 | | | | | 240 |
| Ile | Arg | Glu | Ala | Val | Gly | Glu | Asp | Ala | Ser | Leu | Lys | Ser | Arg | Asp | Val |
| | | | | 245 | | | | | 250 | | | | | 255 | |
| Ala | Ala | Leu | Asp | Thr | Arg | Lys | Ser | Lys | Gln | His | Val | Asp | Pro | Glu | Ile |
| | | | 260 | | | | | 265 | | | | | 270 | | |
| Arg | Met | Ala | Glu | Trp | Met | Gln | Thr | Leu | Lys | Glu | Thr | Gly | Phe | Asp | Ile |
| | | 275 | | | | | 280 | | | | | 285 | | | |
| Arg | Ala | Tyr | Arg | Asp | Ala | Ala | Asp | Gln | Arg | Thr | Glu | Ile | Arg | Thr | Gln |
| | 290 | | | | | 295 | | | | | 300 | | | | |
| Ala | Pro | Gly | Pro | Ala | Ser | Gln | Asp | Gly | Pro | Asp | Val | Gln | Gln | Ala | Val |
| 305 | | | | | 310 | | | | | 315 | | | | | 320 |
| Thr | Gln | Ala | Ile | Ala | Gly | Leu | Ser | Glu | Arg | Lys | Val | Gln | Phe | Thr | Tyr |
| | | | | 325 | | | | | 330 | | | | | 335 | |
| Thr | Asp | Val | Leu | Ala | Arg | Thr | Val | Gly | Ile | Leu | Pro | Pro | Glu | Asn | Gly |
| | | | 340 | | | | | 345 | | | | | 350 | | |
| Val | Ile | Glu | Arg | Ala | Arg | Ala | Gly | Ile | Asp | Glu | Ala | Ile | Ser | Arg | Glu |
| | | 355 | | | | | 360 | | | | | 365 | | | |
| Gln | Leu | Ile | Pro | Leu | Asp | Arg | Glu | Lys | Gly | Leu | Phe | Thr | Ser | Gly | Ile |
| | 370 | | | | | 375 | | | | | 380 | | | | |

```
His Val Leu Asp Glu Leu Ser Val Arg Ala Leu Ser Arg Asp Ile Met
385                 390                 395                 400

Lys Gln Asn Arg Val Thr Val His Pro Glu Lys Ser Val Pro Arg Thr
            405                 410                 415

Ala Gly Tyr Ser Asp Ala Val Ser Val Leu Ala Gln Asp Arg Pro Ser
            420                 425                 430

Leu Ala Ile Val Ser Gly Gln Gly Ala Ala Gly Gln Arg Glu Arg
        435                 440                 445

Val Ala Glu Leu Val Met Met Ala Arg Glu Gln Gly Arg Glu Val Gln
    450                 455                 460

Ile Ile Ala Ala Asp Arg Arg Ser Gln Met Asn Leu Lys Gln Asp Glu
465                 470                 475                 480

Arg Leu Ser Gly Glu Leu Ile Thr Gly Arg Arg Gln Leu Leu Glu Gly
            485                 490                 495

Met Ala Phe Thr Pro Gly Ser Thr Val Ile Val Asp Gln Gly Glu Lys
            500                 505                 510

Leu Ser Leu Lys Glu Thr Leu Thr Leu Leu Asp Gly Ala Ala Arg His
        515                 520                 525

Asn Val Gln Val Leu Ile Thr Asp Ser Gly Gln Arg Thr Gly Thr Gly
    530                 535                 540

Ser Ala Leu Met Ala Met Lys Asp Ala Gly Val Asn Thr Tyr Arg Trp
545                 550                 555                 560

Gln Gly Gly Glu Gln Arg Pro Ala Thr Ile Ile Ser Glu Pro Asp Arg
            565                 570                 575

Asn Val Arg Tyr Ala Arg Leu Ala Gly Asp Phe Ala Ala Ser Val Lys
            580                 585                 590

Ala Gly Glu Glu Ser Val Ala Gln Val Ser Gly Val Arg Glu Gln Ala
        595                 600                 605

Ile Leu Thr Gln Ala Ile Arg Ser Glu Leu Lys Thr Gln Gly Val Leu
    610                 615                 620

Gly His Pro Glu Val Thr Met Thr Ala Leu Ser Pro Val Trp Leu Asp
625                 630                 635                 640

Ser Arg Ser Arg Tyr Leu Arg Asp Met Tyr Arg Pro Gly Met Val Met
            645                 650                 655

Glu Gln Trp Asn Pro Glu Thr Arg Ser His Asp Arg Tyr Val Ile Asp
            660                 665                 670

Arg Val Thr Ala Gln Ser His Ser Leu Thr Leu Arg Asp Ala Gln Gly
        675                 680                 685

Glu Thr Gln Val Val Arg Ile Ser Ser Leu Asp Ser Ser Trp Ser Leu
    690                 695                 700

Phe Arg Pro Glu Lys Met Pro Val Ala Asp Gly Glu Arg Leu Arg Val
705                 710                 715                 720

Thr Gly Lys Ile Pro Gly Leu Arg Val Ser Gly Asp Arg Leu Gln
            725                 730                 735

Val Ala Ser Val Ser Glu Asp Ala Met Thr Val Val Pro Gly Arg
            740                 745                 750

Ala Glu Pro Ala Ser Leu Pro Val Ser Asp Ser Pro Phe Thr Ala Leu
        755                 760                 765

Lys Leu Glu Asn Gly Trp Val Glu Thr Pro Gly His Ser Val Ser Asp
    770                 775                 780

Ser Ala Thr Val Phe Ala Ser Val Thr Gln Met Ala Met Asp Asn Ala
785                 790                 795                 800

Thr Leu Asn Gly Leu Ala Arg Ser Gly Arg Asp Val Arg Leu Tyr Ser
```

```
                805                 810                 815
Ser Leu Asp Glu Thr Arg Thr Ala Glu Lys Leu Ala Arg His Pro Ser
            820                 825                 830

Phe Thr Val Val Ser Glu Gln Ile Lys Ala Arg Ala Gly Glu Thr Leu
            835                 840                 845

Leu Glu Thr Ala Ile Ser Leu Gln Lys Ala Gly Leu His Thr Pro Ala
    850                 855                 860

Gln Gln Ala Ile His Leu Ala Leu Pro Val Leu Glu Ser Lys Asn Leu
865                 870                 875                 880

Ala Phe Ser Met Val Asp Leu Leu Thr Glu Ala Lys Ser Phe Ala Ala
                885                 890                 895

Glu Gly Thr Gly Phe Thr Glu Leu Gly Gly Glu Ile Asn Ala Gln Ile
            900                 905                 910

Lys Arg Gly Asp Leu Leu Tyr Val Asp Val Ala Lys Gly Tyr Gly Thr
            915                 920                 925

Gly Leu Leu Val Ser Arg Ala Ser Tyr Glu Ala Glu Lys Ser Ile Leu
    930                 935                 940

Arg His Ile Leu Glu Gly Lys Glu Ala Val Thr Pro Leu Met Glu Arg
945                 950                 955                 960

Val Pro Gly Glu Leu Met Glu Thr Leu Thr Ser Gly Gln Arg Ala Ala
                965                 970                 975

Thr Arg Met Ile Leu Glu Thr Ser Asp Arg Phe Thr Val Gln Gly
            980                 985                 990

Tyr Ala Gly Val Gly Lys Thr Thr  Gln Phe Arg Ala Val  Met Ser Ala
            995                 1000                1005

Val Asn  Met Leu Pro Ala Ser  Glu Arg Pro Arg  Val Val Gly Leu
    1010                1015                1020

Gly Pro  Thr His Arg Ala Val  Gly Glu Met Arg  Ser Ala Gly Val
    1025                1030                1035

Asp Ala  Gln Thr Leu Ala Ser  Phe Leu His Asp Thr  Gln Leu Gln
    1040                1045                1050

Gln Arg  Ser Gly Glu Thr Pro  Asp Phe Ser Asn Thr  Leu Phe Leu
    1055                1060                1065

Leu Asp  Glu Ser Ser Met Val  Gly Asn Thr Glu Met  Ala Arg Ala
    1070                1075                1080

Tyr Ala  Leu Ile Ala Ala Gly  Gly Gly Arg Ala Val  Ala Ser Gly
    1085                1090                1095

Asp Thr  Asp Gln Leu Gln Ala  Ile Ala Pro Gly Gln  Ser Phe Arg
    1100                1105                1110

Leu Gln  Gln Thr Arg Ser Ala  Ala Asp Val Val Ile  Met Lys Glu
    1115                1120                1125

Ile Val  Arg Gln Thr Pro Glu  Leu Arg Glu Ala Val  Tyr Ser Leu
    1130                1135                1140

Ile Asn  Arg Asp Val Glu Arg  Ala Leu Ser Gly Leu  Glu Ser Val
    1145                1150                1155

Lys Pro  Ser Gln Val Pro Arg  Leu Glu Gly Ala Trp  Ala Pro Glu
    1160                1165                1170

His Ser  Val Thr Glu Phe Ser  His Ser Gln Glu Ala  Lys Leu Ala
    1175                1180                1185

Glu Ala  Gln Gln Lys Ala Met  Leu Lys Gly Glu Ala  Phe Pro Asp
    1190                1195                1200

Ile Pro  Met Thr Leu Tyr Glu  Ala Ile Val Arg Asp  Tyr Thr Gly
    1205                1210                1215
```

```
Arg Thr Pro Glu Ala Arg Glu Gln Thr Leu Ile Val Thr His Leu
1220           1225                1230

Asn Glu Asp Arg Arg Val Leu Asn Ser Met Ile His Asp Ala Arg
1235            1240                1245

Glu Lys Ala Gly Glu Leu Gly Lys Glu Gln Val Met Val Pro Val
1250            1255                1260

Leu Asn Thr Ala Asn Ile Arg Asp Gly Glu Leu Arg Arg Leu Ser
1265            1270                1275

Thr Trp Glu Lys Asn Pro Asp Ala Leu Ala Leu Val Asp Asn Val
1280            1285                1290

Tyr His Arg Ile Ala Gly Ile Ser Lys Asp Asp Gly Leu Ile Thr
1295            1300                1305

Leu Gln Asp Ala Glu Gly Asn Thr Arg Leu Ile Ser Pro Arg Glu
1310            1315                1320

Ala Val Ala Glu Gly Val Thr Leu Tyr Thr Pro Asp Lys Ile Arg
1325            1330                1335

Val Gly Thr Gly Asp Arg Met Arg Phe Thr Lys Ser Asp Arg Glu
1340            1345                1350

Arg Gly Tyr Val Ala Asn Ser Val Trp Thr Val Thr Ala Val Ser
1355            1360                1365

Gly Asp Ser Val Thr Leu Ser Asp Gly Gln Gln Thr Arg Val Ile
1370            1375                1380

Arg Pro Gly Gln Glu Arg Ala Glu Gln His Ile Asp Leu Ala Tyr
1385            1390                1395

Ala Ile Thr Ala His Gly Ala Gln Gly Ala Ser Glu Thr Phe Ala
1400            1405                1410

Ile Ala Leu Glu Gly Thr Glu Gly Asn Arg Lys Leu Met Ala Gly
1415            1420                1425

Phe Glu Ser Ala Tyr Val Ala Leu Ser Arg Met Lys Gln His Val
1430            1435                1440

Gln Val Tyr Thr Asp Asn Arg Gln Gly Trp Thr Asp Ala Ile Asn
1445            1450                1455

Asn Ala Val Gln Lys Gly Thr Ala His Asp Val Leu Glu Pro Lys
1460            1465                1470

Pro Asp Arg Glu Val Met Asn Ala Gln Arg Leu Phe Ser Thr Ala
1475            1480                1485

Arg Glu Leu Arg Asp Val Ala Ala Gly Arg Ala Val Leu Arg Gln
1490            1495                1500

Ala Gly Leu Ala Gly Gly Asp Ser Pro Ala Arg Phe Ile Ala Pro
1505            1510                1515

Gly Arg Lys Tyr Pro Gln Pro Tyr Val Ala Leu Pro Ala Phe Asp
1520            1525                1530

Arg Asn Gly Lys Ser Ala Gly Ile Trp Leu Asn Pro Leu Thr Thr
1535            1540                1545

Asp Asp Gly Asn Gly Leu Arg Gly Phe Ser Gly Glu Gly Arg Val
1550            1555                1560

Lys Gly Ser Gly Asp Ala Gln Phe Val Ala Leu Gln Gly Ser Arg
1565            1570                1575

Asn Gly Glu Ser Leu Leu Ala Asp Asn Met Gln Asp Gly Val Arg
1580            1585                1590

Ile Ala Arg Asp Asn Pro Asp Ser Gly Val Val Val Arg Ile Ala
1595            1600                1605
```

-continued

```
Gly Glu Gly Arg Pro Trp Asn Pro Gly Ala Ile Thr Gly Gly Arg
    1610                1615                1620

Val Trp Gly Asp Ile Pro Asp Asn Ser Val Gln Pro Gly Ala Gly
    1625                1630                1635

Asn Gly Glu Pro Val Thr Ala Glu Val Leu Ala Gln Arg Gln Ala
    1640                1645                1650

Glu Glu Ala Ile Arg Arg Glu Thr Glu Arg Arg Ala Asp Glu Ile
    1655                1660                1665

Val Arg Lys Met Ala Glu Asn Lys Pro Asp Leu Pro Asp Gly Lys
    1670                1675                1680

Thr Glu Leu Ala Val Arg Asp Ile Ala Gly Gln Glu Arg Asp Arg
    1685                1690                1695

Ser Ala Ile Ser Glu Arg Glu Thr Ala Leu Pro Glu Ser Val Leu
    1700                1705                1710

Arg Glu Ser Gln Arg Glu Arg Glu Ala Val Arg Glu Val Ala Arg
    1715                1720                1725

Glu Asn Leu Leu Gln Glu Arg Leu Gln Gln Met Glu Arg Asp Met
    1730                1735                1740

Val Arg Asp Leu Gln Lys Glu Lys Thr Leu Gly Gly Asp
    1745                1750                1755

<210> SEQ ID NO 86
<211> LENGTH: 8
<212> TYPE: PRT
<213> ORGANISM: Artificial sequence
<220> FEATURE:
<223> OTHER INFORMATION: RecD-like motif I of TraI Eco

<400> SEQUENCE: 86

Gly Tyr Ala Gly Val Gly Lys Thr
1               5

<210> SEQ ID NO 87
<211> LENGTH: 10
<212> TYPE: PRT
<213> ORGANISM: Artificial sequence
<220> FEATURE:
<223> OTHER INFORMATION: RecD-like motif V of TraI Eco

<400> SEQUENCE: 87

Tyr Ala Ile Thr Ala His Gly Ala Gln Gly
1               5                   10

<210> SEQ ID NO 88
<211> LENGTH: 14
<212> TYPE: PRT
<213> ORGANISM: Artificial sequence
<220> FEATURE:
<223> OTHER INFORMATION: MobF  motif III of TraI Eco

<400> SEQUENCE: 88

His Asp Thr Ser Arg Asp Gln Glu Pro Gln Leu His Thr His
1               5                   10

<210> SEQ ID NO 89
<211> LENGTH: 9
<212> TYPE: PRT
<213> ORGANISM: Artificial Sequence
<220> FEATURE:
<223> OTHER INFORMATION: XPD motif V
<220> FEATURE:
<221> NAME/KEY: MISC_FEATURE
<222> LOCATION: (1)..(1)
```

```
<223> OTHER INFORMATION: Any amino acid except D, E, K or R.  Preferably
      not charged or H. More preferably V, L, I, S or Y.
<220> FEATURE:
<221> NAME/KEY: MISC_FEATURE
<222> LOCATION: (2)..(2)
<223> OTHER INFORMATION: Any amino acid except D, E, K or R.  Preferably
      not charged or H.
<220> FEATURE:
<221> NAME/KEY: MISC_FEATURE
<222> LOCATION: (3)..(3)
<223> OTHER INFORMATION: Any amino acid.
<220> FEATURE:
<221> NAME/KEY: MISC_FEATURE
<222> LOCATION: (5)..(5)
<223> OTHER INFORMATION: Any amino acid.  Preferably K, R or T.
<220> FEATURE:
<221> NAME/KEY: MISC_FEATURE
<222> LOCATION: (6)..(6)
<223> OTHER INFORMATION: Any amino acid except D, E, K or R.  Preferably
      not charged or H. More preferably V, L, I, N or F.
<220> FEATURE:
<221> NAME/KEY: MISC_FEATURE
<222> LOCATION: (7)..(7)
<223> OTHER INFORMATION: Any amino acid except D, E, K or R.  Preferably
      not charged or H. More preferably S or A.

<400> SEQUENCE: 89

Xaa Xaa Xaa Gly Xaa Xaa Xaa Glu Gly
1               5

<210> SEQ ID NO 90
<211> LENGTH: 22
<212> TYPE: PRT
<213> ORGANISM: Artificial Sequence
<220> FEATURE:
<223> OTHER INFORMATION: XPD motif VI
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (3)..(3)
<223> OTHER INFORMATION: Any amino acid except D, E, K, R.  Typically G,
      P, A, V, L, I, M, C, F, Y, W, H, Q, N, S or T.  Preferably not
      charged.  Preferably not H.  More preferably V, A, L, I or M.
<220> FEATURE:
<221> NAME/KEY: MISC_FEATURE
<222> LOCATION: (6)..(6)
<223> OTHER INFORMATION: Any amino acid except D, E, K, R.  Typically G,
      P, A, V, L, I, M, C, F, Y, W, H, Q, N, S or T.  Preferably not
      charged.  Preferably not H.  More preferably V, A, L, I, M or C.
<220> FEATURE:
<221> NAME/KEY: MISC_FEATURE
<222> LOCATION: (7)..(7)
<223> OTHER INFORMATION: Any amino acid except D, E, K, R.  Typically G,
      P, A, V, L, I, M, C, F, Y, W, H, Q, N, S or T.  Preferably not
      charged.  Preferably not H.  More preferably I, H, L, F, M or V.
<220> FEATURE:
<221> NAME/KEY: MISC_FEATURE
<222> LOCATION: (9)..(11)
<223> OTHER INFORMATION: Any amino acid.
<220> FEATURE:
<221> NAME/KEY: MISC_FEATURE
<222> LOCATION: (12)..(12)
<223> OTHER INFORMATION: D or E
<220> FEATURE:
<221> NAME/KEY: MISC_FEATURE
<222> LOCATION: (13)..(13)
<223> OTHER INFORMATION: Any amino acid.
<220> FEATURE:
<221> NAME/KEY: MISC_FEATURE
<222> LOCATION: (14)..(14)
<223> OTHER INFORMATION: Any amino acid.  Preferably G, A, S or C
<220> FEATURE:
<221> NAME/KEY: MISC_FEATURE
<222> LOCATION: (15)..(16)
```

<223> OTHER INFORMATION: Any amino acid.
<220> FEATURE:
<221> NAME/KEY: MISC_FEATURE
<222> LOCATION: (17)..(17)
<223> OTHER INFORMATION: Any amino acid. Preferably F, V, L, I, M, A, W or Y
<220> FEATURE:
<221> NAME/KEY: MISC_FEATURE
<222> LOCATION: (18)..(18)
<223> OTHER INFORMATION: Any amino acid. Preferably L, F, Y, M, I or V.
<220> FEATURE:
<221> NAME/KEY: MISC_FEATURE
<222> LOCATION: (19)..(19)
<223> OTHER INFORMATION: Any amino acid. Preferably A, C, V, L, I, M or S.

<400> SEQUENCE: 90

Gln Xaa Xaa Gly Arg Xaa Xaa Arg Xaa Xaa Xaa Xaa Xaa Xaa Xaa Xaa
1               5                   10                  15

Xaa Xaa Xaa Asp Asn Arg
            20

<210> SEQ ID NO 91
<211> LENGTH: 726
<212> TYPE: PRT
<213> ORGANISM: Methanococcoides burtonii

<400> SEQUENCE: 91

Met Ser Asp Lys Pro Ala Phe Met Lys Tyr Phe Thr Gln Ser Ser Cys
1               5                   10                  15

Tyr Pro Asn Gln Gln Glu Ala Met Asp Arg Ile His Ser Ala Leu Met
            20                  25                  30

Gln Gln Gln Leu Val Leu Phe Glu Gly Ala Cys Gly Thr Gly Lys Thr
        35                  40                  45

Leu Ser Ala Leu Val Pro Ala Leu His Val Gly Lys Met Leu Gly Lys
    50                  55                  60

Thr Val Ile Ile Ala Thr Asn Val His Gln Gln Met Val Gln Phe Ile
65                  70                  75                  80

Asn Glu Ala Arg Asp Ile Lys Lys Val Gln Asp Val Lys Val Ala Val
                85                  90                  95

Ile Lys Gly Lys Thr Ala Met Cys Pro Gln Glu Ala Asp Tyr Glu Glu
            100                 105                 110

Cys Ser Val Lys Arg Glu Asn Thr Phe Glu Leu Met Glu Thr Glu Arg
        115                 120                 125

Glu Ile Tyr Leu Lys Arg Gln Glu Leu Asn Ser Ala Arg Asp Ser Tyr
    130                 135                 140

Lys Lys Ser His Asp Pro Ala Phe Val Thr Leu Arg Asp Glu Leu Ser
145                 150                 155                 160

Lys Glu Ile Asp Ala Val Glu Glu Lys Ala Arg Gly Leu Arg Asp Arg
                165                 170                 175

Ala Cys Asn Asp Leu Tyr Glu Val Leu Arg Ser Asp Ser Glu Lys Phe
            180                 185                 190

Arg Glu Trp Leu Tyr Lys Glu Val Arg Ser Pro Glu Glu Ile Asn Asp
        195                 200                 205

His Ala Ile Lys Asp Gly Met Cys Gly Tyr Glu Leu Val Lys Arg Glu
    210                 215                 220

Leu Lys His Ala Asp Leu Leu Ile Cys Asn Tyr His His Val Leu Asn
225                 230                 235                 240

Pro Asp Ile Phe Ser Thr Val Leu Gly Trp Ile Glu Lys Glu Pro Gln
                245                 250                 255

Glu Thr Ile Val Ile Phe Asp Glu Ala His Asn Leu Glu Ser Ala Ala
            260                 265                 270

Arg Ser His Ser Ser Leu Ser Leu Thr Glu His Ser Ile Glu Lys Ala
            275                 280                 285

Ile Thr Glu Leu Glu Ala Asn Leu Asp Leu Leu Ala Asp Asp Asn Ile
290                 295                 300

His Asn Leu Phe Asn Ile Phe Leu Glu Val Ile Ser Asp Thr Tyr Asn
305                 310                 315                 320

Ser Arg Phe Lys Phe Gly Glu Arg Glu Val Arg Lys Asn Trp Tyr
                325                 330                 335

Asp Ile Arg Ile Ser Asp Pro Tyr Glu Arg Asn Asp Ile Val Arg Gly
            340                 345                 350

Lys Phe Leu Arg Gln Ala Lys Gly Asp Phe Gly Glu Lys Asp Ile
            355                 360                 365

Gln Ile Leu Leu Ser Glu Ala Ser Glu Leu Gly Ala Lys Leu Asp Glu
            370                 375                 380

Thr Tyr Arg Asp Gln Tyr Lys Lys Gly Leu Ser Ser Val Met Lys Arg
385                 390                 395                 400

Ser His Ile Arg Tyr Val Ala Asp Phe Met Ser Ala Tyr Ile Glu Leu
            405                 410                 415

Ser His Asn Leu Asn Tyr Tyr Pro Ile Leu Asn Val Arg Arg Asp Met
            420                 425                 430

Asn Asp Glu Ile Tyr Gly Arg Val Glu Leu Phe Thr Cys Ile Pro Lys
            435                 440                 445

Asn Val Thr Glu Pro Leu Phe Asn Ser Leu Phe Ser Val Ile Leu Met
450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
            485                 490                 495

Lys Arg Leu Ser Ile Ala Val Ser Ile Pro Pro Leu Phe Ala Lys Asn
            500                 505                 510

Arg Asp Asp Arg His Val Thr Glu Leu Leu Gln Val Leu Leu Asp
            515                 520                 525

Ser Ile Glu Asn Ser Lys Gly Asn Val Ile Leu Phe Phe Gln Ser Ala
530                 535                 540

Phe Glu Ala Lys Arg Tyr Tyr Ser Lys Ile Glu Pro Leu Val Asn Val
545                 550                 555                 560

Pro Val Phe Leu Asp Glu Val Gly Ile Ser Ser Gln Asp Val Arg Glu
            565                 570                 575

Glu Phe Phe Ser Ile Gly Glu Gly Asn Gly Lys Ala Val Leu Leu Ser
            580                 585                 590

Tyr Leu Trp Gly Thr Leu Ser Glu Gly Ile Asp Tyr Arg Asp Gly Arg
            595                 600                 605

Gly Arg Thr Val Ile Ile Gly Val Gly Tyr Pro Ala Leu Asn Asp
            610                 615                 620

Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
            645                 650                 655

Gln Ala Met Gly Arg Val Val Arg Ser Pro Thr Asp Tyr Gly Ala Arg
            660                 665                 670

```
Ile Leu Leu Asp Gly Arg Phe Leu Thr Asp Ser Lys Lys Arg Phe Gly
        675                 680                 685

Lys Phe Ser Val Phe Glu Val Phe Pro Pro Ala Glu Arg Ser Glu Phe
    690                 695                 700

Val Asp Val Asp Pro Glu Lys Val Lys Tyr Ser Leu Met Asn Phe Phe
705                 710                 715                 720

Met Asp Asn Asp Glu Gln
                725

<210> SEQ ID NO 92
<211> LENGTH: 9
<212> TYPE: PRT
<213> ORGANISM: Artificial Sequence
<220> FEATURE:
<223> OTHER INFORMATION: Motif V

<400> SEQUENCE: 92

Tyr Leu Trp Gly Thr Leu Ser Glu Gly
1               5

<210> SEQ ID NO 93
<211> LENGTH: 22
<212> TYPE: PRT
<213> ORGANISM: Artificial Sequence
<220> FEATURE:
<223> OTHER INFORMATION: Motif VI

<400> SEQUENCE: 93

Gln Ala Met Gly Arg Val Val Arg Ser Pro Thr Asp Tyr Gly Ala Arg
1               5                   10                  15

Ile Leu Leu Asp Gly Arg
            20

<210> SEQ ID NO 94
<211> LENGTH: 50
<212> TYPE: DNA
<213> ORGANISM: Artificial Sequence
<220> FEATURE:
<223> OTHER INFORMATION: Double stranded portion of MuA substrate

<400> SEQUENCE: 94
gttttcgcat ttatcgtgaa acgctttcgc gtttttcgtg cgccgcttca                50

<210> SEQ ID NO 95
<211> LENGTH: 50
<212> TYPE: DNA
<213> ORGANISM: Artificial Sequence
<220> FEATURE:
<223> OTHER INFORMATION: Double stranded portion of MuA substrate with U
      at 3' end
<220> FEATURE:
<221> NAME/KEY: misc_feature
<222> LOCATION: (50)..(50)
<223> OTHER INFORMATION: n = U

<400> SEQUENCE: 95
caaaagcgta aatagcactt tgcgaaagcg caaaaagcac gcggcgaagn                50

<210> SEQ ID NO 96
<211> LENGTH: 54
<212> TYPE: DNA
<213> ORGANISM: Artificial Sequence
<220> FEATURE:
<223> OTHER INFORMATION: Overhang strand of double stranded MuA
      substrate
<220> FEATURE:
```

-continued

<221> NAME/KEY: misc_feature
<222> LOCATION: (50)..(50)
<223> OTHER INFORMATION: n = U

<400> SEQUENCE: 96
caaaagcgta aatagcactt tgcgaaagcg caaaaagcac gcggcgaagn ctag    54

<210> SEQ ID NO 97
<211> LENGTH: 439
<212> TYPE: PRT
<213> ORGANISM: Enterobacteria phage T4

<400> SEQUENCE: 97

Met Thr Phe Asp Asp Leu Thr Glu Gly Gln Lys Asn Ala Phe Asn Ile
1               5                   10                  15

Val Met Lys Ala Ile Lys Glu Lys Lys His His Val Thr Ile Asn Gly
            20                  25                  30

Pro Ala Gly Thr Gly Lys Thr Thr Leu Thr Lys Phe Ile Ile Glu Ala
        35                  40                  45

Leu Ile Ser Thr Gly Glu Thr Gly Ile Ile Leu Ala Ala Pro Thr His
    50                  55                  60

Ala Ala Lys Lys Ile Leu Ser Lys Leu Ser Gly Lys Glu Ala Ser Thr
65                  70                  75                  80

Ile His Ser Ile Leu Lys Ile Asn Pro Val Thr Tyr Glu Glu Asn Val
                85                  90                  95

Leu Phe Glu Gln Lys Glu Val Pro Asp Leu Ala Lys Cys Arg Val Leu
            100                 105                 110

Ile Cys Asp Glu Val Ser Met Tyr Asp Arg Lys Leu Phe Lys Ile Leu
        115                 120                 125

Leu Ser Thr Ile Pro Pro Trp Cys Thr Ile Ile Gly Ile Gly Asp Asn
    130                 135                 140

Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
                165                 170                 175

Lys Arg Ser Asn Ala Pro Ile Ile Asp Val Ala Thr Asp Val Arg Asn
            180                 185                 190

Gly Lys Trp Ile Tyr Asp Lys Val Val Asp Gly His Gly Val Arg Gly
        195                 200                 205

Phe Thr Gly Asp Thr Ala Leu Arg Asp Phe Met Val Asn Tyr Phe Ser
    210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Val Met Gln
            260                 265                 270

Glu Pro Leu Phe Lys Thr Tyr Lys Ile Asp Gly Lys Pro Val Ser Glu
        275                 280                 285

Ile Ile Phe Asn Asn Gly Gln Leu Val Arg Ile Glu Ala Glu Tyr
    290                 295                 300

Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Asp Glu Tyr Tyr
                325                 330                 335

Arg Glu Lys Ile Lys Ile Ile Ser Ser Asp Glu Leu Tyr Lys Phe
            340                 345                 350

Asn Leu Phe Leu Gly Lys Thr Ala Glu Thr Tyr Lys Asn Trp Asn Lys
        355                 360                 365

Gly Gly Lys Ala Pro Trp Ser Asp Phe Trp Asp Ala Lys Ser Gln Phe
    370                 375                 380

Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
                405                 410                 415

Asp Val Glu Leu Ala Gln Gln Leu Leu Tyr Val Gly Val Thr Arg Gly
            420                 425                 430

Arg Tyr Asp Val Phe Tyr Val
            435

<210> SEQ ID NO 98
<211> LENGTH: 678
<212> TYPE: PRT
<213> ORGANISM: Rhodothermus marinus

<400> SEQUENCE: 98

Met Glu Glu Leu Ser Asn Glu Gln Gln Arg Val Leu Asp His Val Leu
1               5                   10                  15

Ala Trp Leu Glu Arg Asn Asp Ala Pro Pro Ile Phe Ile Leu Thr Gly
            20                  25                  30

Ser Ala Gly Thr Gly Lys Thr Leu Leu Ile Arg His Leu Val Arg Ala
        35                  40                  45

Leu Gln Asp Arg Arg Ile His Tyr Ala Leu Ala Pro Thr Gly Arg
50                  55                  60

Ala Ala Arg Ile Leu Ser Glu Arg Thr Gly Asp His Ala Arg Thr Leu
65                  70                  75                  80

His Ser Leu Ile Tyr Ile Phe Asp Arg Tyr Gln Leu Val Glu Glu Ala
                85                  90                  95

Asp Arg Gln Thr Asp Glu Pro Leu Ser Leu Gln Leu His Phe Ala Leu
            100                 105                 110

Arg Ser Ala Glu His Asp Ala Arg Leu Ile Ile Val Asp Glu Ala Ser
        115                 120                 125

Met Val Ser Asp Thr Ala Gly Glu Glu Leu Tyr Arg Phe Gly Ser
130                 135                 140

Gly Arg Leu Leu Asn Asp Leu Leu Thr Phe Ala Arg Leu Ile Pro Lys
145                 150                 155                 160

Arg Asp Arg Pro Pro Thr Thr Arg Leu Leu Phe Val Gly Asp Pro Ala
                165                 170                 175

Gln Leu Pro Pro Val Gly Gln Ser Val Ser Pro Ala Leu Ser Ala Gln
            180                 185                 190

Tyr Leu Arg Asp Thr Phe Gly Leu Ser Ala Glu Thr Ala His Leu Arg
        195                 200                 205

Ser Val Tyr Arg Gln Arg Lys Gly His Pro Ile Leu Glu Thr Ala Thr
    210                 215                 220

Ala Leu Arg Asn Ala Leu Glu Lys Gly His Tyr His Thr Phe Arg Leu
225                 230                 235                 240

Pro Glu Gln Pro Pro Asp Leu Arg Pro Val Gly Leu Glu Glu Ala Ile
                245                 250                 255

Glu Thr Thr Ala Thr Asp Phe Arg Arg Gln Asn Pro Ser Val Leu Leu
            260                 265                 270

```
Cys Arg Thr Asn Ala Leu Ala Arg Lys Leu Asn Ala Ala Val Arg Ala
    275                 280                 285

Arg Leu Trp Gly Arg Glu Gly Leu Pro Pro Gln Pro Gly Asp Leu Leu
290                 295                 300

Leu Val Asn Arg Asn Ala Pro Leu His Gly Leu Phe Asn Gly Asp Leu
305                 310                 315                 320

Val Leu Val Glu Thr Val Gly Pro Leu Glu His Arg Arg Val Gly Arg
            325                 330                 335

Arg Gly Arg Pro Pro Val Asp Leu Tyr Phe Arg Asp Val Glu Leu Leu
                340                 345                 350

Tyr Pro His Glu Lys Pro Arg Asn Arg Ile Arg Cys Lys Leu Leu Glu
        355                 360                 365

Asn Leu Leu Glu Ser Pro Asp Gly Gln Leu Ser Pro Asp Ile Ile Gln
370                 375                 380

Ala Leu Leu Ile Asp Phe Tyr Arg Arg His Pro Ser Leu Lys His Gly
385                 390                 395                 400

Ser Ser Glu Phe Arg Leu Met Leu Ala Asn Asp Ala Tyr Phe Asn Ala
            405                 410                 415

Leu His Val Arg Tyr Gly Tyr Ala Met Thr Val His Lys Ala Gln Gly
                420                 425                 430

Gly Glu Trp Lys Arg Ala Thr Val Val Phe Asn Asp Trp Arg His Phe
        435                 440                 445

Arg His Ala Glu Phe Phe Arg Trp Ala Tyr Thr Ala Ile Thr Arg Ala
450                 455                 460

Arg Glu Glu Leu Leu Thr Ile Gly Ala Pro Ser Phe Glu Ala Leu Ser
465                 470                 475                 480

Asp Met Arg Trp Gln Pro Ala Pro Ser Val Pro Ala Pro Glu Gln Ala
            485                 490                 495

Ala Glu Asn Ala Thr Arg Phe Pro Leu Lys Ala Leu Glu Thr Tyr His
                500                 505                 510

Gln Arg Leu Ser Glu Ala Leu Thr Ala Ala Gly Ile Glu Thr Thr Gly
        515                 520                 525

Val Glu Leu Leu Gln Tyr Ala Val Arg Tyr His Leu Ala Arg Ala Asp
530                 535                 540

Arg Thr Thr Arg Ile Gln Tyr Tyr Arg Gly Asp Gly Gln Ile Ser
545                 550                 555                 560

Arg Ile Val Thr Leu Gly Gly Ala Asp Asp Pro Glu Leu Thr Gln Gln
            565                 570                 575

Ala Tyr Ala Leu Phe Glu Arg Ile Leu Ser Glu Pro Pro Ala Asp Ser
                580                 585                 590

Gly Glu Leu Pro Glu Asn Pro Leu Leu Arg Glu Phe Leu Glu Arg Ala
        595                 600                 605

His Leu Arg Leu Glu Gly Ser Gly Ile Arg Ile Val His Trp Lys Glu
610                 615                 620

Met Pro Tyr Ala Leu Arg Leu Tyr Phe Ser Ala Asp Gly Glu Asn Val
625                 630                 635                 640

Thr Ile Asp Phe Tyr Tyr Asn Arg Arg Gly Val Trp Thr His Ala Gln
            645                 650                 655

Glu Val Gly Arg Ser Ser Gly Ala Leu Phe Ala Arg Ile Gln Ser
                660                 665                 670

Leu Leu Gln Ala Asp Ser
        675
```

<210> SEQ ID NO 99
<211> LENGTH: 496
<212> TYPE: PRT
<213> ORGANISM: Cyanothece ATCC51142

<400> SEQUENCE: 99

```
Met Ser Gln Ser Val Val Pro Asp Glu Leu Gly Glu Ile Ile Thr
1               5                   10                  15

Ala Val Ile Glu Phe Tyr Gln Asp Ala Val Asp Lys Ile Glu Pro Lys
            20                  25                  30

Ile Val Phe Leu Glu Leu Arg Lys Asn Val Val Asp Trp Val Ser Arg
            35                  40                  45

Thr Gln Leu Lys Ile Glu Glu Lys Glu Ile Gln Ala Thr Gly Leu Thr
50                  55                  60

Arg Gln Gln Gln Thr Ala Tyr Lys Glu Met Ile Asn Phe Ile Glu Asn
65                  70                  75                  80

Ser Ser Glu Gln Tyr Phe Arg Leu Ser Gly Tyr Ala Gly Thr Gly Lys
            85                  90                  95

Ser Phe Leu Met Ala Lys Val Ile Glu Trp Leu Lys Gln Glu Asp Tyr
            100                 105                 110

Lys Tyr Ser Val Ala Ala Pro Thr Asn Lys Ala Ala Lys Asn Leu Thr
            115                 120                 125

Gln Ile Ala Arg Ser Gln Gly Ile Lys Ile Glu Ala Thr Thr Val Ala
    130                 135                 140

Lys Leu Leu Lys Leu Gln Pro Thr Ile Asp Val Asp Thr Gly Gln Gln
145                 150                 155                 160

Ser Phe Glu Phe Asn Ser Glu Lys Glu Leu Glu Leu Lys Asp Tyr Asp
            165                 170                 175

Val Ile Ile Ile Asp Glu Tyr Ser Met Leu Asn Lys Asp Asn Phe Arg
            180                 185                 190

Asp Leu Gln Gln Ala Val Lys Gly Gly Glu Ser Lys Phe Ile Phe Val
    195                 200                 205

Gly Asp Ser Ser Gln Leu Pro Pro Val Lys Glu Lys Glu Pro Ile Val
210                 215                 220

Ala Asn His Pro Asp Ile Arg Lys Ser Ala Asn Leu Thr Gln Ile Val
225                 230                 235                 240

Arg Tyr Asp Gly Glu Ile Val Lys Val Ala Glu Ser Ile Arg Arg Asn
            245                 250                 255

Pro Arg Trp Asn His Gln Thr Tyr Pro Phe Glu Thr Val Ala Asp Gly
            260                 265                 270

Thr Ile Ile Lys Leu Asn Thr Glu Asp Trp Leu Gln Gln Ala Leu Ser
            275                 280                 285

His Phe Glu Lys Glu Asp Trp Leu Ser Asn Pro Asp Tyr Val Arg Met
    290                 295                 300

Ile Thr Trp Arg Asn Lys Thr Ala Asp Lys Tyr Asn Gln Ala Ile Arg
305                 310                 315                 320

Glu Ala Leu Tyr Gly Glu Asn Val Gly Gln Leu Val Val Gly Asp Arg
            325                 330                 335

Leu Ile Ala Lys Lys Pro Val Phe Arg Ser Leu Pro Gly Gly Lys Lys
            340                 345                 350

Lys Glu Lys Lys Ile Ile Leu Asn Asn Ser Glu Glu Cys Lys Val Ile
            355                 360                 365

Glu Thr Pro Lys Ile Asn Tyr Asn Glu Lys Tyr Lys Trp Glu Phe Tyr
370                 375                 380
```

Gln Val Lys Val Arg Thr Asp Glu Gly Gly Met Ile Glu Leu Arg Ile
385                 390                 395                 400

Leu Thr Ser Glu Ser Glu Lys Arg Gln Lys Leu Lys Glu Leu
            405                 410                 415

Ala Lys Arg Ala Arg Glu Glu Asn Tyr Ser Glu Lys Lys Gln
            420                 425                 430

Trp Ala Ile Tyr Tyr Glu Leu Asp Glu Leu Phe Asp Asn Met Ala Tyr
            435                 440                 445

Ala Tyr Ala Leu Thr Cys His Lys Ala Gln Gly Ser Ser Ile Asp Asn
            450                 455                 460

Val Phe Leu Leu Val Ser Asp Met His Tyr Cys Arg Asp Lys Thr Lys
465                 470                 475                 480

Met Ile Tyr Thr Gly Leu Thr Arg Ala Lys Lys Cys Cys Tyr Val Gly
                485                 490                 495

<210> SEQ ID NO 100
<211> LENGTH: 421
<212> TYPE: PRT
<213> ORGANISM: Salinibacter ruber

<400> SEQUENCE: 100

Met Ser Thr Phe Ala Asp Ala Pro Phe Thr Glu Asp Gln Glu Glu Ala
1               5                   10                  15

Tyr Asp His Val Tyr Asp Arg Leu Ala Gln Gly Glu Arg Phe Thr Gly
                20                  25                  30

Leu Arg Gly Tyr Ala Gly Thr Gly Lys Thr Tyr Leu Val Ser Arg Leu
            35                  40                  45

Val Glu Gln Leu Leu Asp Glu Asp Cys Thr Val Thr Val Cys Ala Pro
50                  55                  60

Thr His Lys Ala Val Gln Val Leu Ser Asp Glu Leu Gly Asp Ala Pro
65                  70                  75                  80

Val Gln Met Gln Thr Leu His Ser Phe Leu Gly Leu Arg Leu Gln Pro
                85                  90                  95

Lys Gln Asp Gly Glu Tyr Glu Leu Val Ala Glu Glu Arg Asn Phe
            100                 105                 110

Ala Glu Gly Val Val Ile Val Asp Glu Ala Ser Met Ile Gly Arg Glu
            115                 120                 125

Glu Trp Ser His Ile Gln Asp Ala Pro Phe Trp Val Gln Trp Leu Phe
            130                 135                 140

Val Gly Asp Pro Ala Gln Leu Pro Pro Val Asn Glu Asp Pro Ser Pro
145                 150                 155                 160

Ala Leu Asp Val Pro Gly Pro Thr Leu Glu Thr Ile His Arg Gln Ala
                165                 170                 175

Ala Asp Asn Pro Ile Leu Glu Leu Ala Thr Lys Ile Arg Thr Gly Ala
            180                 185                 190

Asp Gly Arg Phe Gly Ser Thr Phe Glu Asp Gly Lys Gly Val Ala Val
            195                 200                 205

Thr Arg Asn Arg Glu Glu Phe Leu Asp Ser Ile Leu Arg Ala Phe Asp
210                 215                 220

Ala Asp Ala Phe Ala Glu Asp Ala Thr His Ala Arg Val Leu Ala Tyr
225                 230                 235                 240

Arg Asn Lys Thr Val Arg Arg Tyr Asn Arg Glu Ile Arg Ala Glu Arg
                245                 250                 255

Tyr Gly Ala Asp Ala Asp Arg Phe Val Glu Gly Glu Trp Leu Val Gly

```
                        260                 265                 270
Thr Glu Thr Trp Tyr Tyr Asp Gly Val Gln Arg Leu Thr Asn Ser Glu
            275                 280                 285

Glu Val Arg Val Lys Ala Gln Val Glu Thr Phe Glu Ala Asp Asp
        290                 295                 300

Gln Ser Glu Trp Thr Val Trp Glu Leu Lys Ile Arg Thr Pro Gly Arg
305                 310                 315                 320

Gly Leu Thr Arg Thr Ile His Val Leu His Glu Glu Arg Glu Arg
                325                 330                 335

Tyr Glu Asn Ala Leu Glu Arg Arg Gly Lys Ala Glu Asp Asp Pro
                340                 345                 350

Ser Lys Trp Asp Arg Phe Phe Glu Leu Arg Glu Arg Phe Ala Arg Val
            355                 360                 365

Asp Tyr Ala Tyr Ala Thr Thr Val His Arg Ala Gln Gly Ser Thr Tyr
                370                 375                 380

Asp Thr Val Phe Val Asp His Arg Asp Leu Arg Val Cys Arg Gly Glu
385                 390                 395                 400

Glu Arg Gly Ala Leu Leu Tyr Val Ala Val Thr Arg Pro Ser Arg Arg
                405                 410                 415

Leu Ala Leu Leu Val
            420

<210> SEQ ID NO 101
<211> LENGTH: 500
<212> TYPE: PRT
<213> ORGANISM: Sulfurimonas gotlandica GD1

<400> SEQUENCE: 101

Met Lys Ile Leu Asn Lys Glu Thr Tyr Lys Leu Ser Leu His Gln Glu
1               5                   10                  15

Glu Val Phe Thr Gln Ile Val Ser Gln Leu Asp Thr Lys Val Ser Ser
            20                  25                  30

Ile Leu Lys Ser Thr Asn Ile Glu Asp Tyr Leu Leu Ser Leu Thr Gly
        35                  40                  45

Pro Ala Gly Thr Gly Lys Thr Phe Leu Thr Thr Gln Ile Ala Lys Tyr
    50                  55                  60

Leu Val Glu Lys Arg Lys Glu Ser Glu Tyr Pro Met Ser Ser Asp Phe
65                  70                  75                  80

Asp Phe Thr Ile Thr Ala Pro Thr His Lys Ala Val Gly Val Leu Ser
                85                  90                  95

Lys Leu Leu Arg Glu Asn Asn Ile Gln Ser Ser Cys Lys Thr Ile His
            100                 105                 110

Ser Phe Leu Gly Ile Lys Pro Phe Ile Asp Tyr Thr Thr Gly Glu Glu
        115                 120                 125

Lys Phe Val Val Asp Lys Thr Asn Lys Arg Lys Asp Arg Thr Ser Ile
    130                 135                 140

Leu Ile Val Asp Glu Ser Ser Met Ile Gly Asn Thr Leu Tyr Glu Tyr
145                 150                 155                 160

Ile Leu Glu Ala Ile Glu Asp Lys Arg Val Asn Val Leu Phe Ile
                165                 170                 175

Gly Asp Pro Tyr Gln Leu Leu Pro Ile Glu Asn Ser Lys Asn Glu Ile
            180                 185                 190

Tyr Asp Leu Pro Asn Arg Phe Phe Leu Ser Glu Val Val Arg Gln Ala
        195                 200                 205
```

Glu Asn Ser Tyr Ile Ile Arg Val Ala Thr Lys Leu Arg Glu Arg Ile
            210                 215                 220

Lys Asn Gln Asp Phe Ile Ser Leu Gln Gln Phe Phe Gln Glu Asn Met
225                 230                 235                 240

Glu Asp Glu Ile Thr Phe Phe His Asn Lys Glu Ala Phe Leu Glu Asp
            245                 250                 255

Phe Tyr Lys Glu Glu Glu Trp Tyr Lys Glu Asn Lys Ile Leu Ala Thr
            260                 265                 270

Tyr Lys Asn Lys Asp Val Asp Ala Phe Asn Lys Ile Ile Arg Asn Lys
            275                 280                 285

Phe Trp Glu Gln Lys Gly Asn Thr Thr Pro Ser Thr Leu Leu Ala Gly
290                 295                 300

Asp Met Ile Arg Phe Lys Asp Ala Tyr Thr Val Gly Asp Ile Thr Ile
305                 310                 315                 320

Tyr His Asn Gly Gln Glu Leu Gln Leu Gly Ser Thr Glu Val Lys Tyr
            325                 330                 335

His Asp Ser Leu His Ile Glu Tyr Trp Glu Cys Lys Ser Ile Tyr Ala
            340                 345                 350

Leu Glu Gln Gln Val Phe Arg Val Val Asn Pro Asp Ser Glu Ala Val
            355                 360                 365

Phe Asn Gln Lys Leu Gln Ser Leu Ala Thr Lys Ala Lys Gln Ala Lys
370                 375                 380

Phe Pro Asp Asn Lys Lys Leu Trp Lys Leu Tyr Tyr Glu Thr Arg Asn
385                 390                 395                 400

Met Phe Ala Asn Val Gln Tyr Ile His Ala Ser Thr Ile His Lys Leu
            405                 410                 415

Gln Gly Ser Thr Tyr Asp Val Ser Tyr Ile Asp Ile Phe Ser Leu Val
            420                 425                 430

His Asn His Tyr Met Ser Asp Glu Glu Lys Tyr Arg Leu Leu Tyr Val
            435                 440                 445

Ala Ile Thr Arg Ala Ser Lys Asp Ile Lys Ile Phe Met Ser Ala Phe
            450                 455                 460

Asp Arg Thr Ser Asp Glu Lys Val Ile Ile Asn Asn Gln Asn Ser Glu
465                 470                 475                 480

Thr Met Asn Thr Leu Lys Gln Leu His Asp Ile Asp Ile Leu Lys
            485                 490                 495

Asp Leu Asp Leu
            500

<210> SEQ ID NO 102
<211> LENGTH: 450
<212> TYPE: PRT
<213> ORGANISM: Vibrio phage henriette 12B8

<400> SEQUENCE: 102

Met Ala Asp Phe Glu Leu Thr Leu Gly Gln Lys Thr Val Leu Gly Glu
1               5                   10                  15

Val Ile Ser Thr Ile Leu Lys Pro Val Asn Leu Asn Asp Thr Ser Arg
            20                  25                  30

Phe His Thr Met His Gly Pro Ala Gly Ser Gly Lys Thr Thr Val Leu
            35                  40                  45

Gln Arg Ile Ile Ser Gln Ile Pro Ala Tyr Lys Thr Ile Gly Phe Cys
        50                  55                  60

Ser Pro Thr His Lys Ser Val Lys Val Ile Arg Arg Met Ala Arg Glu
65                  70                  75                  80

Ala Gly Ile Ser His Arg Val Asp Ile Arg Thr Ile His Ser Ala Leu
                85                  90                  95

Gly Leu Val Met Lys Pro Val Arg Gly Asp Glu Val Leu Val Lys Glu
            100                 105                 110

Pro Phe Ala Glu Glu Arg Ile Tyr Asp Val Leu Ile Ile Asp Glu Ala
        115                 120                 125

Gly Met Leu Asn Asp Glu Leu Ile Met Tyr Ile Leu Glu Ser Gln Ser
    130                 135                 140

Ser Lys Val Ile Phe Val Gly Asp Met Cys Gln Ile Gly Pro Ile Gln
145                 150                 155                 160

Ser Asn Leu Pro Glu Glu Asp Gly Tyr Thr Pro Thr Ser Thr Asp Asp
                165                 170                 175

Val Ser Lys Val Phe Thr Glu Val Glu Met Met Ser Ala Leu Thr Glu
            180                 185                 190

Val Val Arg Gln Ala Glu Gly Ser Pro Ile Ile Gln Leu Ala Thr Glu
        195                 200                 205

Phe Arg Leu Ala Gln Asp Asp Ile Tyr Ala Asp Leu Pro Arg Ile Val
    210                 215                 220

Thr Asn Thr Thr Pro Asp Gly Asn Gly Ile Ile Thr Met Pro Asn Gly
225                 230                 235                 240

Asn Trp Val Asp Ser Ala Val Ala Arg Phe Gln Ser Asp Gln Phe Lys
                245                 250                 255

Glu Asp Pro Asp His Cys Arg Ile Val Cys Tyr Thr Asn Ala Met Val
            260                 265                 270

Asp Leu Cys Asn Asp Leu Val Arg Lys Arg Leu Phe Gly Ala Asp Val
        275                 280                 285

Pro Glu Trp Leu Glu Asp Glu Ile Leu Val Ala Gln Glu Met Gly Ser
    290                 295                 300

Thr Trp Asn Asn Ala Asp Glu Leu Arg Ile Val Ser Ile Asp His
305                 310                 315                 320

Phe Asp Gln Gln Tyr Glu Val Pro Cys Trp Arg Met Gln Leu Glu Ser
                325                 330                 335

Val Glu Asp His Lys Leu His Asn Ala Leu Val Val Lys Gly Asp Tyr
            340                 345                 350

Ile Glu Asp Phe Lys Phe Arg Leu Asn Ala Ile Ala Glu Arg Ala Asn
        355                 360                 365

Thr Asp Lys Asn Met Ser Gly Met His Trp Lys Glu Phe Trp Gly Met
    370                 375                 380

Arg Lys Lys Phe Asn Thr Phe Lys Asn Val Tyr Ala Gly Thr Ala His
385                 390                 395                 400

Lys Ser Gln Gly Ser Thr Phe Asp Tyr Thr Tyr Val Phe Thr Pro Asp
                405                 410                 415

Phe Tyr Lys Phe Gly Ala Thr Met Thr Ile Lys Arg Leu Leu Tyr Thr
            420                 425                 430

Ala Ile Thr Arg Ser Arg Tyr Thr Thr Tyr Phe Ala Met Asn Thr Gly
        435                 440                 445

Ala Gln
    450

<210> SEQ ID NO 103
<211> LENGTH: 421
<212> TYPE: PRT
<213> ORGANISM: Vibrio phage phi-pp2

<400> SEQUENCE: 103

```
Met Gly Leu Thr Asn Cys Gln Gln Gly Ala Met Asp Ala Phe Leu Glu
1               5                   10                  15

Ser Asp Gly His Met Thr Ile Ser Gly Pro Ala Gly Ser Gly Lys Thr
            20                  25                  30

Phe Leu Met Lys Ser Ile Leu Glu Ala Leu Glu Ser Lys Gly Lys Asn
        35                  40                  45

Val Thr Met Val Thr Pro Thr His Gln Ala Lys Asn Val Leu His Lys
    50                  55                  60

Ala Thr Gly Gln Glu Val Ser Thr Ile His Ser Leu Leu Lys Ile His
65                  70                  75                  80

Pro Asp Thr Tyr Glu Asp Gln Lys His Phe Thr Gln Ser Gly Glu Val
                85                  90                  95

Glu Gly Leu Asp Glu Ile Asp Val Leu Val Glu Glu Ala Ser Met
            100                 105                 110

Val Asp Glu Glu Leu Phe Gln Ile Thr Gly Arg Thr Met Pro Arg Lys
        115                 120                 125

Cys Arg Ile Leu Ala Val Gly Asp Lys Tyr Gln Leu Gln Pro Val Lys
130                 135                 140

His Asp Pro Gly Val Ile Ser Pro Phe Phe Thr Lys Phe Thr Thr Phe
145                 150                 155                 160

Glu Met Asn Glu Val Val Arg Gln Ala Lys Asp Asn Pro Leu Ile Gln
                165                 170                 175

Val Ala Thr Glu Val Arg Asn Gly Gln Trp Leu Arg Thr Asn Trp Ser
            180                 185                 190

Lys Glu Arg Arg Gln Gly Val Leu His Val Pro Asn Val Asn Lys Met
        195                 200                 205

Leu Asp Thr Tyr Leu Ser Lys Val Asn Ser Pro Glu Asp Leu Leu Asp
    210                 215                 220

Tyr Arg Ile Leu Ala Tyr Thr Asn Asp Cys Val Asp Thr Phe Asn Gly
225                 230                 235                 240

Ile Ile Arg Glu His Val Tyr Asn Thr Ser Glu Pro Phe Ile Pro Gly
                245                 250                 255

Glu Tyr Leu Val Thr Gln Met Pro Val Met Val Ser Asn Gly Lys Tyr
            260                 265                 270

Pro Val Cys Val Ile Glu Asn Gly Glu Val Val Lys Ile Leu Asp Val
        275                 280                 285

Arg Gln Lys Thr Ile Asp Gly Met Leu Pro Lys Val Asp Asn Glu Ala
    290                 295                 300

Phe Asp Val Ala Val Leu Thr Val Glu Lys Glu Asp Gly Asn Val Tyr
305                 310                 315                 320

Glu Phe Thr Val Leu Trp Asp Asp Leu Gln Lys Glu Arg Phe Ala Arg
                325                 330                 335

Tyr Leu Ser Val Ala Ala Gly Thr Tyr Lys Ser Met Arg Gly Asn Thr
            340                 345                 350

Lys Arg Tyr Trp Arg Ala Phe Trp Gly Leu Lys Glu Gln Met Ile Glu
        355                 360                 365

Thr Lys Ser Leu Gly Ala Ser Thr Val His Lys Ser Gln Gly Thr Thr
    370                 375                 380

Val Lys Gly Val Cys Leu Tyr Thr Gln Asp Met Gly Tyr Ala Glu Pro
385                 390                 395                 400

Glu Ile Leu Gln Gln Leu Val Tyr Val Gly Leu Thr Arg Pro Thr Asp
                405                 410                 415
```

Trp Ala Leu Tyr Asn
            420

<210> SEQ ID NO 104
<211> LENGTH: 434
<212> TYPE: PRT
<213> ORGANISM: Aeromonas phage 65

<400> SEQUENCE: 104

Met Ser Glu Ser Glu Ile Thr Leu Thr Pro Ser Gln Asn Met Ala Val
1               5                   10                  15

Asn Glu Val Lys Asn Gly Thr Gly His Ile Thr Ile Ser Gly Pro Pro
            20                  25                  30

Gly Ser Gly Lys Thr Phe Leu Val Lys Tyr Leu Ile Lys Met Leu Gly
            35                  40                  45

Asp Glu Leu Gly Thr Val Leu Ala Ala Pro Thr His Gln Ala Lys Ile
        50                  55                  60

Val Leu Thr Glu Met Ser Gly Ile Glu Ala Cys Thr Ile His Ser Leu
65                  70                  75                  80

Met Lys Ile His Pro Glu Thr Leu Glu Asp Ile Gln Ile Phe Asp Gln
                85                  90                  95

Ser Lys Leu Pro Asp Leu Ser Asn Ile Arg Tyr Leu Ile Val Glu Glu
            100                 105                 110

Ala Ser Met His Ser Lys Thr Leu Phe Lys Ile Thr Met Lys Ser Ile
        115                 120                 125

Pro Pro Thr Cys Arg Ile Ile Ala Ile Gly Asp Lys Asp Gln Ile Gln
130                 135                 140

Pro Glu Glu His Ala Gln Gly Glu Leu Ser Pro Tyr Phe Thr Asp Pro
145                 150                 155                 160

Arg Phe Ser Gln Ile Arg Leu Thr Asp Ile Met Arg Gln Ser Leu Asp
                165                 170                 175

Asn Pro Ile Ile Gln Val Ala Thr Lys Ile Arg Glu Gly Gly Trp Ile
            180                 185                 190

Glu Pro Asn Trp Asn Arg Asp Thr Lys Thr Gly Val Tyr Lys Val Ser
        195                 200                 205

Gly Ile Thr Asp Leu Val Asn Ser Tyr Leu Arg Ala Val Lys Thr Pro
210                 215                 220

Glu Asp Leu Thr Lys Tyr Arg Phe Leu Ala Tyr Thr Asn Lys Val Val
225                 230                 235                 240

Asn Lys Val Asn Ser Ile Val Arg Glu His Val Tyr Lys Thr Lys Leu
                245                 250                 255

Pro Phe Ile Glu Gly Glu Lys Ile Val Leu Gln Glu Pro Val Met Val
            260                 265                 270

Glu His Glu Asp Asp Thr Ile Glu Thr Ile Phe Thr Asn Gly Glu Val
        275                 280                 285

Val Thr Ile Asn Glu Ile Glu Val Phe Asp Arg Thr Ile Arg Ile Asp
290                 295                 300

Gly Ser Pro Glu Phe Lys Val Asn Ala Ala Lys Leu Ser Val Ser Ser
305                 310                 315                 320

Asp Tyr Ser Gly Ile Glu His Asp Phe Cys Val Leu Tyr Gly Ser Glu
                325                 330                 335

Ser Arg Leu Glu Phe Glu Tyr Gln Leu Ser Glu Ser Ala Gly Asn Ile
            340                 345                 350

Lys Gln Met Gly Lys Gly Gly Asn Gln Arg Ser Ala Trp Lys Ser Phe

```
            355                 360                 365
Trp Ala Ala Lys Lys Met Phe Ile Glu Thr Lys Ser Leu Gly Ala Ser
        370                 375                 380

Thr Ile His Lys Ser Gln Gly Ser Thr Val Lys Gly Val Trp Leu Ala
385                 390                 395                 400

Leu His Asp Ile His Tyr Ala Asp Glu Glu Leu Lys Gln Gln Leu Val
                405                 410                 415

Tyr Val Gly Val Thr Arg Pro Thr Asp Phe Cys Leu Tyr Phe Asp Gly
            420                 425                 430

Thr Lys

<210> SEQ ID NO 105
<211> LENGTH: 420
<212> TYPE: PRT
<213> ORGANISM: Aeromonas phage CC2

<400> SEQUENCE: 105

Met Ala Val Asp Ala Val Gln Ser Gly Thr Gly His Ile Thr Ile Ser
1               5                   10                  15

Gly Pro Pro Gly Ser Gly Lys Thr Phe Leu Val Lys Tyr Ile Ile Lys
            20                  25                  30

Met Leu Gly Asp Glu Leu Gly Thr Val Leu Ala Ala Pro Thr His Gln
        35                  40                  45

Ala Lys Ile Val Leu Thr Glu Met Ser Gly Ile Glu Ala Cys Thr Ile
    50                  55                  60

His Ser Leu Met Lys Ile His Pro Glu Thr Leu Glu Asp Ile Gln Ile
65                  70                  75                  80

Phe Asp Gln Ser Lys Met Pro Asp Leu Ser Thr Val Arg Tyr Leu Ile
                85                  90                  95

Ile Glu Glu Ala Ser Met His Ser Lys Ala Leu Phe Asn Ile Thr Met
            100                 105                 110

Lys Ser Ile Pro Pro Thr Cys Arg Ile Ile Ala Ile Gly Asp Lys Asp
        115                 120                 125

Gln Ile Gln Pro Val Asp His Ala Pro Gly Glu Leu Ser Pro Tyr Phe
    130                 135                 140

Thr Asp Ser Arg Phe Thr Gln Ile Arg Met Thr Asp Ile Met Arg Gln
145                 150                 155                 160

Ser Leu Asp Asn Pro Ile Ile Gln Val Ala Thr Thr Ile Arg Glu Gly
                165                 170                 175

Gly Trp Ile Tyr Gln Asn Trp Asn Lys Glu Lys Ser Gly Val Tyr
            180                 185                 190

Lys Val Lys Ser Ile Thr Asp Leu Ile Asn Ser Tyr Leu Arg Val Val
        195                 200                 205

Lys Thr Pro Glu Asp Leu Thr Lys Tyr Arg Phe Leu Ala Phe Thr Asn
    210                 215                 220

Lys Val Val Asp Lys Val Asn Ser Ile Val Arg Lys His Val Tyr Lys
225                 230                 235                 240

Thr Asp Leu Pro Phe Ile Glu Gly Glu Lys Leu Val Leu Gln Glu Pro
                245                 250                 255

Val Met Val Glu Tyr Asp Asp Thr Ile Glu Thr Ile Phe Thr Asn
            260                 265                 270

Gly Glu Val Val Thr Val Asp Glu Ile Glu Val Ser Asp Met Asn Ile
        275                 280                 285

Arg Ile Asp Gly Ser Pro Ala Phe Ser Ile Ser Val Ala Lys Leu Lys
```

```
                290                 295                 300
Val Thr Ser Asp Phe Ser Gly Val Thr His Asp Ile Met Ser Val Tyr
305                 310                 315                 320

Gly Glu Asp Ser Lys Ala Glu Phe Asn Tyr Gln Leu Ser Glu Ala Ala
                325                 330                 335

Ala Val Ile Lys Gln Met Gln Arg Gly Gln Thr Lys Ala Ala Trp Ala
                340                 345                 350

Ser Phe Trp Asp Ala Lys Lys Thr Phe Thr Glu Thr Lys Ser Leu Gly
                355                 360                 365

Ala Cys Thr Ile His Lys Ser Gln Gly Ser Thr Val Lys Gly Val Trp
                370                 375                 380

Leu Gly Leu His Asp Ile Ser Tyr Ala Asp Thr Asp Leu Gln Gln Gln
385                 390                 395                 400

Leu Val Tyr Val Gly Val Thr Arg Pro Thr Asp Phe Cys Leu Tyr Phe
                405                 410                 415

Asp Gly Ser Lys
                420

<210> SEQ ID NO 106
<211> LENGTH: 443
<212> TYPE: PRT
<213> ORGANISM: Cronobacter phage vB CsaM GAP161

<400> SEQUENCE: 106

Met Ser Glu Leu Thr Phe Asp Asp Leu Ser Asp Asp Gln Lys Ser Ala
1               5                   10                  15

His Asp Arg Val Ile His Asn Ile Gln Asn Ala Ile His Thr Thr Ile
                20                  25                  30

Thr Gly Gly Pro Gly Val Gly Lys Thr Thr Leu Val Lys Phe Val Phe
            35                  40                  45

Asn Thr Leu Lys Gly Leu Gly Ile Ser Gly Ile Trp Leu Thr Ala Pro
50                  55                  60

Thr His Gln Ala Lys Asn Val Leu Ala Ala Ala Thr Gly Met Asp Ala
65                  70                  75                  80

Thr Thr Ile His Ser Ala Leu Lys Ile Ser Pro Val Thr Asn Glu Glu
                85                  90                  95

Leu Arg Val Phe Glu Gln Gln Lys Gly Lys Lys Ala Pro Asp Leu Ser
                100                 105                 110

Thr Cys Arg Val Phe Val Val Glu Glu Val Ser Met Val Asp Met Asp
            115                 120                 125

Leu Phe Arg Ile Ile Arg Arg Ser Ile Pro Ser Asn Ala Val Ile Leu
130                 135                 140

Gly Leu Gly Asp Lys Asp Gln Ile Arg Pro Val Asn Ala Asp Gly Arg
145                 150                 155                 160

Val Glu Leu Ser Pro Phe Phe Asp Glu Ile Phe Asp Val Ile Arg
                165                 170                 175

Met Asp Lys Ile Met Arg Gln Ala Glu Gly Asn Pro Ile Ile Gln Val
                180                 185                 190

Ser Arg Ala Val Arg Asp Gly Lys Met Leu Lys Pro Met Ser Val Gly
            195                 200                 205

Asp Leu Gly Val Phe Gln His Ala Asn Ala Val Asp Phe Leu Arg Gln
            210                 215                 220

Tyr Phe Arg Arg Val Lys Thr Pro Asp Asp Leu Ile Glu Asn Arg Met
225                 230                 235                 240
```

-continued

```
Phe Ala Tyr Thr Asn Asp Asn Val Asp Lys Leu Asn Ala Thr Ile Arg
                245                 250                 255

Lys His Leu Tyr Lys Thr Thr Glu Pro Phe Ile Leu Asp Glu Val Ile
            260                 265                 270

Val Met Gln Glu Pro Leu Val Gln Glu Met Arg Leu Asn Gly Gln Ile
        275                 280                 285

Phe Thr Glu Ile Val Tyr Asn Asn Glu Lys Ile Arg Val Leu Glu
    290                 295                 300

Ile Ile Pro Arg Arg Glu Val Ile Lys Ala Glu Lys Cys Asp Glu Lys
305                 310                 315                 320

Ile Glu Ile Glu Phe Tyr Leu Leu Lys Thr Val Ser Leu Glu Glu
                325                 330                 335

Thr Glu Ala Gln Ile Gln Val Val Asp Pro Val Met Lys Asp Arg
            340                 345                 350

Leu Gly Asn Tyr Leu Ala Tyr Val Ala Ser Thr Tyr Lys Arg Ile Lys
        355                 360                 365

Gln Gln Thr Gly Tyr Lys Ala Pro Trp His Ser Phe Trp Ala Ile Lys
    370                 375                 380

Asn Lys Phe Gln Asp Val Lys Pro Leu Pro Val Cys Thr Tyr His Lys
385                 390                 395                 400

Ser Gln Gly Ser Thr Tyr Asp His Ala Tyr Met Tyr Thr Arg Asp Ala
                405                 410                 415

Tyr Ala Phe Ala Asp Tyr Asp Leu Cys Lys Gln Leu Ile Tyr Val Gly
            420                 425                 430

Val Thr Arg Ala Arg Tyr Thr Val Asp Tyr Val
        435                 440

<210> SEQ ID NO 107
<211> LENGTH: 442
<212> TYPE: PRT
<213> ORGANISM: Klebsiella phage KP15

<400> SEQUENCE: 107

Met Ser Glu Leu Thr Phe Asp Asp Leu Ser Glu Asp Gln Lys Asn Ala
1               5                   10                  15

His Asp Arg Val Ile Lys Asn Ile Arg Asn Lys Ile His Thr Thr Ile
            20                  25                  30

Thr Gly Gly Pro Gly Val Gly Lys Thr Thr Leu Val Lys Phe Val Phe
        35                  40                  45

Glu Thr Leu Lys Lys Leu Gly Ile Ser Gly Ile Trp Leu Thr Ala Pro
    50                  55                  60

Thr His Gln Ala Lys Asn Val Leu Ser Glu Ala Val Gly Met Asp Ala
65                  70                  75                  80

Thr Thr Ile His Ser Ala Leu Lys Ile Ser Pro Val Thr Asn Glu Glu
                85                  90                  95

Leu Arg Val Phe Glu Gln Gln Lys Gly Lys Lys Ala Ala Asp Leu Ser
            100                 105                 110

Glu Cys Arg Val Phe Val Val Glu Glu Val Ser Met Val Asp Lys Glu
        115                 120                 125

Leu Phe Arg Ile Ile Lys Arg Thr Ile Pro Ser Cys Ala Val Ile Leu
    130                 135                 140

Gly Leu Gly Asp Lys Asp Gln Ile Arg Pro Val Asn Thr Glu Gly Ile
145                 150                 155                 160

Thr Glu Leu Ser Pro Phe Phe Asp Glu Glu Ile Phe Ala Val Ile Arg
                165                 170                 175
```

```
Met Asp Lys Ile Met Arg Gln Ala Glu Gly Asn Pro Ile Ile Gln Val
            180                 185                 190

Ser Arg Ala Ile Arg Asp Gly Lys Pro Leu Met Pro Leu Met Asn Gly
        195                 200                 205

Glu Leu Gly Val Met Lys His Glu Asn Ala Ser Asp Phe Leu Arg Arg
    210                 215                 220

Tyr Phe Ser Arg Val Lys Thr Pro Asp Leu Asn Asn Arg Met
225                 230                 235                 240

Phe Ala Tyr Thr Asn Ala Asn Val Asp Lys Leu Asn Ala Val Ile Arg
                245                 250                 255

Lys His Leu Tyr Lys Thr Asp Gln Pro Phe Ile Val Gly Glu Val Val
            260                 265                 270

Val Met Gln Glu Pro Leu Val Thr Glu Gly Arg Val Asn Gly Val Ser
        275                 280                 285

Phe Val Glu Val Ile Tyr Asn Asn Asn Glu Gln Ile Lys Ile Leu Glu
    290                 295                 300

Ile Ile Pro Arg Ser Asp Thr Ile Lys Ala Asp Arg Cys Asp Pro Val
305                 310                 315                 320

Gln Ile Asp Tyr Phe Leu Met Lys Thr Glu Ser Met Phe Glu Asp Thr
                325                 330                 335

Lys Ala Asp Ile Gln Val Ile Ala Asp Pro Val Met Gln Glu Arg Leu
            340                 345                 350

Gly Asp Tyr Leu Asn Tyr Val Ala Phe Gln Tyr Lys Lys Met Lys Gln
        355                 360                 365

Glu Thr Gly Tyr Lys Ala Pro Trp Tyr Ser Phe Trp Gln Ile Lys Asn
    370                 375                 380

Lys Phe Gln Thr Val Lys Ala Leu Pro Val Cys Thr Tyr His Lys Gly
385                 390                 395                 400

Gln Gly Ser Thr Tyr Asp His Ser Tyr Met Tyr Thr Arg Asp Ala Tyr
                405                 410                 415

Ala Tyr Ala Asp Tyr Glu Leu Cys Lys Gln Leu Leu Tyr Val Gly Thr
            420                 425                 430

Thr Arg Ala Arg Phe Thr Val Asp Tyr Val
        435                 440

<210> SEQ ID NO 108
<211> LENGTH: 438
<212> TYPE: PRT
<213> ORGANISM: Stenotrophomonas phage IME13

<400> SEQUENCE: 108

Met Val Thr Tyr Asp Asp Leu Thr Val Gly Gln Lys Asp Ala Ile Glu
1               5                  10                  15

Lys Ala Leu Gln Ala Met Arg Thr Lys Arg His Ile Thr Ile Arg Gly
            20                  25                  30

Pro Ala Gly Ser Gly Lys Thr Thr Met Thr Arg Phe Leu Leu Glu Arg
        35                  40                  45

Leu Phe Gln Thr Gly Gln Gln Gly Ile Val Leu Thr Ala Pro Thr His
    50                  55                  60

Gln Ala Lys Lys Glu Leu Ser Lys His Ala Leu Arg Lys Ser Tyr Thr
65                  70                  75                  80

Ile Gln Ser Val Leu Lys Ile Asn Pro Ser Thr Leu Glu Glu Asn Gln
                85                  90                  95

Ile Phe Glu Gln Lys Gly Thr Pro Asp Phe Ser Lys Thr Arg Val Leu
```

```
            100                 105                 110
Ile Cys Asp Glu Val Ser Phe Tyr Thr Arg Lys Leu Phe Asp Ile Leu
            115                 120                 125

Met Arg Asn Val Pro Ser His Cys Val Val Ile Gly Ile Gly Asp Lys
            130                 135             140

Ala Gln Ile Arg Gly Val Ser Glu Asp Asp Thr His Glu Leu Ser Pro
145                 150                 155                 160

Phe Phe Thr Asp Asn Arg Phe Glu Gln Val Glu Leu Thr Glu Val Lys
                165                 170                 175

Arg His Gln Gly Pro Ile Ile Glu Val Ala Thr Asp Ile Arg Asn Gly
            180                 185                 190

Lys Trp Ile Tyr Glu Lys Leu Asp Asp Ser Gly Asn Val Lys Gln
            195                 200                 205

Phe His Thr Val Lys Asp Phe Leu Ser Lys Tyr Phe Arg Thr Lys
            210                 215                 220

Thr Pro Asn Asp Leu Leu Glu Asn Arg Ile Met Ala Tyr Thr Asn Asn
225                 230                 235                 240

Ser Val Asp Lys Leu Asn Ser Val Ile Arg Lys Gln Leu Tyr Gly Ala
                245                 250                 255

Asn Ala Ala Pro Phe Leu Pro Asp Glu Ile Leu Val Met Gln Glu Pro
            260                 265                 270

Leu Met Phe Asp Ile Asp Ile Gly Gly Gln Thr Leu Lys Glu Val Ile
            275                 280                 285

Phe Asn Asn Gly Gln Asn Val Arg Val Ile Asn Val Lys Pro Ser Arg
            290                 295                 300

Lys Thr Leu Lys Ala Lys Gly Val Gly Glu Ile Glu Val Glu Cys Thr
305                 310                 315                 320

Met Leu Glu Cys Glu Ser Tyr Glu Glu Asp Gly Asp Tyr Arg Arg
                325                 330                 335

Ala Trp Phe Thr Val Val His Asp Gln Asn Thr Gln Tyr Ala Ile Asn
            340                 345                 350

Glu Phe Leu Ser Ile Ile Ala Glu Lys Tyr Arg Ser Arg Glu Val Phe
            355                 360                 365

Pro Asn Trp Lys Asp Phe Trp Ala Ile Arg Asn Thr Phe Val Lys Val
            370                 375                 380

Arg Pro Leu Gly Ala Met Thr Phe His Lys Ser Gln Gly Ser Thr Phe
385                 390                 395                 400

Asp Asn Ala Tyr Leu Phe Thr Pro Cys Leu His Gln Tyr Cys Arg Asp
                405                 410                 415

Pro Asp Val Ala Gln Glu Leu Ile Tyr Val Gly Asn Thr Arg Ala Arg
            420                 425                 430

Lys Asn Val Cys Phe Val
            435

<210> SEQ ID NO 109
<211> LENGTH: 442
<212> TYPE: PRT
<213> ORGANISM: Acinetobacter phage Ac42

<400> SEQUENCE: 109

Met Asn Phe Glu Asp Leu Thr Glu Gly Gln Lys Asn Ala Tyr Thr Ala
1               5                   10                  15

Ala Ile Lys Ala Ile Glu Thr Val Pro Ser Ser Ala Glu Lys Arg
            20                  25                  30
```

```
His Leu Thr Ile Asn Gly Pro Ala Gly Thr Gly Lys Thr Thr Leu Thr
     35                  40                  45
Lys Phe Leu Ile Ala Glu Leu Ile Arg Arg Gly Glu Arg Gly Val Tyr
 50                  55                  60
Leu Ala Ala Pro Thr His Gln Ala Lys Lys Val Leu Ser Gln His Ala
 65                  70                  75                  80
Gly Met Glu Ala Ser Thr Ile His Ser Leu Leu Lys Ile Asn Pro Thr
                 85                  90                  95
Thr Tyr Glu Asp Ser Thr Thr Phe Glu Gln Lys Asp Val Pro Asp Met
             100                 105                 110
Ser Glu Cys Arg Val Leu Ile Cys Asp Glu Ala Ser Met Tyr Asp Leu
         115                 120                 125
Lys Leu Phe Gln Ile Leu Met Ser Ser Ile Pro Leu Cys Cys Thr Val
130                 135                 140
Ile Ala Leu Gly Asp Ile Ala Gln Ile Arg Pro Val Glu Pro Gly Ala
145                 150                 155                 160
Phe Glu Gly Gln Val Ser Pro Phe Phe Thr Tyr Glu Lys Phe Glu Gln
                 165                 170                 175
Val Ser Leu Thr Glu Val Met Arg Ser Asn Ala Pro Ile Ile Asp Val
             180                 185                 190
Ala Thr Ser Ile Arg Thr Gly Asn Trp Ile Tyr Glu Asn Val Ile Asp
         195                 200                 205
Gly Ala Gly Val His Asn Leu Thr Ser Glu Arg Ser Val Lys Ser Phe
    210                 215                 220
Met Glu Lys Tyr Phe Ser Ile Val Lys Thr Pro Glu Asp Leu Phe Glu
225                 230                 235                 240
Asn Arg Leu Leu Ala Phe Thr Asn Lys Ser Val Asp Asp Leu Asn Lys
                 245                 250                 255
Ile Val Arg Lys Lys Ile Tyr Asn Thr Leu Glu Pro Phe Ile Asp Gly
             260                 265                 270
Glu Val Leu Val Met Gln Glu Pro Leu Ile Lys Ser Tyr Thr Tyr Glu
         275                 280                 285
Gly Lys Lys Val Ser Glu Ile Val Phe Asn Asn Gly Glu Met Val Lys
    290                 295                 300
Val Leu Cys Cys Ser Gln Thr Ser Asp Glu Ile Ser Val Arg Gly Cys
305                 310                 315                 320
Ser Thr Lys Tyr Met Val Arg Tyr Trp Gln Leu Asp Leu Gln Ser Leu
                 325                 330                 335
Asp Asp Pro Asp Leu Thr Gly Ser Ile Asn Val Ile Val Asp Glu Ala
             340                 345                 350
Glu Ile Asn Lys Leu Asn Leu Val Leu Gly Lys Ser Ala Glu Gln Phe
         355                 360                 365
Lys Ser Gly Ala Val Lys Ala Ala Trp Ala Asp Trp Trp Lys Leu Lys
    370                 375                 380
Arg Asn Phe His Lys Val Lys Ala Leu Pro Cys Ser Thr Ile His Lys
385                 390                 395                 400
Ser Gln Gly Thr Ser Val Asp Asn Val Phe Leu Tyr Thr Pro Cys Ile
                 405                 410                 415
His Lys Ala Asp Ser Gln Leu Ala Gln Leu Leu Tyr Val Gly Ala
             420                 425                 430
Thr Arg Ala Arg His Asn Val Tyr Tyr Ile
         435                 440
```

<210> SEQ ID NO 110
<211> LENGTH: 442
<212> TYPE: PRT
<213> ORGANISM: Shigella phage SP18

<400> SEQUENCE: 110

```
Met Ile Lys Phe Glu Asp Leu Asn Thr Gly Gln Lys Glu Ala Phe Asp
1               5                   10                  15

Tyr Ile Thr Glu Ala Ile Gln Arg Arg Ser Gly Glu Cys Ile Thr Leu
            20                  25                  30

Asn Gly Pro Ala Gly Thr Gly Lys Thr Thr Leu Thr Lys Phe Val Ile
        35                  40                  45

Asp His Leu Val Arg Asn Gly Val Met Gly Ile Val Leu Ala Ala Pro
    50                  55                  60

Thr His Gln Ala Lys Lys Val Leu Ser Lys Leu Ser Gly Gln Thr Ala
65                  70                  75                  80

Asn Thr Ile His Ser Ile Leu Lys Ile Asn Pro Thr Thr Tyr Glu Asp
                85                  90                  95

Gln Asn Ile Phe Glu Gln Arg Glu Met Pro Asp Met Ser Lys Cys Asn
            100                 105                 110

Val Leu Val Cys Asp Glu Ala Ser Met Tyr Asp Gly Ser Leu Phe Lys
        115                 120                 125

Ile Ile Cys Asn Ser Val Pro Glu Trp Cys Thr Ile Leu Gly Ile Gly
    130                 135                 140

Asp Met His Gln Leu Gln Pro Val Asp Pro Gly Ser Thr Gln Gln Lys
145                 150                 155                 160

Ile Ser Pro Phe Phe Thr His Pro Lys Phe Lys Gln Ile His Leu Thr
                165                 170                 175

Glu Val Met Arg Ser Asn Ala Pro Ile Ile Glu Val Ala Thr Glu Ile
            180                 185                 190

Arg Asn Gly Gly Trp Phe Arg Asp Cys Met Tyr Asp Gly His Gly Val
        195                 200                 205

Gln Gly Phe Thr Ser Gln Thr Ala Leu Lys Asp Phe Met Val Asn Tyr
    210                 215                 220

Phe Gly Ile Val Lys Asp Ala Asp Met Leu Met Glu Asn Arg Met Tyr
225                 230                 235                 240

Ala Tyr Thr Asn Lys Ser Val Glu Lys Leu Asn Asn Ile Ile Arg Arg
                245                 250                 255

Lys Leu Tyr Glu Thr Asp Lys Ala Phe Leu Pro Tyr Glu Val Leu Val
            260                 265                 270

Met Gln Glu Pro His Met Lys Glu Leu Glu Phe Glu Gly Lys Lys Phe
        275                 280                 285

Ser Glu Thr Ile Phe Asn Asn Gly Gln Leu Val Arg Ile Lys Asp Cys
    290                 295                 300

Lys Tyr Thr Ser Thr Ile Leu Arg Cys Lys Gly Glu Ser His Gln Leu
305                 310                 315                 320

Val Ile Asn Tyr Trp Asp Leu Glu Val Glu Ser Ile Asp Glu Asp Glu
                325                 330                 335

Glu Tyr Gln Val Asp Arg Ile Lys Val Leu Pro Glu Asp Gln Gln Pro
            340                 345                 350

Lys Phe Gln Ala Tyr Leu Ala Lys Val Ala Asp Thr Tyr Lys Gln Met
        355                 360                 365

Lys Ala Ala Gly Lys Arg Pro Glu Trp Lys Asp Phe Trp Lys Ala Arg
    370                 375                 380
```

-continued

Arg Thr Phe Leu Lys Val Arg Ala Leu Pro Val Ser Thr Ile His Lys
385                 390                 395                 400

Ala Gln Gly Val Ser Val Asp Lys Ala Phe Ile Tyr Thr Pro Cys Ile
            405                 410                 415

His Met Ala Glu Ala Ser Leu Ala Ser Gln Leu Ala Tyr Val Gly Ile
            420                 425                 430

Thr Arg Ala Arg Tyr Asp Ala Tyr Tyr Val
            435                 440

<210> SEQ ID NO 111
<211> LENGTH: 439
<212> TYPE: PRT
<213> ORGANISM: Yersinia phage phiR1-RT

<400> SEQUENCE: 111

Met Ile Thr Tyr Asp Asp Leu Thr Asp Gly Gln Lys Ser Ala Phe Asp
1               5                   10                  15

Asn Thr Met Glu Ala Ile Lys Asn Lys Lys Gly His Ile Thr Ile Asn
            20                  25                  30

Gly Pro Ala Gly Thr Gly Lys Thr Thr Leu Thr Lys Phe Ile Ile Asp
        35                  40                  45

His Leu Ile Lys Thr Gly Glu Ala Gly Ile Ile Leu Cys Ala Pro Thr
50                  55                  60

His Gln Ala Lys Lys Val Leu Ser Lys Leu Ser Gly Met Asp Ala Ser
65                  70                  75                  80

Thr Ile His Ser Val Leu Lys Ile Asn Pro Thr Thr Tyr Glu Glu Asn
            85                  90                  95

Gln Ile Phe Glu Gln Arg Glu Val Pro Asp Leu Ala Ala Cys Arg Val
        100                 105                 110

Leu Ile Cys Asp Glu Ala Ser Phe Tyr Asp Arg Lys Leu Phe Gly Ile
        115                 120                 125

Ile Leu Ala Thr Val Pro Ser Trp Cys Thr Val Ile Ala Leu Gly Asp
130                 135                 140

Lys Asp Gln Leu Arg Pro Val Thr Pro Gly Glu Ser Glu Gln Gln Leu
145                 150                 155                 160

Ser Pro Phe Phe Ser His Ala Lys Phe Lys Gln Val His Leu Thr Glu
            165                 170                 175

Ile Lys Arg Ser Asn Gly Pro Ile Ile Gln Val Ala Thr Asp Ile Arg
        180                 185                 190

Asn Gly Gly Trp Leu Ser Glu Asn Ile Val Asp Gly Glu Gly Val His
        195                 200                 205

Ala Phe Asn Ser Asn Thr Ala Leu Lys Asp Phe Met Ile Arg Tyr Phe
210                 215                 220

Asp Val Val Lys Thr Ala Asp Asp Leu Ile Glu Ser Arg Met Leu Ala
225                 230                 235                 240

Tyr Thr Asn Lys Ser Val Asp Lys Leu Asn Gly Ile Ile Arg Arg Lys
            245                 250                 255

Leu Tyr Glu Thr Asp Lys Pro Phe Ile Asn Gly Glu Val Leu Val Met
        260                 265                 270

Gln Glu Pro Leu Met Lys Glu Leu Glu Phe Asp Gly Lys Lys Phe His
        275                 280                 285

Glu Ile Val Phe Asn Asn Gly Gln Leu Val Lys Ile Leu Tyr Ala Ser
        290                 295                 300

Glu Thr Ser Thr Phe Ile Ser Ala Arg Asn Val Pro Gly Glu Tyr Met
305                 310                 315                 320

-continued

```
Ile Arg Tyr Trp Asn Leu Glu Val Glu Thr Ala Asp Ser Asp Asp Asp
            325                 330                 335

Tyr Ala Thr Ser Gln Ile Gln Val Ile Cys Asp Pro Ala Glu Met Thr
            340                 345                 350

Lys Phe Gln Met Phe Leu Ala Lys Thr Ala Asp Thr Tyr Lys Asn Ser
            355                 360                 365

Gly Val Lys Ala Tyr Trp Lys Asp Phe Trp Ser Val Lys Asn Lys Phe
            370                 375                 380

Lys Lys Val Lys Ala Leu Pro Val Ser Thr Ile His Lys Ser Gln Gly
385                 390                 395                 400

Cys Thr Val Asn Asn Thr Phe Leu Tyr Thr Pro Cys Ile His Met Ala
                405                 410                 415

Asp Ala Gln Leu Ala Lys Gln Leu Leu Tyr Val Gly Ala Thr Arg Ala
            420                 425                 430

Arg Thr Asn Leu Tyr Tyr Ile
            435

<210> SEQ ID NO 112
<211> LENGTH: 441
<212> TYPE: PRT
<213> ORGANISM: Salmonella phage S16

<400> SEQUENCE: 112

Met Ile Thr Phe Glu Gln Leu Thr Ser Gly Gln Lys Leu Ala Phe Asp
1               5                   10                  15

Glu Thr Ile Arg Ala Ile Lys Glu Lys Lys Asn His Val Thr Ile Asn
            20                  25                  30

Gly Pro Ala Gly Thr Gly Lys Thr Thr Leu Thr Lys Phe Ile Met Glu
            35                  40                  45

His Leu Val Ser Thr Gly Glu Thr Gly Ile Ile Leu Thr Ala Pro Thr
        50                  55                  60

His Ala Ala Lys Lys Val Leu Thr Lys Leu Ser Gly Met Glu Ala Asn
65                  70                  75                  80

Thr Ile His Lys Ile Leu Lys Ile Asn Pro Thr Thr Tyr Glu Glu Ser
                85                  90                  95

Met Leu Phe Glu Gln Lys Glu Val Pro Asp Leu Ala Ser Cys Arg Val
            100                 105                 110

Leu Ile Cys Asp Glu Ala Ser Met Trp Asp Arg Lys Leu Phe Lys Ile
            115                 120                 125

Leu Met Ala Ser Ile Pro Lys Trp Cys Thr Ile Val Ala Ile Gly Asp
            130                 135                 140

Val Ala Gln Ile Arg Pro Val Asp Pro Gly Glu Thr Glu Ala His Ile
145                 150                 155                 160

Ser Pro Phe Phe Ile His Lys Asp Phe Lys Gln Leu Asn Leu Thr Glu
                165                 170                 175

Val Met Arg Ser Asn Ala Pro Ile Ile Asp Val Ala Thr Asp Ile Arg
            180                 185                 190

Asn Gly Ser Trp Ile Tyr Glu Lys Thr Val Asp Gly His Gly Val His
            195                 200                 205

Gly Phe Thr Ser Thr Thr Ala Leu Lys Asp Phe Met Met Gln Tyr Phe
        210                 215                 220

Ser Ile Val Lys Ser Pro Glu Asp Leu Phe Glu Asn Arg Met Leu Ala
225                 230                 235                 240

Phe Thr Asn Lys Ser Val Asp Lys Leu Asn Ser Ile Ile Arg Arg Arg
```

```
               245                 250                 255
Leu Tyr Gln Thr Glu Glu Ala Phe Val Val Gly Glu Val Ile Val Met
            260                 265                 270
Gln Glu Pro Leu Met Arg Glu Leu Val Phe Glu Gly Lys Lys Phe His
            275                 280                 285
Glu Thr Leu Phe Thr Asn Gly Gln Tyr Val Arg Ile Leu Ser Ala Asp
            290                 295                 300
Tyr Thr Ser Ser Phe Leu Gly Ala Lys Gly Val Ser Gly Glu His Leu
305                 310                 315                 320
Ile Arg His Trp Val Leu Asp Val Glu Thr Tyr Asp Asp Glu Tyr
                325                 330                 335
Ala Arg Glu Lys Ile Asn Val Ile Ser Asp Glu Gln Glu Met Asn Lys
            340                 345                 350
Phe Gln Phe Phe Leu Ala Lys Thr Ala Asp Thr Tyr Lys Asn Trp Asn
            355                 360                 365
Lys Gly Gly Lys Ala Pro Trp Ser Glu Phe Trp Asp Ala Lys Arg Lys
370                 375                 380
Phe His Lys Val Lys Ala Leu Pro Cys Ser Thr Phe His Lys Ala Gln
385                 390                 395                 400
Gly Ile Ser Val Asp Ser Ser Phe Ile Tyr Thr Pro Cys Ile His Val
                405                 410                 415
Ser Ser Asp Asn Lys Phe Lys Leu Glu Leu Leu Tyr Val Gly Ala Thr
            420                 425                 430
Arg Gly Arg His Asp Val Phe Phe Val
            435                 440

<210> SEQ ID NO 113
<211> LENGTH: 786
<212> TYPE: DNA
<213> ORGANISM: Escherichia coli

<400> SEQUENCE: 113
tgtctgaccg caccgccgaa agaagcggca cgtccgaccc tgatgccgcg tgcacagtct     60
tataaagatc tgacccatct gccggctccg acgggcaaaa ttttgttag cgtctataac    120
atccaggacg aaaccggtca atttaaaccg tacccggcga gtaatttctc cacggccgtt    180
ccgcagagtg caaccgctat gctggtcacg gcactgaaag attcccgttg gttcattccg    240
ctggaacgcc agggcctgca aaacctgctg aatgaacgta aaattatccg cgcagctcag    300
gaaaacggta ccgtggccat taacaatcgt attccgctgc aaagcctgac cgccgcaaac    360
atcatggttg aaggctctat catcggttac gaatcaaacg tcaaatcggg cggtgtgggc    420
gcacgttatt ttggcattgg tgctgatacc cagtaccaac tggaccagat cgcagttaac    480
ctgcgcgtgg ttaatgtcag caccggcgaa attctgagct ctgtgaatac cagcaaaacg    540
atcctgtctt acgaagtgca ggctggtgtt tttcgtttca ttgattatca acgcctgctg    600
gaaggcgaag tcggttacac ctcaaacgaa ccggtgatgc tgtgtctgat gtcggcgatt    660
gaaacgggtg ttatttttcct gatcaatgat ggcatcgacc gtggtctgtg ggatctgcag    720
aacaaagccg aacgtcaaaa tgacattctg gtgaaatacc gccacatgag tgttccgccg    780
gaatcc                                                               786

<210> SEQ ID NO 114
<211> LENGTH: 262
<212> TYPE: PRT
<213> ORGANISM: Escherichia coli
```

<400> SEQUENCE: 114

Cys Leu Thr Ala Pro Pro Lys Glu Ala Ala Arg Pro Thr Leu Met Pro
1               5                   10                  15

Arg Ala Gln Ser Tyr Lys Asp Leu Thr His Leu Pro Ala Pro Thr Gly
            20                  25                  30

Lys Ile Phe Val Ser Val Tyr Asn Ile Gln Asp Glu Thr Gly Gln Phe
        35                  40                  45

Lys Pro Tyr Pro Ala Ser Asn Phe Ser Thr Ala Val Pro Gln Ser Ala
    50                  55                  60

Thr Ala Met Leu Val Thr Ala Leu Lys Asp Ser Arg Trp Phe Ile Pro
65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Thr Val Ala Ile Asn Asn Arg Ile Pro
            100                 105                 110

Leu Gln Ser Leu Thr Ala Ala Asn Ile Met Val Glu Gly Ser Ile Ile
        115                 120                 125

Gly Tyr Glu Ser Asn Val Lys Ser Gly Gly Val Gly Ala Arg Tyr Phe
130                 135                 140

Gly Ile Gly Ala Asp Thr Gln Tyr Gln Leu Asp Gln Ile Ala Val Asn
145                 150                 155                 160

Leu Arg Val Val Asn Val Ser Thr Gly Glu Ile Leu Ser Ser Val Asn
                165                 170                 175

Thr Ser Lys Thr Ile Leu Ser Tyr Glu Val Gln Ala Gly Val Phe Arg
            180                 185                 190

Phe Ile Asp Tyr Gln Arg Leu Leu Gly Gly Glu Val Gly Tyr Thr Ser
        195                 200                 205

Asn Glu Pro Val Met Leu Cys Leu Met Ser Ala Ile Glu Thr Gly Val
    210                 215                 220

Ile Phe Leu Ile Asn Asp Gly Ile Asp Arg Gly Leu Trp Asp Leu Gln
225                 230                 235                 240

Asn Lys Ala Glu Arg Gln Asn Asp Ile Leu Val Lys Tyr Arg His Met
                245                 250                 255

Ser Val Pro Pro Glu Ser
            260

<210> SEQ ID NO 115
<211> LENGTH: 50
<212> TYPE: DNA
<213> ORGANISM: Artificial Sequence
<220> FEATURE:
<223> OTHER INFORMATION: Transposon top strand

<400> SEQUENCE: 115
gttttcgcat ttatcgtgaa acgctttcgc gtttttcgtg cgccgcttca                50

<210> SEQ ID NO 116
<211> LENGTH: 54
<212> TYPE: DNA
<213> ORGANISM: Artificial Sequence
<220> FEATURE:
<223> OTHER INFORMATION: Adapter annealing sequence to form transposon 1
<220> FEATURE:
<221> NAME/KEY: misc_feature
<222> LOCATION: (50)..(50)
<223> OTHER INFORMATION: n = U

<400> SEQUENCE: 116
caaaagcgta aatagcactt tgcgaaagcg caaaaagcac gcggcgaagn ctag    54

<210> SEQ ID NO 117
<211> LENGTH: 64
<212> TYPE: DNA
<213> ORGANISM: Artificial Sequence
<220> FEATURE:
<223> OTHER INFORMATION: Adapter annealing sequence to form transposon 2

<400> SEQUENCE: 117
gatctgaagc ggcgcacgaa aaacgcgaaa gcgtttcacg ataaatgcga aactttttt    60 tttt    64

<210> SEQ ID NO 118
<211> LENGTH: 12
<212> TYPE: DNA
<213> ORGANISM: Artificial Sequence
<220> FEATURE:
<223> OTHER INFORMATION: Adapter annealing sequence attached at 5' end
      to 3' end of iSpC3 spacers

<400> SEQUENCE: 118
tttttttttt tt    12

<210> SEQ ID NO 119
<211> LENGTH: 77
<212> TYPE: DNA
<213> ORGANISM: Artificial Sequence
<220> FEATURE:
<223> OTHER INFORMATION: Adapter annealing sequence attached at 5' end
      to 3' end of iSp18 spacers

<400> SEQUENCE: 119
ggttgtttct gttggtgctg atattgcgtt ttcgcattta tcgtgaaacg ctttcgcgtt    60
tttcgtgcgc cgcttca    77

<210> SEQ ID NO 120
<211> LENGTH: 29
<212> TYPE: DNA
<213> ORGANISM: Artificial Sequence
<220> FEATURE:
<223> OTHER INFORMATION: Polynucleotide used in the Examples

<400> SEQUENCE: 120
gcaatatcag caccaacaga aacaacctt    29

<210> SEQ ID NO 121
<211> LENGTH: 62
<212> TYPE: DNA
<213> ORGANISM: Artificial Sequence
<220> FEATURE:
<223> OTHER INFORMATION: Polynucleotide used in the Examples

<400> SEQUENCE: 121
tgctgatatt gcgttttcgc atttatcgtg aaacgctttc gcgttttcg tgcgccgctt    60 ca    62

<210> SEQ ID NO 122
<211> LENGTH: 753
<212> TYPE: PRT
<213> ORGANISM: Escherichia coli

<400> SEQUENCE: 122

```
Met Asp Val Ser Tyr Leu Leu Asp Ser Leu Asn Asp Lys Gln Arg Glu
1               5                   10                  15

Ala Val Ala Ala Pro Arg Ser Asn Leu Leu Val Leu Ala Gly Ala Gly
            20                  25                  30

Ser Gly Lys Thr Arg Val Leu Val His Arg Ile Ala Trp Leu Met Ser
            35                  40                  45

Val Glu Asn Cys Ser Pro Tyr Ser Ile Met Ala Val Thr Phe Thr Asn
50                  55                  60

Lys Ala Ala Ala Glu Met Arg His Arg Ile Gly Gln Leu Met Gly Thr
65                  70                  75                  80

Ser Gln Gly Gly Met Trp Val Gly Thr Phe His Gly Leu Ala His Arg
                85                  90                  95

Leu Leu Arg Ala His His Met Asp Ala Asn Leu Pro Gln Asp Phe Gln
            100                 105                 110

Ile Leu Asp Ser Glu Asp Gln Leu Arg Leu Leu Lys Arg Leu Ile Lys
            115                 120                 125

Ala Met Asn Leu Asp Glu Lys Gln Trp Pro Pro Arg Gln Ala Met Trp
130                 135                 140

Tyr Ile Asn Ser Gln Lys Asp Glu Gly Leu Arg Pro His His Ile Gln
145                 150                 155                 160

Ser Tyr Gly Asn Pro Val Glu Gln Thr Trp Gln Lys Val Tyr Gln Ala
                165                 170                 175

Tyr Gln Glu Ala Cys Asp Arg Ala Gly Leu Val Asp Phe Ala Glu Leu
            180                 185                 190

Leu Leu Arg Ala His Glu Leu Trp Leu Asn Lys Pro His Ile Leu Gln
            195                 200                 205

His Tyr Arg Glu Arg Phe Thr Asn Ile Leu Val Asp Glu Phe Gln Asp
210                 215                 220

Thr Asn Asn Ile Gln Tyr Ala Trp Ile Arg Leu Leu Ala Gly Asp Thr
225                 230                 235                 240

Gly Lys Val Met Ile Val Gly Asp Asp Gln Ser Ile Tyr Gly Trp
                245                 250                 255

Arg Gly Ala Gln Val Glu Asn Ile Gln Arg Phe Leu Asn Asp Phe Pro
            260                 265                 270

Gly Ala Glu Thr Ile Arg Leu Glu Gln Asn Tyr Arg Ser Thr Ser Asn
            275                 280                 285

Ile Leu Ser Ala Ala Asn Ala Leu Ile Glu Asn Asn Asn Gly Arg Leu
290                 295                 300

Gly Lys Lys Leu Trp Thr Asp Gly Ala Asp Gly Glu Pro Ile Ser Leu
305                 310                 315                 320

Tyr Cys Ala Phe Asn Glu Leu Asp Glu Ala Arg Phe Val Val Asn Arg
            325                 330                 335

Ile Lys Thr Trp Gln Asp Asn Gly Gly Ala Leu Ala Glu Cys Ala Ile
            340                 345                 350

Leu Tyr Arg Ser Asn Ala Gln Ser Arg Val Leu Glu Glu Ala Leu Leu
            355                 360                 365

Gln Ala Ser Met Pro Tyr Arg Ile Tyr Gly Gly Met Arg Phe Phe Glu
370                 375                 380

Arg Gln Glu Ile Lys Asp Ala Leu Ser Tyr Leu Arg Leu Ile Ala Asn
385                 390                 395                 400

Arg Asn Asp Asp Ala Ala Phe Glu Arg Val Val Asn Thr Pro Thr Arg
                405                 410                 415

Gly Ile Gly Asp Arg Thr Leu Asp Val Val Arg Gln Thr Ser Arg Asp
```

-continued

```
                420                 425                 430
Arg Gln Leu Thr Leu Trp Gln Ala Cys Arg Glu Leu Leu Gln Glu Lys
            435                 440                 445

Ala Leu Ala Gly Arg Ala Ala Ser Ala Leu Gln Arg Phe Met Glu Leu
        450                 455                 460

Ile Asp Ala Leu Ala Gln Glu Thr Ala Asp Met Pro Leu His Val Gln
465                 470                 475                 480

Thr Asp Arg Val Ile Lys Asp Ser Gly Leu Arg Thr Met Tyr Glu Gln
                485                 490                 495

Glu Lys Gly Glu Lys Gly Gln Thr Arg Ile Glu Asn Leu Glu Glu Leu
            500                 505                 510

Val Thr Ala Thr Arg Gln Phe Ser Tyr Asn Glu Glu Asp Glu Asp Leu
        515                 520                 525

Met Pro Leu Gln Ala Phe Leu Ser His Ala Ala Leu Glu Ala Gly Glu
    530                 535                 540

Gly Gln Ala Asp Thr Trp Gln Asp Ala Val Gln Leu Met Thr Leu His
545                 550                 555                 560

Ser Ala Lys Gly Leu Glu Phe Pro Gln Val Phe Ile Val Gly Met Glu
                565                 570                 575

Glu Gly Met Phe Pro Ser Gln Met Ser Leu Asp Glu Gly Gly Arg Leu
            580                 585                 590

Glu Glu Glu Arg Arg Leu Ala Tyr Val Gly Val Thr Arg Ala Met Gln
        595                 600                 605

Lys Leu Thr Leu Thr Tyr Ala Glu Thr Arg Arg Leu Tyr Gly Lys Glu
    610                 615                 620

Val Tyr His Arg Pro Ser Arg Phe Ile Gly Glu Leu Pro Glu Glu Cys
625                 630                 635                 640

Val Glu Glu Val Arg Leu Arg Ala Thr Val Ser Arg Pro Val Ser His
                645                 650                 655

Gln Arg Met Gly Thr Pro Met Val Glu Asn Asp Ser Gly Tyr Lys Leu
            660                 665                 670

Gly Gln Arg Val Arg His Ala Lys Phe Gly Glu Gly Thr Ile Val Asn
        675                 680                 685

Met Glu Gly Ser Gly Glu His Ser Arg Leu Gln Val Ala Phe Gln Gly
    690                 695                 700

Gln Gly Ile Lys Trp Leu Val Ala Ala Tyr Ala Arg Leu Glu Ser Val
705                 710                 715                 720

Ser Gly Gly Ser Ala Trp Ser His Pro Gln Phe Glu Lys Gly Gly Gly
                725                 730                 735

Ser Gly Gly Gly Ser Gly Gly Ser Ala Trp Ser His Pro Gln Phe Glu
            740                 745                 750

Lys
```